(12) United States Patent
Timm et al.

(10) Patent No.: US 7,588,175 B2
(45) Date of Patent: Sep. 15, 2009

(54) SURGICAL STAPLING AND CUTTING INSTRUMENT WITH IMPROVED FIRING SYSTEM

(75) Inventors: Richard W. Timm, Cincinnati, OH (US); Frederick E. Shelton, IV, New Vienna, OH (US); Eugene L. Timperman, Cincinnati, OH (US); Leslie M. Fugikawa, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/820,049

(22) Filed: Jun. 18, 2007

(65) Prior Publication Data

US 2008/0308606 A1 Dec. 18, 2008

(51) Int. Cl.
*A61B 17/068* (2006.01)
(52) U.S. Cl. ............... 227/179.1; 227/180.1; 227/19
(58) Field of Classification Search ............. 227/176.1, 227/179.1, 180.1, 19
See application file for complete search history.

(56) References Cited

U.S. PATENT DOCUMENTS

| | | | |
|---|---|---|---|
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 3,892,228 A * | 7/1975 | Mitsui | 600/149 |
| 4,027,746 A | 6/1977 | Kine | |
| 4,100,820 A | 7/1978 | Evett | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,500,024 A | 2/1985 | DiGiovanni et al. | |
| 4,505,273 A | 3/1985 | Braun et al. | |

(Continued)

FOREIGN PATENT DOCUMENTS

CA 2458946 A1 3/2003

(Continued)

OTHER PUBLICATIONS

U.S. Appl. No. 11/820,119, filed Jun. 18, 2007.

(Continued)

*Primary Examiner*—Brian D Nash

(57) ABSTRACT

A surgical instrument comprising an elongate channel assembly that has a distal end and a proximal end and is constructed to operably support a staple cartridge assembly therein. The instrument may further include a knife assembly that is oriented for travel within the elongate channel assembly. At least one first cable transition support is operably mounted to the distal end of the elongate channel and at least one second cable transition support is operably attached to the knife assembly. A first cable is affixed to the distal end of the elongate channel assembly and extends around the first and second cable transition supports to interface with a cable drive system. In various embodiments, the cable drive system may comprise a winch assembly or a pinion driven rack.

18 Claims, 71 Drawing Sheets

U.S. PATENT DOCUMENTS

| | | |
|---|---|---|
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,629,107 A | 12/1986 | Fedotov et al. |
| 4,643,173 A | 2/1987 | Bell et al. |
| 4,655,222 A | 4/1987 | Florez et al. |
| 4,664,305 A | 5/1987 | Blake, III et al. |
| 4,671,445 A | 6/1987 | Barker et al. |
| 4,679,460 A | 7/1987 | Yoshigai |
| 4,715,520 A | 12/1987 | Roehr, Jr. et al. |
| 4,728,020 A * | 3/1988 | Green et al. .................. 227/19 |
| 4,754,909 A * | 7/1988 | Barker et al. .................. 227/19 |
| 4,767,044 A | 8/1988 | Green |
| 4,809,695 A | 3/1989 | Gwathmey et al. |
| 4,817,643 A | 4/1989 | Olson |
| 4,817,847 A | 4/1989 | Redtenbacher et al. |
| 4,821,939 A | 4/1989 | Green |
| 4,833,937 A | 5/1989 | Nagano |
| 4,869,414 A | 9/1989 | Green et al. |
| 4,869,415 A | 9/1989 | Fox |
| 4,915,100 A | 4/1990 | Green |
| 4,941,623 A | 7/1990 | Pruitt |
| 4,944,443 A | 7/1990 | Oddsen et al. |
| 4,951,861 A | 8/1990 | Schulze et al. |
| 4,955,959 A | 9/1990 | Tompkins et al. |
| 4,964,559 A | 10/1990 | Deniega et al. |
| 4,978,049 A | 12/1990 | Green |
| 5,005,754 A | 4/1991 | Van Overloop |
| 5,014,899 A | 5/1991 | Presty et al. |
| 5,018,657 A | 5/1991 | Pedlick et al. |
| 5,040,715 A | 8/1991 | Green et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,084,057 A | 1/1992 | Green et al. |
| 5,100,042 A | 3/1992 | Gravener et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,156,315 A | 10/1992 | Green et al. |
| 5,158,567 A | 10/1992 | Green |
| 5,171,247 A | 12/1992 | Hughett et al. |
| 5,171,249 A | 12/1992 | Stefanchik et al. |
| 5,211,649 A | 5/1993 | Kohler et al. |
| 5,221,036 A | 6/1993 | Takase |
| 5,222,963 A | 6/1993 | Brinkerhoff et al. |
| 5,222,975 A | 6/1993 | Crainich |
| 5,246,156 A | 9/1993 | Rothfuss et al. |
| 5,253,793 A | 10/1993 | Green et al. |
| 5,258,009 A | 11/1993 | Conners |
| 5,261,922 A | 11/1993 | Hood |
| 5,271,543 A * | 12/1993 | Grant et al. ............... 227/179.1 |
| 5,271,544 A | 12/1993 | Fox et al. |
| RE34,519 E | 1/1994 | Fox et al. |
| 5,275,323 A | 1/1994 | Schulze et al. |
| 5,282,806 A | 2/1994 | Haber et al. |
| 5,282,829 A | 2/1994 | Hermes |
| 5,289,963 A * | 3/1994 | McGarry et al. ......... 227/175.1 |
| 5,304,204 A | 4/1994 | Bregen |
| 5,307,976 A | 5/1994 | Olson et al. |
| 5,312,023 A * | 5/1994 | Green et al. ............. 227/175.1 |
| 5,312,024 A * | 5/1994 | Grant et al. ............... 227/179.1 |
| 5,318,221 A | 6/1994 | Green et al. |
| 5,326,013 A | 7/1994 | Green et al. |
| 5,332,142 A | 7/1994 | Robinson et al. |
| 5,342,380 A | 8/1994 | Hood |
| 5,342,395 A | 8/1994 | Jarrett et al. |
| 5,342,396 A | 8/1994 | Cook |
| 5,344,060 A | 9/1994 | Gravener et al. |
| 5,350,400 A | 9/1994 | Esposito et al. |
| 5,366,134 A | 11/1994 | Green et al. |
| 5,366,479 A | 11/1994 | McGarry et al. |
| 5,379,933 A | 1/1995 | Green et al. |
| 5,383,880 A | 1/1995 | Hooven |
| 5,395,034 A | 3/1995 | Allen et al. |
| 5,397,046 A | 3/1995 | Savage et al. |
| 5,397,324 A | 3/1995 | Carroll et al. |
| 5,411,508 A | 5/1995 | Bessler et al. |
| 5,413,267 A | 5/1995 | Solyntjes et al. |
| 5,413,268 A | 5/1995 | Green et al. |
| 5,415,334 A | 5/1995 | Williamson, IV et al. |
| 5,415,335 A | 5/1995 | Knodell, Jr. |
| 5,425,745 A | 6/1995 | Green et al. |
| 5,431,322 A | 7/1995 | Green et al. |
| 5,439,156 A * | 8/1995 | Grant et al. ............... 227/179.1 |
| 5,441,193 A | 8/1995 | Gravener |
| 5,443,197 A | 8/1995 | Malis et al. |
| 5,445,304 A | 8/1995 | Plyley et al. |
| 5,447,265 A | 9/1995 | Vidal et al. |
| 5,449,365 A | 9/1995 | Green et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,465,896 A | 11/1995 | Allen et al. |
| 5,470,006 A | 11/1995 | Rodak |
| 5,470,008 A | 11/1995 | Rodak |
| 5,470,009 A | 11/1995 | Rodak |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,482,197 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,489,058 A | 2/1996 | Plyley et al. |
| 5,492,671 A | 2/1996 | Krafft |
| 5,497,933 A | 3/1996 | DeFonzo et al. |
| 5,503,320 A | 4/1996 | Webster et al. |
| 5,503,635 A | 4/1996 | Sauer et al. |
| 5,509,596 A | 4/1996 | Green et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,542,594 A | 8/1996 | McKean et al. |
| 5,553,765 A | 9/1996 | Knodel et al. |
| 5,554,169 A | 9/1996 | Green et al. |
| 5,560,532 A | 10/1996 | DeFonzo et al. |
| 5,562,241 A | 10/1996 | Knodel et al. |
| 5,562,682 A | 10/1996 | Oberlin et al. |
| 5,562,702 A | 10/1996 | Huitema et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,586,711 A | 12/1996 | Plyley et al. |
| 5,588,579 A | 12/1996 | Schnut et al. |

| | | | | | | |
|---|---|---|---|---|---|---|
| 5,588,580 A | 12/1996 | Paul et al. | | 5,865,361 A | 2/1999 | Milliman et al. |
| 5,588,581 A | 12/1996 | Conlon et al. | | 5,868,760 A | 2/1999 | McGuckin, Jr. |
| 5,601,224 A | 2/1997 | Bishop et al. | | 5,871,135 A | 2/1999 | Williamson, IV et al. |
| 5,603,443 A | 2/1997 | Clark et al. | | 5,893,506 A | 4/1999 | Powell |
| 5,605,273 A | 2/1997 | Hamblin et al. | | 5,897,562 A | 4/1999 | Bolanos et al. |
| 5,607,094 A | 3/1997 | Clark et al. | | 5,901,895 A | 5/1999 | Heaton et al. |
| 5,609,285 A | 3/1997 | Grant et al. | | 5,906,625 A | 5/1999 | Bito et al. |
| 5,624,452 A | 4/1997 | Yates | | 5,911,353 A | 6/1999 | Bolanos et al. |
| 5,628,446 A | 5/1997 | Geiste et al. | | 5,915,616 A | 6/1999 | Viola et al. |
| 5,630,539 A | 5/1997 | Plyley et al. | | 5,918,791 A | 7/1999 | Sorrentino et al. |
| 5,630,540 A | 5/1997 | Blewett | | 5,938,667 A | 8/1999 | Peyser et al. |
| 5,632,432 A | 5/1997 | Schulze et al. | | 5,941,442 A | 8/1999 | Geiste et al. |
| 5,632,433 A | 5/1997 | Grant et al. | | 5,946,978 A | 9/1999 | Yamashita |
| 5,634,584 A | 6/1997 | Okorocha et al. | | 5,954,259 A | 9/1999 | Viola et al. |
| 5,636,780 A | 6/1997 | Green et al. | | 6,010,054 A * | 1/2000 | Johnson et al. .......... 227/176.1 |
| 5,639,008 A | 6/1997 | Gallagher et al. | | 6,024,748 A | 2/2000 | Manzo et al. |
| 5,649,937 A | 7/1997 | Bito et al. | | 6,032,849 A | 3/2000 | Mastri et al. |
| 5,651,491 A | 7/1997 | Heaton et al. | | 6,045,560 A | 4/2000 | McKean et al. |
| 5,653,373 A | 8/1997 | Green et al. | | 6,083,234 A | 7/2000 | Nicholas et al. |
| 5,653,374 A | 8/1997 | Young et al. | | 6,083,242 A | 7/2000 | Cook |
| 5,655,698 A | 8/1997 | Yoon | | 6,086,600 A | 7/2000 | Kortenbach |
| 5,657,921 A | 8/1997 | Young et al. | | 6,102,271 A | 8/2000 | Longo et al. |
| 5,658,238 A | 8/1997 | Suzuki et al. | | 6,119,913 A | 9/2000 | Adams et al. |
| 5,662,258 A | 9/1997 | Knodel et al. | | 6,126,058 A * | 10/2000 | Adams et al. ............ 227/180.1 |
| 5,662,260 A | 9/1997 | Yoon | | 6,171,330 B1 | 1/2001 | Benchetrit |
| 5,667,527 A | 9/1997 | Cook | | 6,202,914 B1 | 3/2001 | Geiste et al. |
| 5,669,544 A | 9/1997 | Schulze et al. | | 6,209,414 B1 | 4/2001 | Uneme |
| 5,673,840 A | 10/1997 | Schulze et al. | | 6,241,139 B1 | 6/2001 | Milliman et al. |
| 5,673,841 A | 10/1997 | Schulze et al. | | 6,250,532 B1 | 6/2001 | Green et al. |
| 5,680,981 A | 10/1997 | Mililli et al. | | 6,258,107 B1 | 7/2001 | Balázs et al. |
| 5,680,982 A | 10/1997 | Schulze et al. | | 6,264,086 B1 | 7/2001 | McGuckin, Jr. |
| 5,680,983 A | 10/1997 | Plyley et al. | | 6,264,087 B1 | 7/2001 | Whitman |
| 5,685,474 A | 11/1997 | Seeber | | 6,273,897 B1 | 8/2001 | Dalessandro et al. |
| 5,690,269 A | 11/1997 | Bolanos et al. | | 6,302,311 B1 | 10/2001 | Adams et al. |
| 5,692,668 A | 12/1997 | Schulze et al. | | 6,315,184 B1 | 11/2001 | Whitman |
| 5,697,543 A | 12/1997 | Burdorff | | 6,330,965 B1 | 12/2001 | Milliman et al. |
| 5,697,943 A | 12/1997 | Sauer et al. | | 6,387,113 B1 | 5/2002 | Hawkins et al. |
| 5,700,270 A | 12/1997 | Peyser et al. | | 6,398,797 B2 | 6/2002 | Bombard et al. |
| 5,702,408 A | 12/1997 | Wales et al. | | RE37,814 E | 8/2002 | Allgeyer |
| 5,704,534 A | 1/1998 | Huitema et al. | | 6,440,146 B2 | 8/2002 | Nicholas et al. |
| 5,706,998 A | 1/1998 | Plyley et al. | | 6,443,973 B1 | 9/2002 | Whitman |
| 5,709,334 A | 1/1998 | Sorrentino et al. | | 6,488,197 B1 | 12/2002 | Whitman |
| 5,711,472 A | 1/1998 | Bryan | | 6,491,201 B1 | 12/2002 | Whitman |
| 5,713,505 A | 2/1998 | Huitema | | 6,500,194 B2 | 12/2002 | Benderev et al. |
| 5,715,987 A | 2/1998 | Kelley et al. | | 6,503,259 B2 | 1/2003 | Huxel et al. |
| 5,716,366 A | 2/1998 | Yates | | 6,505,768 B2 | 1/2003 | Whitman |
| 5,725,536 A * | 3/1998 | Oberlin et al. .............. 606/139 | | 6,517,565 B1 | 2/2003 | Whitman et al. |
| 5,725,554 A | 3/1998 | Simon et al. | | 6,578,751 B2 | 6/2003 | Hartwick |
| 5,732,821 A * | 3/1998 | Stone et al. ................. 206/370 | | 6,601,749 B2 | 8/2003 | Sullivan et al. |
| 5,732,871 A | 3/1998 | Clark et al. | | 6,616,686 B2 | 9/2003 | Coleman et al. |
| 5,741,271 A | 4/1998 | Nakao et al. | | 6,619,529 B2 | 9/2003 | Green et al. |
| 5,743,456 A | 4/1998 | Jones et al. | | 6,629,988 B2 | 10/2003 | Weadock |
| 5,752,644 A | 5/1998 | Bolanos et al. | | 6,644,532 B2 | 11/2003 | Green et al. |
| 5,758,814 A | 6/1998 | Gallagher et al. | | 6,681,978 B2 | 1/2004 | Geiste et al. |
| 5,762,255 A * | 6/1998 | Chrisman et al. ........ 227/175.2 | | 6,681,979 B2 | 1/2004 | Whitman |
| 5,762,256 A | 6/1998 | Mastri et al. | | 6,695,199 B2 | 2/2004 | Whitman |
| 5,779,130 A | 7/1998 | Alesi et al. | | 6,698,643 B2 | 3/2004 | Whitman |
| 5,779,132 A | 7/1998 | Knodel et al. | | 6,716,233 B1 | 4/2004 | Whitman |
| 5,782,396 A | 7/1998 | Mastri et al. | | 6,754,959 B1 * | 6/2004 | Guiette et al. ................. 30/90.1 |
| 5,782,397 A | 7/1998 | Koukline | | 6,755,338 B2 | 6/2004 | Hahnen et al. |
| 5,785,232 A | 7/1998 | Vidal et al. | | 6,773,438 B1 | 8/2004 | Knodel et al. |
| 5,797,536 A | 8/1998 | Smith et al. | | 6,786,382 B1 | 9/2004 | Hoffman |
| 5,797,537 A * | 8/1998 | Oberlin et al. ........... 227/176.1 | | 6,805,273 B2 | 10/2004 | Bilotti et al. |
| 5,797,538 A | 8/1998 | Heaton et al. | | 6,817,508 B1 | 11/2004 | Racenet et al. |
| 5,799,857 A | 9/1998 | Robertson et al. | | 6,817,509 B2 | 11/2004 | Geiste et al. |
| 5,816,471 A | 10/1998 | Plyley et al. | | 6,830,174 B2 | 12/2004 | Hillstead et al. |
| 5,820,009 A * | 10/1998 | Melling et al. ........... 227/176.1 | | 6,835,199 B2 | 12/2004 | McGuckin, Jr. et al. |
| 5,826,776 A | 10/1998 | Schulze et al. | | 6,843,403 B2 | 1/2005 | Whitman |
| 5,833,695 A | 11/1998 | Yoon | | RE38,708 E | 3/2005 | Bolanos et al. |
| 5,836,503 A | 11/1998 | Ehrenfels et al. | | 6,872,214 B2 | 3/2005 | Sonnenschein et al. |
| 5,839,639 A | 11/1998 | Sauer et al. | | 6,877,647 B2 | 4/2005 | Green et al. |
| 5,849,011 A | 12/1998 | Jones et al. | | 6,899,593 B1 | 5/2005 | Moeller et al. |
| 5,855,311 A | 1/1999 | Hamblin et al. | | 6,905,057 B2 | 6/2005 | Swayze et al. |

| | | |
|---|---|---|
| 6,945,444 B2 | 9/2005 | Gresham et al. |
| 6,953,138 B1 | 10/2005 | Dworak et al. |
| 6,953,139 B2 | 10/2005 | Milliman et al. |
| 6,960,220 B2 | 11/2005 | Marino et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,063,712 B2 | 6/2006 | Vargas et al. |
| 7,070,083 B2 | 7/2006 | Jankowski |
| 7,077,856 B2 | 7/2006 | Whitman |
| 7,083,075 B2 | 8/2006 | Swayze et al. |
| 7,090,684 B2 | 8/2006 | McGuckin, Jr. et al. |
| 7,108,701 B2 | 9/2006 | Evens et al. |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,128,253 B2 | 10/2006 | Mastri et al. |
| 7,140,527 B2 | 11/2006 | Ehrenfels et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,188,758 B2 | 3/2007 | Viola et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,563 B1 * | 10/2007 | Green .................. 227/180.1 |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,328,828 B2 | 2/2008 | Ortiz et al. |
| 7,328,829 B2 | 2/2008 | Arad et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,410,086 B2 | 8/2008 | Ortiz et al. |
| 7,422,136 B1 | 9/2008 | Marczyk |
| 7,431,730 B2 | 10/2008 | Viola |
| 7,438,209 B1 | 10/2008 | Hess et al. |
| 7,441,685 B1 | 10/2008 | Boudreaux |
| 7,490,749 B2 | 2/2009 | Schall et al. |
| 7,494,039 B2 | 2/2009 | Racenet et al. |
| 7,510,107 B2 | 3/2009 | Timm et al. |
| 2002/0117534 A1 | 8/2002 | Green et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2005/0006432 A1 * | 1/2005 | Racenet et al. ............ 227/176.1 |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0216055 A1 | 9/2005 | Scirica et al. |
| 2005/0234472 A1 | 10/2005 | Huebner |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0151567 A1 | 7/2006 | Roy |
| 2006/0180634 A1 | 8/2006 | Shelton, IV et al. |
| 2006/0226196 A1 | 10/2006 | Hueil et al. |
| 2006/0241655 A1 | 10/2006 | Viola |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023477 A1 | 2/2007 | Whitman et al. |
| 2007/0027469 A1 * | 2/2007 | Smith et al. .................. 606/205 |
| 2007/0034668 A1 | 2/2007 | Holsten et al. |
| 2007/0045379 A1 | 3/2007 | Shelton, IV |
| 2007/0055219 A1 * | 3/2007 | Whitman et al. .................. 606/1 |
| 2007/0073340 A1 | 3/2007 | Shelton, IV et al. |
| 2007/0075114 A1 | 4/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102476 A1 | 5/2007 | Shelton, IV et al. |
| 2007/0106317 A1 | 5/2007 | Shelton, IV et al. |
| 2007/0108252 A1 * | 5/2007 | Racenet et al. ............ 227/176.1 |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |

| | | | |
|---|---|---|---|
| 2007/0262116 A1 | 11/2007 | Hueil et al. | |
| 2007/0295780 A1 | 12/2007 | Shelton et al. | |
| 2008/0015598 A1 | 1/2008 | Prommersberger | |
| 2008/0029570 A1 | 2/2008 | Shelton et al. | |
| 2008/0029571 A1 | 2/2008 | Shelton et al. | |
| 2008/0029572 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0029576 A1 | 2/2008 | Shelton et al. | |
| 2008/0029577 A1 | 2/2008 | Shelton et al. | |
| 2008/0035701 A1 | 2/2008 | Racenet et al. | |
| 2008/0041917 A1 | 2/2008 | Racenet et al. | |
| 2008/0078800 A1 | 4/2008 | Hess et al. | |
| 2008/0078801 A1 | 4/2008 | Shelton et al. | |
| 2008/0078802 A1 | 4/2008 | Hess et al. | |
| 2008/0078803 A1 | 4/2008 | Shelton et al. | |
| 2008/0078804 A1 | 4/2008 | Shelton et al. | |
| 2008/0078805 A1 | 4/2008 | Omaits et al. | |
| 2008/0078806 A1 | 4/2008 | Omaits et al. | |
| 2008/0078807 A1 | 4/2008 | Hess et al. | |
| 2008/0078808 A1 | 4/2008 | Hess et al. | |
| 2008/0082115 A1 | 4/2008 | Morgan et al. | |
| 2008/0082124 A1 | 4/2008 | Hess et al. | |
| 2008/0082125 A1 | 4/2008 | Murray et al. | |
| 2008/0082126 A1 | 4/2008 | Murray et al. | |
| 2008/0164296 A1 | 7/2008 | Shelton et al. | |
| 2008/0167522 A1 | 7/2008 | Giordano et al. | |
| 2008/0167644 A1 | 7/2008 | Shelton et al. | |
| 2008/0167670 A1 | 7/2008 | Shelton et al. | |
| 2008/0167671 A1 | 7/2008 | Giordano et al. | |
| 2008/0167672 A1 | 7/2008 | Giordano et al. | |
| 2008/0167736 A1 | 7/2008 | Swayze et al. | |
| 2008/0169327 A1 | 7/2008 | Shelton et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0210738 A1 | 9/2008 | Shelton et al. | |
| 2008/0237296 A1 | 10/2008 | Boudreaux et al. | |
| 2008/0237298 A1 | 10/2008 | Schall et al. | |
| 2008/0296343 A1 | 12/2008 | Schall et al. | |
| 2008/0296345 A1 | 12/2008 | Shelton, IV et al. | |
| 2008/0296346 A1 | 12/2008 | Shelton, IV et al. | |
| 2008/0296347 A1 | 12/2008 | Shelton, IV et al. | |
| 2008/0300579 A1 | 12/2008 | Broehl et al. | |
| 2008/0300580 A1 | 12/2008 | Shelton, IV et al. | |
| 2008/0300613 A1 | 12/2008 | Shelton, IV et al. | |
| 2008/0308601 A1 | 12/2008 | Timm et al. | |
| 2008/0308602 A1 | 12/2008 | Timm et al. | |
| 2008/0308603 A1 | 12/2008 | Shelton, IV et al. | |
| 2008/0308607 A1 | 12/2008 | Timm et al. | |
| 2008/0314954 A1 | 12/2008 | Boudreaux | |
| 2008/0314955 A1 | 12/2008 | Boudreaux et al. | |
| 2008/0314956 A1 | 12/2008 | Boudreaux | |
| 2008/0314957 A1 | 12/2008 | Boudreaux | |
| 2008/0314961 A1 | 12/2008 | Boudreaux et al. | |
| 2008/0314962 A1 | 12/2008 | Boudreaux | |
| 2009/0001121 A1 | 1/2009 | Hess et al. | |
| 2009/0001123 A1 | 1/2009 | Morgan et al. | |
| 2009/0001124 A1 | 1/2009 | Hess et al. | |
| 2009/0001125 A1 | 1/2009 | Hess et al. | |
| 2009/0001126 A1 | 1/2009 | Hess et al. | |
| 2009/0001128 A1 | 1/2009 | Weisenburgh, II et al. | |
| 2009/0001130 A1 | 1/2009 | Hess et al. | |
| 2009/0005807 A1 | 1/2009 | Hess et al. | |
| 2009/0005808 A1 | 1/2009 | Hess et al. | |
| 2009/0005809 A1 | 1/2009 | Hess et al. | |
| 2009/0012556 A1 | 1/2009 | Boudreaux et al. | |
| 2009/0076534 A1 | 3/2009 | Shelton, IV et al. | |

FOREIGN PATENT DOCUMENTS

| | | | |
|---|---|---|---|
| CA | 2512960 A1 | 1/2006 | |
| CA | 2514274 A1 | 1/2006 | |
| DE | 273689 C | 5/1914 | |
| DE | 1775926 A | 1/1972 | |
| DE | 9412228 U | 9/1994 | |
| DE | 19924311 A1 | 11/2000 | |
| DE | 69328576 T2 | 1/2001 | |
| DE | 20112837 U1 | 10/2001 | |
| DE | 20121753 U1 | 4/2003 | |
| DE | 10314072 A1 | 10/2004 | |
| EP | 0122046 A1 | 10/1984 | |
| EP | 0033548 B1 | 5/1986 | |
| EP | 0276104 A2 | 7/1988 | |
| EP | 0639349 A2 | 2/1994 | |
| EP | 0593920 A1 | 4/1994 | |
| EP | 0600182 A2 | 6/1994 | |
| EP | 0630612 A1 | 12/1994 | |
| EP | 0634144 A1 | 1/1995 | |
| EP | 0646356 A2 | 4/1995 | |
| EP | 0646357 A1 | 4/1995 | |
| EP | 0669104 A1 | 8/1995 | |
| EP | 0679367 A2 | 11/1995 | |
| EP | 0392547 B1 | 12/1995 | |
| EP | 0685204 A1 | 12/1995 | |
| EP | 0699418 A1 | 3/1996 | |
| EP | 0702937 A1 | 3/1996 | |
| EP | 0705571 A1 | 4/1996 | |
| EP | 0484677 B2 | 6/1996 | |
| EP | 0541987 B1 | 7/1996 | |
| EP | 0667119 B1 | 7/1996 | |
| EP | 0770355 A1 | 5/1997 | |
| EP | 0503662 B1 | 6/1997 | |
| EP | 0625335 B1 | 11/1997 | |
| EP | 0552423 B1 | 1/1998 | |
| EP | 0592244 B1 | 1/1998 | |
| EP | 0648476 B1 | 1/1998 | |
| EP | 0603472 B1 | 11/1998 | |
| EP | 0605351 B1 | 11/1998 | |
| EP | 0878169 A1 | 11/1998 | |
| EP | 0879742 A1 | 11/1998 | |
| EP | 0760230 B1 | 2/1999 | |
| EP | 0537572 B1 | 6/1999 | |
| EP | 0552050 B1 | 5/2000 | |
| EP | 1090592 A1 | 4/2001 | |
| EP | 1256318 B1 | 5/2001 | |
| EP | 0908152 B1 | 1/2002 | |
| EP | 0872213 B1 | 5/2002 | |
| EP | 1238634 A2 | 9/2002 | |
| EP | 0656188 B1 | 1/2003 | |
| EP | 0829235 B1 | 6/2003 | |
| EP | 0813843 B1 | 10/2003 | |
| EP | 0741996 B1 | 2/2004 | |
| EP | 0705570 B1 | 4/2004 | |
| EP | 1086713 B1 | 5/2004 | |
| EP | 1426012 A1 | 6/2004 | |
| EP | 0888749 B1 | 9/2004 | |
| EP | 1477119 A1 | 11/2004 | |
| EP | 1479345 A1 | 11/2004 | |
| EP | 1479347 A1 | 11/2004 | |
| EP | 1479348 A1 | 11/2004 | |
| EP | 1520523 A1 | 4/2005 | |
| EP | 1520525 A1 | 4/2005 | |
| EP | 1522264 A1 | 4/2005 | |
| EP | 1550408 A1 | 7/2005 | |
| EP | 1557129 A1 | 7/2005 | |
| EP | 1064883 B1 | 8/2005 | |
| EP | 1621138 A2 | 2/2006 | |
| EP | 1621141 A2 | 2/2006 | |
| EP | 1652481 A2 | 5/2006 | |

| | | | |
|---|---|---|---|
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1300117 B1 | 8/2007 |
| EP | 1813199 A1 | 8/2007 |
| EP | 1813207 A1 | 8/2007 |
| EP | 1839596 A1 | 10/2007 |
| EP | 1897502 A1 | 3/2008 |
| FR | 999646 A | 2/1952 |
| FR | 1112936 A | 3/1956 |
| FR | 2765794 A | 1/1999 |
| GB | 939929 A | 10/1963 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/35464 A1 | 11/1996 |
| WO | WO 97/34533 A1 | 9/1997 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/096954 A2 | 10/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/132992 A1 | 12/2006 |
| WO | WO 2007/016290 A2 | 2/2007 |
| WO | WO 2007/121579 A1 | 11/2007 |
| WO | WO 2007/142625 A2 | 12/2007 |
| WO | WO 2008/045383 A2 | 4/2008 |

OTHER PUBLICATIONS

U.S. Appl. No. 11/820,161, filed Jun. 18, 2007.
U.S. Appl. No. 11/820,124, filed Jun. 18, 2007.
U.S. Appl. No. 11/820,077, filed Jun. 18, 2007.
U.S. Appl. No. 11/820,121, filed Jun. 18, 2007.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/ abstract?CRETRY=1&SRETRY=0; [online] accessed: Sep. 22, 2008 (2 pages).
European Search Report, Application No. 08252077.6, dated Dec. 19, 2008 (8 pages).

* cited by examiner

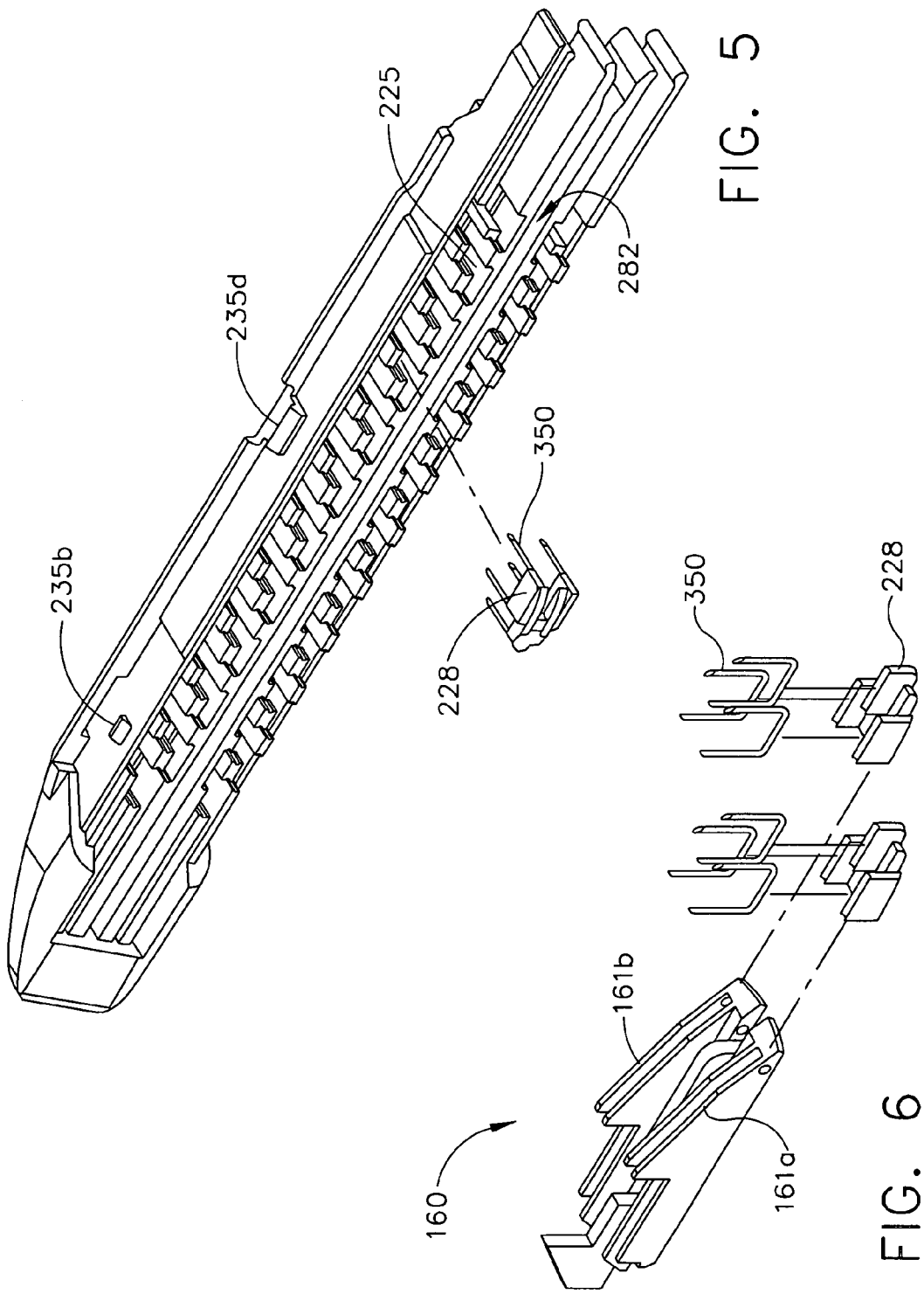

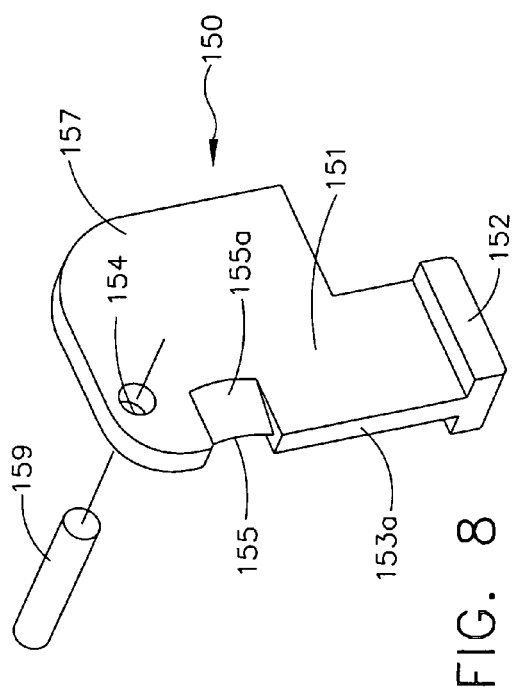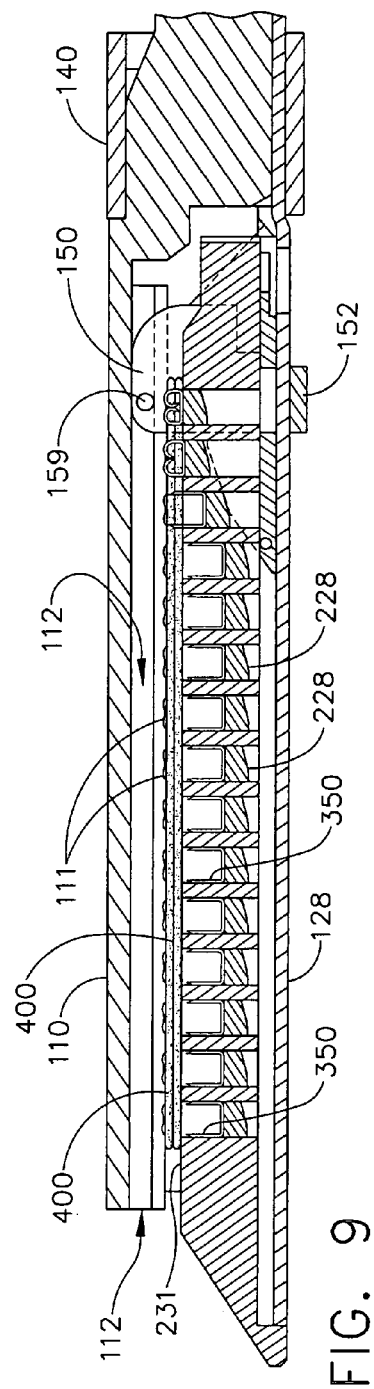

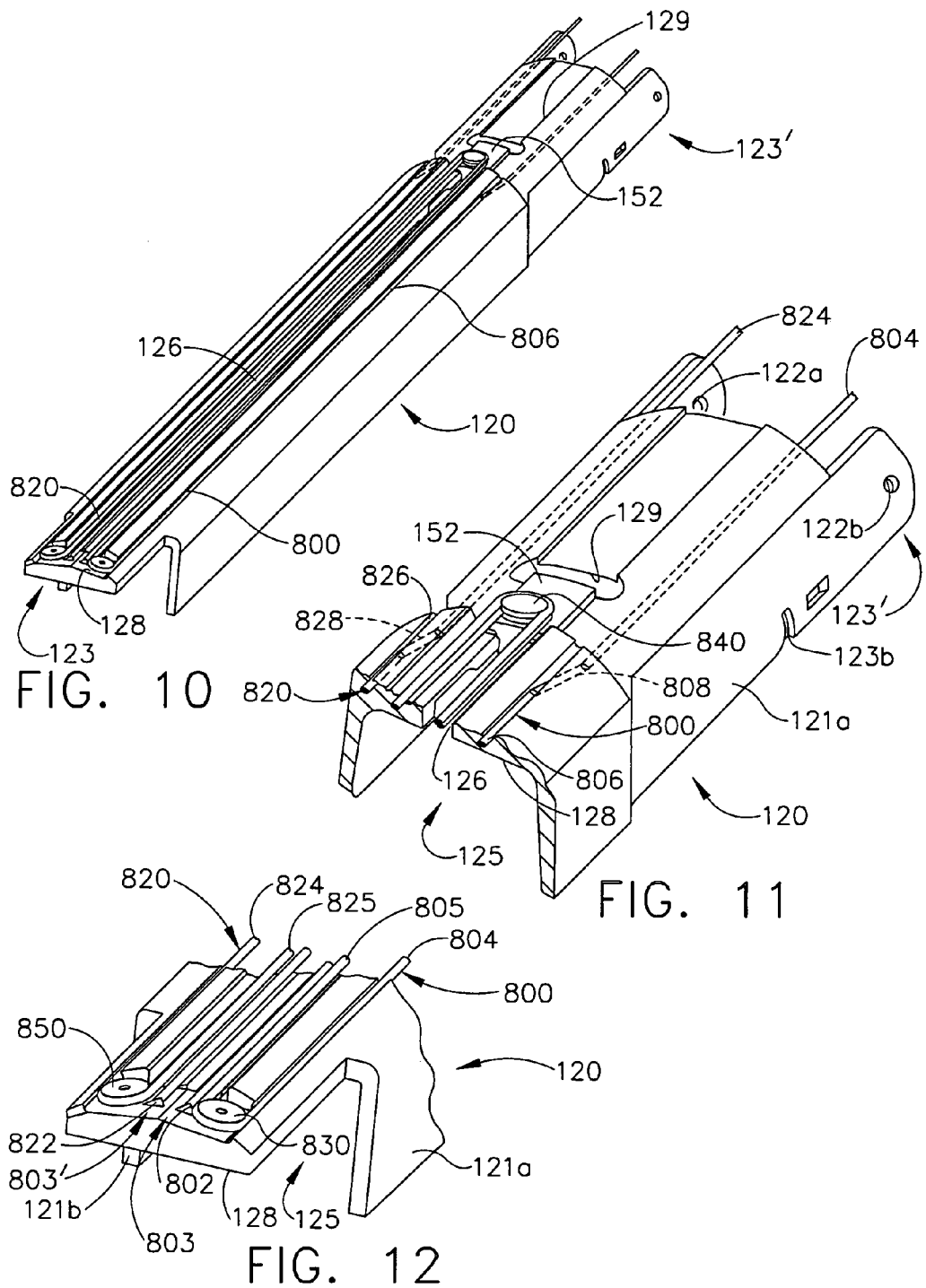

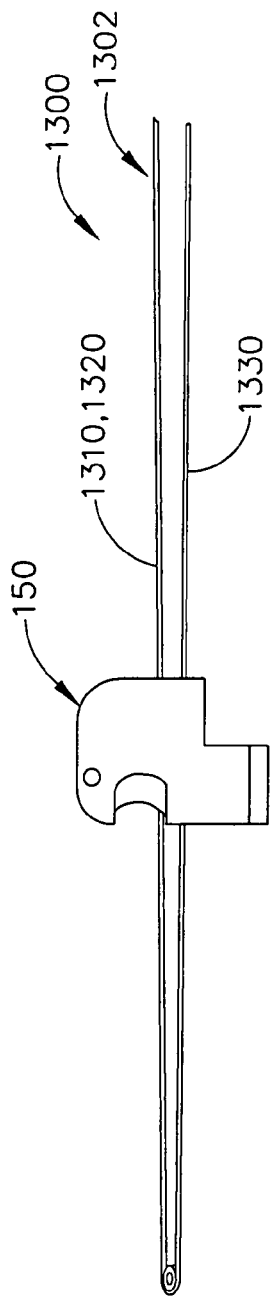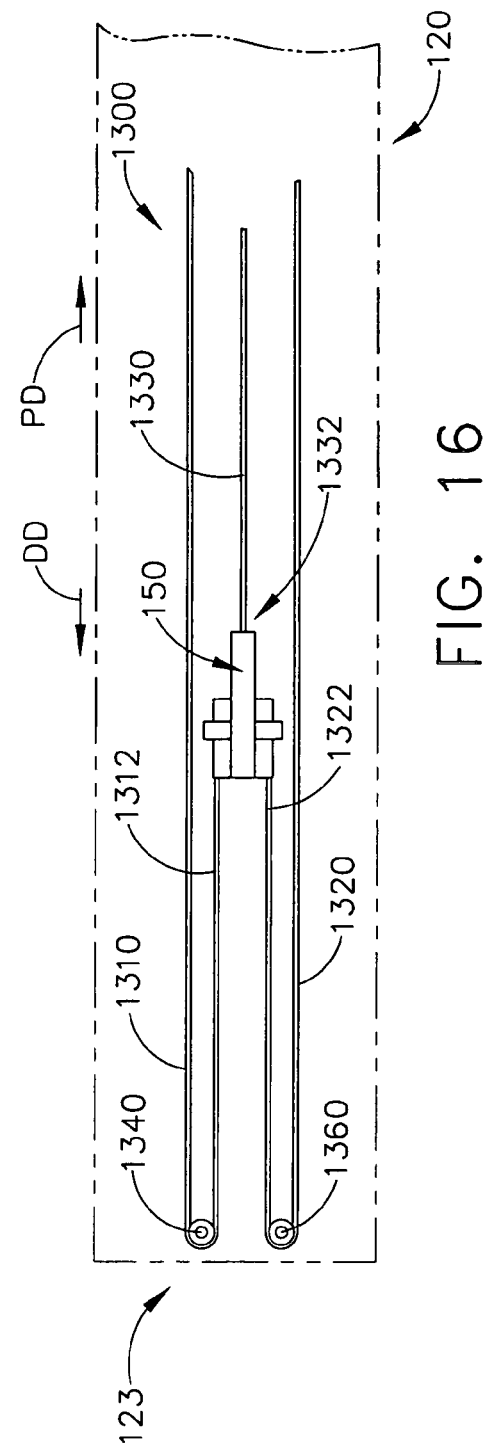

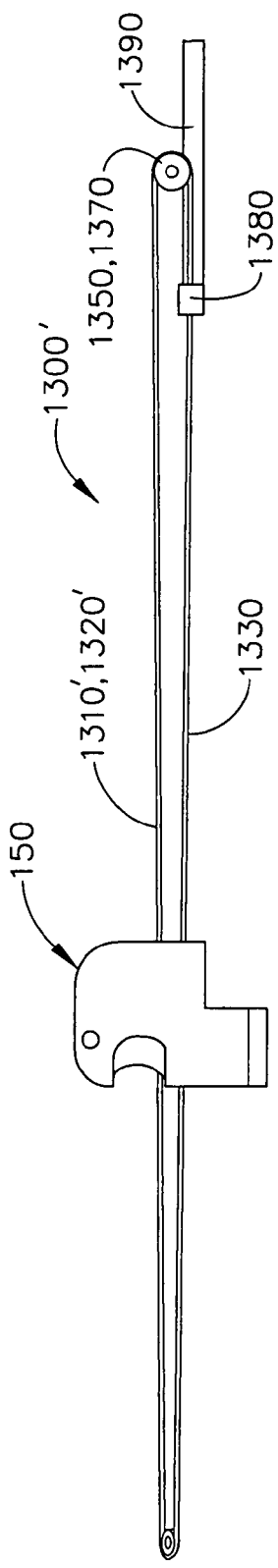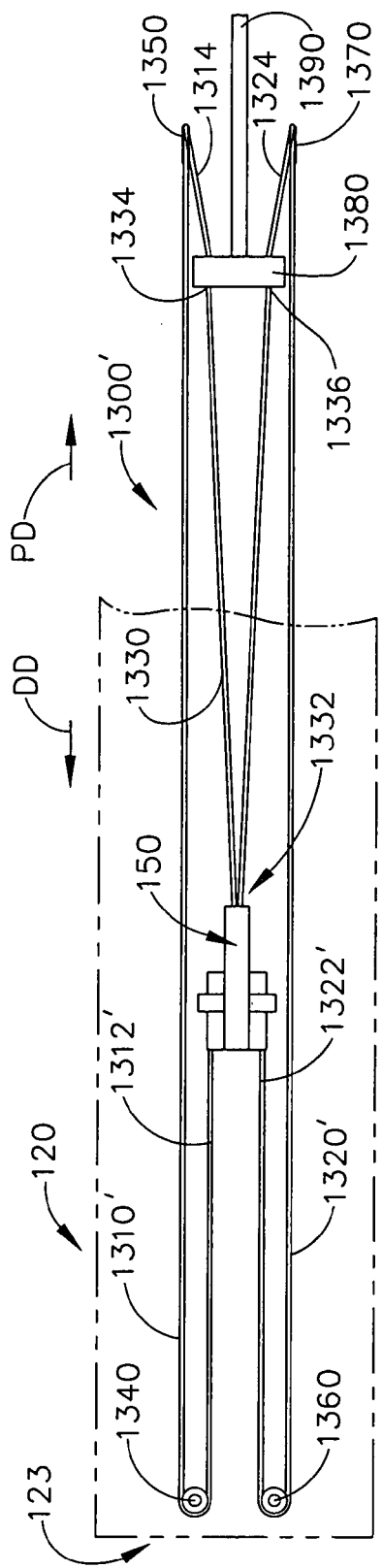

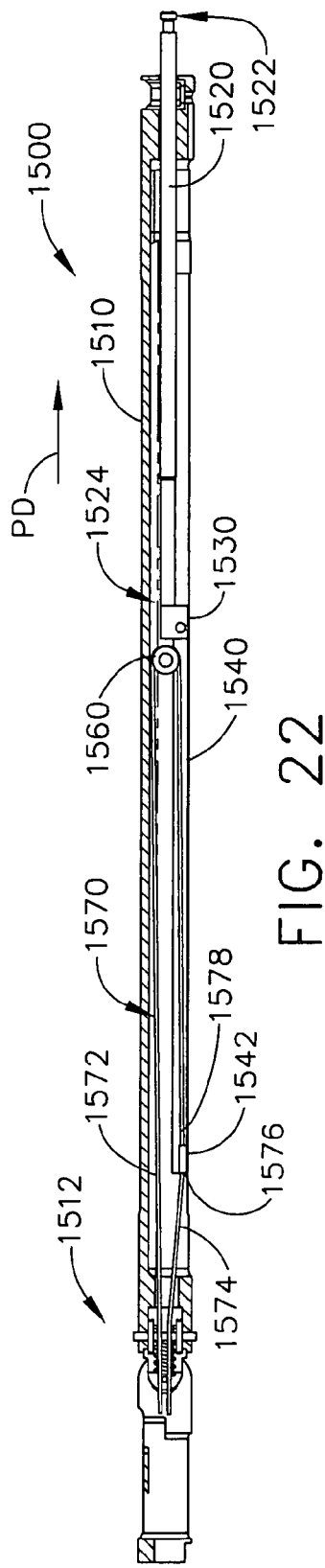
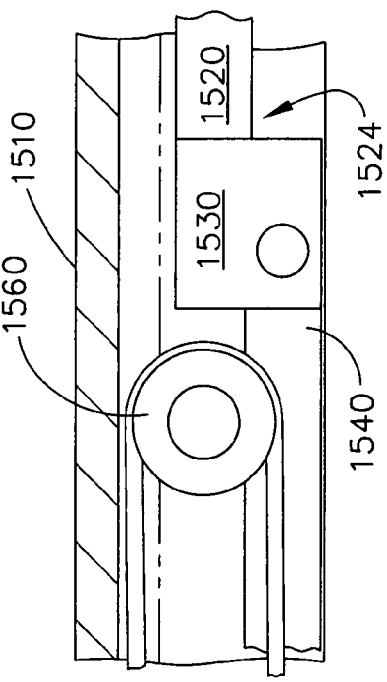
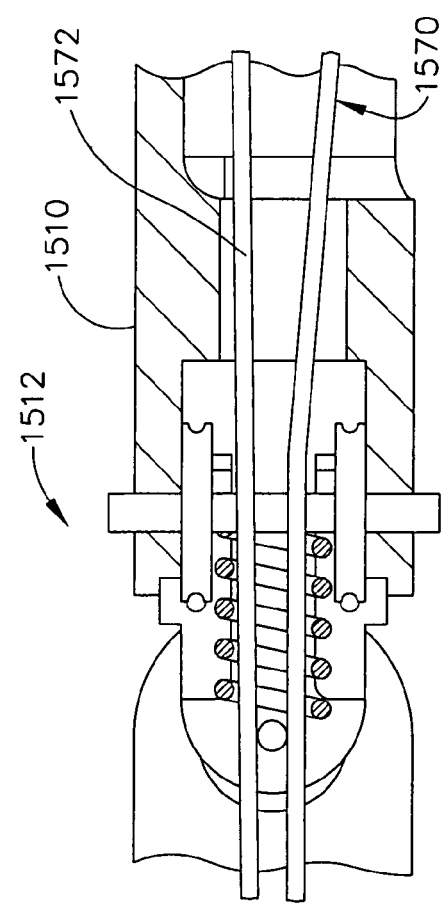
FIG. 22
FIG. 24
FIG. 23

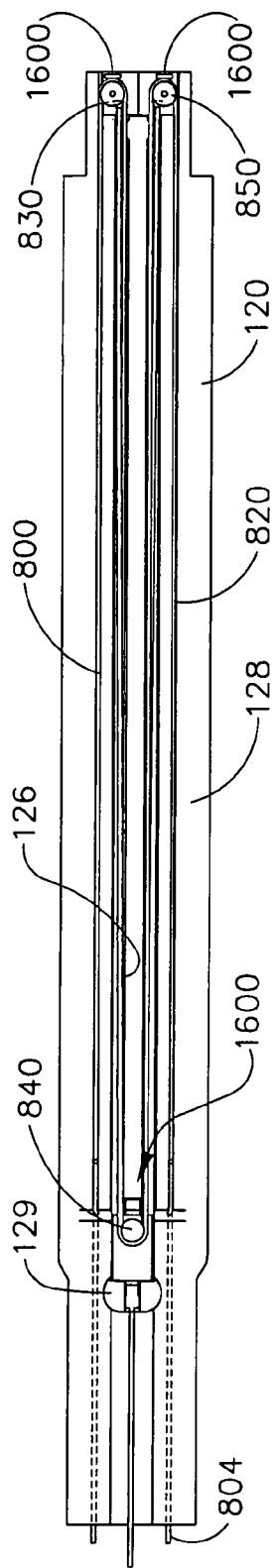
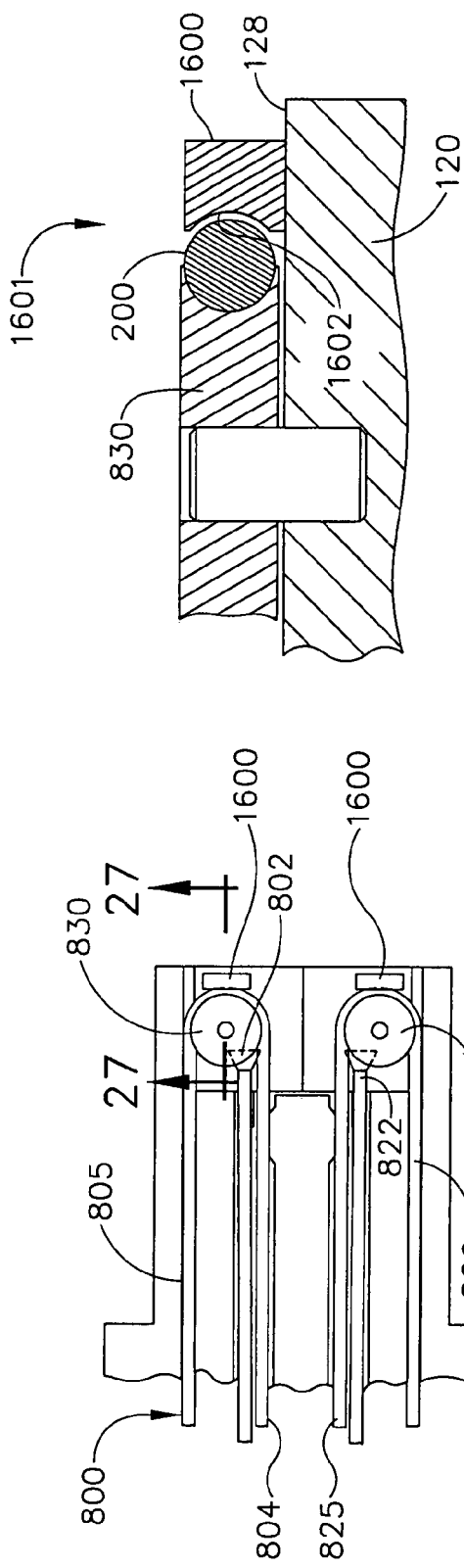

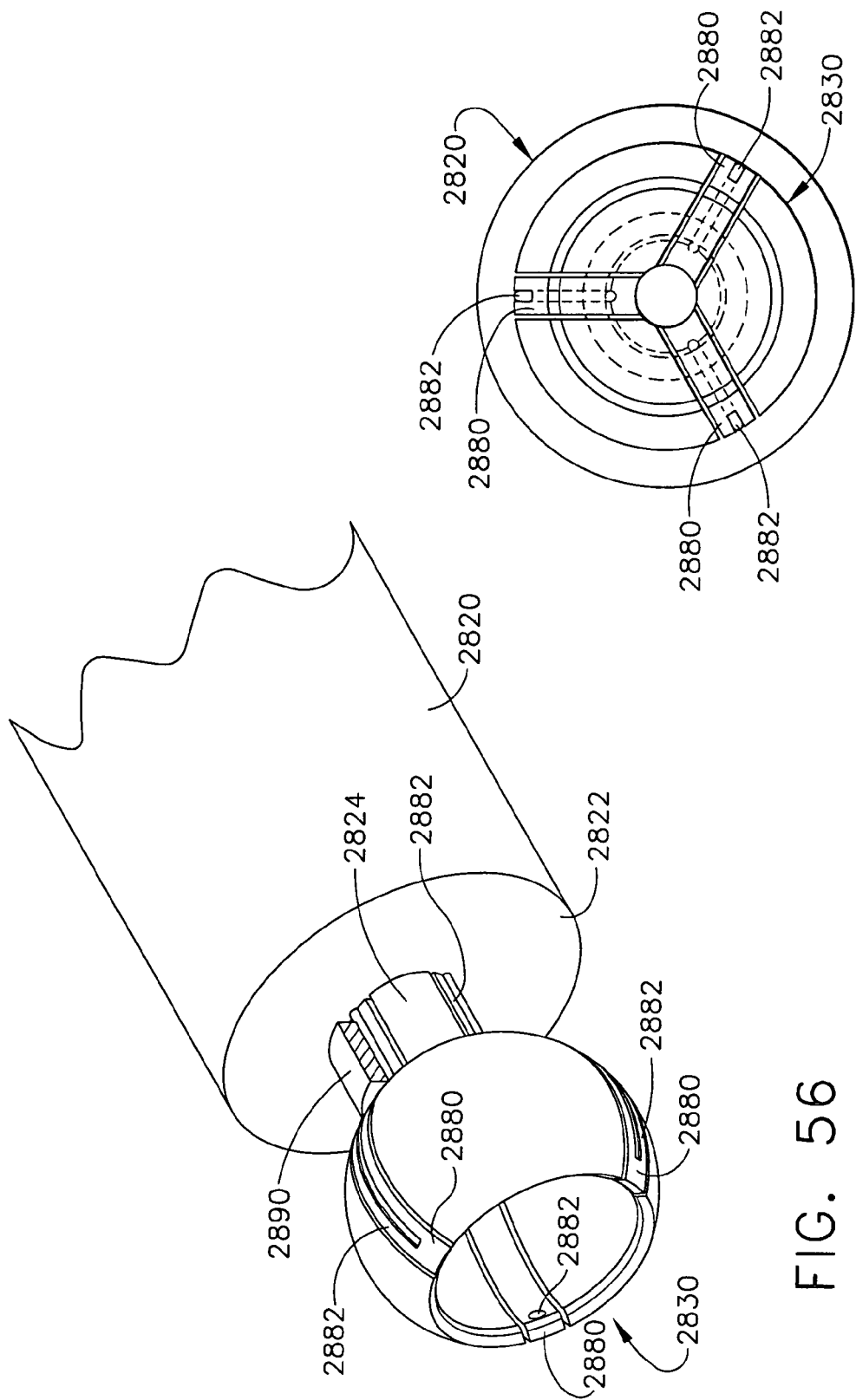

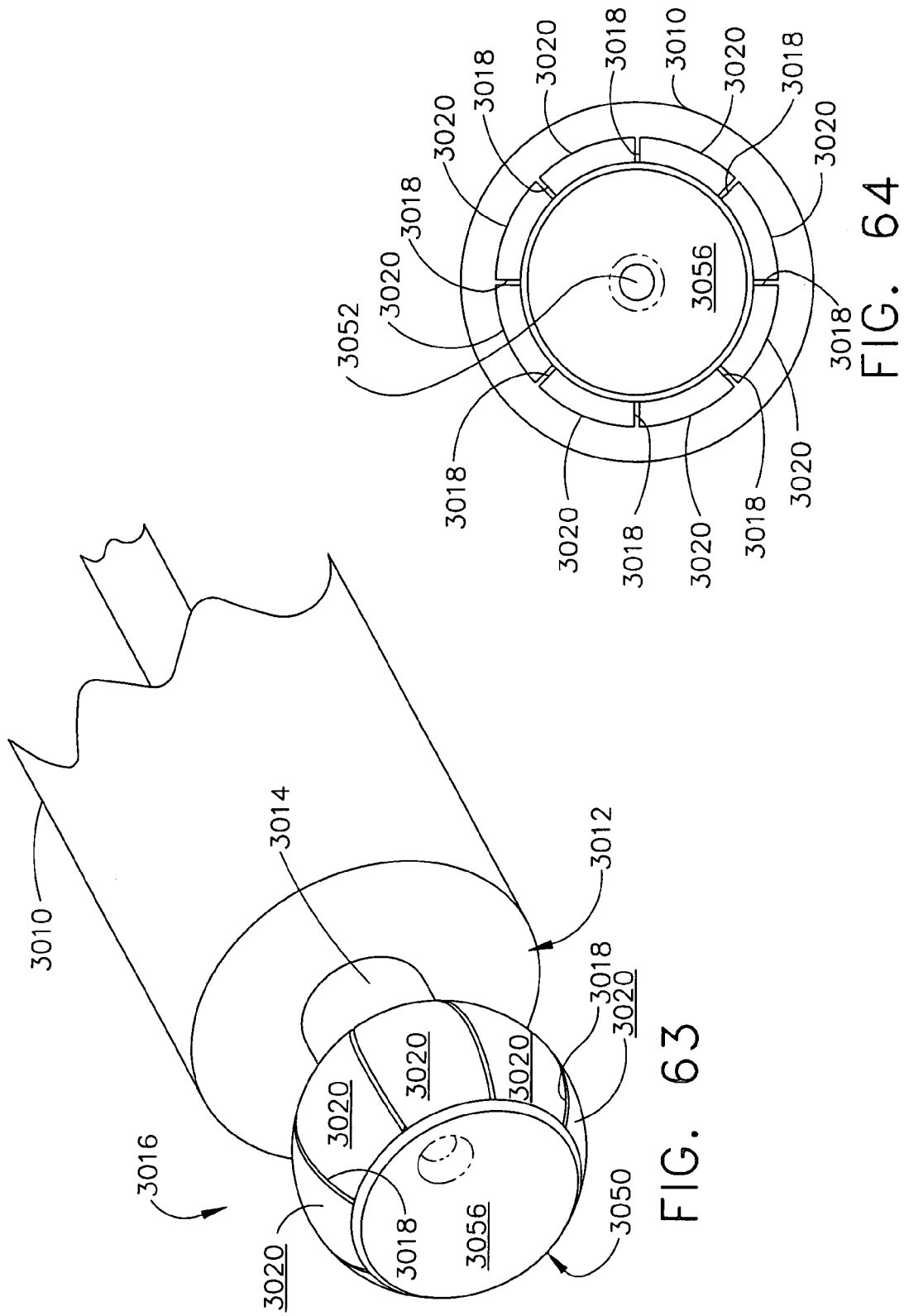

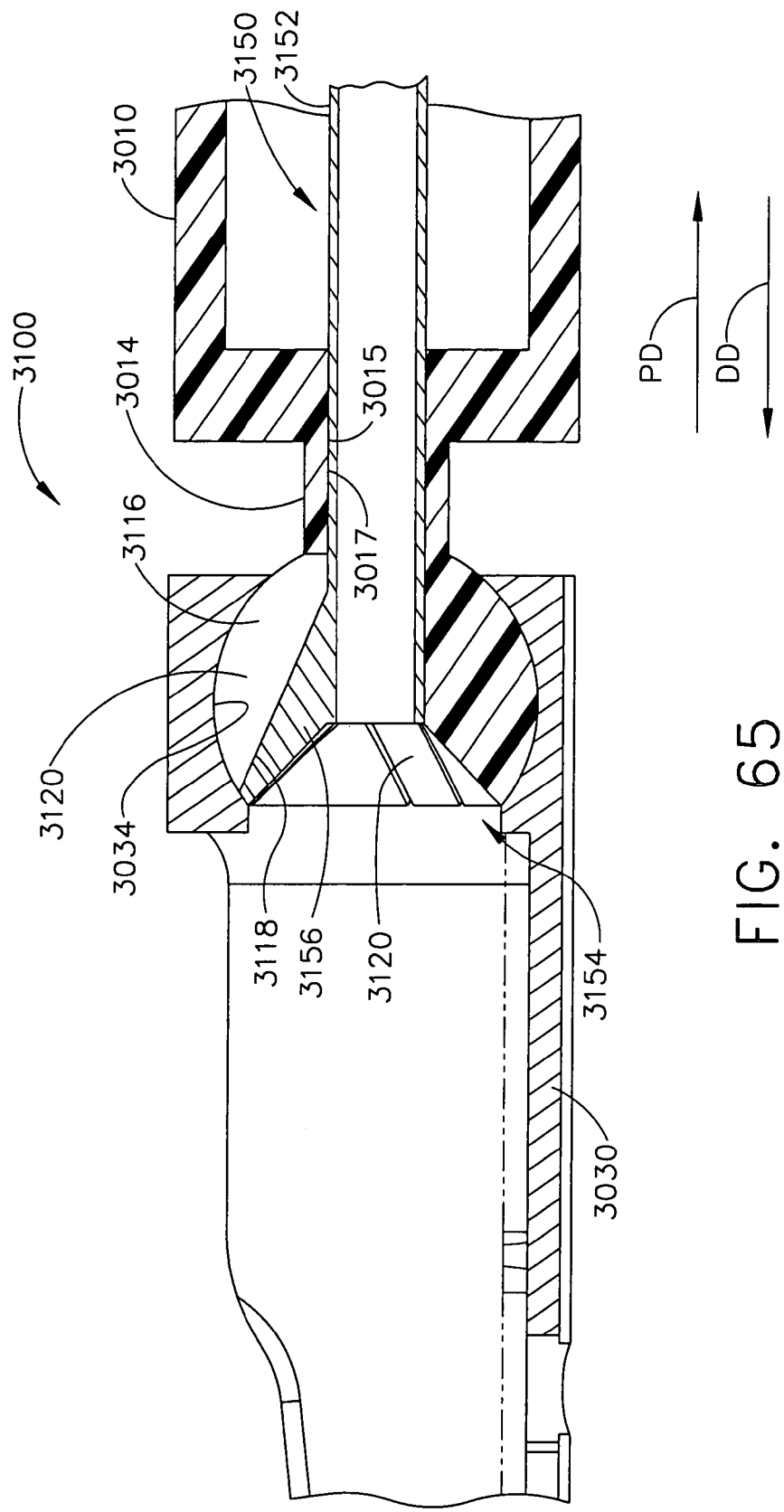

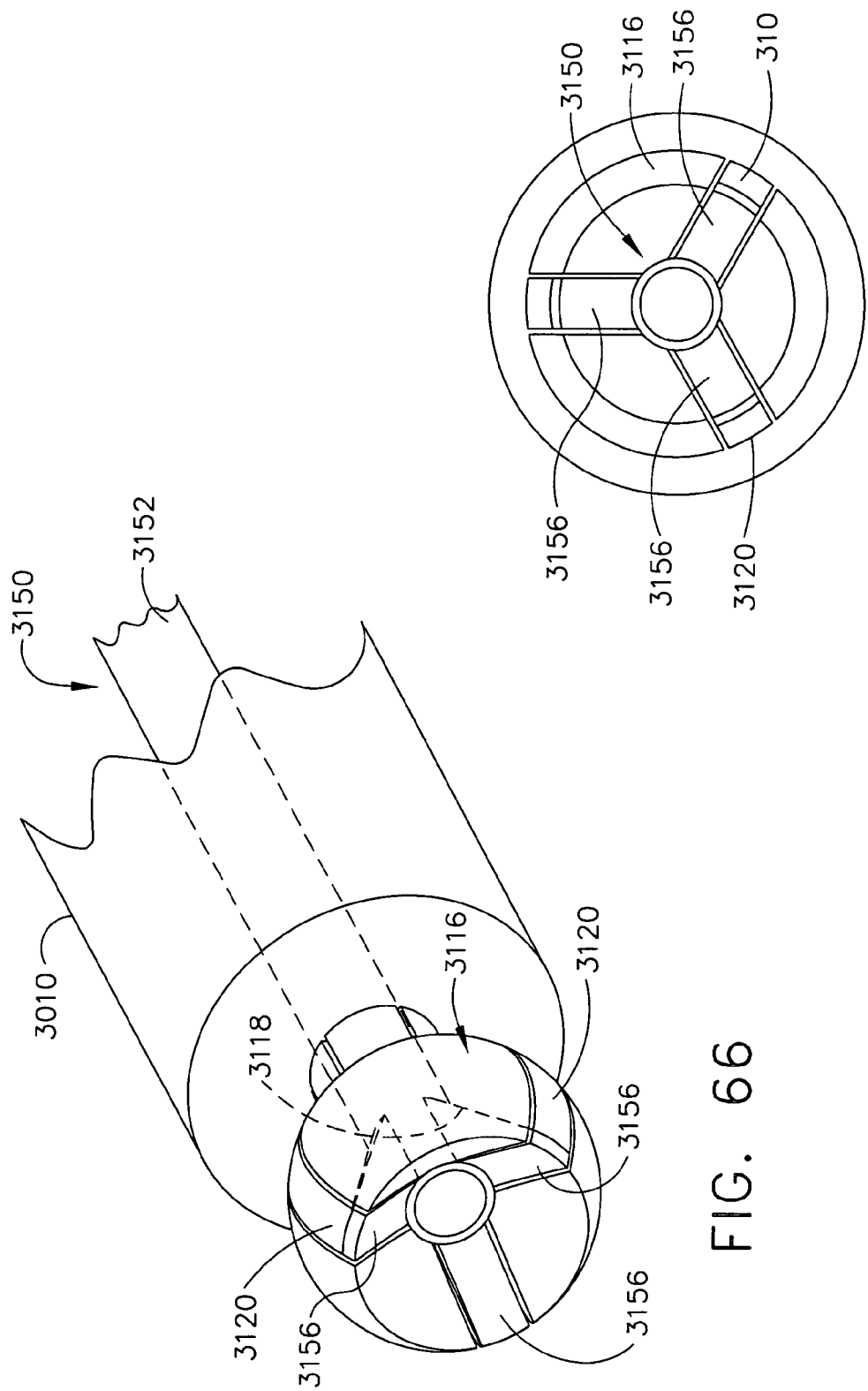

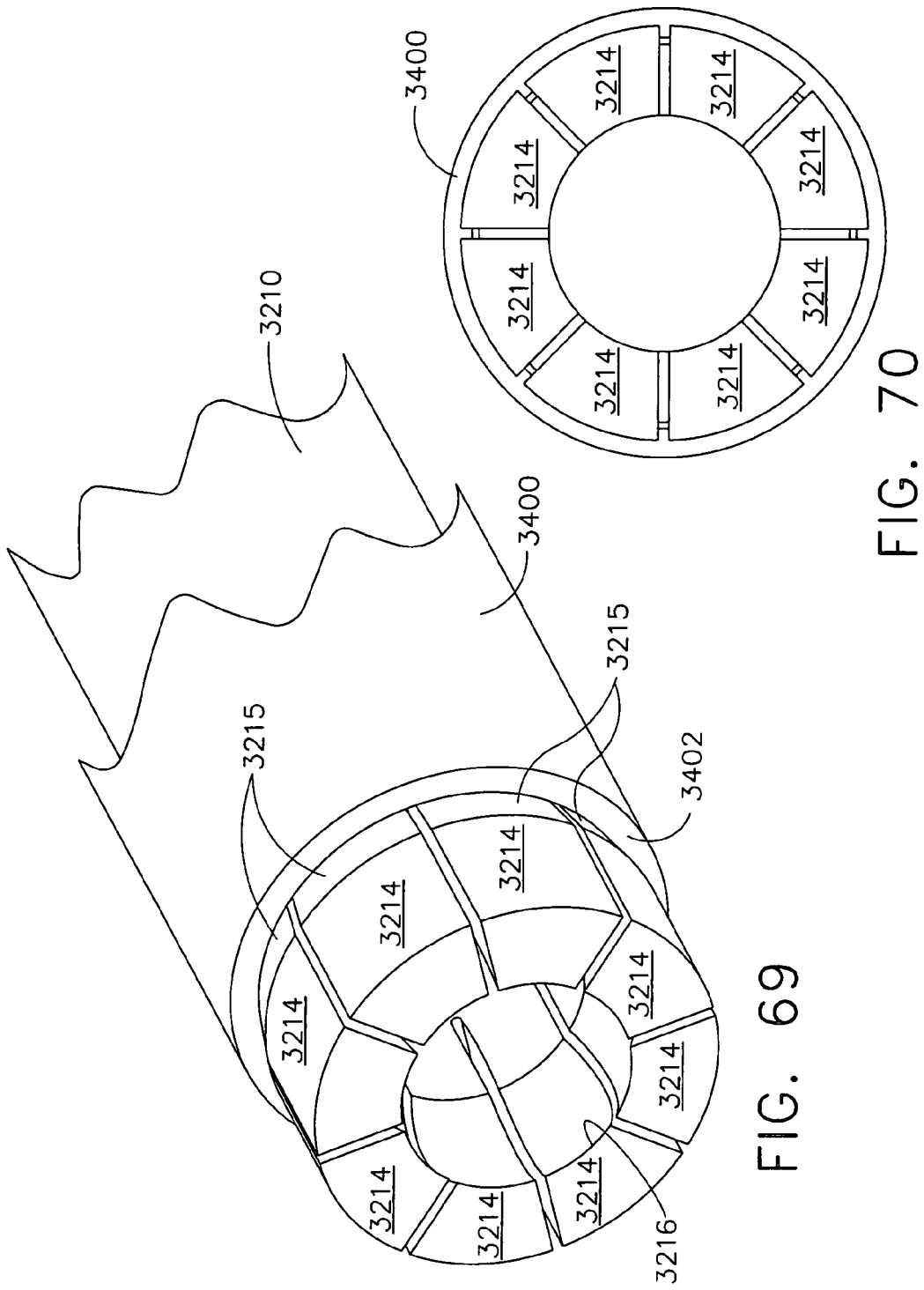

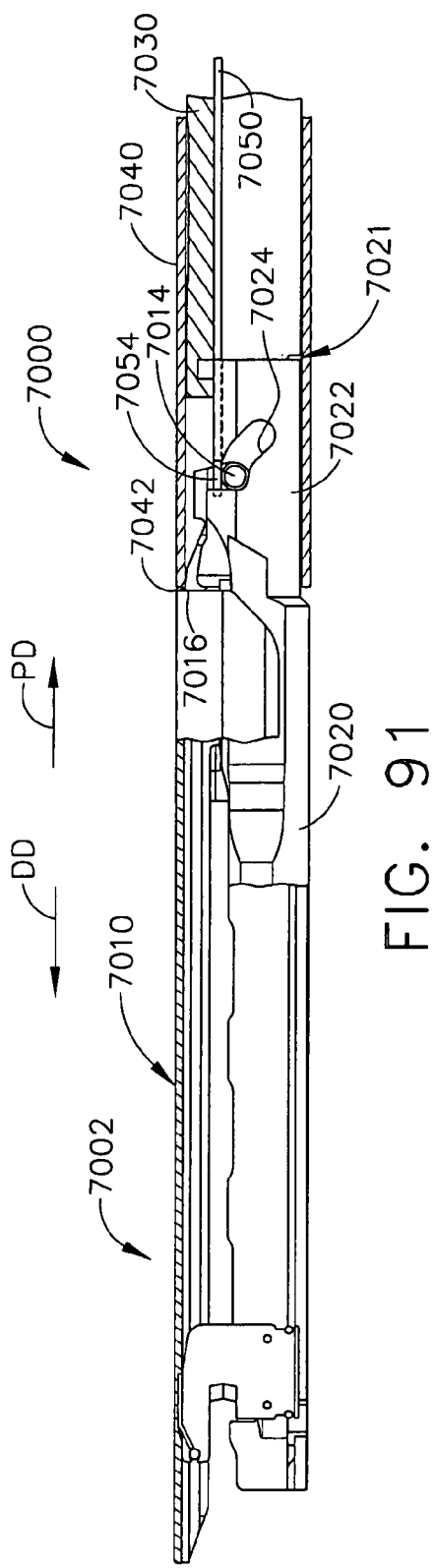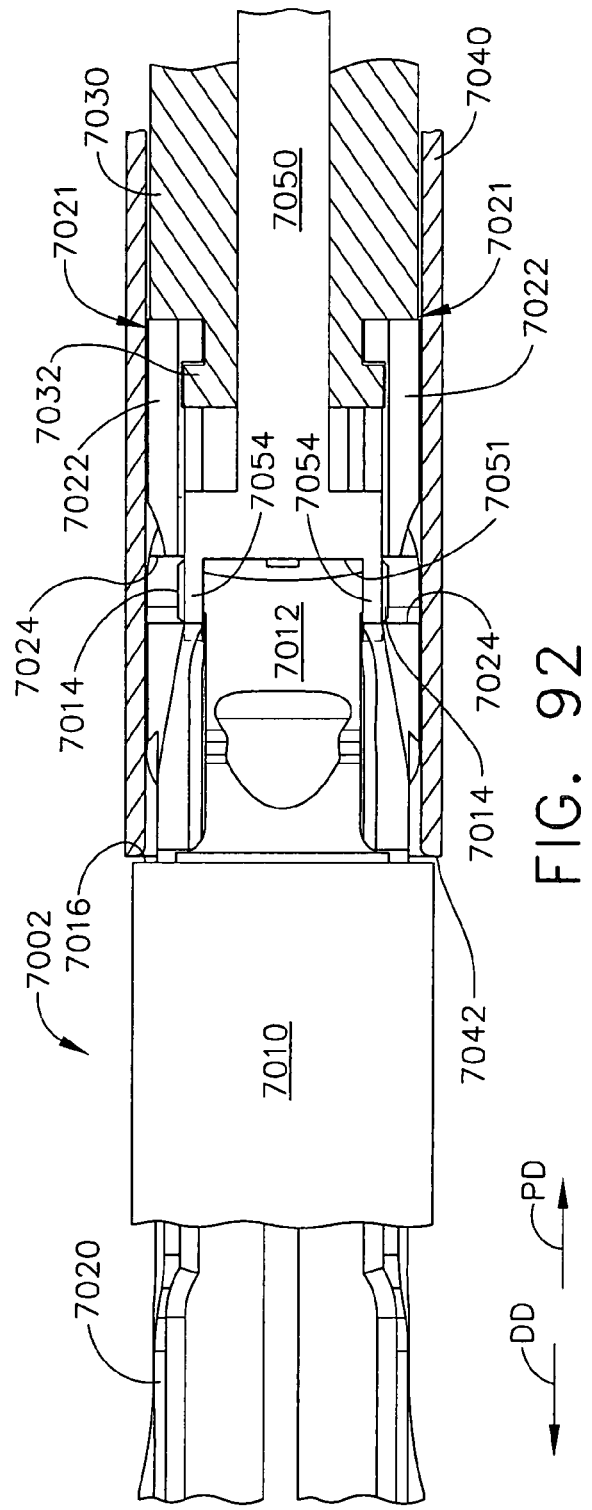

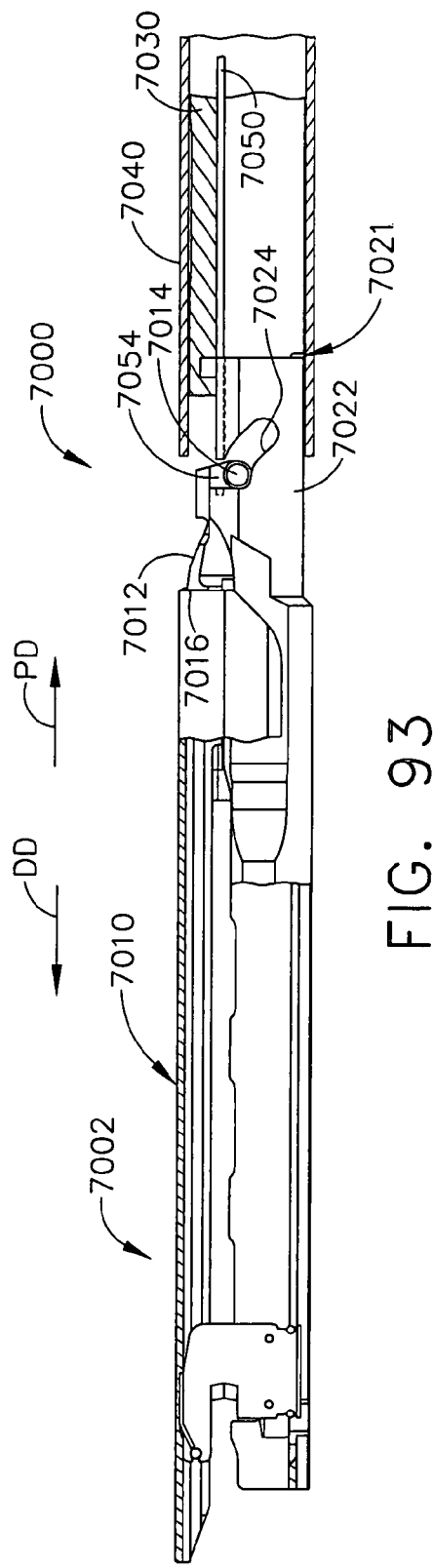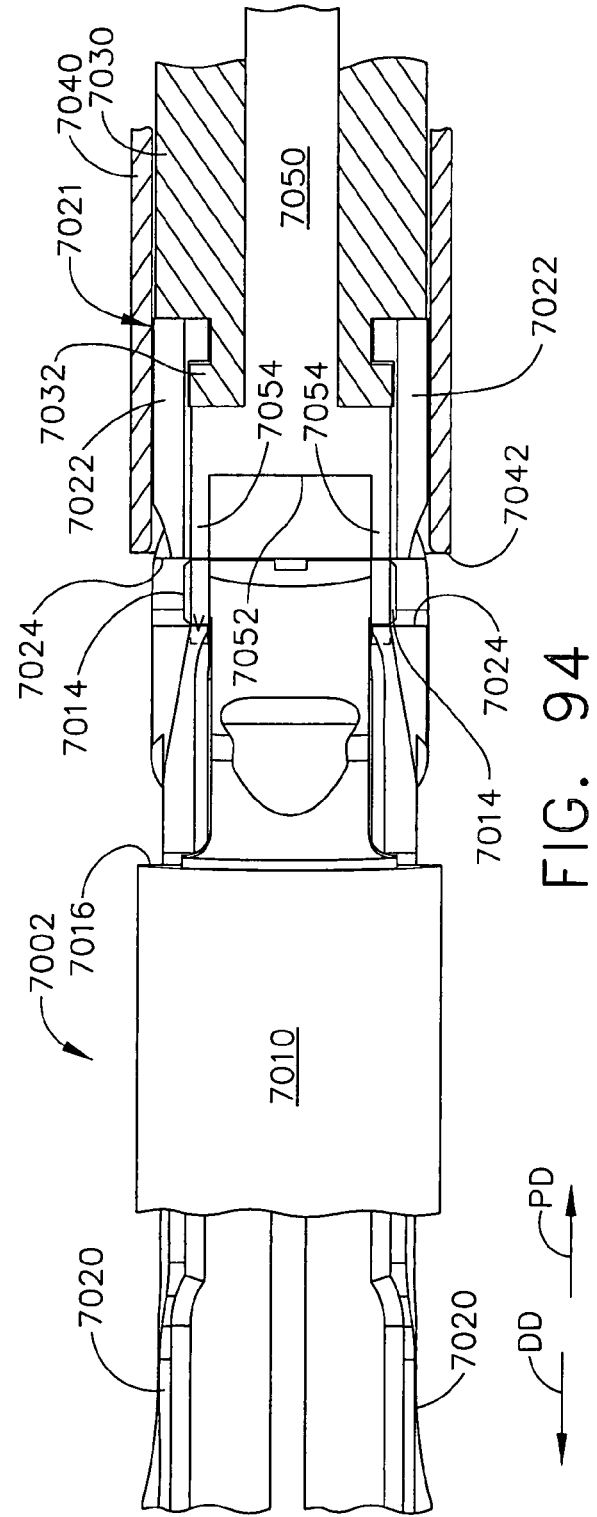

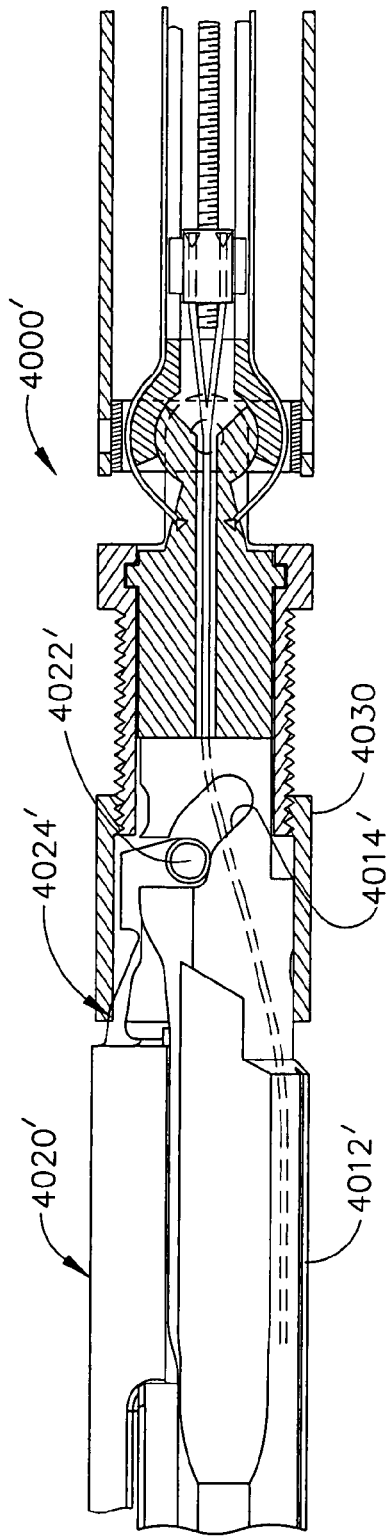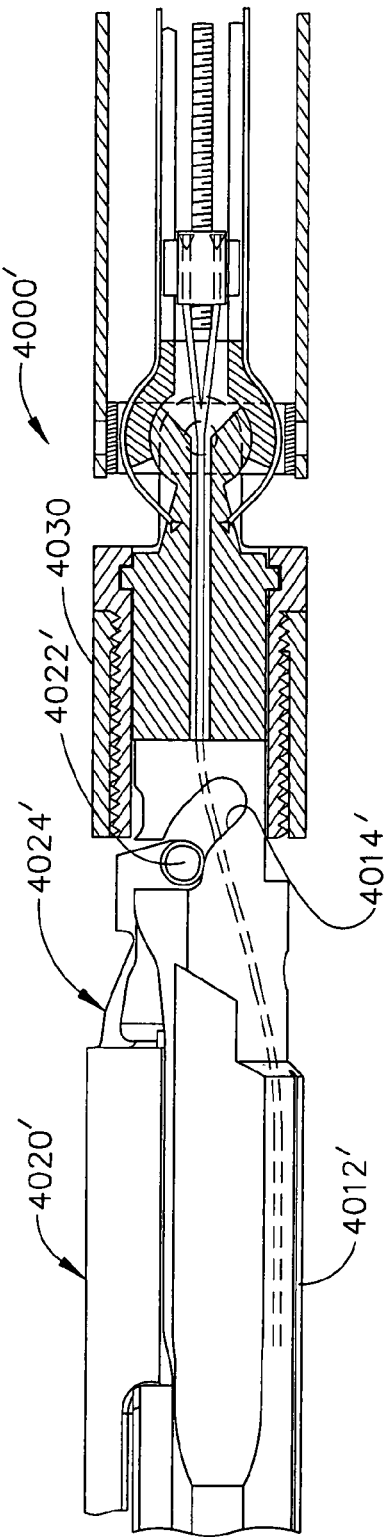

SURGICAL STAPLING AND CUTTING INSTRUMENT WITH IMPROVED FIRING SYSTEM

FIELD OF THE INVENTION

The present invention relates in general to endoscopic surgical instruments including, but not limited to, surgical stapler instruments that are capable of applying lines of staples to tissue while cutting the tissue between those staple lines and, more particularly, to improvements relating to firing and drive systems therefor.

BACKGROUND

The present application is related to the following commonly-owned U.S. Patent Applications filed on even date herewith, the disclosures of which are hereby incorporated by reference in their entirety:

(1) U.S. Patent Application entitled "Surgical Stapling and Cutting Instrument With Improved Closure System" to Richard W. Timm and Frederick E. Shelton, I V, Eugene L. Timperman, and Leslie M. Fugikawa, Ser. No. 11/820,119, Filed Jun. 18, 2007;

(2) U.S. Patent Application entitled "Cable Driven Surgical Stapling and Cutting Instrument With Apparatus For Preventing Inadvertent Cable Disengagement" to Richard W. Timm and Frederick E. Shelton, I V, Ser. No. 11/820,161, Filed Jun. 18, 2007;

(3) U.S. Patent Application entitled "Cable Driven Surgical Stapling and Cutting Instrument With Improved Cable Attachment Arrangements" to Frederick E. Shelton, I V and Richard W. Timm, Ser. No. 11/820,124, Filed Jun. 18, 2007;

(4) U.S. Patent Application entitled "Surgical Stapling and Cutting Instrument With Improved Anvil Opening Features" to Richard W. Timm, Frederick E. Shelton, I V, and Jeffrey S. Swayze, Ser. No. 11/820,077, Filed Jun. 18, 2007; and (5) U.S. Patent Application entitled "Surgical Stapling and Cutting Instruments" to Richard W. Timm, Frederick E. Shelton, I V, Charles J. Scheib, Christopher J. Schall, Glen A. Armstrong, Eugene L. Timperman, and Leslie M. Fugikawa, Ser. No. 11/820,121, Filed Jun. 18, 2007.

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument commonly includes a plurality of wedges that, when driven distally, pass through openings in the staple cartridge and engage drivers supporting the staples to effect the firing of the staples toward the anvil.

An example of such surgical staplers is disclosed in U.S. Patent Publication No. US 2006/0011699 A1 to Olson et al., the disclosure of which is herein incorporated by reference. The stapling devices disclosed therein employs a cable or cables that are positioned around distally located pins or pulleys and are fixed to the knife. The ends of the cables are pulled in a proximal direction. Such system, however, suffers from a low mechanical advantage and tends to require relatively high forces to pull the knife through its stroke.

Thus, there is a need for an improved drive and firing system for use with cable driven surgical staplers.

SUMMARY

In one aspect of the invention, there is provided a surgical instrument that comprises an elongate channel assembly that has a distal end and a proximal end. The elongate channel assembly may be constructed to operably support a staple cartridge assembly therein. Various embodiments may further include a knife assembly that is oriented for travel within the elongate channel assembly. A first distal transition support may be operably mounted to the distal end of the elongate channel. A second cable transition support may be operably attached to the knife assembly. A first cable having a distal end that is affixed to the distal end of the elongate channel assembly may extend around the second cable transition support on the knife assembly and the first distal cable transition support. The first cable may further have a proximal end that interfaces with a cable drive system. A second distal cable transition support may be operably mounted to the distal end of the elongate channel assembly. A second cable having a distal end affixed to the distal end of the elongate channel assembly may extend around the second cable transition support on the knife assembly and the second distal cable transition support. The second cable may have a proximal end that interfaces with the cable drive system.

In another general aspect of various embodiments of the present invention there is provided a surgical instrument that comprises an elongate channel assembly that has a distal end and a proximal end and is constructed to operably support a staple cartridge therein. A knife assembly may be oriented for travel within the elongate channel assembly. First and second distal cable transition supports may be provided on the distal end of the elongate channel assembly. First and second proximal cable transition supports may be operably attached to a proximal end of the elongate channel assembly. The instrument may further comprise a reciprocatable drive member and a first cable that is attached to the knife assembly and the reciprocatable drive member. The first cable is received on the first distal cable transition support and the first proximal cable transition support. The instrument may further include second cable that is attached to the knife assembly and the reciprocatable drive member and extends around the second distal transition support and the second proximal transition support.

In still another general aspect of various embodiments of the present invention there is provided a surgical instrument that comprises a handle assembly and an elongate closure tube assembly that is operably coupled to the handle assembly. An elongate channel assembly is coupled to the elongate closure tube assembly and is constructed to operably support a staple cartridge therein. The instrument may further comprise a knife assembly that is oriented for travel within the elongate channel assembly. Two first cable transition supports are operably attached to the distal end of the elongate channel assembly. At least one second cable transition support is operably attached to the knife assembly. A first cable is affixed to the distal end of the elongate channel assembly and extends around one of the first cable transition supports and the second cable transition support to interface with a cable drive assembly operably supported by the handle assembly. A second cable is affixed to the distal end of the elongate channel assembly and extends around the other one of the first cable transition supports and the second cable transition support to interface with the cable drive assembly.

In another general aspect of various embodiments of the present invention there is provided a surgical instrument that comprises a handle assembly and an elongate spine operably coupled to said handle assembly. The instrument may further comprise a knife assembly that is oriented for travel within the elongate channel assembly. First and second distal cable transition supports may be provided on the distal end of the elongate channel assembly. First and second proximal cable transition supports may be provided on the proximal end of the elongate channel assembly. The instrument may further include a reciprocatable drive member and a first cable that is attached to the knife assembly and the reciprocatable drive member. The first cable extends around the first distal cable transition support and the first proximal cable transition support. A second cable is attached to the knife assembly and the reciprocatable drive member. The second cable extends around the second distal transition support and the second proximal transition support.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain various principles of the present invention.

FIG. 5 is a bottom perspective view with some parts separated therefrom of a cartridge assembly of various embodiments of the present invention.

FIG. 6 is an exploded assembly view of a sled, staples and staple pushers of various embodiments of the present invention.

FIG. 8 is a perspective view of a dynamic clamping member of various embodiments of the present invention.

FIG. 9 is a side cross-sectional view of the tool assembly depicted in FIGS. 1-4 with tissue clamped therein.

FIG. 10 is a bottom perspective view of an elongate channel assembly of various embodiments of the present invention.

FIG. 11 is a perspective view of a proximal portion of the elongate channel assembly of FIG. 10.

FIG. 12 is a perspective view of distal portion of the elongate channel assembly of FIGS. 10 and 11.

FIG. 15 is a diagrammatic side view of a firing system of various embodiments of the present invention.

FIG. 15A is a diagrammatic view of another firing system of various embodiments of the present invention.

FIG. 16 is a diagrammatic top view of the firing system of FIG. 15.

FIG. 16A is a diagrammatic view of the firing system of FIG. 15A.

FIG. 22 is a partial cross-sectional view of another embodiment of the present invention that employs an articulation joint.

FIG. 23 is an enlarged partial cross-sectional view of the articulation joint depicted in FIG. 22.

FIG. 24 is an enlarged cross-sectional view of a portion of the instrument depicted in FIG. 22.

FIG. 25 is a bottom view of another elongate channel assembly embodiment of the present invention.

FIG. 26 is an enlarged view of a distal end portion of the elongate channel assembly of FIG. 25.

FIG. 27 is a cross-sectional view of a portion of the distal end of the elongate channel assembly of FIG. 26 taken along line 27-27 in FIG. 26.

FIG. 56 is a perspective view of a cable controlled lockable articulation joint embodiment of the present invention.

FIG. 57 is an end view of the cable controlled lockable articulation joint embodiment of FIG. 56.

FIG. 63 is a partial perspective end view of a proximal spine segment of the lockable articulation joint of FIG. 62.

FIG. 64 is an end view of the proximal spine segment of FIG. 63.

FIG. 65 a cross-sectional view of another lockable articulation joint of another embodiment of the present invention.

FIG. 66 is a partial perspective end view of a proximal spine segment of the lockable articulation joint of FIG. 65.

FIG. 67 is an end view of the proximal spine segment of FIG. 66.

FIG. 69 is a partial perspective end view of a proximal spine segment of the lockable articulation joint of FIG. 68.

FIG. 70 is an end view of the proximal spine segment of FIG. 69.

FIG. 91 is a cross-sectional elevational view of the tool assembly and closure tube arrangement of FIG. 90 with the trunnion lock bar in a locked position retaining the trunnions in their respective slots.

FIG. 92 is a partial top view of the tool assembly and closure tube arrangement of FIG. 91 with portions thereof shown in cross-section.

FIG. 93 is a cross-sectional elevational view of the tool assembly and closure tube arrangement of FIGS. 90-92 with the trunnion lock bar in an unlocked position.

FIG. 94 is a partial top view of the tool assembly and closure tube arrangement of FIG. 93 with portions thereof shown in cross-section.

FIG. 104 is a side elevational view of a portion of another surgical instrument embodiment of the present invention with a closure ring moved in its distal-most position and with some components thereof shown in cross-section.

FIG. 105 is a side elevational view of the surgical instrument embodiment of FIG. 104 with the closure ring moved in its proximal-most position and with some components thereof shown in cross-section.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 1:
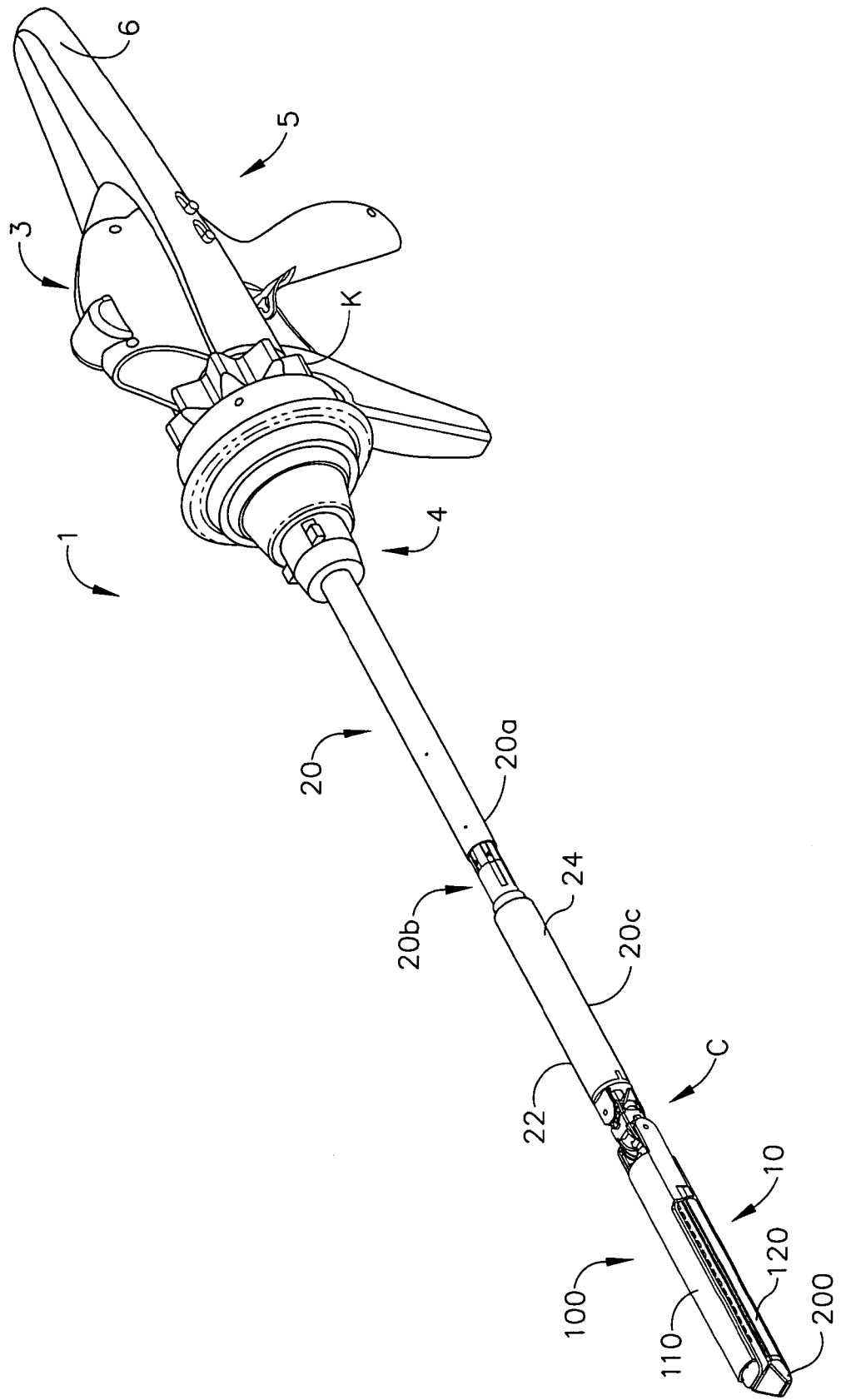
FIG. 1 is a perspective view of a surgical stapling and severing instrument of various embodiments of the present invention.

Turning to the Drawings, wherein like numerals denote like components throughout the several views, FIG. 1 depicts a surgical instrument, which in the illustrative versions is more particularly a surgical stapling and severing instrument 1, capable of practicing certain unique benefits of the present invention. Instrument 1 may essentially comprise a surgical stapler of the form and construction disclosed in the previously cited U.S. Patent Publication No. 2006/0011699 A1, which has been herein incorporated by reference in its entirety, with one or more of the improvements described below. As the present Detailed Description proceeds, however, those of ordinary skill in the art will appreciate that the various embodiments and improvements described herein may be incorporated in connection with other surgical stapler constructions without departing from the spirit and scope of the present invention.

As shown in FIG. 1, the instrument 1 may include a housing 3 that has distal and proximal ends 4 and 6, respectively, an elongated shaft 20 mounted to housing 3, preferably to its distal end 4, and a handle assembly generally designated as 5. Shaft 20 may have a distal end 20a to which may be operatively attached by attachment mechanism 20b to a disposable loading unit 10. As also shown in FIG. 1, disposable loading unit (DLU) 10 may comprise a tool assembly 100 and a shaft connector portion 20c which may be pivotally and operatively attached to each other through connector mechanism C.

It is within the scope of this disclosure that tool assembly 100 may be pivotally, operatively, or integrally attached, for example, through a connection mechanism such as C permanently and directly to distal end 20a of shaft 20 of a disposable surgical stapler. As is known, a used or spent disposable loading unit 10 can be removed from shaft 20 of a reusable or disposable open, endoscopic or laparoscopic surgical stapler, and replaced with an unused disposable unit. In various embodiments, it is contemplated that shaft 20 with or without an integral or removably attached disposable loading unit can be selectively removable from the housing 3.

Shaft connector portion 20c includes a proximal end 24 and a distal end 22. As mentioned above, the proximal end 24 can be permanently or removably associated with a handle or other actuating assemblies of a manually (or other, e.g., robotic or computer) operated open or endoscopic surgical stapler 1. Distal end 22 of shaft connector portion 20c is operatively connected to tool assembly 100. Tool assembly 100, in general, may include an elongate channel assembly 120, an anvil assembly 110, and a staple cartridge assembly 200. Tool assembly 100 may also preferably include an actuator, preferably a dynamic clamping member 150, a sled 160, as well as staple pushers 228 and staples 350 once an unspent or unused cartridge 200 is mounted in elongate channel assembly 120. See FIGS. 2, 5, and 6.

It will be appreciated that the terms "proximal" and "distal" are used herein with reference to a clinician gripping a handle of an instrument. Thus, the tool assembly 100 is distal with respect to the more proximal handle assembly 5. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

Shaft connector portion 20c may be cylindrical in shape and define an internal channel 25 which may be dimensioned to receive a tube adapter 40. See FIG. 2. Shaft connector portion 20c may also receive or house actuators for actuating tool assembly 100. Tool assembly 100 may mount to distal end 22 of shaft connector 20c (or the distal end 20a of shaft 20). In various embodiments, tool assembly 100 may be mounted onto tube adapter 40 which includes an outer cylindrical surface 47 that may be slidingly received in friction-fit engagement with the internal channel 25 of shaft connector 20c (or, again, to shaft 20). Herein, the description of the proximal connection or attachment of tool assembly 100 to shaft connector 20c may also apply to its connection to shaft 20. The outer surface 47 of the tube adapter 40 may further include at least one mechanical interface, e.g., a cutout or notch 45, oriented to mate with a corresponding mechanical interface, e.g., a radially inwardly extending protrusion or detent (not shown), disposed on the inner periphery of internal channel 25 to lock the tube adapter 40 to the shaft connector 20c.

In various embodiments, the distal end of tube adapter 40 may include a pair of opposing flanges 42a and 42b which define a cavity 41 for pivotably receiving a pivot block 50 therein. Each flange 42a and 42b may include an aperture 44a and 44b oriented to receive a pivot pin 57 that extends through an aperture in pivot block 50 to allow pivotable movement of pivot block 50 about a "Z" axis defined as perpendicular to longitudinal axis "X" of tool assembly 100. See FIG. 3. As will be explained in more detail below, the channel assembly may be formed with two upwardly extending flanges 121a, 121b that have an aperture 122a, 122b, respectively, which are dimensioned to receive a pivot pin 59. In turn, pivot pin 59 mounts through apertures 53a, 53b of pivot block 50 to permit rotation of the tool assembly 100 about the "Y" axis as needed during a given surgical procedure. Rotation of pivot block 50 about pin 57 along "Z" axis rotates tool assembly 100 about the "Z" axis. Other methods of fastening the channel 120 to the pivot block and of fastening the anvil to the channel may be effectively employed without departing from the spirit and scope of the present invention.

In various embodiments, an actuator or a plurality of actuators (not shown) preferably pass through shaft connector portion 20c, tube adapter 40, and pivot block 50 and operably connect to tool assembly 100 to permit the surgeon to articulate tool assembly 100 about the "Y" and "Z" axes as needed during a surgical procedure. In addition, shaft 20 of surgical stapler 1 may be rotatable 360° by the rotation of knob "K". As a result, tool assembly 100 may be articulatable at least 90° in all directions. Various actuators, hand assemblies, and pivot blocks are envisioned which can be utilized to accomplish this task some of which are identified in U.S. Pat. Nos. 6,250,532 and 6,330,965, the entire contents of which are each hereby incorporated by reference herein.

As mentioned above, in various embodiments, tool assembly 100 may include anvil assembly 110 and elongate channel assembly 120. See FIG. 2. Elongate channel assembly 120 may support the staple cartridge assembly 200, an actuator, e.g., a dynamic clamping member 150, and a sled 160. As such, these various assemblies and their respective internal components, when assembled, cooperate to allow the tool assembly to manipulate, grasp, clamp, fasten and, preferably, sever tissue during a given surgical procedure as explained below. Elongate channel assembly 120 may include a bottom surface 128 having upwardly extending side walls or flanges 121a and 121b which define elongated support channel 125 which, in turn, is dimensioned to mountingly receive staple cartridge assembly 200 therein. Elongate channel assembly 120 may also include a plurality of mechanical interfaces 127a, 127b, 127c, 127d oriented to receive a corresponding plurality of mechanical interfaces 235a, 235b, 235c, and 235d disposed in the outer-facing surfaces of staple cartridge assembly 200. See FIGS. 2 and 6.

Staple cartridge assembly 200 mounts within the elongate channel assembly 120 and includes an upper tissue contacting or facing surface 231 which, as will become further apparent as the present Detailed Description proceeds, opposes a tissue contacting or facing bottom anvil surface 114b of anvil assembly 110. Staple cartridge assembly 200 can be assembled and mounted within elongate channel assembly 120 during the manufacturing or assembly process and sold as part of overall tool assembly 100, or staple cartridge assembly 200 may be designed for selective mounting to channel assembly 120 as needed and sold separately, e.g., as a single use replacement, replaceable or disposable staple cartridge assembly 200. For example, staple cartridge assembly 200 may be manufactured to include sled 160 and dynamic clamping member 150. Alternatively dynamic clamping member 150 with a knife 155 may be sold as part of the replaceable staple cartridge assembly 200 without a knife blade 155a (but preferably with a knife blade 155a) to enhance and/or insure accurate cutting of tissue after staple formation. Tool assembly 100 may also be sold as a kit that includes a variety of staple cartridges 200 containing surgical fasteners 350 of different sizes, and/or arranged to be ejected in different patterns, any of which may be selectively-coupled to the elongate channel assembly 120 as desired for use during a particular operation.

As best seen in FIG. 6, sled 160 may include a pair of upwardly-extending cam wedges 161a and 161b which, when actuated to move by the user, cam a series of surgical fasteners 350 or staples into and through the tissue and against staple forming pockets 111 (shown in FIG. 9) of anvil assembly 110 to form the fasteners 350 and fasten tissue therewith. Dynamic clamping member 150 is associated with, e.g., mounted on and rides on, or with or is connected to or integral with and/or rides behind sled 160. It is envisioned that dynamic clamping member 150 can have cam wedges or cam surfaces attached or integrally formed or be pushed by a leading distal surface thereof.

In various embodiments, dynamic clamping member 150 may include an upper portion 157 having a transverse aperture 154 with a pin 159 mountable or mounted therein, a central support or upward extension 151 and substantially T-shaped bottom flange 152 which cooperate to slidingly retain dynamic clamping member 150 along an ideal cutting path during longitudinal, distal movement of sled 160. See FIG. 8. The leading cutting edge 155, here, knife blade 155a, is dimensioned to ride within slot 282 of staple cartridge assembly 200 and separate tissue 400 once stapled. It is envisioned that leading edge 153a of the dynamic clamping member 150 may be serrated, beveled or notched to facilitate tissue cutting. In some embodiments, for example, the upper camming member need not be a pin but can be any integral or removable suitable outwardly protruding cam surface(s). The same applies to bottom flange 152 which can be any suitable camming surface, including a pin or a removable pin, a button to facilitate mounting of the dynamic clamping member into the sled 160 or elongate channel assembly 120. As used herein, the term "knife assembly" 170 may include the aforementioned dynamic clamping member 150, knife 155, and sled 160 or other knife/ beam/sled drive arrangements. In addition, the various embodiments of the present invention may be employed with knife assembly arrangements that may be entirely supported in the staple cartridge or partially supported in the staple cartridge and elongate channel assembly or entirely supported within the elongate channel assembly.

Figure 13:
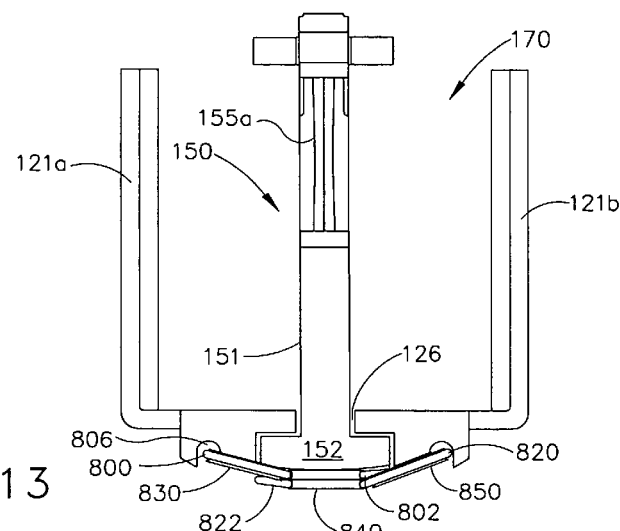
FIG. 13 is a cross-sectional elevational view of a distal portion of the elongate channel assembly of FIGS. 10-12 with the dynamic clamping member supported therein.
Figure 14:
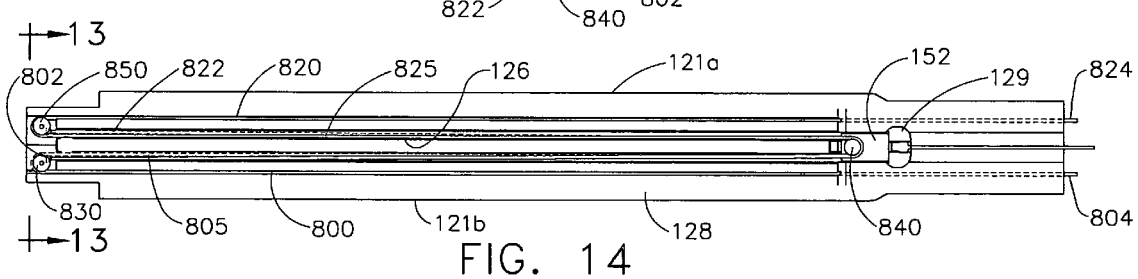
FIG. 14 is another bottom view of the elongate channel assembly of FIGS. 10-13.

As best shown in FIG. 10, the elongate channel assembly 120 has a distal end 123 and proximal end 123'. The bottom surface 128 of the elongate channel assembly 120 also includes an elongated longitudinal slot 126 which includes and communicates at its proximal end with a cut out or notch 129. Notch 129 is dimensioned to allow bottom flange 152 of dynamic clamping member 150 to pass therethrough. The narrower portion of slot 126 is dimensioned to slidingly receive and allow upward support or extension 151 to pass therethrough. See FIG. 13. Other dynamic clamping members 150, channel slots, and sled configurations may be employed.

Figure 3:
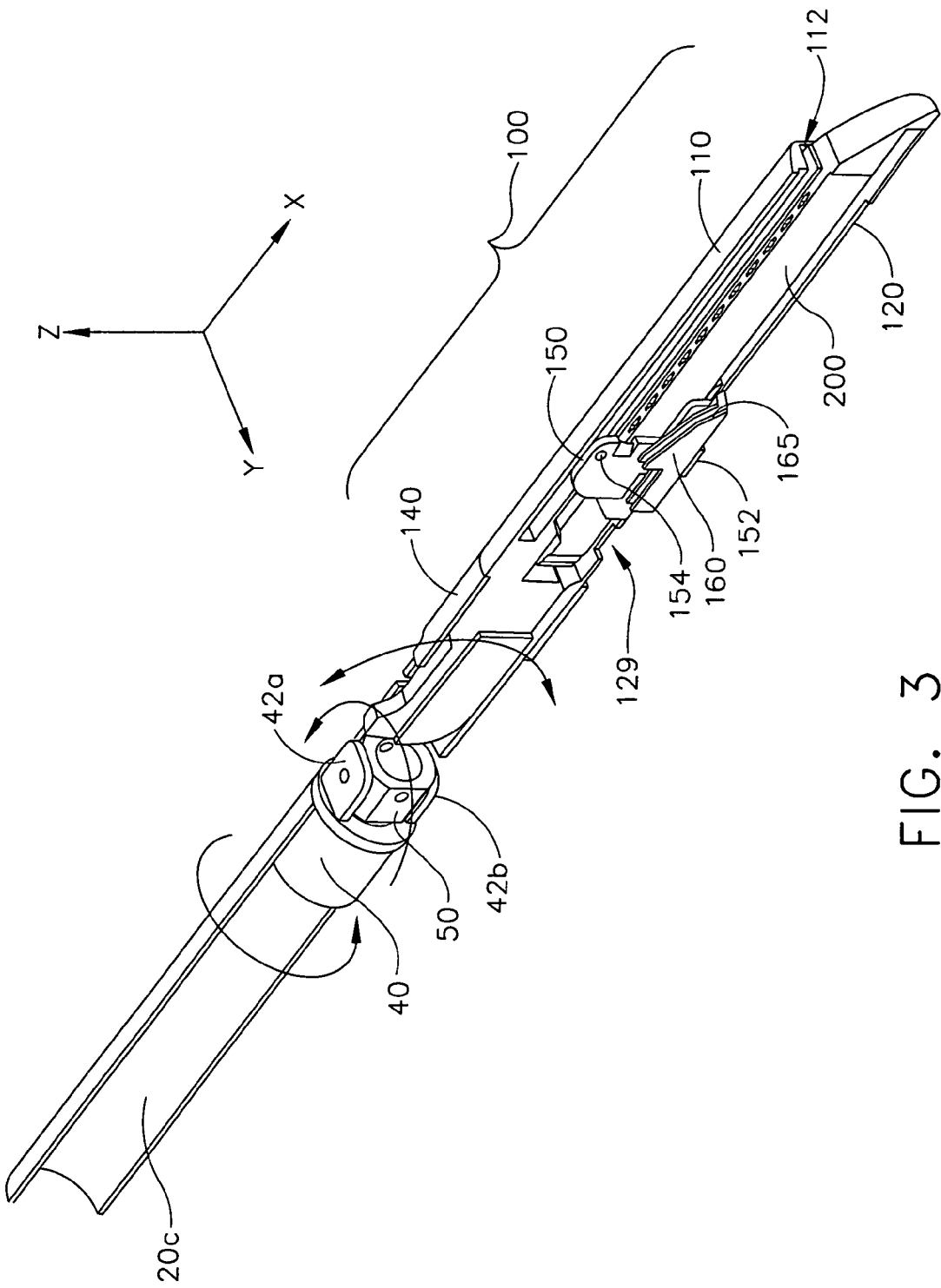
FIG. 3 is a right perspective view of the tool assembly of FIG. 1 with some components thereof shown in cross-section.

When tool assembly 100 is assembled, sled 160 may be slidingly positioned between the staple cartridge assembly 200 and the elongate channel assembly 120 (See FIG. 3). Sled 160 and the inner-working components of staple cartridge assembly 200 detailed above operatively cooperate to deform staples 350. More particularly, as indicated above, sled 160 may include upwardly extending, bifurcated cam wedges 161a and 161b which engage and cooperate with a series of staple pushers 228 to drive staples 350 through slots 225 from cartridge assembly 200 and deform against staple forming pockets 11 of anvil assembly 100. Further details of a sled 160, dynamic clamping member 150 and the staple cartridge assembly 200 of various embodiments are further described in U.S. Publication No. US 2006/0011699 A1.

Figure 2:
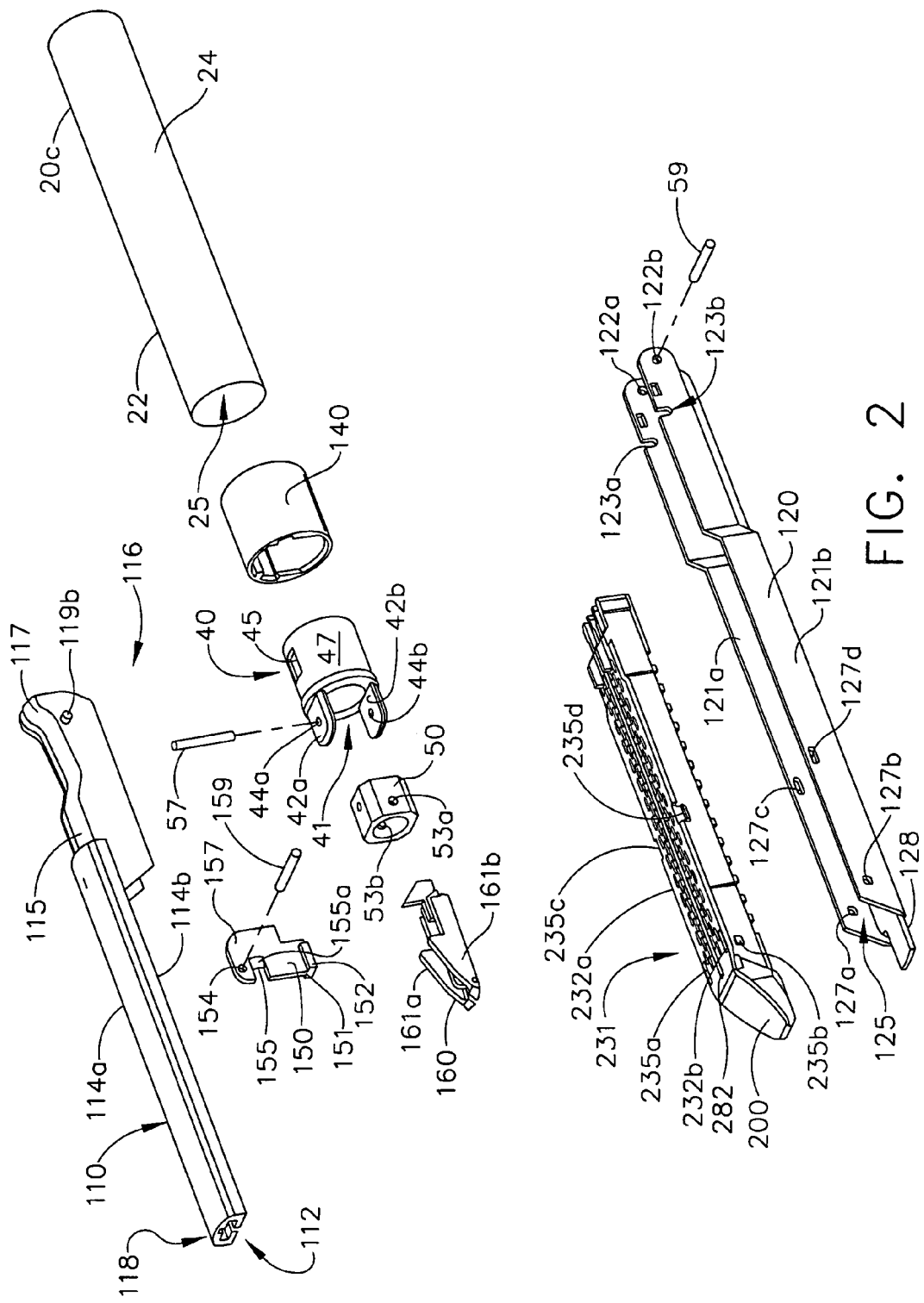
FIG. 2 is an exploded perspective view of a tool assembly depicted in FIG. 1.
Figure 7:
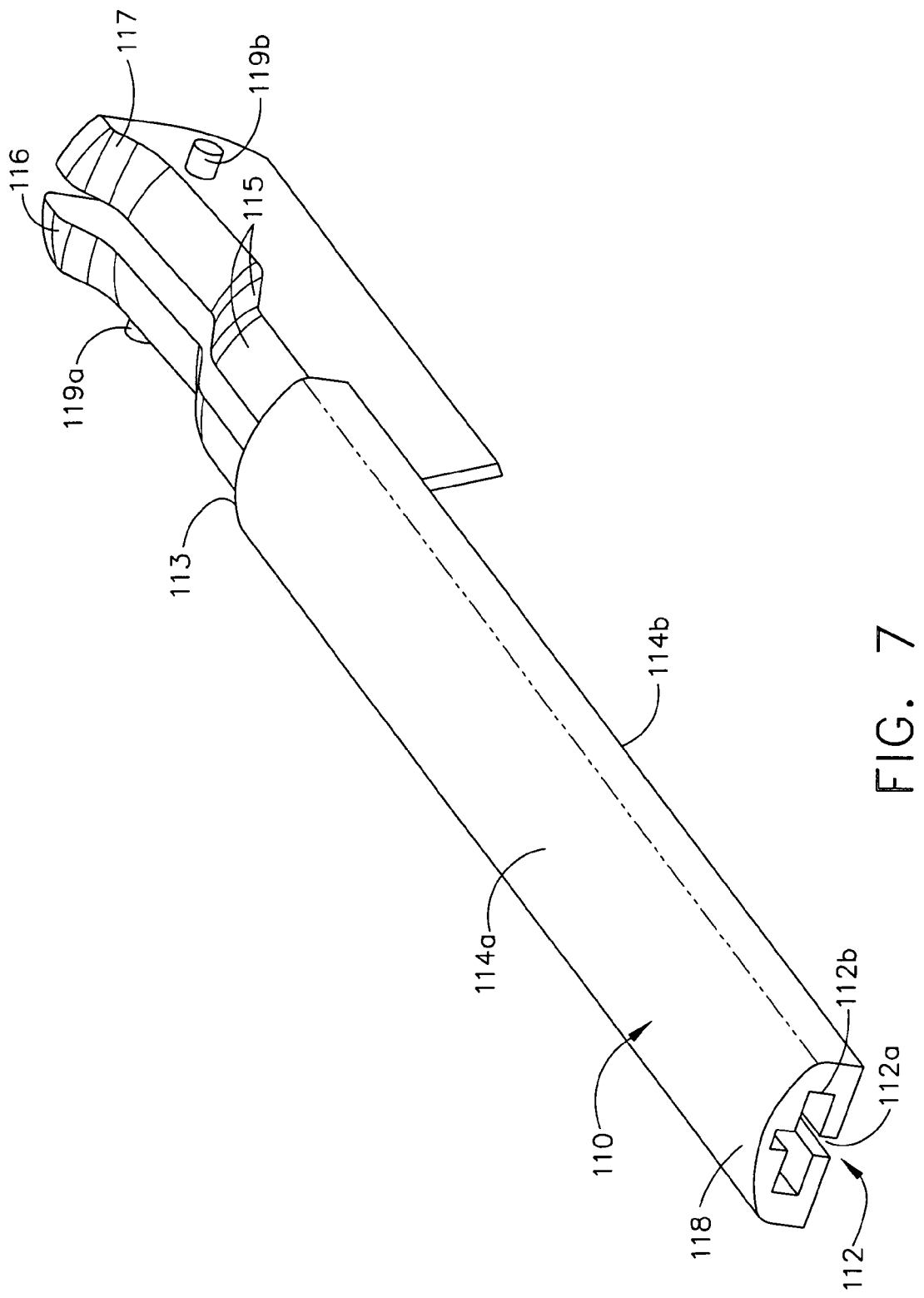
FIG. 7 is a perspective view of an anvil assembly of various embodiments of the present invention.

As shown in FIGS. 2 and 7, anvil assembly 110 may be elongated and include a proximal end 116, a distal end 118, and top and bottom surfaces 114a and 114b, respectively. A pair of trunnions 119a and 119b may be disposed near proximal end 116 and are designed for pivotable engagement with corresponding pair of notches 123a and 123b provided in the sidewalls 121a, 121b near the proximal end of the elongate channel assembly 120. It is contemplated that actuation by conventional means (e.g., activated remotely, e.g., by a handle assembly 5 will cause clamping collar 140 to move in a distal direction and engage forward cam surface 115 of anvil assembly 110. This will cause the anvil assembly 110 to pivot from an open first position wherein the anvil assembly 110 and the elongate channel assembly 120 are disposed in spaced relation relative to one another to a second closed position wherein anvil assembly 110 and staple cartridge assembly 200 cooperate to grasp tissue therebetween, i.e., pre-clamp the tissue between tissue engaging surface 114b of anvil assembly 110 and opposing tissue engaging surface 231 of staple cartridge assembly 200. However, other anvil assembly arrangements may be successfully employed.

In various embodiments, anvil assembly 110 may include an elongated cross or T-shaped channel or slot generally designated 112 having a depending central portion or leg 112a and a transverse upper portion 112b. See FIG. 7. Slot 112 preferably extends longitudinally from proximal end 113 of upper portion 114a of the anvil assembly 110 to the distal end 118 thereof. Leg 112a starts from or enters proximal end 113 of anvil assembly 110 and extends to distal end 118 and upper transverse portion 112b starts proximal cam 115 and extends to distal end 118. See FIG. 7. Preferably, upper portion 112b is dimensioned to slidingly receive transverse pin 159 that extends within aperture 154 in upper portion 157 of central support or extension 157 of dynamic clamping member 150 (see FIG. 9). Pin 159 is dimensioned to slidingly lock the upper portion 157 of dynamic clamping member 150 within the T-shaped slot 112 such that the dynamic clamping member 150 is longitudinally-reciprocatable within slot 112.

In various embodiments, pre-clamping collar 140 may be designed to encompass and clamp or pre-clamp the channel assembly 120 and the anvil assembly 110 together in an approximated and clamped position prior to tissue fastening. By moving pre-clamping collar 140 distally, the user can actuate/move the anvil assembly 110 from an open, first position toward channel assembly 120 to approximate the jaws, i.e., the anvil assembly 110 and staple cartridge 200, to a second, closed position to grasp tissue therebetween. The sled 160 can be actuated by the user to staple and subsequently incise the tissue.

Figure 4:
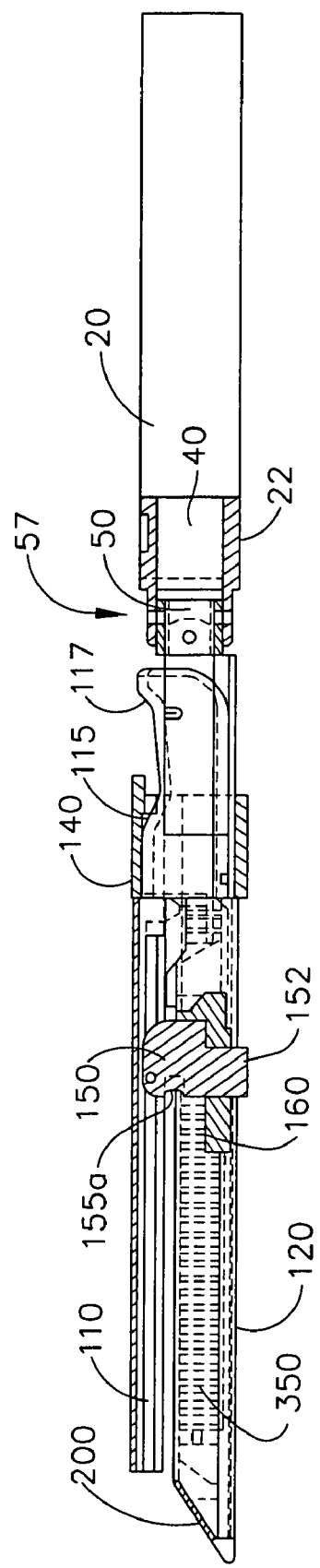
FIG. 4 is a left side partial cross-sectional view of the tool assembly depicted in FIGS. 2 and 3.

As best illustrated by FIGS. 4, 8, and 9, during distal translation of the dynamic clamping member 150 through tissue 400, the combination of the heavy gauge material of the anvil assembly 110 and the substantially vertical alignment of the flange 152, knife edge 155, and camming pin 159 operate to further proximate (i.e., further clamp) the opposing tissue engaging surfaces (i.e., anvil bottom surface 114b and upper facing surface 231 of staple cartridge assembly 200) at a moving point which is distal to the leading edge 155 of the knife 155a. The further clamping of the tissue 400 distally relative to the translating dynamic clamping member 150 acts to maintain a maximum acceptable gap between the opposing surfaces 114b and 231 and forces fluid from the tissue 400 which may enhance stapling and reduce the likelihood of hydraulically displacing the staples 350 during deformation. It is contemplated that the combination of the enhanced closure force as a result of the heavy gauge material of the anvil assembly 110, together with the above described dynamic clamping member 150, permits relatively accurate cutting of tissue 400 when leading edge 155 is advanced through tissue 400.

From the foregoing and with reference to the various Figures, those skilled in the art will appreciate that certain modifications can also be made to the present disclosure without departing from the scope of the present disclosure. For example, the above-described tool assembly 100 may be part of or incorporated into a disposable loading unit (DLU) such as disclosed in U.S. Pat. No. 6,330,965 or attached directly to the distal end of any known surgical stapling device. A handle assembly for actuating the approximation member(s) can be selected from a variety of actuating mechanisms including toggles, rotatable and slideable knobs, pivotable levers or triggers, and any combination thereof. The use of the above-described tool assembly 100 as part of a robotic system is also envisioned.

FIGS. 10-18 illustrate a single use tool assembly arrangement. As can be seen in those Figures, a pair of cables, ropes, threads, bands or belts 800, 820 may be supported by the channel assembly 120. As can be seen in FIGS. 11 and 12, a first cable 800 may include an anchor segment 802 that is fixed to a first point of attachment 803 on the bottom 128 of the elongate channel assembly 120 at the distal end 123 thereof, an activation portion 804 that extends to the drive system (not shown) located in the housing portion 5, and a moving portion 805. As can be most particularly seen in FIG. 12, the first cable 800 is operably supported on a first distal cable transition support 830 that may comprise, for example, a pulley, rod, capstan, etc. mounted to the bottom 128 at the distal end 123 of the elongate channel assembly 120. The first cable 800 may also be operably supported on a second cable transition support 840, which may comprise, for example, a double pulley 840 mounted to the knife assembly 170. In one embodiment, for example, the second cable transition support is mounted to the bottom flange portion 152 of the dynamic clamping member 150. See FIGS. 12 and 13. The first cable 800 may pass through a longitudinally extending first groove 806 provided in the bottom 128 of the elongate channel assembly 120. The moving portion 805 may move freely back and forth axially adjacent the slot 126. The activation portion 804 may pass through a first transition passage 808 in the bottom 128 of the elongate channel assembly 120 as shown in FIG. 11.

Also in this embodiment, a second cable 820 may have an anchor portion 822 that is fixed to the bottom 128 of the elongate channel assembly 120 at the distal end 123 thereof at a second point of attachment 803', an activation portion 824 that extends to the drive system located in the handle housing 5, and a moving portion 825. The second cable 820 may be operably supported on a second distal cable transition support 850 which may, for example, comprise a second pulley, rod, capstan, etc. that is attached to the distal end 123 of the elongate channel assembly 120 and is also operably supported on the second cable transition support 840. The second cable 820 may pass through a longitudinally extending second groove 826 provided in the bottom 128 of the elongate channel assembly 120. The moving portion 825 may freely move back and forth axially adjacent the slot 126. The activation portion 824 may pass through a second transition passage 828 in the bottom 128 of the elongate channel assembly 120. See FIG. 11. Those of ordinary skill in the art will appreciate that such arrangement may provide improved mechanical advantages over prior cable arrangements and thereby reduce the amount of firing forces that must be generated to advance the knife assembly 170 in the form of the dynamic clamping member 150, knife 155, and sled 160 to fire the staples 350.

As indicated above, the advancement and retraction of the knife assembly 170 (i.e., dynamic clamping assembly 150, knife 155, and sled 160) is controlled by the cables 800, 820 that each have proximal ends which may be attached, for example, to a cable drive system which may include, for example, a rotatable take up drum or drums (not shown) operably supported in the handle 5. The take up drum or drums may be mechanically or manually rotated or powered by a motor to rotate the cables 800, 820 thereon. As the cables 800, 820 are taken up on those drums, the knife assembly 170 (dynamic clamping assembly 150/sled 160 are driven from the proximal end of the elongate channel 120 to the distal end thereof to complete the severing and stapling operations. In various embodiments no means are provided to retract the knife assembly 170 back to the proximal end of the channel 120, so the tool assembly may not be reused.

Figure 17:
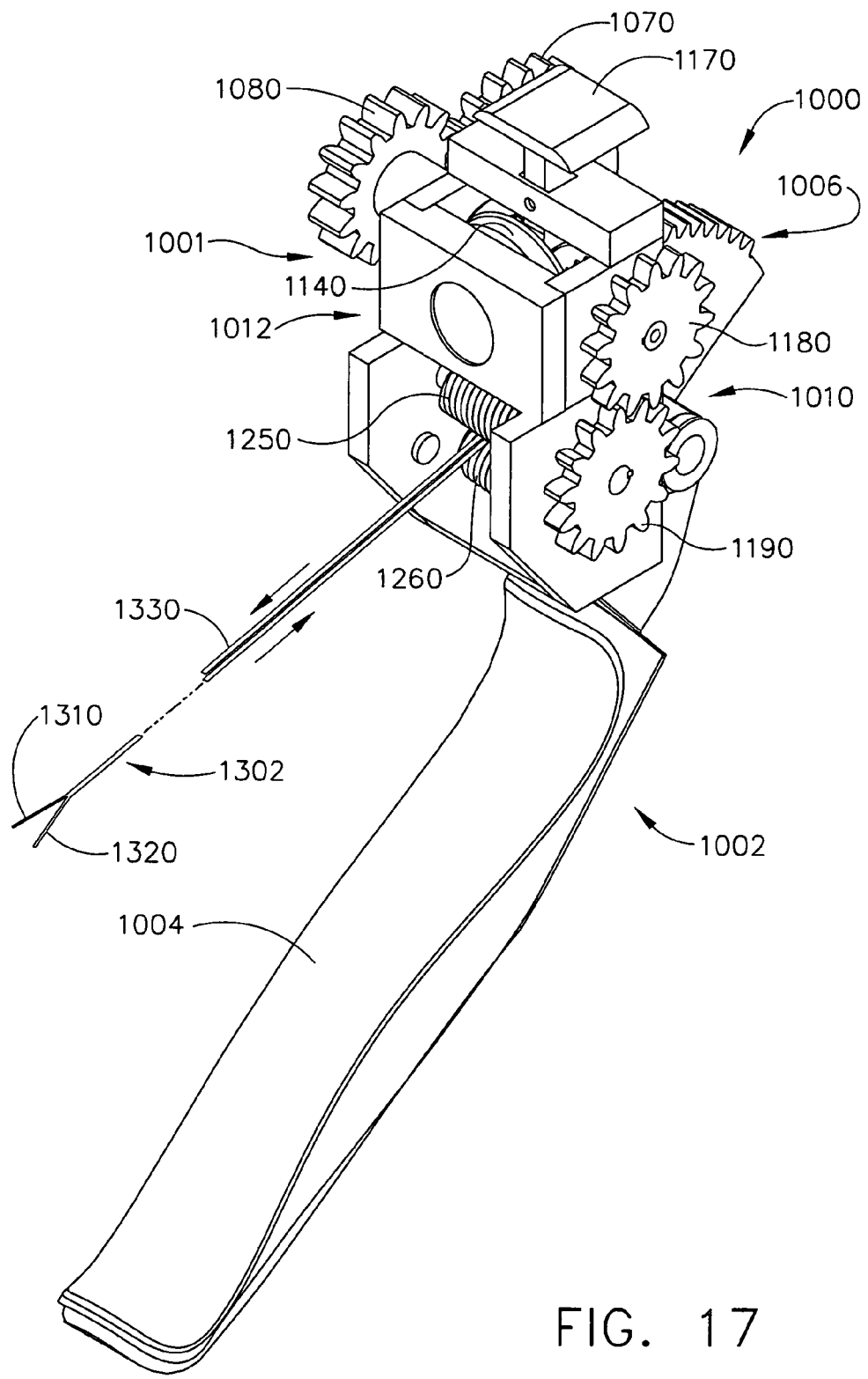
FIG. 17 is a front perspective view of a winch assembly of various embodiments of the present invention.

An alternative firing system 1300 embodiment is disclosed in FIGS. 15-20. As can be seen in FIGS. 15-17, this embodiment employs an advance cable 1302 that is bifurcated into a pair of advance cable portions 1310, 1320 and a retract cable 1330 which are illustrated in diagrammatic form. As can be most particularly seen in FIG. 16, a first advance cable portion 1310 may be operably supported on a first distal cable transition support 1340 which may comprise, for example, a pulley, rod, capstan, etc. that is attached to the distal end 123 of the elongate channel assembly 120 as was described above. A distal end 1312 of the first advance cable portion 1310 may be affixed to the knife assembly 170 (dynamic clamping assembly 150). The second advance cable portion 1320 may be operably supported on a second distal cable transition support 1360 which may, for example, comprise a pulley, rod, capstan etc. that is mounted to the distal end 123 of the elongate channel assembly 120. A distal end 1322 of the second advance cable portion 1320 is attached to the knife assembly 170 (dynamic clamping assembly 150). Also in these embodiments, a retract cable 1330 is employed. In one embodiment, the retract cable 1330 may be formed in a loop such that the distal looped end 1332 is fixedly attached (swaged, etc.) to the dynamic clamping assembly 150.

In various embodiments, the advance cable 1302 and the retract cable 1330 may be driven by, for example, a cable drive system 1000 which, for example, may comprise a manually actuatable winch assembly 1001 mounted in or otherwise supported by the handle assembly 5. See FIGS. 17-20. The winch assembly 1000 may include, for example, an actuator 1002 in the form of a firing trigger 1004 that is pivotally supported by the handle assembly 5. While this embodiment employs a grippable trigger 1004, those of ordinary skill in the art will appreciate that the actuator 1002 may comprise a push button, lever, slide, etc. without departing from the spirit and scope of the present invention. In the embodiment depicted in FIGS.17-20, the winch assembly 1001 may include a transmission 1010 and first and second rotatable spools 1250, 1260, respectively, that are supported on a frame assembly 1012.

Figure 18:
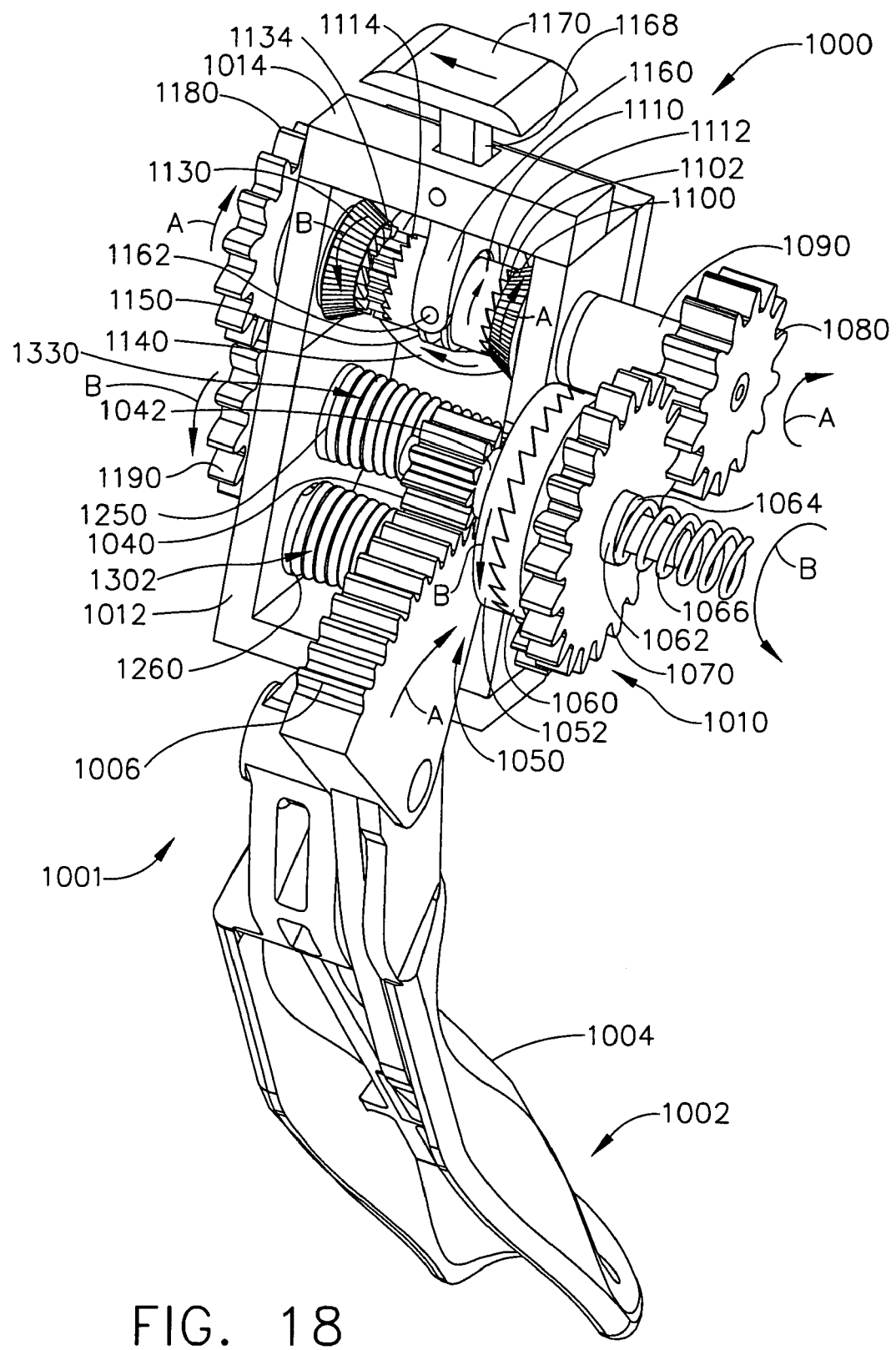
FIG. 18 is a rear perspective view of the winch assembly embodiment of FIG. 17.
Figure 19:
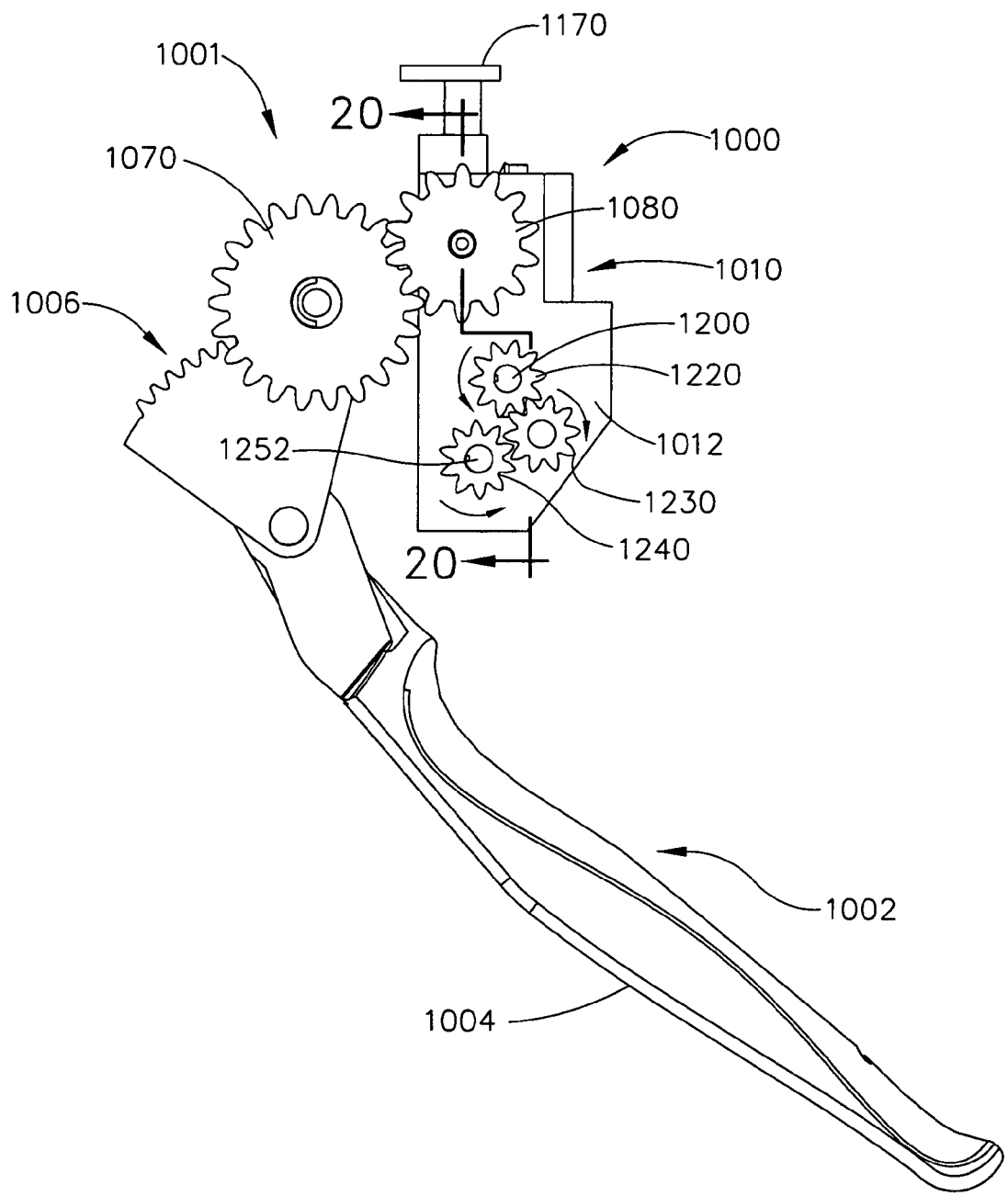
FIG. 19 is a right side elevational view of the winch assembly embodiment of FIGS. 17 and 18.
Figure 20:
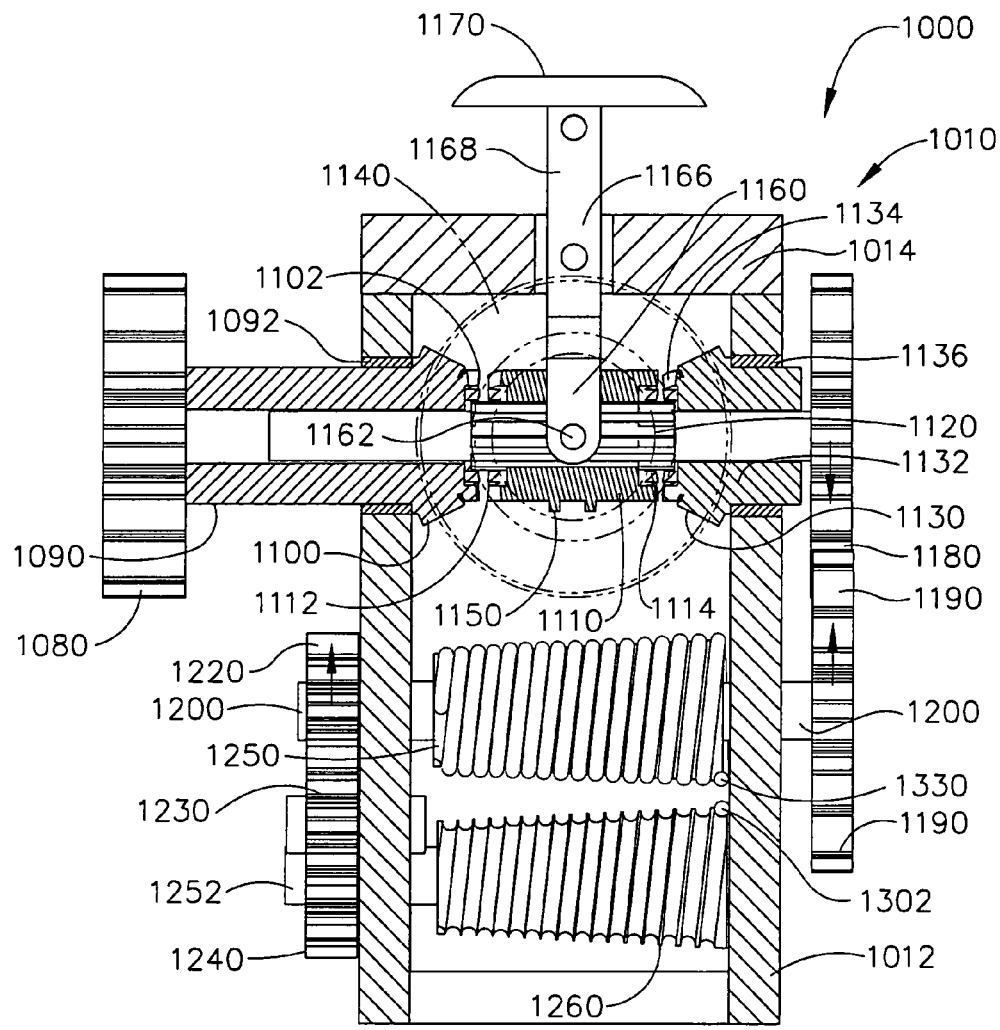
FIG. 20 is a cross-sectional view of the winch assembly embodiment of FIGS. 17-19 in a neutral position.

In various embodiments, a handle gear segment 1006 may be formed or otherwise provided on the firing trigger 1004. The handle gear segment 1006 is mounted in meshing engagement with a primary drive gear 1040 that is mounted to a shaft 1042 attached to a first ratchet clutch plate 1052 of a clutch assembly 1050. See FIG. 18. A second ratchet clutch plate 1060 is supported on a clutch shaft 1062 that is rotatably supported within the handle assembly 5. The clutch shaft 1062 may be provided with a shoulder portion 1064 and have a clutch spring 1066 journaled thereon and in contact with a portion of the housing 3 to bias the second ratchet clutch plate 1060 into meshing engagement with the first ratchet clutch plate 1052. As can also be seen in FIG. 18, a second drive gear 1070 is journaled on the clutch shaft 1062 and is in meshing engagement with a third drive gear 1080 that is attached to a first transmission shaft 1090 that is rotatably supported by a first transmission bearing or sleeve 1092 mounted in the frame assembly 1012. See FIG. 18. The first transmission shaft 1090 may have a first pinion gear portion 1100 and a series of first gear teeth 1102 formed thereon for selective meshing engagement with a series of primary gear teeth 1112 on an axially and rotatably movable shaft spool 1110. As can be seen in FIG. 20, the shaft spool 1110 is received on a splined shaft 1120 that is rotatably received within the first transmission shaft 1090 and a second pinion gear 1130. The second pinion gear 1130 has a second pinion gear portion 1132 and a series of second gear teeth 1134 for selective meshing engagement with secondary gear teeth 1114 on the shaft spool 1110. The second pinion gear 1130 may be rotatably supported by a second bearing 1136 mounted 1136 in the frame assembly 1012 as shown. As can be seen in FIGS. 18 and 20, a reversing bevel gear 1140 is supported by the frame assembly 1012 in meshing engagement with the first and second pinion gears 1100, 1130, respectively.

As can also be seen in FIGS. 18 and 20, the shaft spool 1110 may have a collar portion 1150 formed thereon for receiving two opposing pins 1162 extending from a yoke 1160 formed on a bottom portion of a switch bar 1166. The switch bar 1166 may have a shaft portion 1168 that is pivotally pinned to a crossbar portion 1014 of the frame assembly 1012. A portion of the shaft 1168 protrudes out through an opening in the handle case (not shown) and a switch button 1170 may be attached to the end of the shaft 1168 to enable the user to shift the shaft 1168 axially back and forth to reverse the transmission 1010 as will be further discussed below. Those of ordinary skill in the art will appreciate that the yoke arrangement 1160 enables the shaft spool 1110 to freely rotate relative to the yoke 1160 while enabling the yoke 1160 to shift the shaft spool 1110 axially on the splined shaft 1120.

As can be seen in FIG. 20, a shifter output gear 1180 is keyed or otherwise attached to the splined shaft 1120 for rotation therewith. The shifter output gear 1180 is arranged in meshing engagement with a first spool gear 1190 that is attached to the shaft 1200 of the first rotatable spool 1250. Attached to the other end of the first rotatable spool shaft 1200 is a first spool transfer gear 1220. The first spool transfer gear 1220 is in meshing engagement with a reversing gear 1230 which is meshing engagement with a second spool drive gear 1240 that is attached to the shaft 1252 of the second rotatable spool 1260. See FIG. 17. In various embodiments, the advance cable 1302 may be received on second (bottom) rotatable spool 1260 and the retraction cable 1330 may be received on the first rotatable spool 1250.

A method of operating the winch 1000 will now be described with reference to FIGS. 17-20. Turning to FIG. 20 first, in that Figure, the shaft spool 1110 is in the neutral position. Thus, actuation of the firing trigger 1004 will not result in any movement of the dynamic clamping member 150, knife 155 or sled 160. To fire the device (advance the dynamic clamping member 150, knife 155, and sled 160 from the proximal end of the elongate channel assembly 120 to the distal end of the elongate channel assembly 120), the clinician shifts the shifter button 1170 to the position shown in FIG. 18. In doing so, the primary gear teeth 1112 of the shaft spool 1110 are brought into meshing engagement with the first gear teeth 1102 of the first pinion gear 1100. After the shaft spool 1110 has been moved to that position, the clinician may begin to pull/pivot the firing trigger 1004 to cause the handle gear segment 1006 to move in the direction represented by arrow "A" in FIG. 18. As the firing trigger 1004 continues to pivot, the gear segment 1006 rotates the primary drive gear 1040 as well as the clutch assembly 1050 and the second drive gear 1070 in the "B" direction. As the second drive gear 1070 rotates in that direction, the third drive gear 1080 is rotated in the opposite "A" direction which also causes the first pinion gear 1100 to rotate in that direction. Because the first teeth 1102 of the first pinion gear 1100 are in meshing engagement with the primary teeth 1112 of the shaft spool 1110, the shaft spool 1110 also rotates in the "A" direction. As the shaft spool 1110 rotates in the "A" direction, the splined shaft 1120 and the shifter output gear 1180 also rotate in that direction. The shifter output gear 1180 is in meshing engagement with the first spool gear 1190 that is attached to the shaft 1200 of the first payout spool 1250. As the shifter output gear is rotated in the "A" direction, the first spool gear 1190 is rotated in the "B" direction. The first spool transfer gear 1220 is attached to the shaft 1200 and also rotates in the "B" direction. As the first spool 1250 rotates in the "B" direction, the retract cable 1330 is paid off of the first spool 1250. As the first spool rotates 1250, the first spool transfer gear 1220 rotates in the same direction. The first spool transfer gear 1220, reversing gear 1230, and second spool drive gear 1240 cause the second spool 1260 to wind up the advance cable 1302 thereon.

After the firing trigger 1004 has been depressed as far as it can go (to the end of its stroke), the clinician releases the firing trigger 1004 and a spring (not shown) or other suitable arrangement supported by the handle assembly 5 biases the firing trigger back 1004 to the starting (unfired position). As the firing trigger 1004 returns to the starting position, the first clutch plate 1052 rotates backwards ("A" direction) relative to the second clutch plate 1060 while the second clutch plate 1060 remains stationary and does not move. The user can then depress the firing trigger 1004 again until the dynamic clamping member 150, knife 155, and sled 160 have been completely advanced to the end distal position within the channel assembly 120 by the advance cable 1302.

To retract (move the knife assembly 170 in the proximal direction "PD" to a starting position) the dynamic clamping assembly 150, the knife 155, and the sled 160 (knife assembly 170), the clinician shifts the shifter button 1170 to bring the secondary gear teeth 1114 of the shaft spool 1110 into meshing engagement with the second gear teeth 1134 on the second pinion gear 1130. After the shaft spool 1110 has been moved to that position, the clinician may begin to pull/pivot the firing trigger 1004 in the manner described above. As the firing trigger 1004 continues to pivot, the gear segment 1006 rotates the primary drive gear 1040 as well as the clutch assembly 1050 and the second drive gear 1070 in the "B" direction. As the second drive gear 1070 rotates in that direction, the third drive gear 1080 is rotated in the opposite "A" direction which also causes the first pinion gear 1100 to rotate in that direction. As the first pinion gear 1100 rotates, it causes the reversing bevel gear 1140 to rotate and cause the second pinion gear 1130 to rotate in the "B" direction. Because the secondary teeth 1114 of the shaft spool 1110 are in meshing engagement with the second teeth 1134 of the second pinion gear 1130, the shaft spool 1110 and the splined shaft 1120 rotate in the "B" direction. The shift output gear 1180 causes the first spool transfer gear 1220 to rotate in the "A" direction. As the first spool transfer gear 1220 rotates in the "A" direction, the retract cable 1330 is wound onto the first spool 1250. As the first spool rotates 1250, the first spool transfer gear 1220 rotates in the same direction. The first spool transfer gear 1220, reversing gear 1230 and second spool drive gear 1240 cause the second spool 1260 to rotate to payout the advance cable 1302 therefrom.

After the firing trigger 1004 has been depressed as far as it can go (to the end of its stroke), the user releases the firing trigger 1004 and a spring (not shown) supported by the handle assembly 5 biases the firing trigger back 1004 to the staring (unfired position). As the firing trigger 1004 returns to the starting position, the first clutch plate 1052 rotates backwards relative to the second clutch plate 1060 while the second clutch plate 1060 remains stationary and does not move. The user can then depress the firing trigger 1004 again until the dynamic clamping member 150, knife 155, and sled 160 have been completely retracted into a starting position within the elongate channel assembly 120 by the retract cable 1330.

In an embodiment depicted in FIGS. 18 and 20, the first rotatable spool 1250 and the second rotatable spool 1260 are tapered. That is, they have a decreasing diameter along their respective axial directions. Thus, the winch assembly 1001 has the ability to change the mechanical advantage as it takes up cable. In this embodiment, the advance cable 1302 is attached to spool 1260 and the retract cable 1330 is attached to spool 1250 such that the greatest take up force is generated at the beginning of the firing process. If the winch assembly 1001 is turned at a constant torque, cable is taken up on the spool and the change in the spool's diameter would change the force transmitted to the cable. Such arrangement is particularly advantageous when the largest frictional or resistive forces that must be overcome during the firing process occur at the beginning of the firing sequence. If, however, the largest frictional and resistive forces are expected to be encountered toward the end of the firing process, the cables 1302, 1330 could be attached to the other ends (the smaller ends) of their respective spools 1260, 1250. In still other embodiments, if the largest resistive and friction forces are encountered midway during the firing process, each of the spools 1250, 1260 may have a central portion that has a larger diameter than the diameters of the end portions of the spools. Such unique and novel spool configurations, along with the unique and novel pulley arrangements describe above, enable the device to be designed to address different frictional and resistive forces encountered during the firing sequence and represent a vast improvement over prior cable related drive systems employed in connection with surgical stapling instruments.

While the cable drive system 1000 described above comprises a manually actuatable drive system, other contemplated embodiments of the present invention may employ a battery powered motor or motors, alternating current powered motor or motors or pneumatically powered motors to power the cable drive systems. Thus, the protection afforded to the various embodiments of the present invention should not solely be limited to surgical instruments that are manually actuatable.

Figure 21:
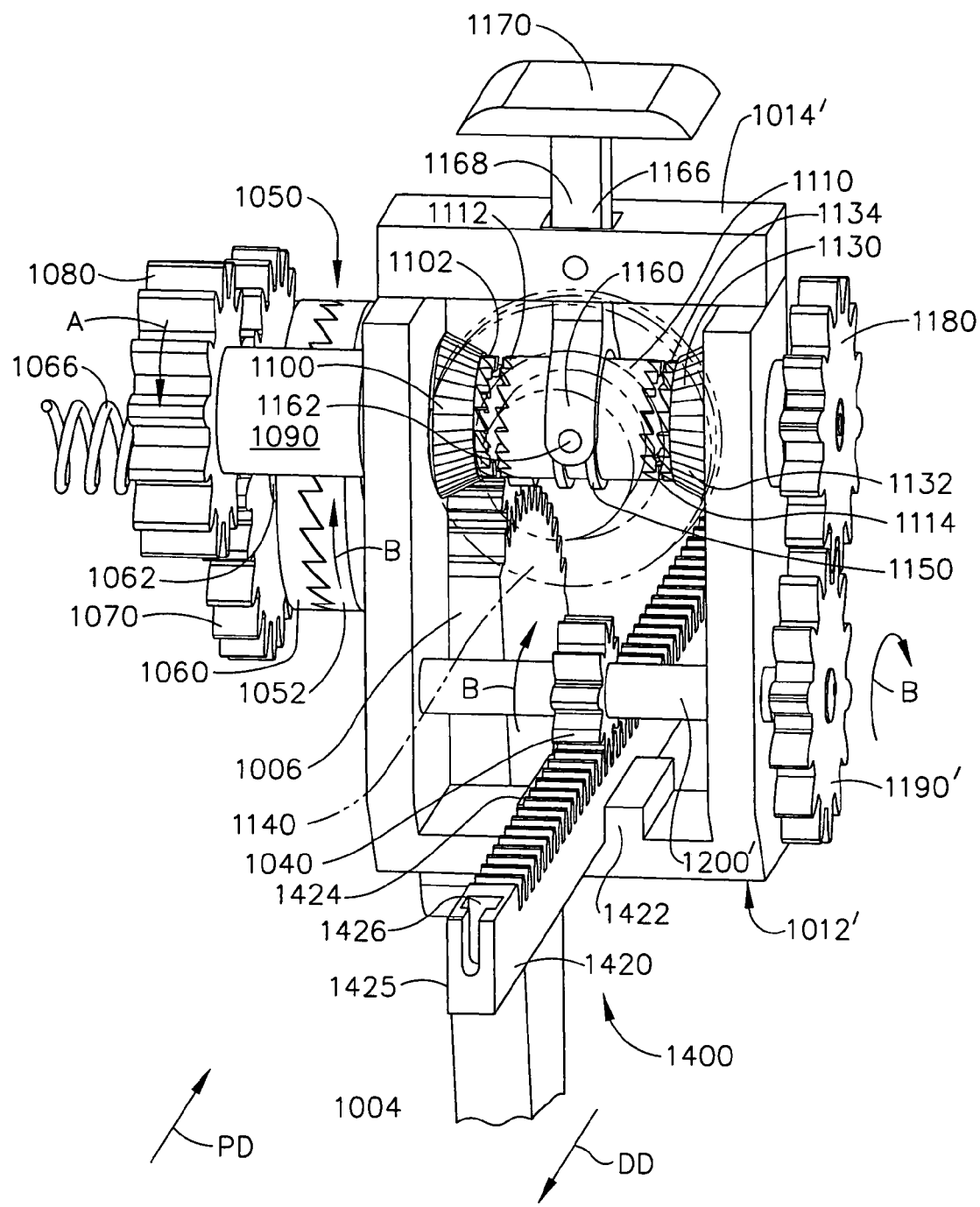
FIG. 21 is a perspective view of a drive system embodiment of the present invention.

FIGS. 15A, 16A, and 21 illustrate another improved firing system embodiment 1300' of the present invention. As can be seen in FIGS. 15A and 16A, this embodiment employs a pair of advance cables 1310', 1320' and a retract cable 1330. FIGS. 15A and 16A, illustrate the cables 1310', 1320', and 1330 in diagrammatic form. As can be seen in those Figures, a first advance cable 1310' is operably supported on a first distal cable transition support 1340 which may comprise, for example, a pulley, rod, capstan, etc. that is attached to the distal end 123 of the elongate channel assembly 120 as was described above and a first proximal cable transition support 1350 which may comprise, for example, a pulley, rod, capstan, etc. 1350 that is operably supported by the elongate channel assembly 120. A distal end 1312' of the first advance cable 1310' is affixed to the knife assembly 170 (dynamic clamping assembly 150) and the proximal end 1314' of the first advance cable 1310' is attached to a connector 1380 attached to a reciprocatable drive member 1390. As can be seen in FIGS. 15A and 16A, the first distal cable transition support 1340 may be oriented such that its axis of rotation is substantially perpendicular to the axis of rotation of the first proximal cable transition support 1350. The second advance cable 1320' is operably supported on a second distal cable transition support 1360 which may, for example, comprise a pulley, rod, capstan etc. that is mounted to the distal end 123 of the elongate channel assembly 120 and a second proximal cable transition support 1370 which may, for example, comprise a pulley, rod, capstan, etc. mounted to the proximal end of the elongate channel assembly 120. The proximal end 1322' of the second advance cable 1320 may be attached to the knife assembly 170 (dynamic clamping assembly 150) and the proximal end 1324' may be attached to the connector 1380'. Also in these embodiments, a retract cable 1330 is employed. In one embodiment, the retract cable 1300 may be formed in a loop such that the distal looped end 1332 is fixedly attached (swaged, etc.) to the dynamic clamping assembly 150 and the two proximal ends 1334, 1336 are each fixedly attached (swaged, etc.) to the connector 1380.

Those of ordinary skill in the art will understand that the dynamic clamping assembly 150, knife 155, and sled 160 may be advanced in the distal direction ("DD") when the drive rod 1390 is also advanced in the distal direction "DD". To retract the knife in the proximal direction "PD", the drive rod 1390 is moved in the proximal direction "PD". In various embodiments, the drive rod 1390 may be selectively advanced and retracted by a drive system 1400 that is somewhat similar in operation as to the operation of the winch assembly 1001, except for the differences discussed below. In particular, as can be seen in FIG. 21, a handle gear segment 1006 may be formed or otherwise provided on the firing trigger (not shown). The handle gear segment 1006 may be mounted in meshing engagement with a primary drive gear 1040 that is mounted to a shaft (not shown) attached to a first ratchet clutch plate 1052 of a clutch assembly 1050. A second ratchet clutch plate 1060 is supported on a clutch shaft 1062 that is rotatably supported within the handle assembly 5. The clutch shaft 1062 may be provided with a shoulder portion (not shown) and have a clutch spring 1066 journaled thereon to bias the second ratchet clutch plate 1060 into meshing engagement with the first ratchet clutch plate 1050.

A second drive gear 1070 may be journaled on the clutch shaft 1062 and is in meshing engagement with a third drive gear 1080 that is attached to a first transmission shaft 1090 that is rotatably supported by a first transmission bearing or sleeve (not shown) mounted in the frame assembly 1012'. The first transmission shaft 1090 has a first pinion gear portion 1100 and a series of first gear teeth 1102 formed thereon for selective meshing engagement with a series of primary gear teeth 1112 on a an axially and rotatably movable shaft spool 1110. The shaft spool 1110 is received on a splined shaft (not shown) 1120 that is rotatably received within the first transmission shaft 1090 and a second pinion gear 1130. The second pinion gear 1130 has a second pinion gear portion 1132 and a series of second gear teeth 1134 for selective meshing engagement with secondary gear teeth 1114 on the shaft spool 1110. The second pinion gear 1130 may be rotatably supported by a second bearing (not shown) mounted in the frame assembly 1012' as shown.

A reversing bevel gear 1140 is supported by the frame assembly 1012' in meshing engagement with the first and second pinion gears 1100, 1130, respectively. The shaft spool 1110 has a collar portion 1150 formed thereon for receiving two opposing pins 1162 extending from a yoke 1160 formed on a bottom portion of a switch bar 1166. The switch bar 1166 has a shaft portion 1168 that is pivotally pinned to a crossbar portion 1014' of the frame assembly 1012'. A portion of the shaft 1168 protrudes out through an opening in the handle case (not shown) and a switch button 1170 may be attached to the end of the shaft 1168 to enable the user to shift the shaft 1168 axially back and forth to reverse the drive 1400 as will be further discussed below. Those of ordinary skill in the art will appreciate that the yoke arrangement 1160 enables the shaft spool 1110 to freely rotate relative to the yoke 1160 while enabling the yoke 1160 to shift the shaft spool 1110 axially on the splined shaft 1120.

A shifter output gear 1180 is keyed or otherwise attached to the splined shaft 20 for rotation therewith. The shifter output gear 1180 is arranged in meshing engagement with a drive gear 1190' that is attached to a drive shaft 1200'. Attached to the drive shaft 1200' is a drive gear 1410 that is in meshing engagement with a rack 1420 that is constrained to move axially in the distal and proximal directions between two lugs 1422, 1424 formed in the frame 1012'. To affix the proximal end of the drive rod 1390 to the rack 1420, a T-slot 1426 may be formed in the distal end 1425 of the rack 1420. However, other methods of attachment may also be employed.

A method of operating the drive system 1400 will now be described. As can be seen in FIG. 21, the shaft spool 1110 is in the neutral position. Thus, actuation of the firing trigger 1004 will not result in any movement of the dynamic clamping member 150, knife 155 or sled 160. To fire the device (advance the dynamical clamping member 150, knife 155, and sled 160 in the distal direction DD), the clinician shifts the shifter button 1170 such that the first gear teeth 1102 of the first pinion gear 1100 are brought into meshing engagement with the primary gear teeth 1112 of the shaft spool 1110. After the shaft spool 1110 has been moved to that position, the clinician may begin to pull/pivot the firing trigger 1004 to cause the handle gear segment 1006 to move. As the firing trigger 1004 continues to pivot, the gear segment 1006 rotates the primary drive gear of the clutch assembly 1050 and the second drive gear 1070. As the second drive gear 1070 rotates in one direction, the third drive gear 1080 is rotated in the opposite direction which also causes the first pinion gear 1100 to rotate in that direction. Because the first teeth 1102 of the first pinion gear 1100 are in meshing engagement with the primary teeth 1112 of the shaft spool 1110, the shaft spool 1110 also rotates in that direction. As the shaft spool 1110 rotates in that direction, the splined shaft and the shifter output gear 1180 also rotate in that direction. The shifter output gear 1180 causes the drive gear 1190', drive shaft 1200', and drive gear 1410 to rotate in the "B" direction thereby driving the rack in the distal direction DD.

After the firing trigger 1004 has been depressed as far as it can go (to the end of its stroke), the clinician releases the firing trigger 1004 and a spring (not shown) or other suitable arrangement supported by the handle assembly 5 biases the firing trigger back 1004 to the staring (unfired position). As the firing trigger 1004 returns to the starting position, the first clutch plate 1052 rotates backwards (A direction) relative to the second clutch plate 1060 while the second clutch plate 1060 remains stationary and does not move. The clinician can then depress the firing trigger 1004 again until the knife assembly 170 (dynamic clamping member 150, knife 155, and sled 160) have been completely advanced to the end distal position within the elongate channel assembly 120 by the rack 1420 and the drive rod 1390.

To retract (move in the proximal direction "PD" to a starting position) the dynamic clamping assembly 150, the knife 155, and the sled 160, the clinician shifts the shifter button 1170 to bring the secondary gear teeth 1114 of the shaft spool 1110 into meshing engagement with the second gear teeth 1134 on the second pinion gear 1130. After the shaft spool 1110 has been moved to that position, the clinician may begin to pull/pivot the firing trigger 1004 in the manner described above. As the firing trigger 1004 continues to pivot, the gear segment 1006 rotates the primary drive gear 1040 as well as the clutch assembly 1050 and the second drive gear 1070 in the "B" direction. As the second drive gear 1070 rotates in that direction, the third drive gear 1080 is rotated in the opposite "A" direction which also causes the first pinion gear 1100 to rotate in that direction. As the first pinion gear 1100 rotates, it causes the reversing bevel gear 1140 to rotate and cause the second pinion gear 1130 to rotate in the "B" direction. Because the secondary teeth 1114 of the shaft spool 1110 are in meshing engagement with the second teeth 1134 of the second pinion gear 1130, the shaft spool 1110 and the splined shaft 1120 rotate in the "B" direction. The shift output gear 1180 causes the drive gear 1190', drive shaft 1200', and drive gear 1410 to rotate in the "A" direction which causes the rack 1424 to move in the proximal direction "PD".

After the firing trigger 1004 has been depressed as far as it can go (to the end of its stroke), the user releases the firing trigger 1004 and a spring (not shown) supported by the handle assembly 5 biases the firing trigger 1004 back to the starting (unfired) position. As the firing trigger 1004 returns to the starting position, the first clutch plate 1052 rotates backwards (A direction) relative to the second clutch plate 1060 while the second clutch plate 1060 remains stationary and does not move. The user can then depress the firing trigger 1004 again until the dynamic clamping member 150, knife 155, and sled 160 have been completely retracted into a starting position within the elongate channel assembly 120 by the drive rod 1390 and the rack 1424. Those of ordinary skill in the art will understand that changes in the gear ratios—either in the transmission or rack and pinion could be used to attain improved mechanical advantages for driving the knife assembly 170 (dynamic clamping assembly 150, knife 155, sled 160) within the elongate channel assembly 120.

While the cable drive system 1400 described above comprises a manually actuatable drive system, other contemplated embodiments of the present invention may employ a battery powered motor or motors, alternating current powered motor or motors or pneumatically powered motors to power the cable drive system. Thus, the protection afforded to the various embodiments of the present invention should not solely be limited to surgical instruments that are manually actuatable.

FIGS. 22-24 illustrate a portion of another surgical stapling instrument 1500 that may employ certain features of the present invention. This embodiment employs a hollow spine or tube 1510 that extends from the handle (not shown) to the channel assembly (not shown). In the embodiment depicted in FIGS. 22-24, the hollow spine 1510 is coupled to an articulation joint 1512 of the type and construction disclosed in U.S. Patent Publication No. US 2005/0006432 to Racenet et al., the disclosure of which is herein incorporated by reference. Other articulation joint arrangements could also be employed without departing from the spirit and scope of the present invention. As can be seen in FIGS. 22-24, a drive rod 1520 extends through the hollow tube 1510 and has a proximal end 1522 that may be coupled to the rack of a drive arrangement of the type described above and supported by the handle. A transition block 1530 may be attached to or otherwise formed on the distal end 1524 of the drive rod 1520 for attachment to a driven rod 1540. A proximal pulley, rod, capstan, etc. 1560 is mounted within the hollow tube 1510 as shown in FIGS. 22 and 24.

A cable, thread, band, belt, etc. 1570 may be operably supported on one or more pulleys, rods, capstans, etc. (not shown) formed on the channel assembly (not shown) and extend through the articulation joint 1512 and operably supported on the distal pulley 1560 as shown in FIGS. 22-24. The cable 1570 may have an advance portion 1572 and a retract portion 1574. The end 1576 of the retract portion 1574 may be fixedly attached to the distal end 1542 of the driven rod 1540 as shown in FIG. 22. Likewise, the other end 1578 of cable 1570 is attached to the distal end 1542 of the driven rod 1540. FIG. 22 illustrates the position of the driven rod 1540 when the dynamic clamping assembly (not shown), knife (not shown), and sled (not shown) are at the distal end of the elongate channel assembly (not shown). The dynamic clamping assembly, knife, and sled may be moved to a retracted position by operating the drive system described above (FIG. 21) in the retract mode described above which will cause the drive rod 1520 and the driven rod 1540 to move in the proximal direction "PD". The person of ordinary skill in the art will understand that such arrangement represents a vast improvement in mechanical advantage over prior cable arrangements. It will be further appreciated that the cable 1570 may flex as the instrument is articulated. In other embodiments, however, the ends of the cable may be coupled together with a spring coupling arrangement of the type described in further detail below.

As was mentioned above, one problem that may be encountered when using a cable driven surgical cutting and severing instrument is that the cable or cables may become disengaged from a cable transition support or supports such as pulleys, rods, capstans, etc. or the like which could disable the device. Such cable disengagement may, for example, be caused by mechanical vibration during use of the device or may result from shock to the device experienced during use or shipping. FIGS. 25-27 illustrate other embodiments of the present invention that employ cable stop members 1600 which may, for example, comprise cable retention blocks 1601 on the elongate channel assembly 120 that are in close proximity to the cable transition supports 830, 850 to retain the cables 800, 820 thereon, respectively. In various embodiments, the cable transition supports 830, 850 may comprise, for example, pulleys, rods, capstans, etc. Although the cable retention blocks 1610 may be provided in various shapes and configurations, in various embodiments, each cable retention block 1601 may have an arcuate surface 1602 that is complementary-shaped relative to the cable 800, 820, such that the cable 800, 820 cannot become disengaged from the cable transition support 800, 820.

Figure 28:
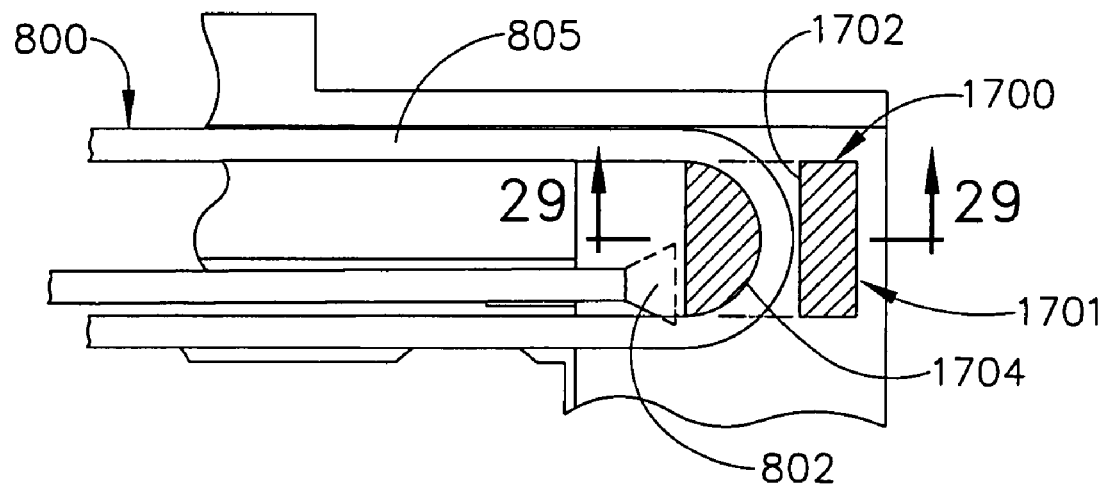
FIG. 28 is a portion of a bottom view of a distal end of another elongate channel assembly embodiment of the present invention with some components shown in cross-section.
Figure 29:
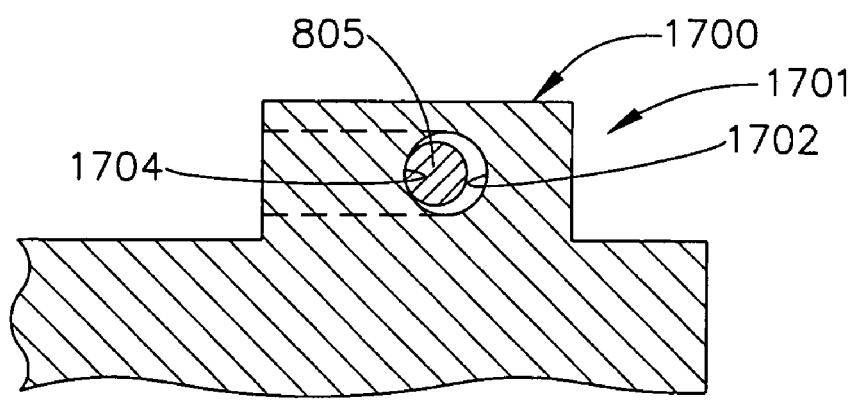
FIG. 29 is a cross-sectional view of the portion of the elongate channel assembly depicted in FIG. 28 taken along line 29-29 in FIG. 28.
Figure 30:
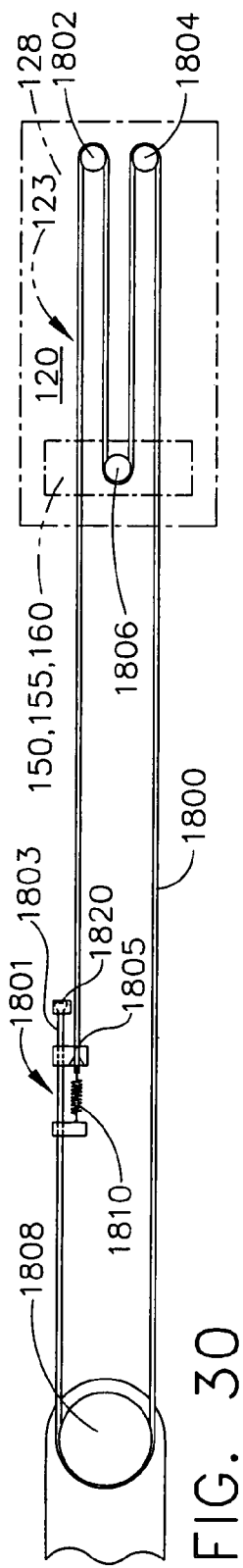
FIG. 30 is a diagrammatical top view of another cable arrangement that employs a cable tensioning joint of various embodiments of the present invention.
Figure 31:
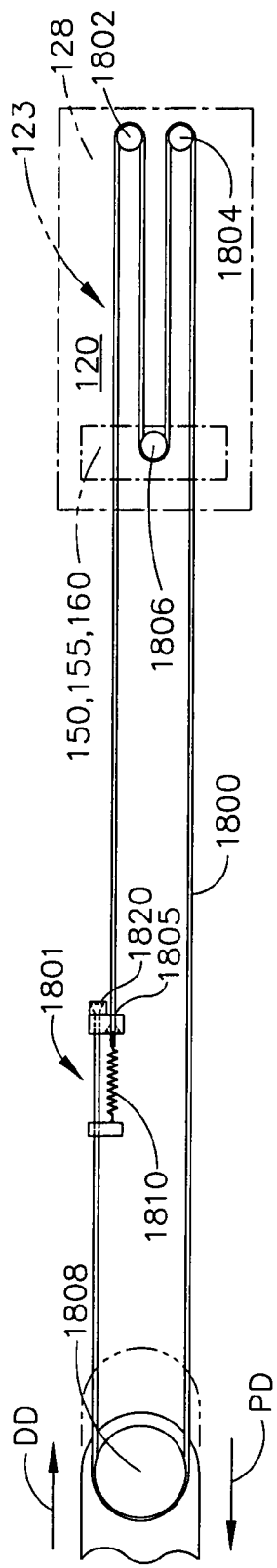
FIG. 31 is another diagrammatical top view of the cable arrangement of FIG. 30 with the cable tensioning joint in a fully expanded position.
Figure 32:
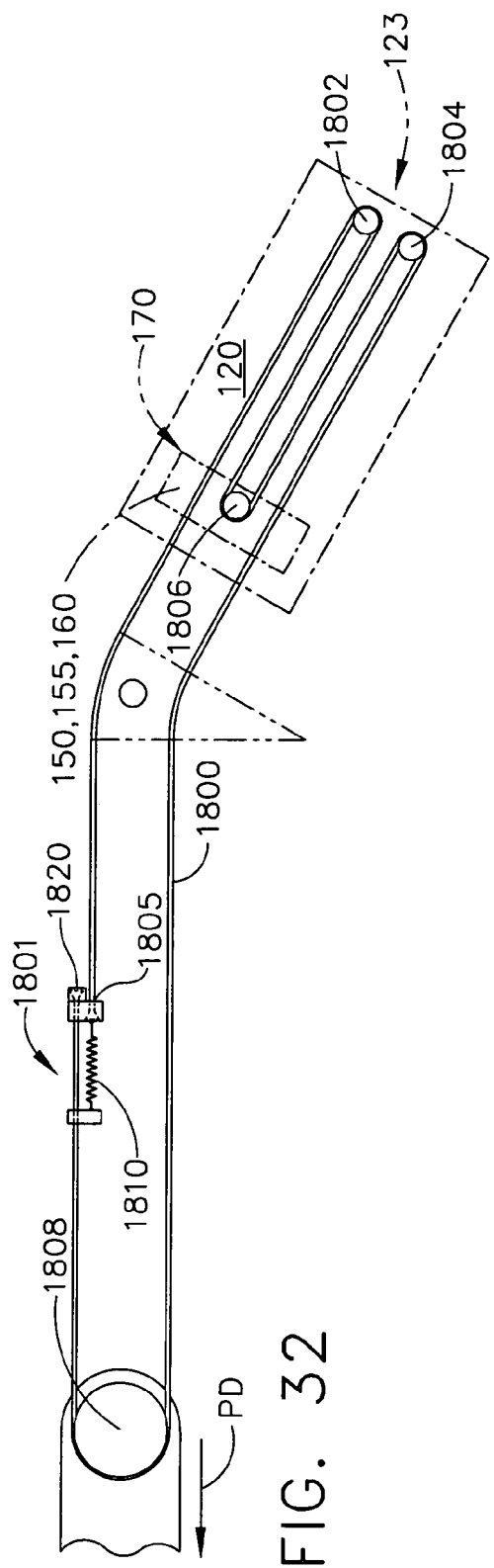
FIG. 32 is another diagrammatical top view of the cable arrangement of FIGS. 30 and 31 in an articulated position.

FIGS. 28 and 29 illustrate another cable stop member 1700 which may, for example, comprise a cable retention block 1701 of other embodiments of the present invention. As can be seen in those Figures, the block 1701 has a passage 1702 therethrough that forms an arcuate bearing surface 1704 over which the cable 800, 820 may pass. In this embodiment, the cable may be threaded into and through the arcuate passage 1702 during installation. Such arrangement avoids the problem of the cable becoming dislodged from a pulley or pulleys, rods, capstans, etc.

FIGS. 30-33 illustrate another embodiment of the present invention in diagrammatic form. This embodiment employs an elongate channel assembly 120 that has a dynamic clamping assembly 150, knife 155, and sled assembly 160 (collectively referred to herein as "knife assembly 170") that is driven by a cable 1800. In particular, the cable 1800 may be operably supported on a pair of cable transition supports 1802, 1804, which may comprise, for example, pulleys, posts, capstans, etc. mounted to the bottom 128 of the distal end 123 of the elongate channel assembly 120 and a third cable transition support 1806 which may comprise, for example, a pulley, post, capstan, etc. on the knife assembly 170. In addition, the cable 1800 may be operably supported on a drive pulley 1808 that is movably supported by the handle assembly 5. The drive pulley 1808 may be selectively movable in the distal direction "DD" and the proximal direction "PD" by a trigger (not shown) or other actuator arrangement (not shown) in the handle assembly 5.

Figure 33:
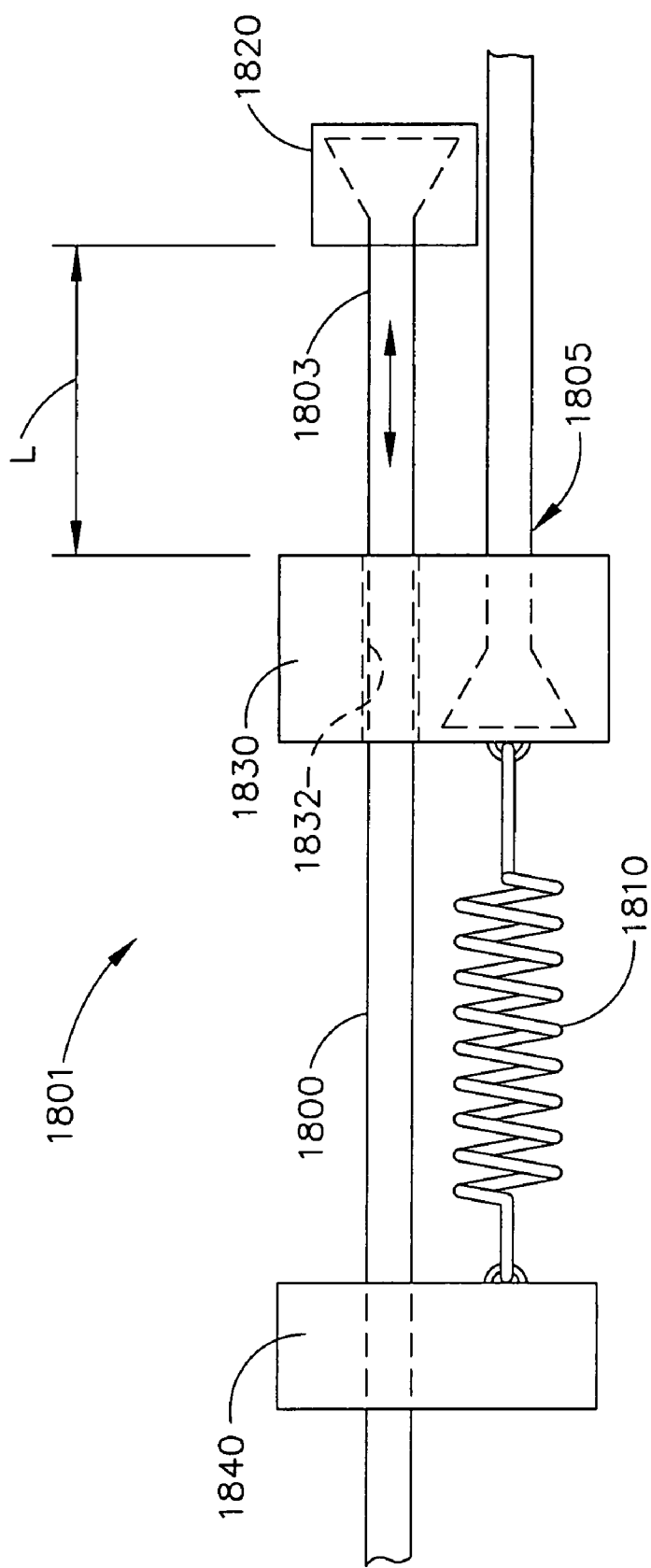
FIG. 33 is an enlarged partial view of the cable tensioning joint depicted in FIGS. 30-32.

Other embodiments of the present invention as illustrated in FIGS. 30-33, employ a unique and novel cable tensioning joint 1801 for connecting the ends of the cable 1800 to maintain the tension in the cable 1800 to prevent the cable 1800 from shifting off the pulleys 1802, 1804, 1806, 1808. In particular, this arrangement employs a tensioning member in the form of a spring 1810 that is oriented in a substantially parallel path to the cable load path. As can be seen in those Figures, a first stop member or block 1820 is fixedly attached (swaged, glued, welded, etc.) to a first end 1803 of the cable 1800. The second end 1805 of the cable 1800 is also fixedly attached (swaged, welded, glued, etc.) to a second stop member or block 1830. As can be seen in FIG. 33, the second stop member 1830 has a passage 1832 therethrough through which a portion of the cable 1800 may slidably pass as represented by the arrow in that Figure. A third stop member or block 1840 is fixedly attached to the cable 1800 and an end of the spring 1810 is attached thereto. The other end of the spring 1810 is attached to the second stop member 1830. Those of ordinary skill in the art will understand that such arrangement permits the cable 1800, when operably supported on cable transition supports in the form of, for example, pulleys, capstans, retention blocks etc., to lengthen a distance "L" (the distance between the first and second stop members 1820, 1830) when the tension spring 1810 is unexpanded. It will be further appreciated that such arrangement is particularly advantageous when an articulated instrument is employed as demonstrated in FIG. 32. In particular, use of the cable tensioning joint 1801 enables the cable to extend or bend around the articulation joint while remaining taught about the various cable transition supports.

Figure 34:
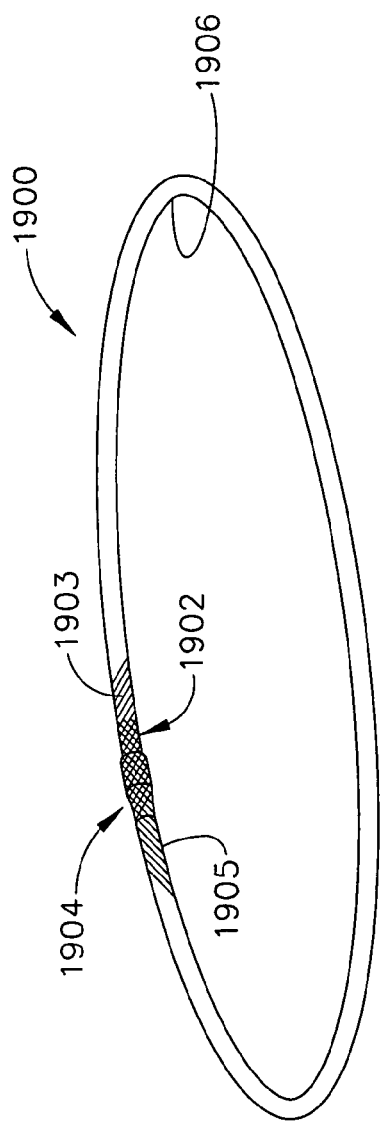
FIG. 34 is a perspective view of a cable embodiment of the present invention.
Figure 35:
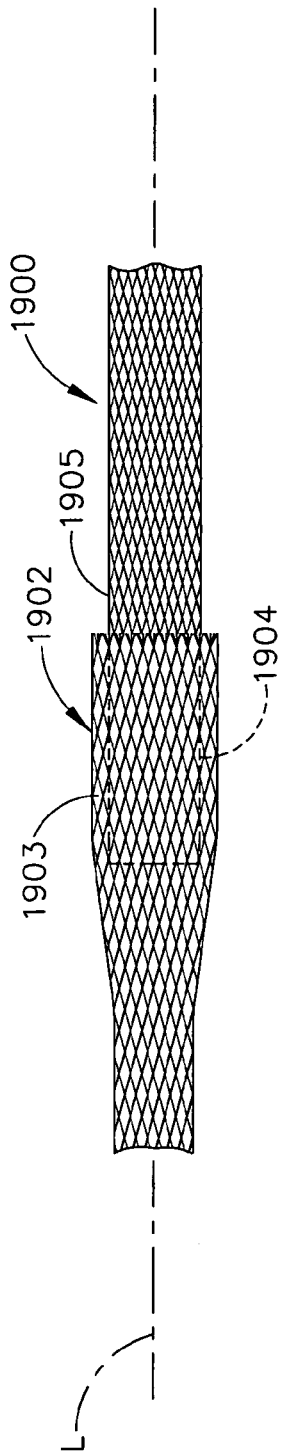
FIG. 35 is an enlarged view of a cable attachment joint embodiment of the present invention.

As indicated above, another challenge commonly encountered when employing cable driven systems relates to connecting the ends of the cable (drive member) in such a manner as to ensure that the cable effectively transmits the desired force to the knife/dynamic clamping member or other surgical instrument component. FIGS. 34 and 35 illustrate an endless cable 1900 of various embodiments of the present invention. In this embodiment, for example, the endless cable 1900 may comprise a woven metal wire or woven plastic member. To form the endless cable, the fibers 1903 of the end 1902 may be interwoven with the fibers 1905 of the end 1904 to form a cable loop. Another embodiment is a Chinese finger cuff (FIG. 35) approach wherein one end is inserted into the other end of a hollow woven cable to form a connection that gets tighter with tension. In various embodiments, some fastening agent/adhesive may be employed during assembly to facilitate such pretentioning of the joint. Such arrangement, for example, may permit the cable 1900 to somewhat constrict about its longitudinal axis "L-L" when tension is applied in the longitudinal direction. One example of such weave pattern is disclosed in U.S. Pat. No. 4,817,643 to Olsen, the disclosure of which is herein incorporated by reference. After the ends 1902, 1904 are braded together as shown, the cable 1900 forms a closed loop 1906. The cable may be looped around a driven pulley or other member and a portion of a movable member such as pins, pulleys, capstans or other portions of the surgical instrument components when the ends 1902, 1904 are braided or interwoven together.

Figure 36:
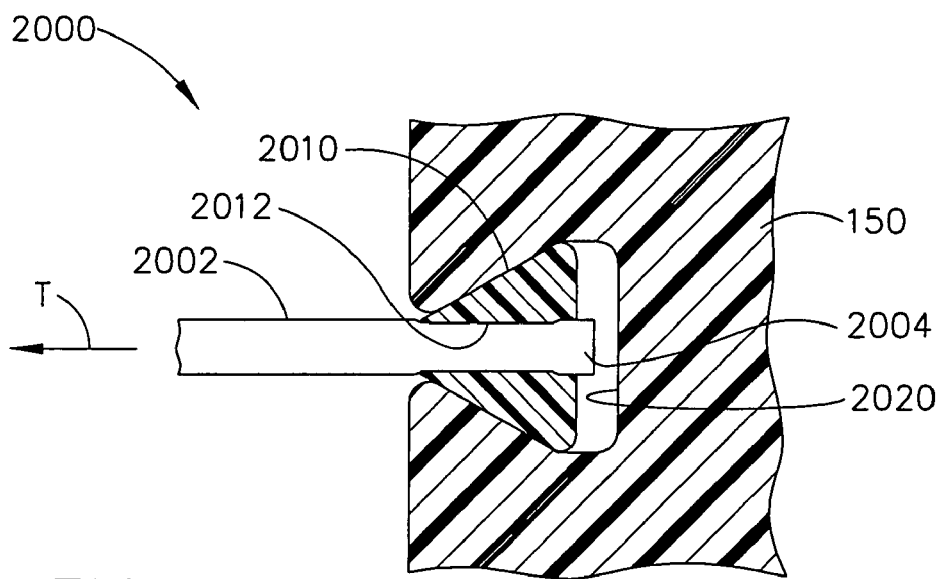
FIG. 36 is a cross-sectional view of a cable anchor joint embodiment of the present invention attached to a dynamic clamping assembly.
Figure 37:
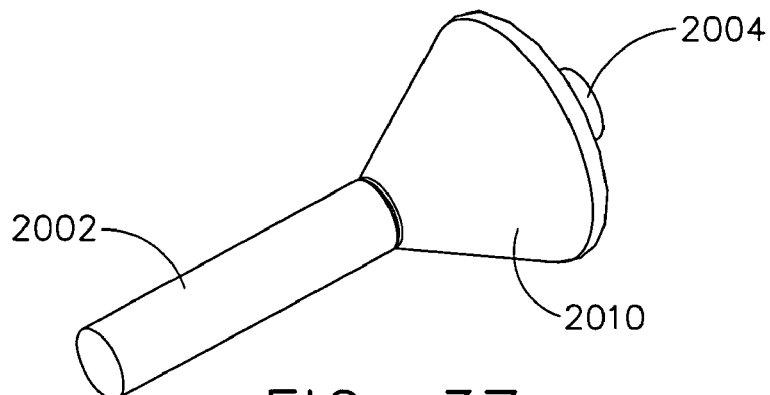
FIG. 37 is a perspective view of the cable anchor joint of FIG. 36.
Figure 38:
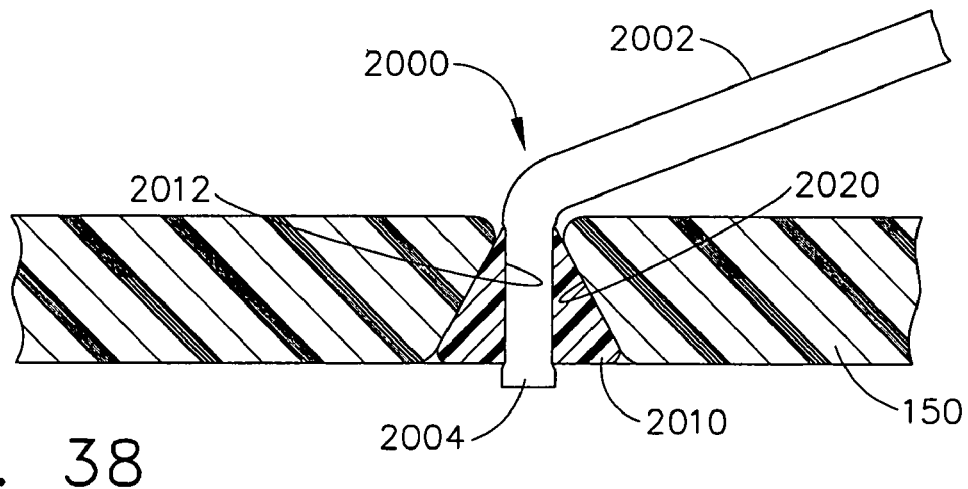
FIG. 38 is a cross-sectional view of another cable anchor joint embodiment of the present invention attached to a dynamic clamping assembly.

FIGS. 36-38 illustrate another cable attachment arrangement 2000 of the present invention for attaching a cable to a surgical instrument component. As can be seen in those Figures, the cable 2002 may have a substantially wedge-shaped or substantially conically shaped slug 2010 that has a hole 2012 extending therethrough for receiving an end 2004 of the cable 2002 as shown in FIG. 36. The slug 2010 may be crimped, swaged, glued, overmolded, ultrasonically welded, etc. onto the cable end 2012 as shown. In various embodiments, for example, the slug 2010 may be fabricated from a somewhat soft material such as lead, copper, brass, stainless steel, titanium, etc. or, for example, a thermoplastic material such as nylon or polycarbonate. The slug 2010 is sized to be received in a complementary shaped pocket 2020 in surgical instrument component to which it is to be attached such as, for example, the dynamic clamping member 150. The pocket 2020 may be sized such that, as tension is applied to the cable 2002 in the "T" direction, the connection gets tighter. That is, as the cable tension increases, the slug 2020 is further compressed on the end 2004 of the cable 2002. In various embodiments, the pocket 2020 may be open on at least one side thereof to permit the slug 2010 to be installed therein.

Figure 39:
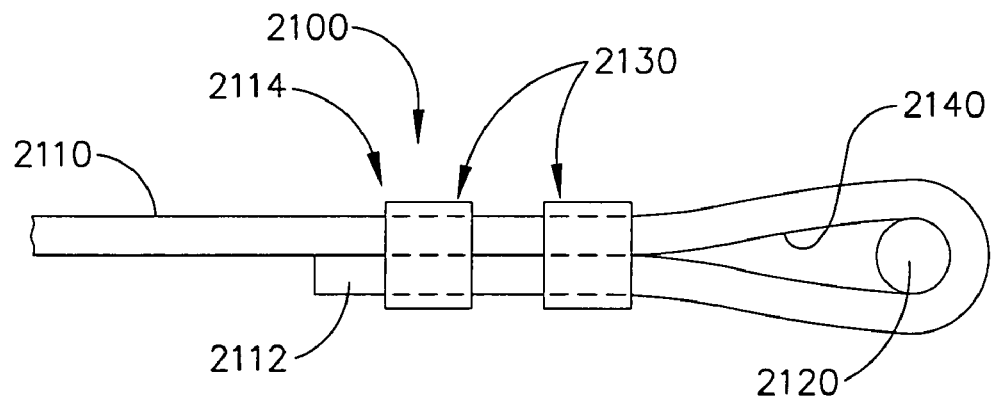
FIG. 39 is a partial view of another cable attachment embodiment of the present invention.

FIG. 39 illustrates another cable attachment arrangement 2100 of various embodiments of the present invention. As can be seen in that Figure, the end 2112 of the cable 2110 may be wrapped around a pin 2120 and be attached to the other portion 2114 of the cable 2110 by one or more clamps 2130 that may be crimped or otherwise cinched thereon to form a loop 2140 for receiving at least a portion of the surgical instrument component such as, for example, a pulley, pin, capstan, etc.

Figure 40:
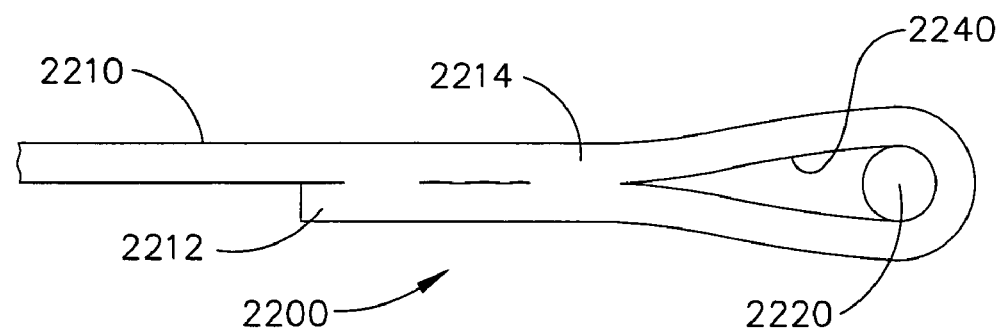
FIG. 40 is a partial view of another cable attachment embodiment of the present invention.

FIG. 40 illustrates another cable attachment arrangement 2200 of various embodiments of the present invention. As can be seen in that Figure, the end portion 2212 of the cable 2210 may be wrapped around a pin 2220 and be melted or glued to another adjacent portion 2214 of the cable 2210 to form a loop 2240 for receiving at least a portion of the surgical instrument component such as, for example, a pulley, pin, capstan, etc.

The endocutter disclosed in U.S. Patent Publication No. US2006/0011699 A1 employs two cable systems: one for closing the anvil; and one that pulls the dynamic clamping assembly, knife, and sled to cut tissue and form staples. In one arrangement, a cable is attached to the clamping collar for pulling the clamping collar distally onto and over cam surface to close the anvil relative to the staple cartridge assembly and compress the tissue. That closure cable must be threaded back through the articulation joint to the handle. When the proximal end of that cable is pulled, the distal end of the cable, which is attached to the clamping collar, causes the clamping collar to move distally and close the anvil. Such arrangement, however, suffers from the limited ability to generate clamping force.

Figure 41:
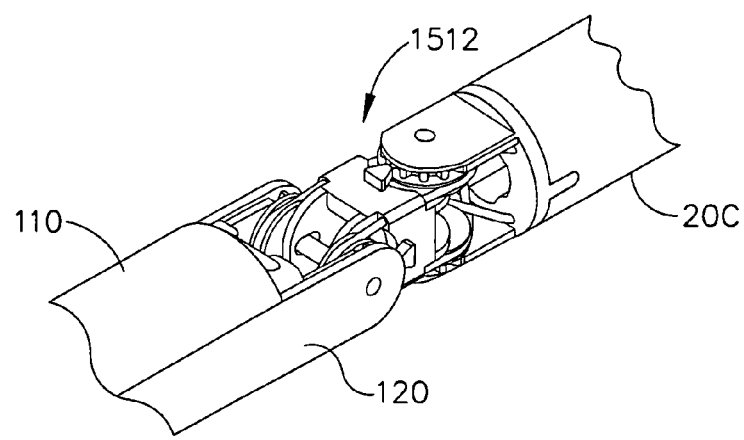
FIG. 41 is a partial perspective view of an articulation joint arrangement.
Figure 42:
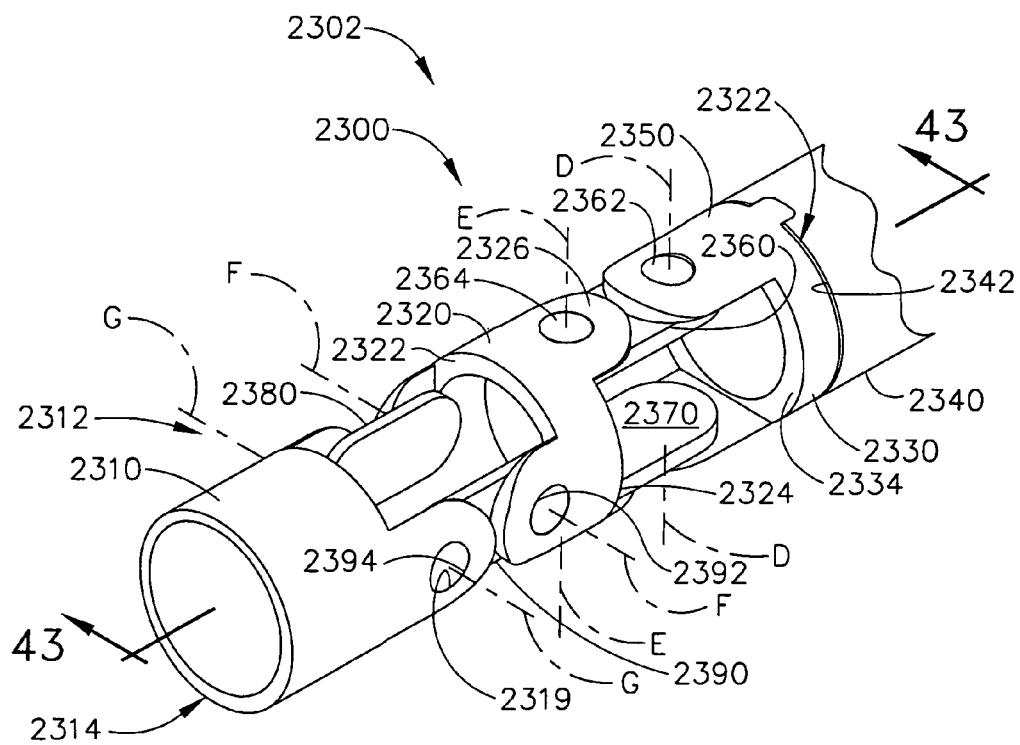
FIG. 42 is a perspective view of a closure tube joint assembly embodiment of the present invention.
Figure 43:
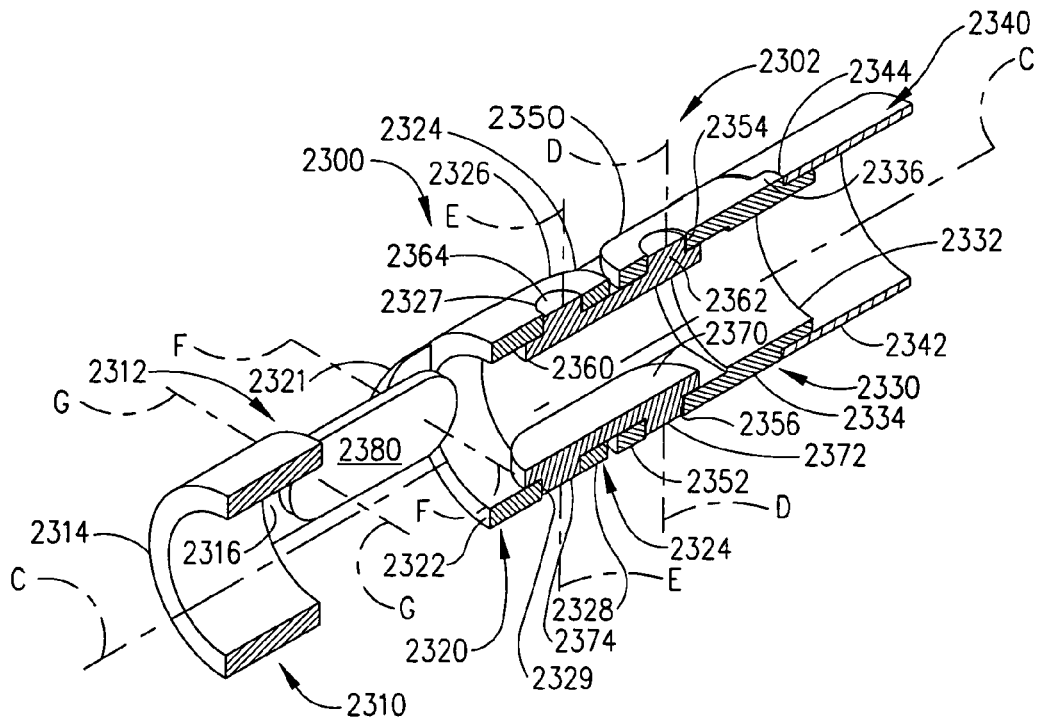
FIG. 43 is a cross-sectional view of the closure tube joint assembly embodiment of FIG. 42 taken along line 43-43.
Figure 44:
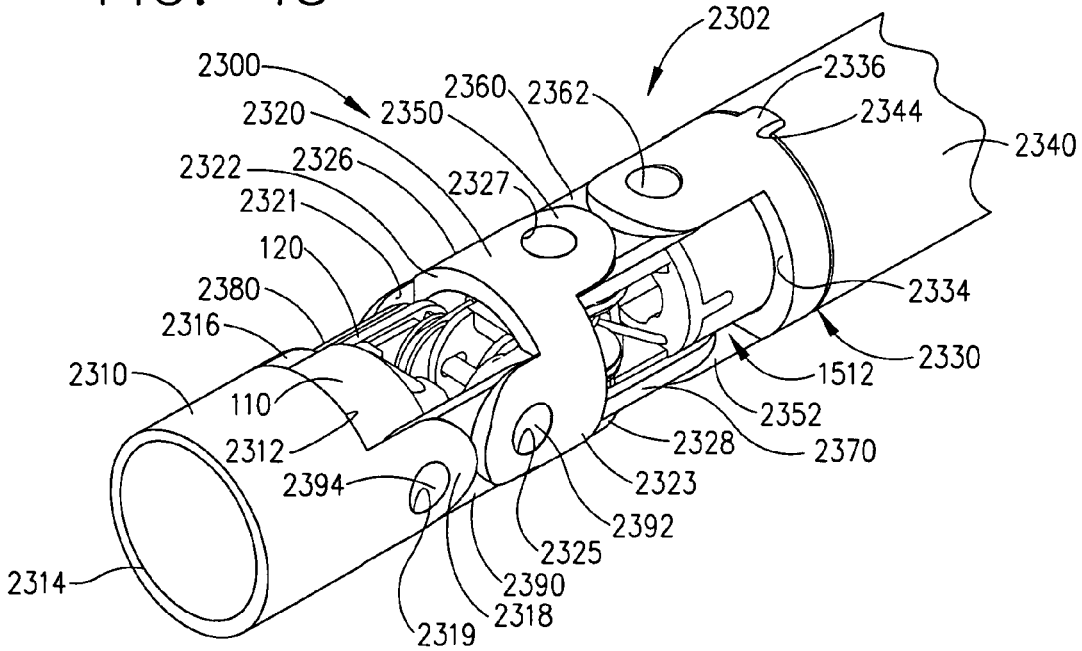
FIG. 44 is a perspective view of the closure tube joint assembly of FIGS. 42 and 43 installed over the articulation joint depicted in FIG. 41.

FIG. 41 illustrates an articulation joint 1512 of the type disclosed in the above-mentioned publication. FIGS. 42 and 43 illustrate the articulation joint assembly 2302 of a closure tube assembly 2300 of various embodiments of the present invention that may be used in connection with the articulation joint 1512 and eliminate the use of a cable to close the anvil 110. FIG. 44 illustrates the closure tube assembly 2300 installed over the articulation joint 1512. As will be discussed in further detail below, in various embodiments, the closure tube assembly 2300 is operably supported adjacent the elongate channel assembly 120 for selectively applying a closing motion to the anvil assembly 110 upon closing contact with the closure tube assembly 2300.

As can be seen in FIG. 42, an embodiment of the closure tube assembly 2300 may include a distal closure tube segment 2310 that has proximal end 2312 and a distal end 2314, a central closure tube segment 2320 that has a distal end 2322 and a proximal end 2324, and a proximal closure tube segment 2330 that has a proximal end 2332 and a distal end 2334. The proximal end 2332 of the proximal closure tube segment 2330 may be non-rotatably coupled to a distal end 2342 of a closure tube segment 2340. As can be seen in FIG. 43, the distal end 2342 of the hollow closure tube segment 2340 may be provided with a notch 2344 therein for receiving a tab 2336 protruding proximally from the distal end 2334 of the proximal closure tube segment 2330. As can also be seen in FIG. 43, the proximal end 2332 may be received within the hollow distal end 2342 of the hollow closure tube segment 2340. The proximal closure tube segment 2330 may be retained in coupling engagement with the closure tube segment 2340 by adhesive, glue, etc. Those of ordinary skill in the art will understand that such unique and novel configuration helps to facilitate assembly of the device. However, in other embodiments for example, the proximal closure tube segment 2330 may be integrally formed with the closure tube segment 2340.

In various embodiments, the closure tube assembly 2300 may further comprise a first upper tab 2350 protruding from the distal end 2334 of the proximal closure tube segment 2330 and a first lower tab 2352 protruding from the distal end 2334 of the proximal closure tube segment 2330 in spaced relation to the first upper tab 2350. The first upper tab 2350 has a first upper pivot hole 2354 therethrough and the first lower tab 2352 has a first lower pivot hole 2356 therethrough that is coaxially aligned with the first upper hole 2354 in various embodiments. The proximal end 2324 of the central closure tube segment 2320 has a second upper tab 2326 protruding therefrom and a second lower tab 2328 protruding therefrom in spaced relation to the second upper tab 2326. The second upper tab 2326 has a second upper pivot hole 2327 therethrough and the second lower tab 2328 has a second lower pivot hole 2329 therethrough that is substantially coaxially aligned with the second upper pivot hole 2327.

As can be seen in FIG. 44, the distal end 2322 of the central closure tube segment 2320 has a first lateral tab 2321 and a second lateral tab 2323 protruding therefrom. The first lateral tab has a first lateral hole (not shown) therethrough and the second lateral tab 2323 has a second lateral hole 2325 therethrough that is coaxially aligned with the first lateral hole 2325. In addition, the proximal end 2312 of the distal closure tube segment 2310 has a third lateral tab 2316 protruding therefrom and a fourth lateral tab 2318 protruding therefrom in spaced relation to the third lateral tab 2316. The third lateral tab 2316 has a third lateral pivot hole (not shown) therethrough and the fourth lateral tab 2318 has a fourth lateral pivot hole 2319 therethrough that is substantially coaxially aligned with the third lateral pivot hole.

In various embodiments, the closure tube joint assembly 2302 further includes an upper double pivot link 2360 that has a first upper pin 2362 and a second upper pin 2364 protruding therefrom. The first upper pin 2362 is sized to be pivotally received in the first upper pivot hole 2354 and the second upper pin 2364 is sized to be pivotally received in the second upper pivot hole 2327. The upper double pivot link 2360 may be retained in position between the proximal end 2324 of the central closure tube segment 2320 and the distal end 2334 of the proximal closure tube segment 2330 by the articulation joint assembly 1512. The closure tube joint assembly 2300 may further include a lower double pivot link 2370 that has a first lower pin 2372 and a second lower pin 2374 protruding therefrom. See FIG. 43. The first lower pin 2372 is sized to be pivotally received within the first lower pivot hole 2356 and the second lower pin 2374 is sized to be pivotally received in the second lower pivot hole 2329. The lower double pivot link 2370 may be retained in position between the proximal end 2324 of the central closure tube segment 2320 and the distal end 2322 of the central closure tube segment 2320 by the articulation joint assembly 1512.

When the upper double pivot link 2360 and the lower double pivot link 2370 are attached to the proximal end 2324 of the central closure tube segment 2320 and the distal end 2334 of the proximal closure tube segment 2330, the first upper pin 2362 and the first lower pin 2372 are coaxially aligned along a first pivot axis D-D that, in various embodiments, may be substantially transverse to an elongated shaft axis C-C that extends through the elongated closure tube assembly 1000. See FIG. 43. Likewise, the second upper pivot pin 2364 and the second lower pivot pin 2374 are coaxially aligned along a second pivot axis E-E. In various embodiments, the second pivot axis E-E is substantially transverse to the elongated shaft axis C-C and substantially parallel to the first pivot axis D-D. The reader will appreciate that such arrangement permits the central closure tube segment 2320 to pivot relative to the proximal closure tube segment 2330 about pivot axes D-D and E-E.

In various embodiments, the closure tube joint assembly 2302 may further include a first lateral double pivot link 2380 that has a first upper pin (not shown) and a second upper pin (not shown) protruding therefrom. The first lateral pin is sized to be pivotally received in the first lateral pivot hole (not shown) in the first lateral tab 2321 and the second lateral pin is sized to be pivotally received in the second lateral pivot hole (not shown) in the third lateral tab 2316. The first lateral double pivot link 2380 may be retained in position between the proximal end 2312 of the distal closure tube segment 2310 and the distal end 2322 of the central closure tube segment 2320 by the articulation joint assembly 1512. The closure tube joint assembly 2300 may further include a second lateral double pivot link 2390 that has a third lateral pin 2392 and a fourth lateral pin 2394 protruding therefrom. The third lateral pin 2392 is sized to be pivotally received within the second lateral hole 2325 in the second lateral tab 2323 and the fourth lateral pin 2394 is sized to be pivotally received in the fourth lateral pivot hole 2319 in the fourth lateral tab 2318. The second lateral double pivot link 2390 may be retained in position between the proximal end 2312 of the distal closure tube segment 2310 and the distal end 2322 of the central closure tube segment 2320 by the articulation joint assembly 1512.

When the first lateral double pivot link 2380 and the second double pivot link 2390 are attached to the proximal end 2312 of the distal closure tube segment 2310 and the distal end 2322 of the central closure tube segment 2320, the first lateral pin and the third lateral pin 2392 are coaxially aligned along a third pivot axis F-F that, in various embodiments, may be substantially transverse or orthogonal to the elongated shaft axis C-C. Likewise, the second lateral pivot pin and the fourth lateral pivot pin 2394 are coaxially aligned along a fourth pivot axis G-G. In various embodiments, the third pivot axis F-F is substantially transverse or orthogonal to the elongated shaft axis C-C and the first axis D-D and the second axis E-E and is substantially parallel to the fourth pivot axis G-G. The reader will appreciate that such arrangement permits the distal closure tube segment 2310 to pivot relative to the central closure tube segment 2320 about pivot axes F-F and G-G. Thus, such arrangement provides a closure tube assembly that can move axially over the joint assembly 1512 and still afford multi-articulation about four axes.

Figure 44A:
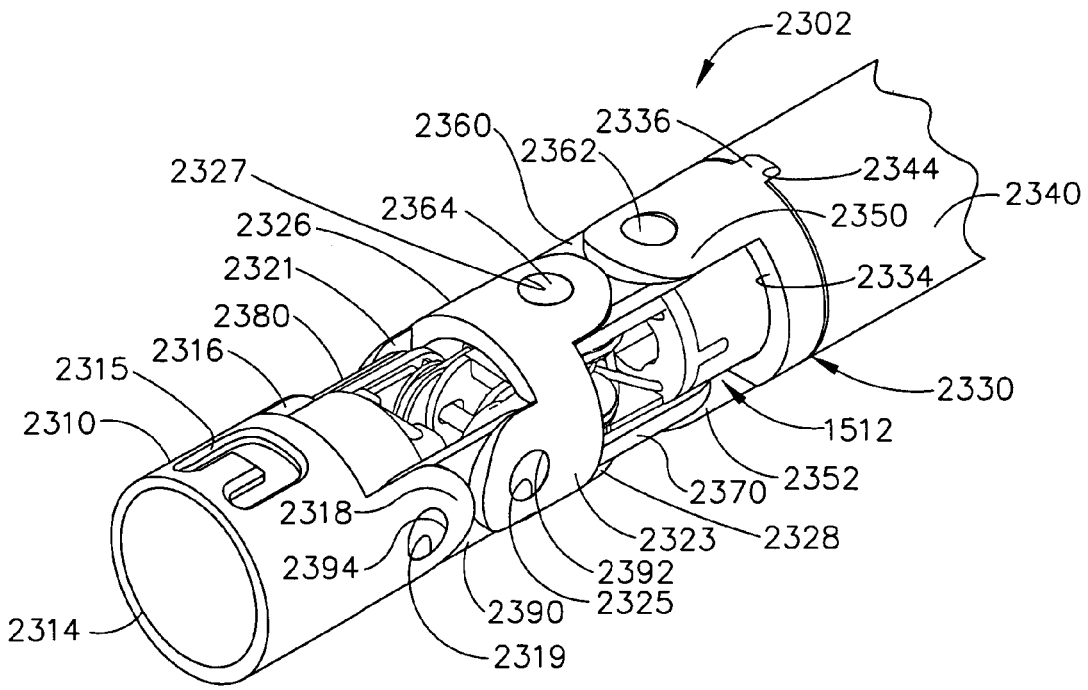
FIG. 44A is a perspective view of another closure tube joint assembly embodiment of the present invention installed over the articulation joint of FIG. 41.
Figure 45:
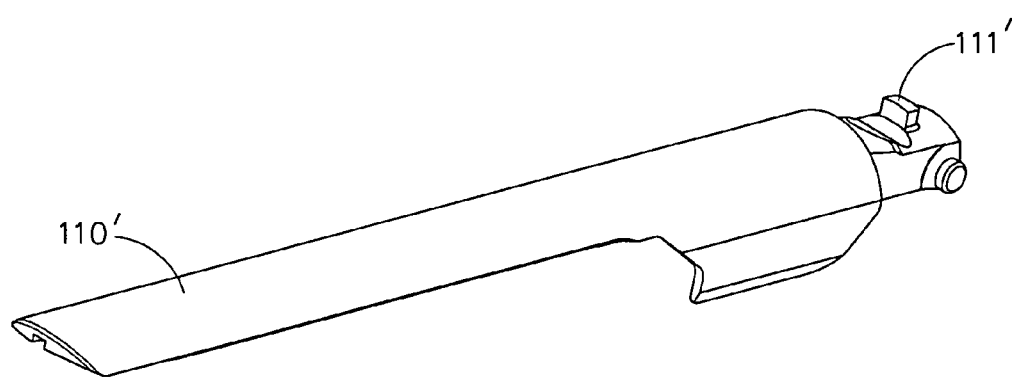
FIG. 45 is a perspective view of another anvil assembly embodiment of the present invention.

Those of ordinary skill in the art will understand that, as the closure tube assembly 2300 is moved (pushed) in the distal direction DD, the distal end 2314 of the distal closure tube segment 2310 applies a closing motion to the anvil assembly 110 by contacting the cam surface 115 of anvil assembly 110 (shown in FIGS. 2, 4 and 7) to close anvil assembly 110 relative to the staple cartridge assembly 200. In various embodiments, a return mechanism, e.g., a spring, cable system or the like (not shown), may be employed to return the closure tube assembly 2300 to a preclamping orientation which causes the anvil assembly 110 to re-open as the closure tube segment 2310 contacts a reverse cam surface 117 on the proximal end of the anvil assembly 110. See FIGS. 2 and 7. In other embodiments as illustrated in FIG. 45, the anvil assembly 110' may be formed with an upstanding actuation tab 111' that is sized to extend into a horse-shoe shaped opening 2315 in the distal end 2314 of the distal closure-tube segment 2310. See FIG. 44A. Thus, as the closure tube assembly 2300 is moved in the distal direction DD, the horse-shoe shaped opening 2315 contacts the ramp 115 and forces the anvil assembly 110' to a closed position. When the closure tube assembly 2300 is moved in the proximal direction PD, the horse-shoe shaped opening 2315 pulls the tab 111' and causes the anvil assembly 110' to pivot to an open position.

Figure 46:
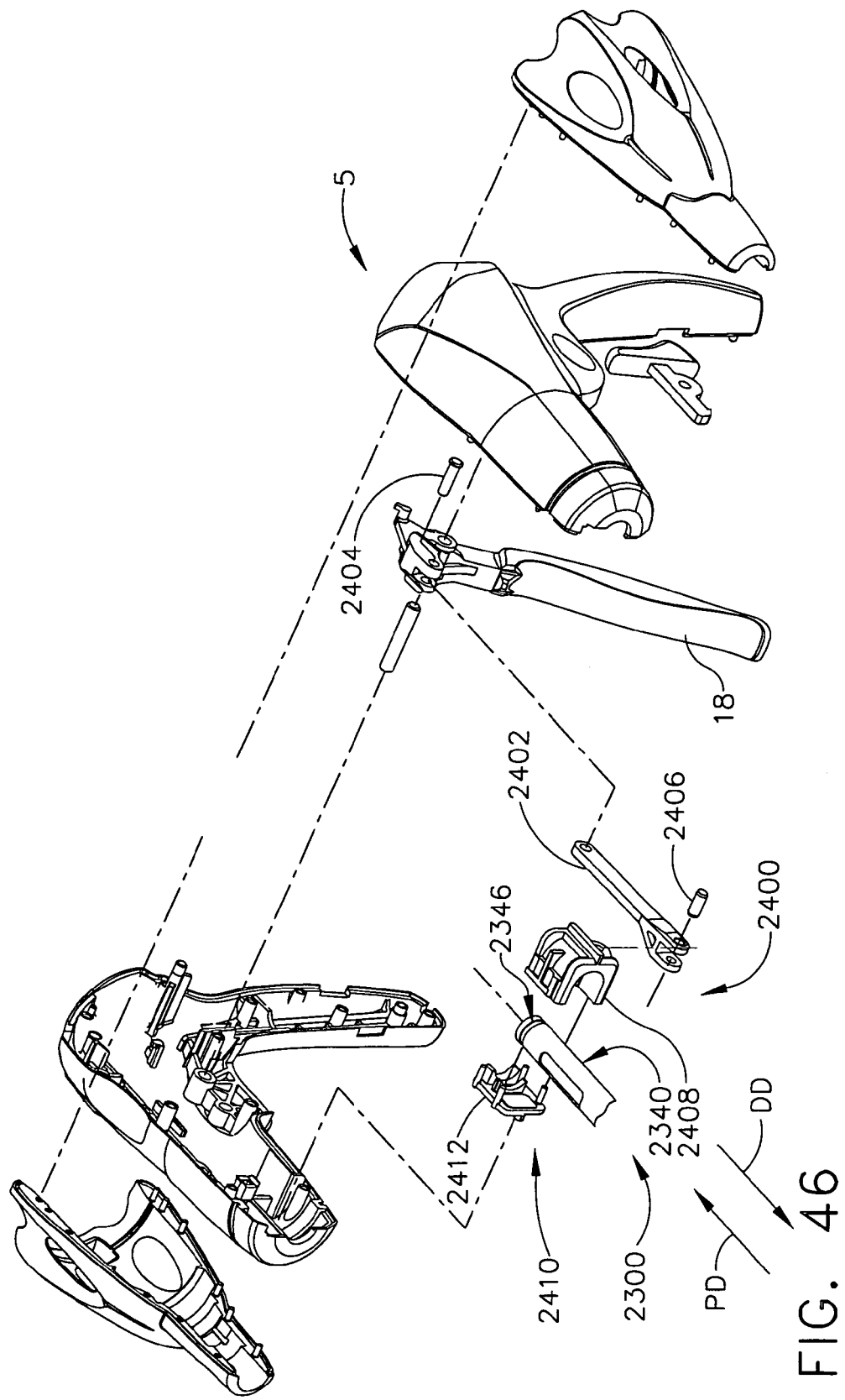
FIG. 46 is an exploded perspective view of a handle assembly and a closure tube actuation arrangement of an embodiment of the present invention.

One closure tube drive system of the present invention is briefly depicted in FIG. 46. However, other systems could also be effectively employed without departing from the spirit and scope of the present invention. As can be seen in FIG. 46, one form of closure tube drive system 2400 includes a yoke 2402 connected to a closure trigger 18. A pivot pin 2404 is inserted through aligned openings in both the closure trigger 18 and the yoke 2402. The distal end of the yoke 2402 is connected, via a pin 2406, to a first portion 2408 of a closure bracket 2410. The first closure bracket portion 2408 connects to a second closure bracket portion 2412. Collectively, the closure bracket 2410 defines an opening in which the proximal end 2346 of the closure tube segment 2340 is seated and held such that longitudinal movement of the closure bracket 2410 essentially pushes or drives the closure tube segment 2340 (and ultimately the elongated closure tube assembly 2300) in the distal direction DD.

In operation, when the yoke 2402 rotates due to retraction of the closure trigger 18, the closure bracket 2410 causes the proximal closure tube segment 2340 to move in the proximal PD direction, which causes the distal closure tube segment 2310 to move proximately. If the anvil assembly 110' is employed, the tab 111' causes the anvil assembly 110' to open when the distal closure tube segment 2310 moves proximately. When the closure trigger 18 is unlocked from the locked position, the proximal closure tube segment 2340 is pushed or otherwise driven in the distal direction DD, which causes the distal closure tube segment 2310 to slide distally. The distal closure tube segment 2310 forces the anvil assembly 110' closed by driving it distally into ramp 115. Such closure system 2400 is further described in commonly owned U.S. patent application Ser. No. 11/343,547 entitled "Endoscopic Surgical Instrument With a Handle That Can Articulate With Respect to the Shaft" to Frederick E. Shelton, IV, et al., the disclosure of which is hereby incorporated by reference in its entirety. Other closure systems may be employed, however, to axially move the closure tube assembly 2300 in the proximal and distal directions.

FIGS. 47-50 illustrate another unique and novel closure system 2500 of various embodiments of the present invention. In the embodiments depicted in these Figures, a manually actuatable drive system 2600 is employed. Such a drive system arrangement is disclosed in commonly owned U.S. patent application Ser. No. 11/475,412, filed Jun. 27, 2006, entitled "Manually Driven Surgical Cutting and Fastening Instrument" to Frederick E. Shelton, et al., the disclosure of which is hereby incorporated by reference in its entirety. Thus, the operation of such drive system arrangement will not be discussed in great detail herein. As the present Detailed Description proceeds, the person of ordinary skill in the art will appreciate, however, that the closure system 2500 of the present invention may also be effectively employed in connection with surgical stapling instruments that employ a cable or cables to drive the dynamic clamping member, knife and sled. In addition, the closure system 2500 may also be effectively employed in connection with other surgical stapling instruments that employ a motor to drive the dynamic clamping member, knife, sled, etc. Thus, the protection afforded to the closure system 2500 as described herein should not be limited to use only in connection with the manually actuatable drive system depicted in the present FIGS. 47-50.

As shown in these Figures, a firing trigger 2610 is operably supported by the handle assembly 5 and has a series of gear teeth 2612 thereon that meshingly interface with the drive gear arrangement (not shown) that operably interfaces with a rotary drive shaft 2614. The rotary drive shaft 2614 may be rotatably supported within a spine 2616 that extends through an elongate hollow closure tube 2510. The rotary drive shaft 2614 may interface with other drive components operably supported by the spine 2616 to convey a rotary driving motion to the tool assembly 100'. Also in various embodiments, a shifter assembly 2620 interfaces with the drive gear arrangement. The shifter assembly may include a selector switch 2622 such that when the switch is in one position and the firing trigger 2610 is pivoted in a ratcheting motion, the rotary drive shaft 2614 rotates in a first direction to ultimately impart a rotary motion to the tool assembly 100' to cause the dynamic clamping member or knife assembly to move in a distal DD direction and, when the selector switch 2622 is moved to a second position, ratcheting of the firing trigger 2610 causes the rotary drive shaft 2614 to rotate in an opposite direction to thereby impart an opposite rotary motion to the tool assembly 100' and cause the dynamic clamping assembly or knife assembly to move in the proximal PD direction.

As can also be seen in these Figures, the closure tube assembly 2500 may further include a closure knob 2520 and a rotation assembly 2550 for rotation of the tool assembly. As can be most particularly seen in FIG. 48, the closure knob 2520 may be supported on the proximal end 2512 of the closure tube 2510 and a spine attachment tube 2618. For assembly purposes, the closure knob 2520 may be provided in half sections that are interconnected by mechanical fasteners or adhesive. In one embodiment, the spine attachment tube 2618 is hollow and has a flanged proximal end 2619. The flanged end 2619 is rotatably supported in a radial slot 2522 provided in the closure knob 2520 such that the closure knob 2520 can freely rotate about the spine attachment tube 2618. As can also be seen in FIG. 48, the spine 2616 may have a proximal end 2617 sized to extend into the spine attachment tube 2618. However, other arrangements may be employed. As can also be seen in FIG. 48, the proximal end 2512 of the closure tube 2510 may be flanged and oriented to be non-rotatably retained within a second radial slot 2524 formed in the closure knob 2520 such that rotation of the closure knob 2520 causes the rotation of the closure tube 2510.

Figure 47:
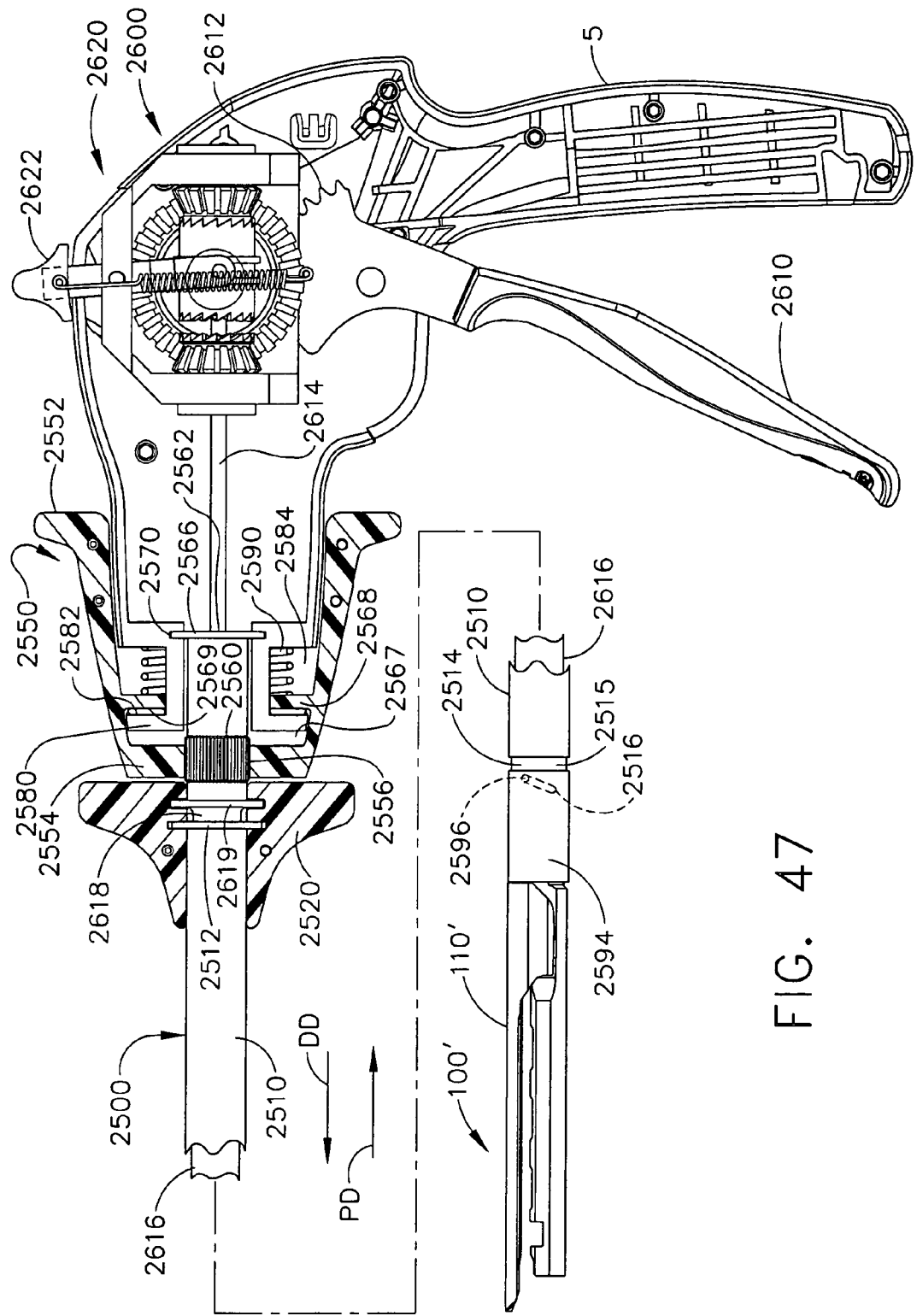
FIG. 47 is a partial cross-sectional view of a handle assembly and tool assembly of an embodiment of the present invention, with some components thereof shown in solid view and the anvil assembly in a closed or clamped position.
Figure 48:
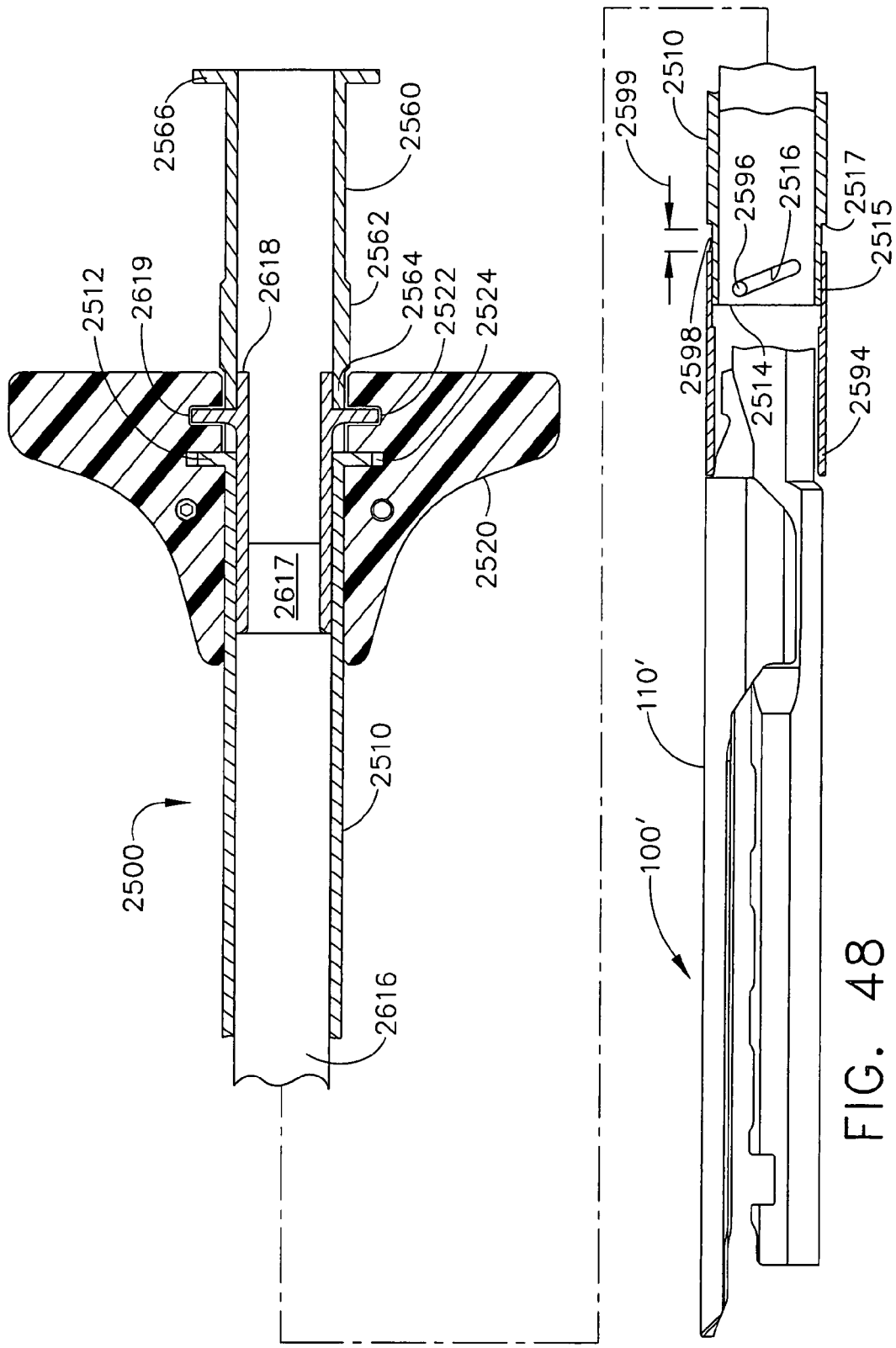
FIG. 48 is a partial cross-sectional view of a closure tube assembly and a tool assembly of an embodiment of the present invention with the anvil assembly in a closed or clamped position.
Figure 49:
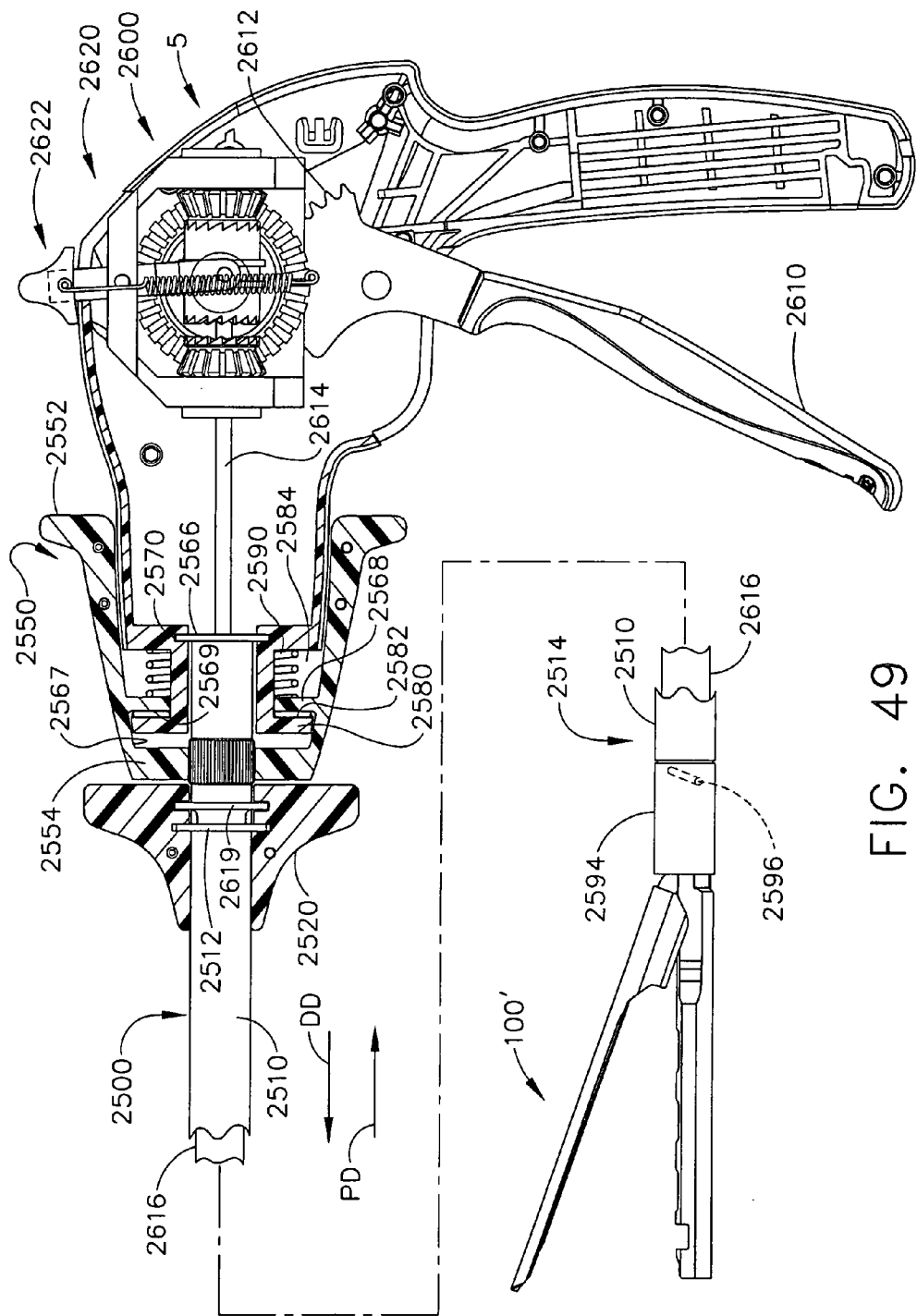
FIG. 49 is another partial cross-sectional view of the handle assembly and tool assembly of FIG. 47 with the anvil assembly thereof in an open position.
Figure 50:
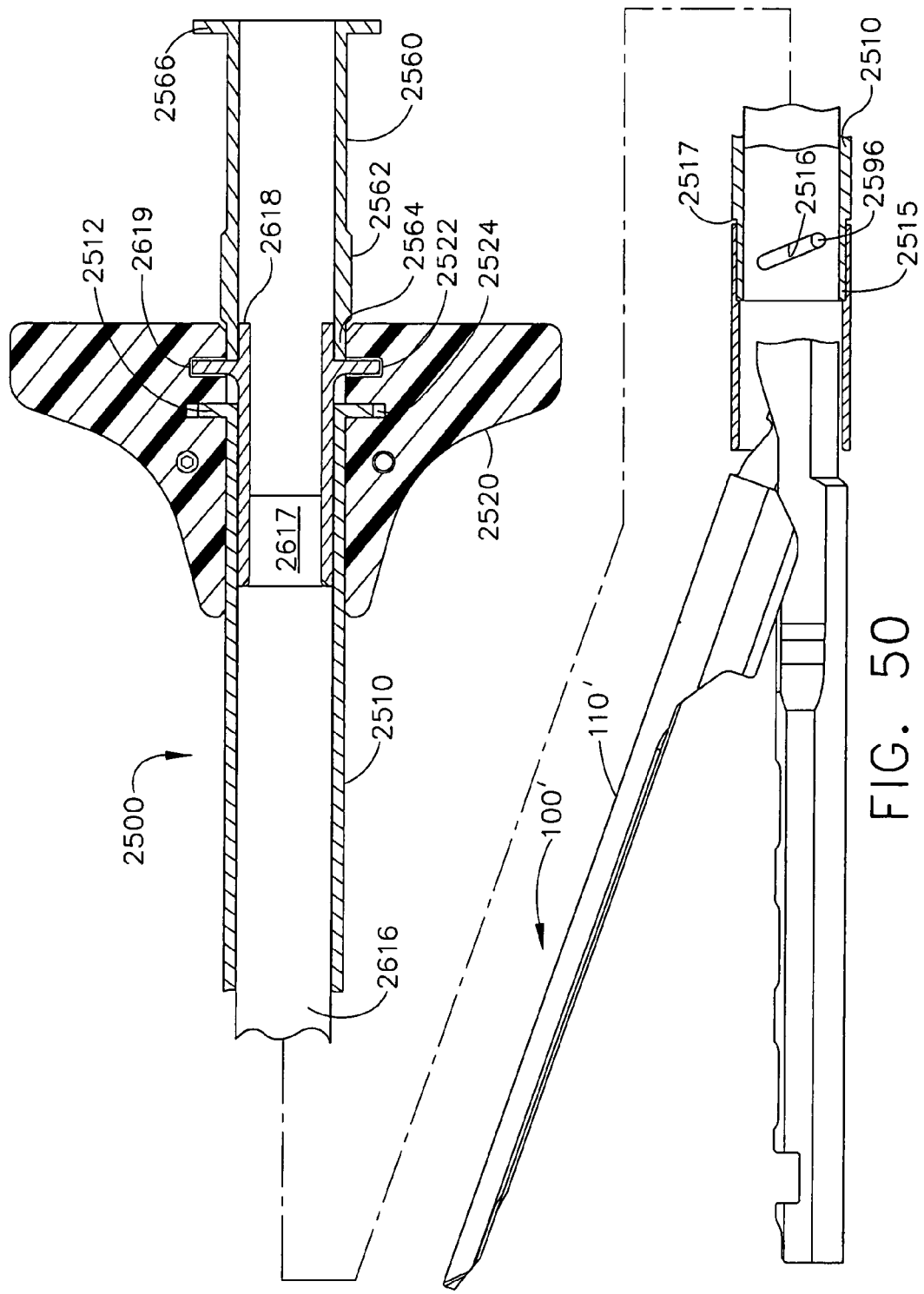
FIG. 50 is another partial cross-sectional view of the closure tube assembly and tool assembly of FIG. 48 with the anvil assembly thereof in an open position.

Various embodiments may also include a rotation assembly 2550. As can be seen in FIGS. 47, 49, and 50, the rotation assembly 2550 may include a rotation knob 2552 that is rotatably received on the handle assembly 5. As with the closure knob 2520 and housing assembly 5, the rotation knob 2552 may be provided in two segments that may be interconnected by mechanical fasteners—screws, snaps, etc. or adhesive for assembly purposes. In various embodiments, the distal end 2554 of the rotation knob 2552 has a hole 2556 therethrough that is adapted to receive therein a spline tube 2560 that has a splined section 2562 that is in axial engagement with the distal end 2554 of the rotation knob 2552 such that the rotation knob 2550 may be moved axially relative to the spline tube 2560, but always be engaged with the splined section 2562 thereof. As can be seen in FIG. 48, the spline tube 2560 has a distal end 2564 that extends into the closure knob 2520 and is non-rotatably attached to the spine attachment tube 2618. by adhesive or other suitable fastener arrangement. A proximal end 2566 of the spline tube 2560 is flanged and is adapted to be received in an annular slot 2570 provided in the handle assembly 5 such that the flanged end 2566 can rotate therein.

As can also be seen in FIG. 47 and 49, the distal end 2580 of the housing assembly is flanged and has a first radial gear 2582 formed thereon. The flanged end 2580 of the housing assembly extends into an annular cavity 2567 formed in the rotation knob 2552. The annular cavity 2567 is formed by an inwardly extending annular flange 2568 that has a second radial gear 2569 formed thereon for selective meshing engagement with the first radial gear 2582. The annular flange 2568 also extends into an annular spring cavity 2584 formed in the housing assembly 5. A locking spring 2590 is provided in the spring cavity 2584 to bias the second radial gear 2569 into meshing engagement with the first radial gear 2582. As will be discussed in further detail below, the clinician can unlock the spine 2616 thereby enabling the clinician to rotate the spine 2616 and ultimately the tool assembly 100' to position the tool assembly 100' in a desired orientation by pulling the rotation knob 2552 proximally to disengage the second radial gear 2569 from the first radial gear 2582 to enable the rotation knob 2550, spline tube 2560 and spine 2616 to rotate.

As shown in FIGS. 47 and 48, the distal end 2514 of the closure tube 2510 may be formed with a reduced diameter portion 2515 for slidably receiving a nonrotatable closure ring 2594 thereon. In various embodiments, a pair of slots 2516 are provided therein that are oriented to receive corresponding pins 2596 that protrude inward from the wall of the closure ring 2594. In various embodiments, at least one pin and slot arrangement is employed. In alternative embodiments, the pins 2596 may be in the closure tube 2510 and the slots 2516 may be provided in the closure ring. FIG. 50 illustrates the anvil 110' of the tool assembly 100' in an open position. To close the anvil 110', the clinician simply rotates the closure knob 2520 in a first direction which also rotates the closure tube 2510 in that direction. The rotation of the closure tube 2510, by virtue of the interaction between the pins 2596 and slots 2516, causes the closure ring 2594 to move distally into contact with a portion of the anvil 110' to pivot the anvil 110' to the closed position depicted in FIG. 47 and 48. As shown in FIG. 48, there is a distance 2599 between the proximal end 2598 of the closure ring 2594 and the ledge 2517 of the reduced diameter portion 2515 of the closure tube 2510. Such distance 2599 represents the amount of axial travel that is available to the closure ring 2594. The person of ordinary skill in the art will appreciate that by providing the slots 2516 at relatively low angles, the pins 2596 will tend to remain in that position and thereby also retain the anvil 110' in the closed position. However, other locking arrangements may be employed.

To open the anvil 110', the clinician again moves the brake knob 2552 in the proximal direction PD and then rotates the closure knob 2520 (and closure tube 2510) in a second direction as shown in FIGS. 49 and 50. In various embodiments, the tissue that was clamped in the tool assembly 100' causes the anvil 110' to move to the open position. In other embodiments, a spring or other biasing member (not shown) may be employed to bias the anvil 110' to the open position when the closure ring 2594 has been moved to the position depicted in FIGS. 49 and 50. In other embodiments, the closure ring 2594 may be provided with the horse-shoe shaped opening described above and the anvil 110' may be configured with a tab 111' as shown in FIG. 45. Thus, in that embodiment, when the closure ring 2594 is drawn proximally, it pulls the anvil 110' to the open position. Once in the open position, the clinician may release the brake knob 2552 and the brake 2550 will lock the closure tube 2510 (and anvil 110') in the open position. The person of ordinary skill in the art will appreciate that the closure system 2500 may also be effectively employed in connection with the closure tube joint assembly 2302 described above. In such arrangement, the slots 2516 may be provided in the distal closure tube segment 2310. Such arrangement would be operated in the same manner as described above, however, the instrument would also be articulatable about multiple axes.

Figure 51:
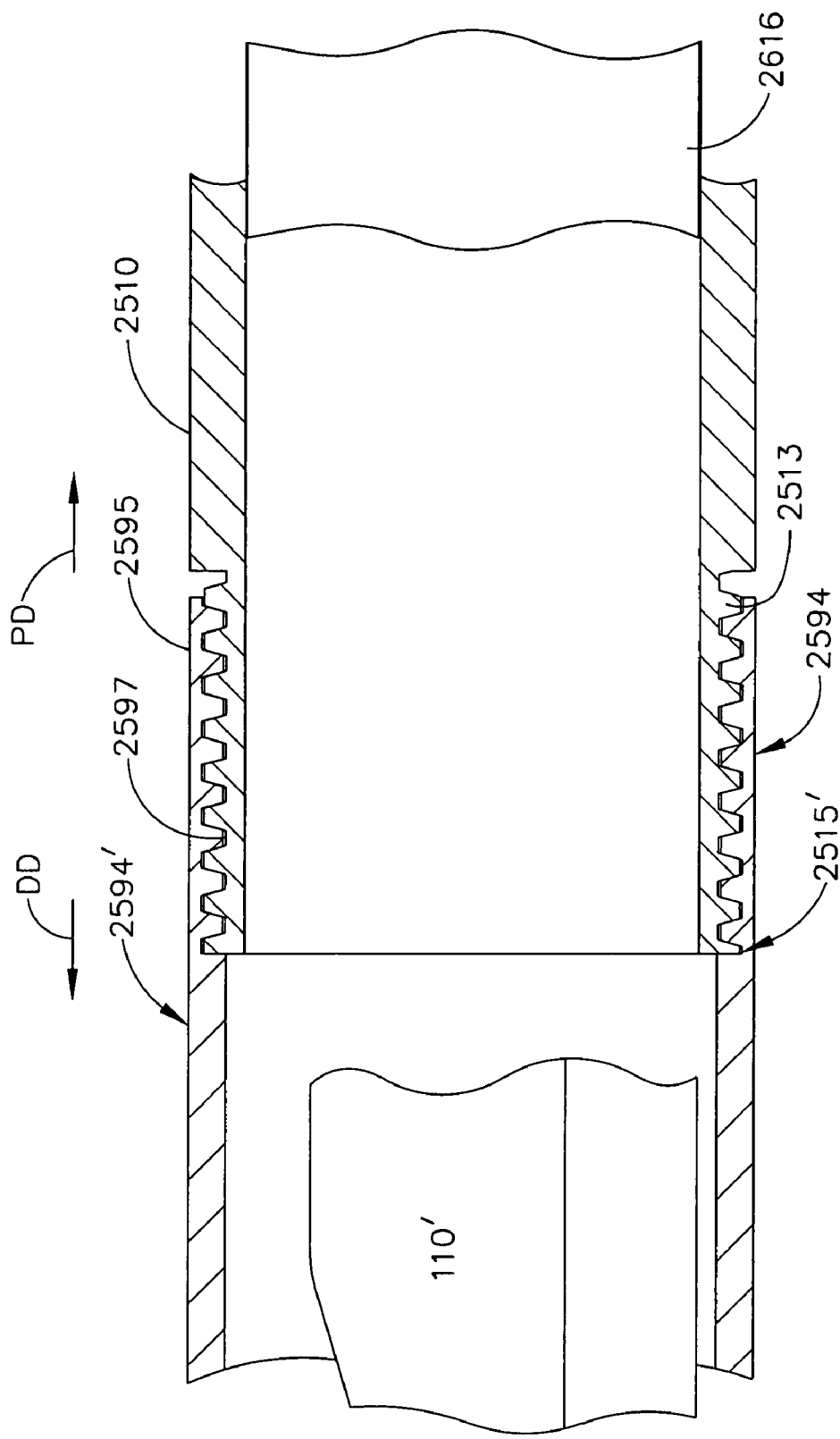
FIG. 51 is a partial cross-sectional view of a closure tube and a closure ring of another embodiment of the present invention.

FIG. 51 illustrates another embodiment of the present invention wherein the distal end 2515' of the closure tube 2510 has threads 2513 thereon for threaded engagement with threads 2597 on the closure ring 2594'. In this embodiment, the closure ring 2594' may be configured to interact with the channel assembly 120 and or spine 2616 such that the closure ring 2594' can move axially relative thereto, but does not rotate. The threads 2597 are formed in the proximal end 2595 of the closure ring 2594' such that as the closure tube 2510 is rotated in one direction, the closure ring 2594' is axially moved in the distal direction DD to contact the anvil 110' and pivot the anvil 110' to the clamped position. Rotation of the closure ring 2594' in the opposite direction causes the closure ring 2594' to move in the proximal direction PD to enable the anvil 110' to be pivoted open by the tissue that was clamped therein, or by springs or other biasing members. Such use of multiple turn threads may provide more closure power than other closure ring arrangements. In alternative embodiments, the closure ring 2594' may be provided with the horse-shoe shaped opening to interact with a closure tab on the anvil. See FIG. 45. The rotation and locking of the closure tube 2510' may be controlled by the closure system 2500 and closure tube brake assembly 2550 as was described above. This embodiment may also be used in connection with the various articulation joints described above without departing from the spirit and scope of the present invention. It will be further appreciated that such embodiment may be effectively used with the manual drive system depicted in FIGS. 47 and 49 or with other drive arrangements, such as cable drive arrangements, etc.

Figure 52:
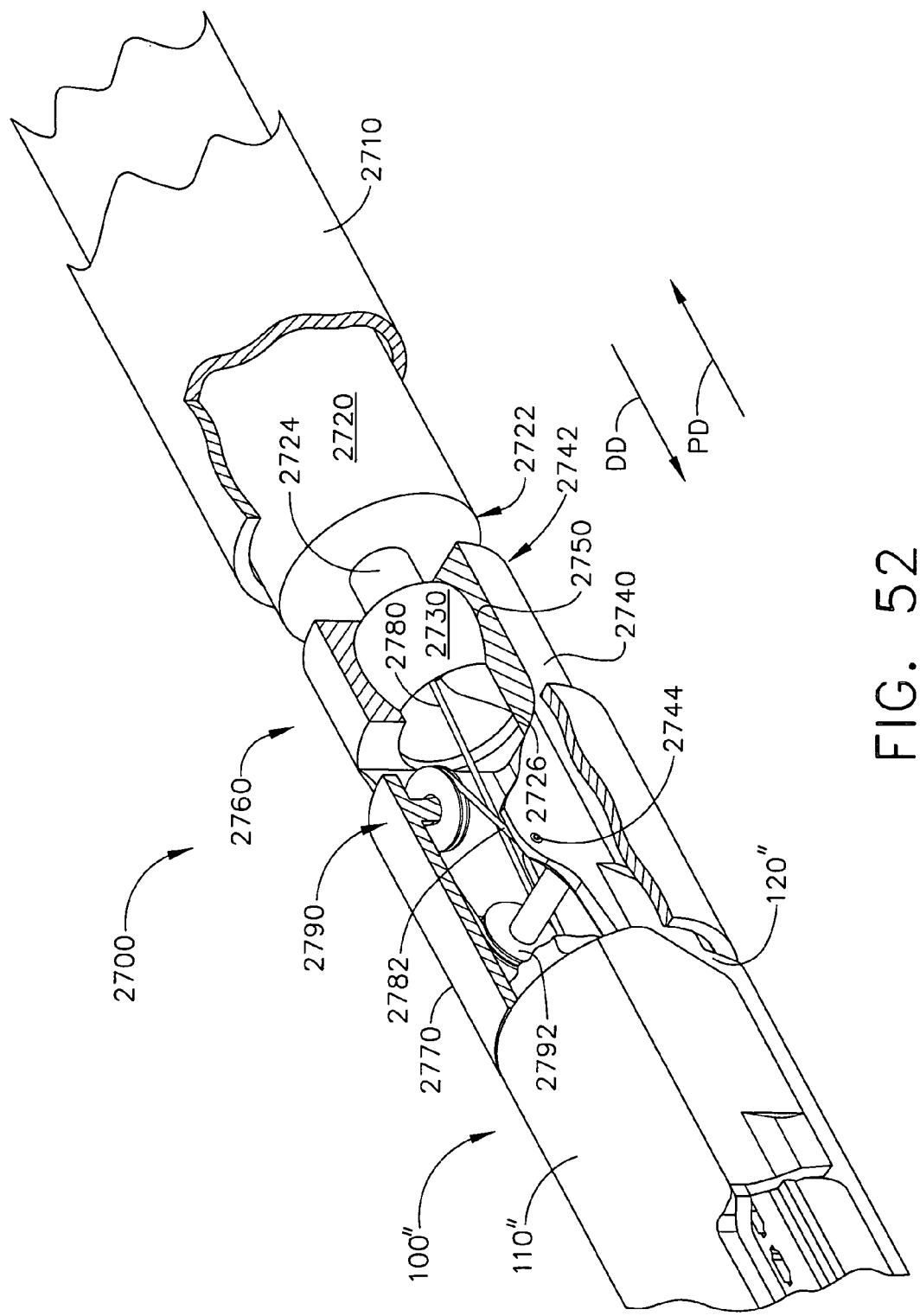
FIG. 52 is a partial perspective cross-sectional view of a universal articulation joint arrangement of another embodiment of the present invention.
Figure 53:
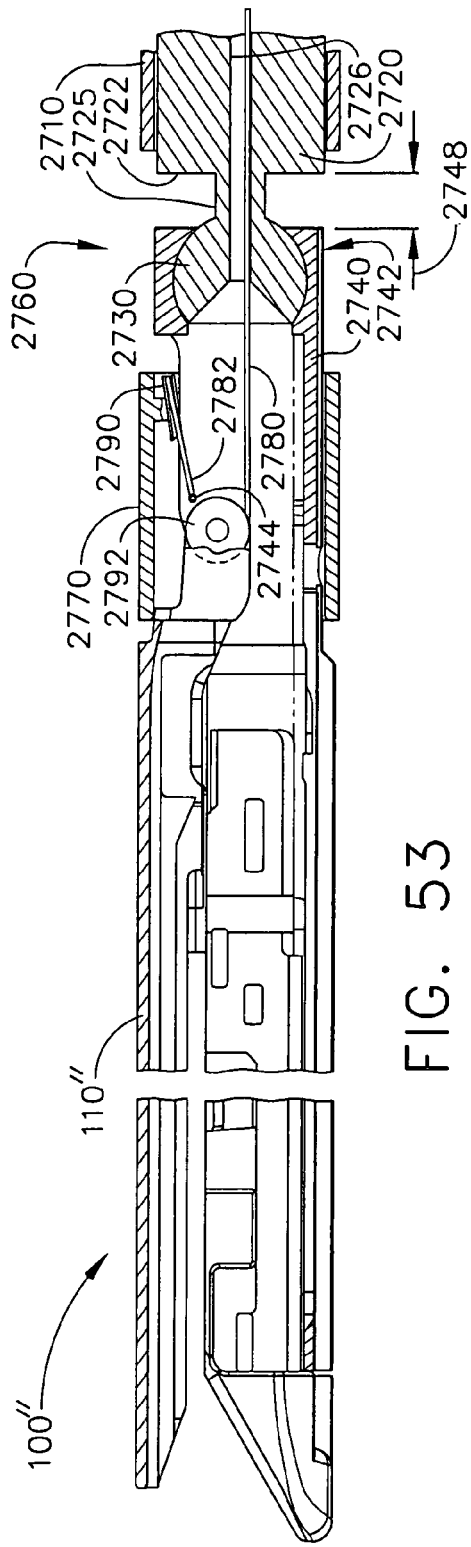
FIG. 53 is a cross-sectional view of a tool assembly and articulation joint of FIG. 52.
Figure 54:
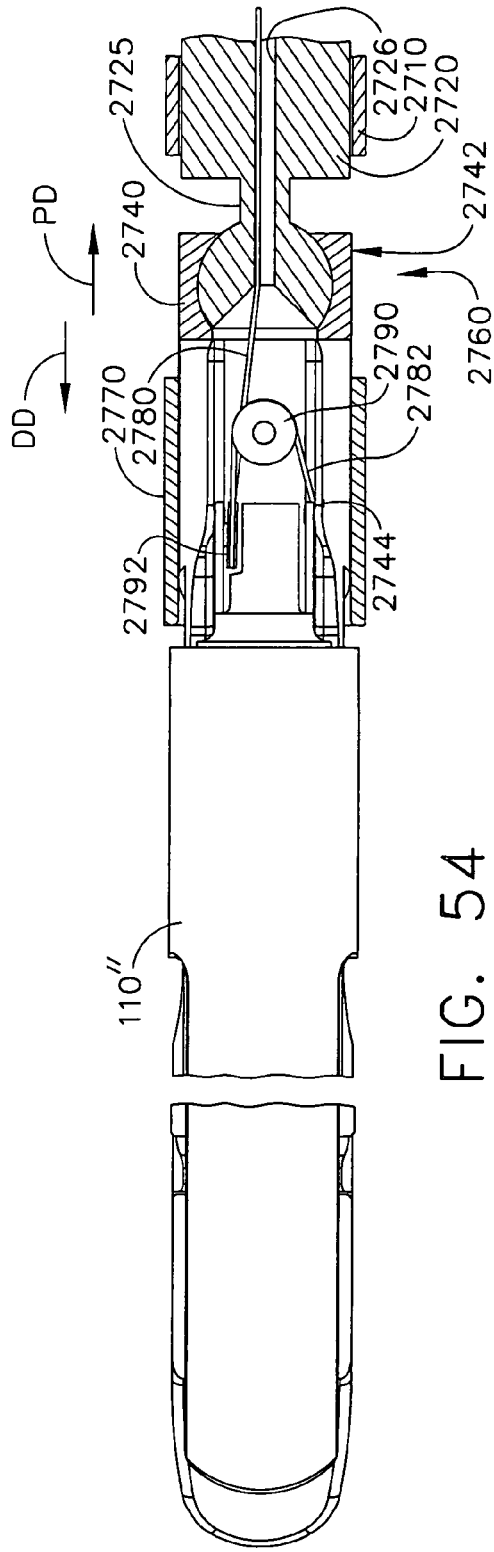
FIG. 54 is a top view of the tool assembly and articulation joint of FIG. 53.

FIGS. 52-54 illustrate another cable-actuated closure system 2700 embodiment of the present invention. As can be seen in those Figures, various embodiments may include a proximal cover tube 2710 that axially supported a proximal spine segment 2720. The proximal spine segment 2720 extends from the handle assembly (not shown) and may be supported thereby in any one of a number of known arrangements without departing from the spirit and scope of the present invention.

In various embodiments, the proximal spine segment 2720 has a distal end 2722 that has a neck portion 2724 protruding therefrom that has a ball-shaped member 2730 attached thereto or otherwise formed therewith. As can also be seen in these Figures, the ball-shaped member 2730 is sized to be received in a socket 2750 formed in a proximal end 2742 of a channel-shaped distal spine segment 2740. The ball-shaped member 2730 and socket 2750 collectively form a ball joint, generally designated as 2760, that affords the distal spine segment 2740 the ability to articulate in multiple directions relative to the proximal spine segment 2720. A sufficient amount of clearance 2748 is provided between the proximal end 2742 of the distal spine segment 2740 and the distal end 2722 of the proximal spine segment 2720 to enable the distal spine segment to articulate in a desired range of motion relative to the proximal spine segment 2720. In various embodiments, the distal spine segment 2740 is attached to the elongate channel assembly 120" to which the anvil 110" is pivotally attached. As can be further seen in FIGS. 52-54, a closure ring 2770 is supported on the distal spine segment 2740 for selective axial travel thereon.

In various embodiments, the opening and closing of the anvil 110' may be accomplished by a closure cable 2780 that extends from the handle assembly (not shown) through a hollow passage 2726 in the proximal spine segment 2720 and neck portion 2724. The proximal end (not shown) of the closure cable 2780 may be attached to one of the cable drive systems described herein or other cable control systems for selectively applying tension to the cable 2780. Those of ordinary skill in the art will further appreciate that a drive cable system of the various types described above may also be employed to drive the dynamic clamping member, knife, and sled.

As can be seen in FIGS. 52-54, the closure ring 2770 may have a first cable transition support 2790 mounted thereon that extends into the open upper end of the channel-shaped distal spine segment 2740 such that the first cable transition support 2790 can move distally and axially back and forth within the distal spine segment 2740 as the closure ring 2770 moves thereon. In various embodiments, the first cable transition support 2790 may comprise a support selected from the group of supports consisting of pulleys, rod, capstans, etc. In addition, a second cable transition support 2792 may be mounted within the distal spine segment 2740 in the orientation shown such that the closure cable 2780 may be operably supported on the first and second cable transition supports 2790, 2792. Similarly, the second cable transition support 2792 may comprise a cable transition support selected from the group of transition supports consisting of pulleys, rods, capstans, etc.

The distal end 2782 of the closure cable 2780 may be fixed to the distal spine segment 2740 at a point of attachment 2744. Thus, applying tension to the closure cable 2780 (pulling the closure cable 2780 in the proximal direction PD) causes the closure ring 2770 to move in the distal direction DD to contact the anvil 110' and pivot it to a closed position in the manner discussed above. In various embodiments, the tissue that was clamped in the tool assembly 100" causes the anvil 110' to move to the open position. In other embodiments, a spring or other biasing member (not shown) may be employed to bias the anvil 110' to the open position when the closure ring 2770 has been axially moved to its proximal unclamped position. Such unique and novel cable actuated closure system enjoys a significant mechanical advantage improvement over prior cable powered closure systems while also providing the ability to articulate the tool assembly 100" relative to the other portion of the instrument. Other embodiments are also contemplated wherein the ball-shaped member is formed in the distal spine segment 2740 and the socket is formed in the proximal spine segment 2720. In still other embodiments, no articulation joint is employed. That is, the proximal spine segment and distal spine segment comprise a single member.

Figure 55:
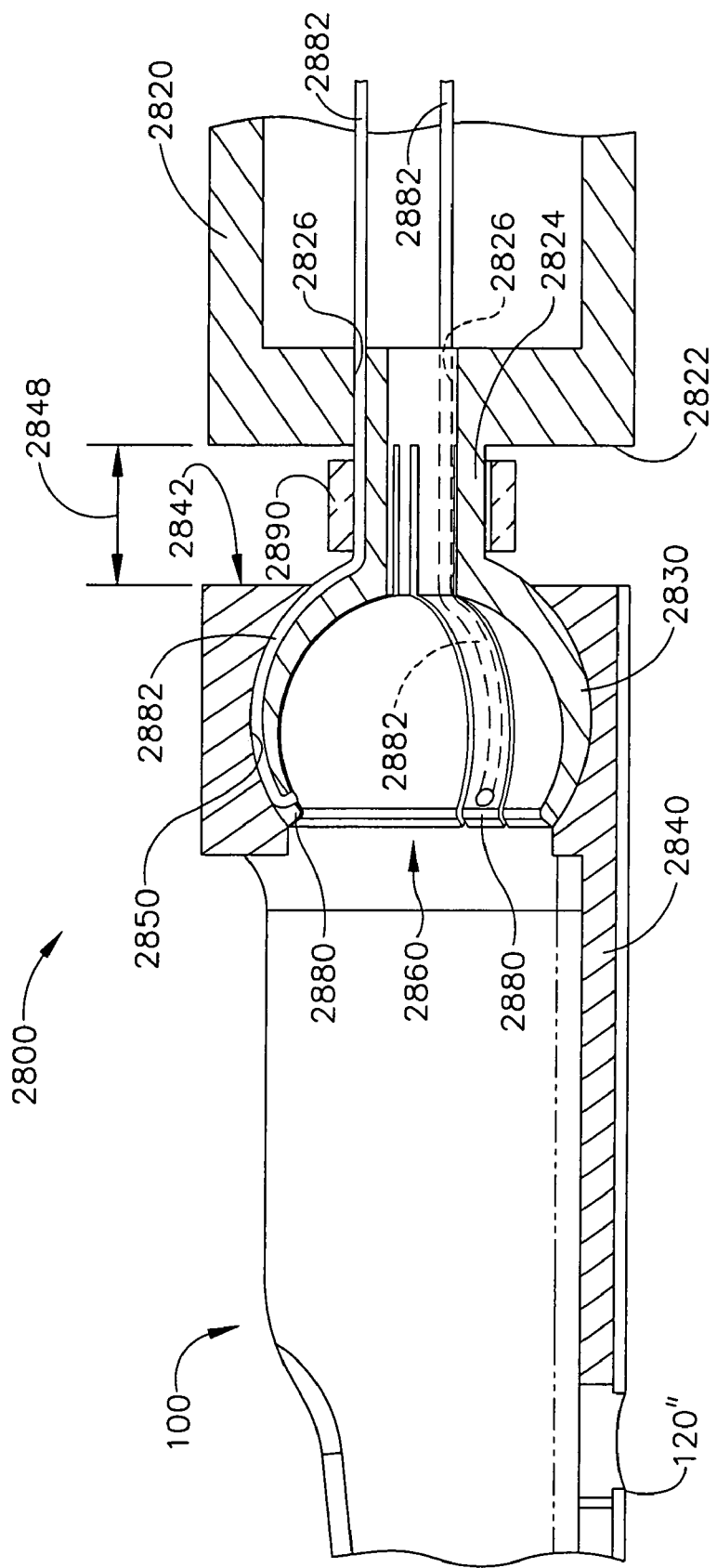
FIG. 55 is a cross-sectional view of another universal articulation joint of another embodiment of the present invention.
Figure 58:
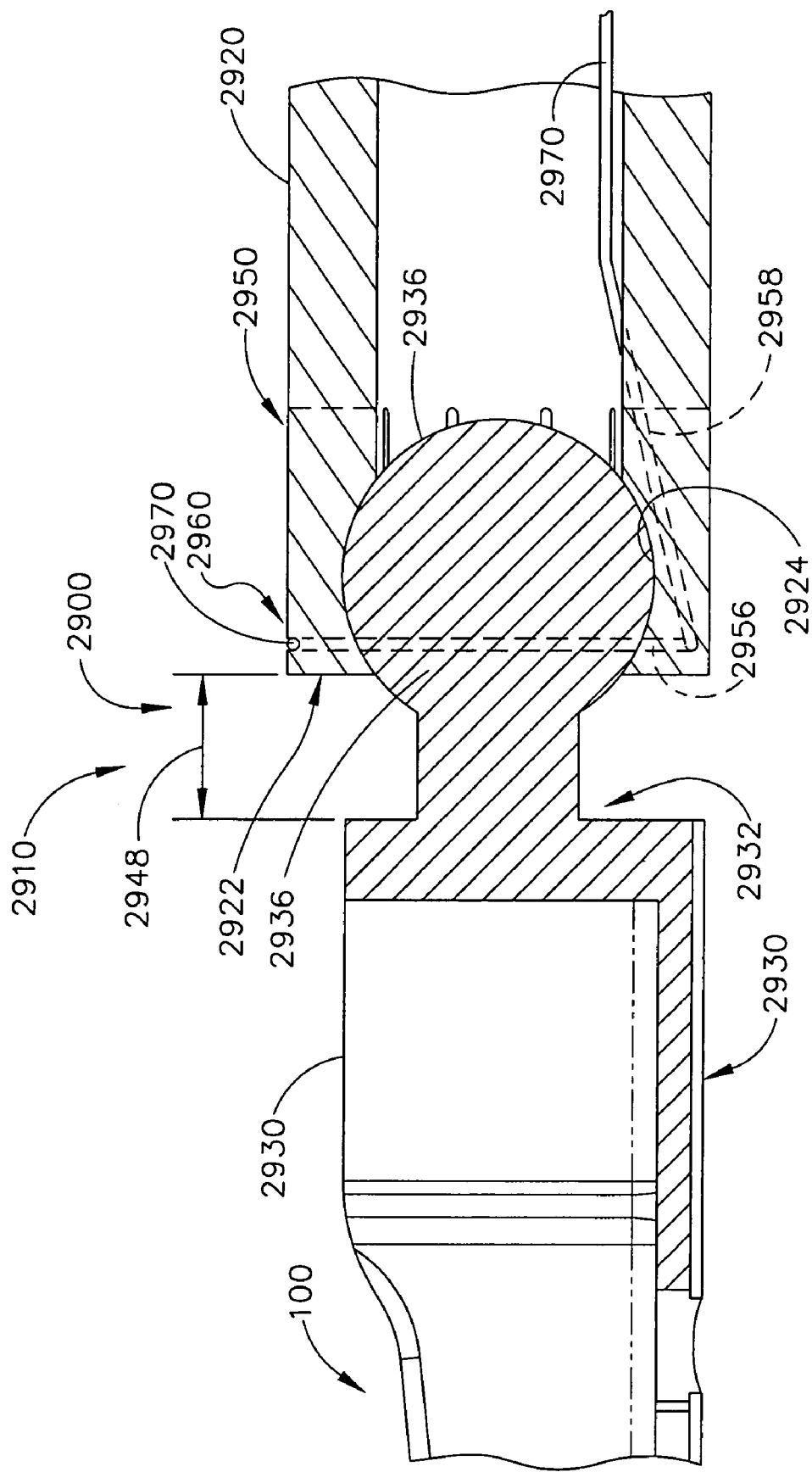
FIG. 58 is a cross-sectional view of another cable controlled lockable articulation joint of another embodiment of the present invention.

FIGS. 55-57 illustrate a cable controlled lockable articulation joint 2800 of various embodiments of the present invention that interfaces between the elongate channel assembly 120" and a proximal spine segment 2820. In various embodiments, the proximal spine segment 2820 may extend from the handle assembly (not shown) and may be supported thereby in any one of a number of known arrangements without departing from the spirit and scope of the present invention. The proximal spine segment 2780 may have a distal end 2822 that has a neck portion 2824 protruding therefrom that has a substantially ball-shaped member 2830 attached thereto or otherwise formed therewith. As can also be seen in these Figures, the ball-shaped member 2830 may be sized to be received in a socket 2850 formed in a proximal end 2842 of a distal spine segment 2840. The ball-shaped member 2830 and socket 2850 collectively form a ball joint, generally designated as 2800, that affords the distal spine segment 2840 with the ability to articulate in multiple directions relative to the proximal spine segment 2820. A sufficient amount of clearance 2848 may be provided between the proximal end 2842 of the distal spine segment 2840 and the distal end 2822 of the proximal spine segment 2820 to enable the distal spine segment 2840 to articulate in a desired range of motion relative to the proximal spine segment 2820. In various embodiments, the distal spine segment 2840 may be attached to the channel assembly 120" to which the anvil (not shown) is pivotally attached.

In various embodiments, one or more radially extendable portions 2880 may be provided in the ball-shaped member 2830. In the embodiment depicted in FIGS. 55-57, three radially extendable fingers 2880 are provided, for example. In various embodiments, the radially extendable fingers 2880 may be equally spaced about the ball-shaped member 2830 (e.g., spaced at 120° intervals). Other numbers of radially extendable fingers 2880 could also be successfully employed. In various embodiments, the ball-shaped member 2830 may be fabricated from, for example, plastic, metal, etc. such that the radially extendable fingers may be pulled or otherwise driven radially outward a distance to lock the ball-shaped member 2830 in a desired orientation within the socket 2850.

In various embodiments, each of the radially extendable fingers 2880 may have a cable 2882 attached thereto that extend adjacent the neck portion 2824 of the proximal spine segment 2820 and through corresponding passages 2826 in the distal end 2822 of the proximal spine segment 2820. The cables 2882 may extend through the hollow proximal spine segment 2820 to a control system supported by the handle (not shown) to selectively apply a tension force to the cables 2882. For example, the cables 2882 may be associated with a locking trigger or other mechanism supported in the handle that can be moved to apply a tension to the cables and be selectively retained in that position until it is desired to release the joint whereby the mechanism may be unlocked to release the tension in the cables 2882. As can be seen in FIG. 55, a hollow cable ring 2890 may be employed as shown to retain the cables 2882 adjacent the neck portion 2824.

To use this embodiment, the clinician positions the tool assembly 100 in the patient and then applies an articulation force to the tool assembly with another surgical instrument or by bringing the tool assembly 100 into contact with a portion of the patient to articulate the tool assembly to a desired position before applying tension to the locking cables 2882. After the tool assembly 100 has been articulated to the desired position, the clinician applies a tension force to the locking cables 2882 which causes the radially extendable fingers 2880 to extend radially outward and lock the ball-shaped member 2830 in that orientation within the socket 2850 to thereby retain the distal spine segment 2840 (and the tool assembly 100 attached thereto) in that articulated position. Such system employs a "passive" articulation technique.

FIGS. 58-61 illustrate another cable controlled lockable articulation joint 2900 of various embodiments of the present invention. As can be seen in those Figures, various embodiments may include a proximal spine segment 2920 that extends from the handle assembly (not shown) and may be supported thereby in any one of a number of known arrangements without departing from the spirit and scope of the present invention. As can also be seen in FIG. 58, a ball-shaped member 2936 may be formed on a proximal end 2932 of a distal spine segment 2930. The ball-shaped member 2936 may be sized to be received in a socket 2924 formed in the distal end 2922 of the proximal spine segment 2920. The ball-shaped member 2936 and socket 2924 collectively form a ball joint, generally designated as 2910, that affords the distal spine segment 2930 with the ability to articulate in multiple directions relative to the proximal spine segment 2920. A sufficient amount of clearance 2948 is provided between the proximal end 2932 of the distal spine segment 2930 and the distal end 2922 of the proximal spine segment 2920 to enable the distal spine segment 2930 to articulate in a desired range of motion relative to the proximal spine segment 2920. In various embodiments, the distal spine segment 2930 may be attached to the channel assembly (not shown) to which the anvil (not shown) is pivotally attached.

Figure 59:
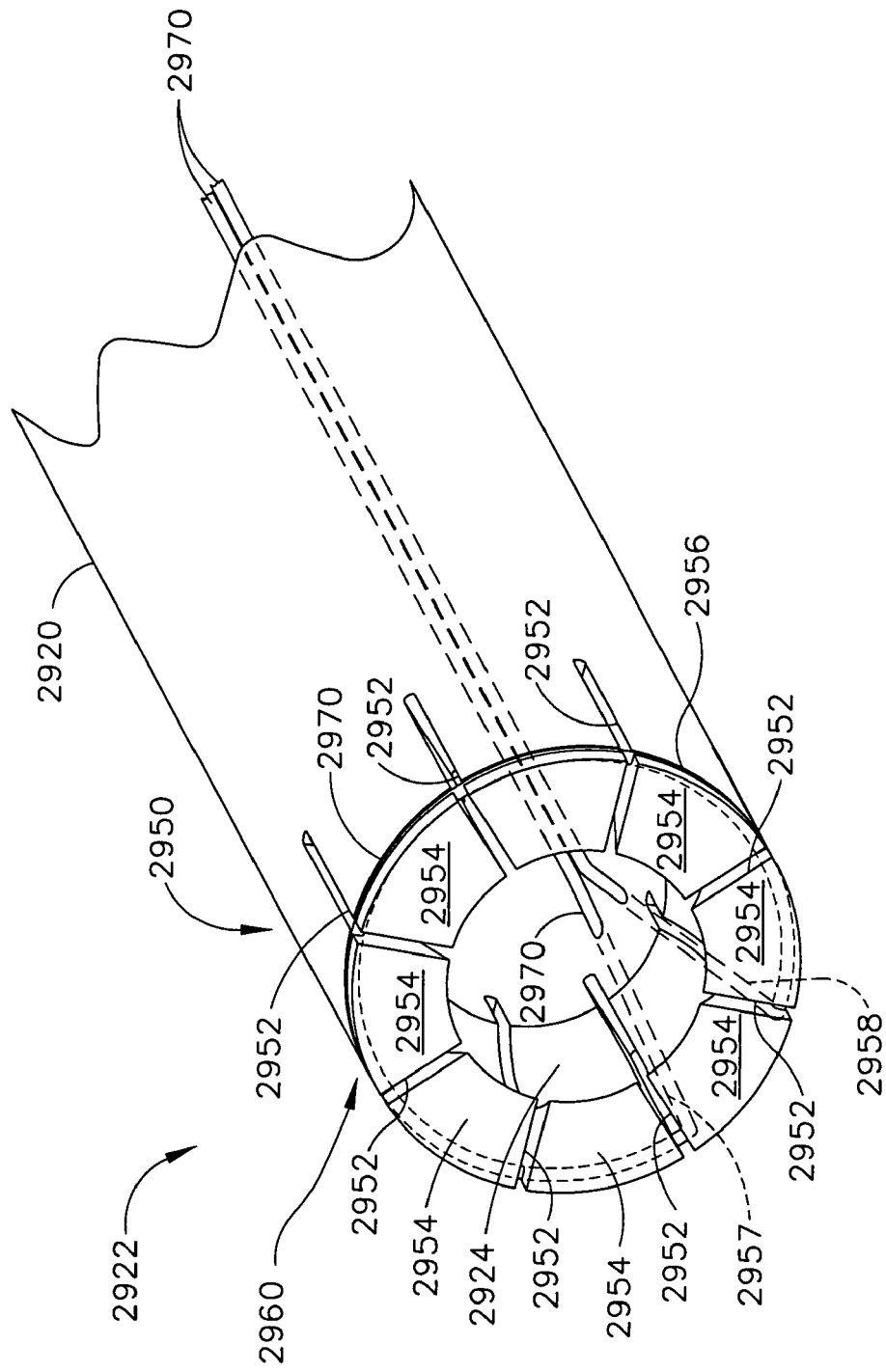
FIG. 59 is a partial perspective end view of a proximal spine segment of the cable-controlled lockable articulation joint of FIG. 58.
Figure 60:
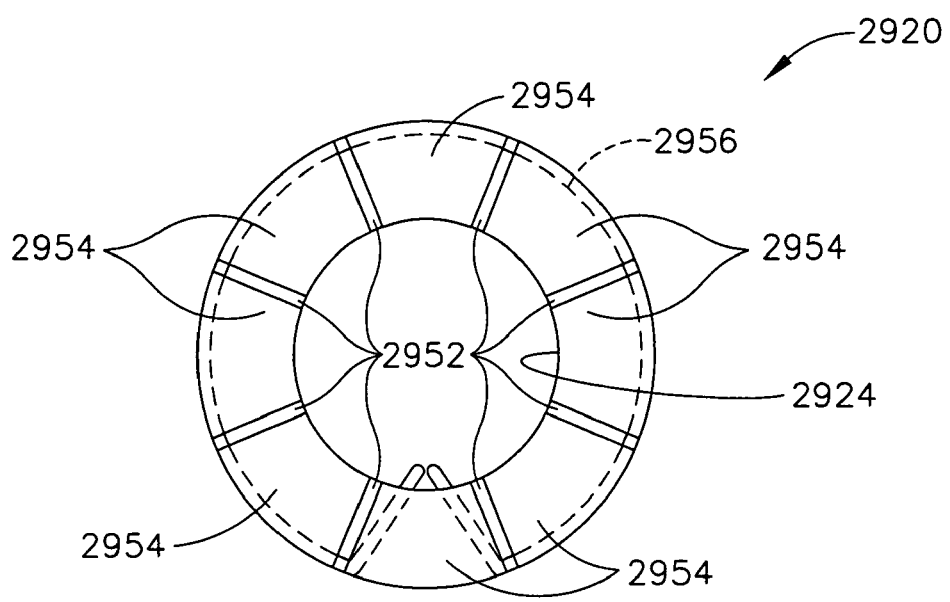
FIG. 60 is an end view of the proximal spine segment of FIG. 59.
Figure 61:
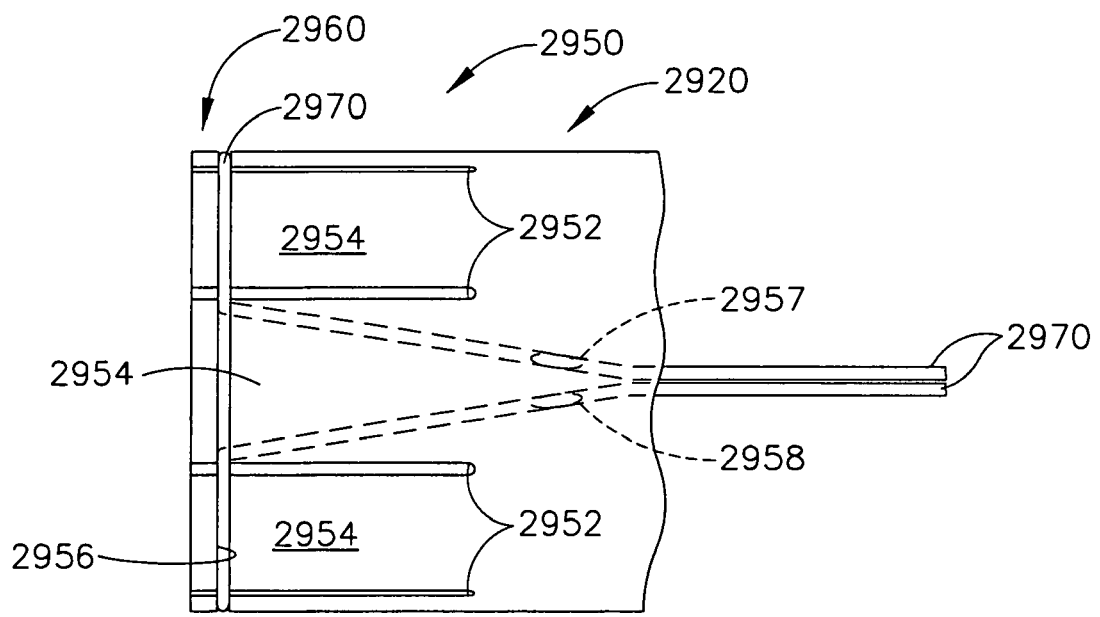
FIG. 61 is a partial side view of the proximal spine segment of FIGS. 59 and 60.

In various embodiments, the distal end 2922 of the proximal spine segment 2920 may have a flexible section 2950 and a cincture section 2960. The proximal spine section may be fabricated from, for example, plastic, metal, etc. The flexible section 2950 may be defined by a series of equally spaced slots 2952 provided into the distal end 2922 of the proximal spine segment 2920 to form a plurality of radially contractable locking portions in the form of, for example, flexible segments 2954 that serve to define the socket 2924 therebetween. In addition, a circumferentially extending groove 2956 may be provided around the circumference of the distal end 2922 of the proximal spine segment 2920. A locking cable 2970 may extend through the hollow proximal spine segment 2920 and be looped around the cincture section 2960 in the circumferentially extending groove 2956 as shown in FIGS. 59 and 61. As can be seen in those Figures, the cable 2970 may pass through two passages 2957, 2958 such that the ends thereof may extend through the proximal spine section 2920 to a cable control system (not shown) supported in the handle assembly (not shown) that may be used to selectively apply a tension force to the cable 2970.

To use this embodiment, the clinician positions the tool assembly 100 in the patient and then applies an articulation force to the tool assembly with another surgical instrument or by bringing the tool assembly 100 into contact with a portion of the patient to articulate the tool assembly to a desired position before applying tension to the locking cable 2970. After the tool assembly 100 has been articulated to the desired position, the clinician applies tension to the locking cables 2970 which causes the flexible segments 2954 to lock around the ball-shaped member 2936 and prevent it from moving relative to the proximal spine segment 2920 to thereby retain the distal spine segment 2840 (and the tool assembly 100 attached thereto) in that articulated position. Such system employs a "passive" articulation technique. To release the ball-shaped member to permit further articulation of the tool assembly, the tension is released from the cable 2970.

Figure 62:
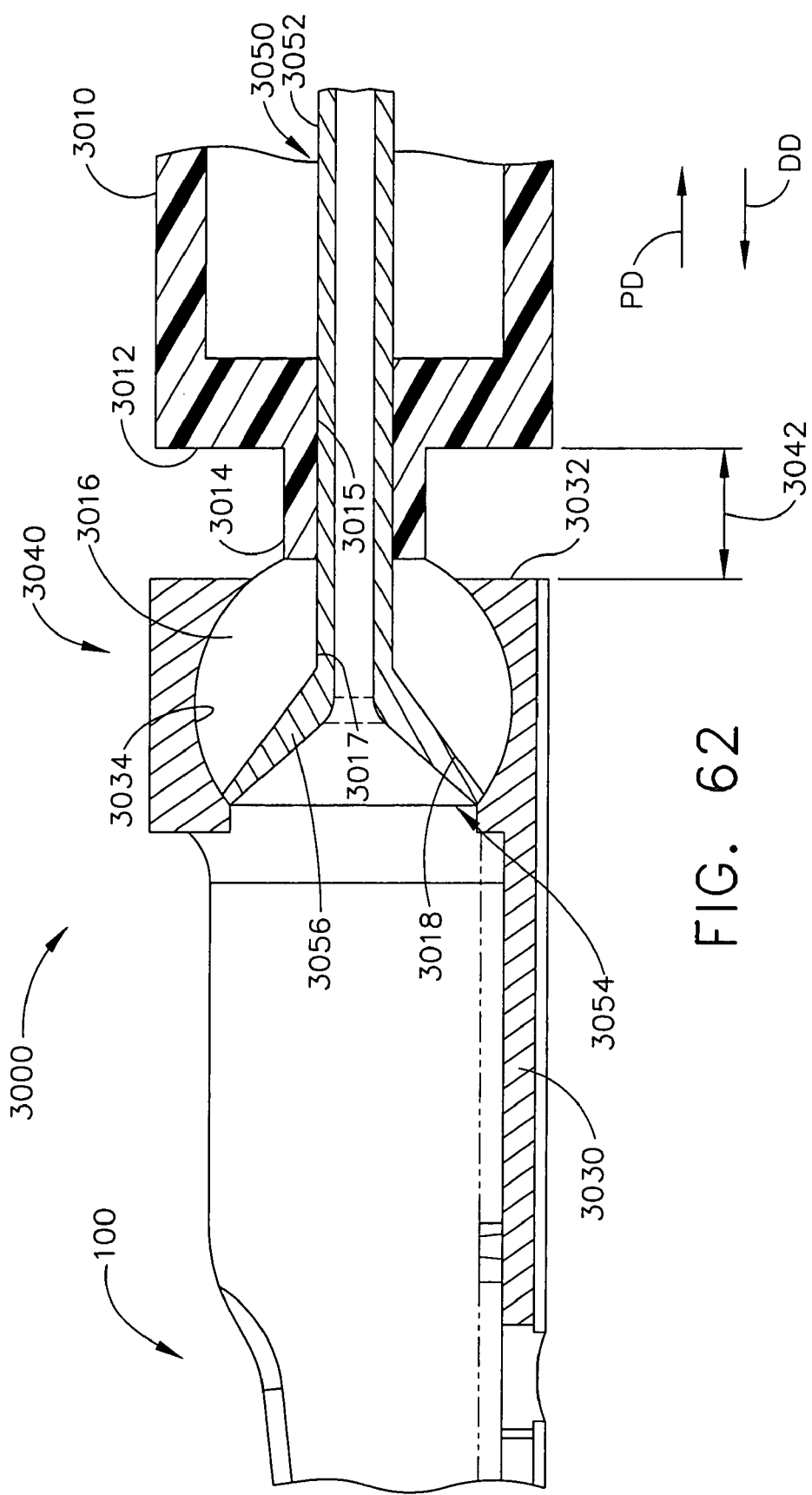
FIG. 62 a cross-sectional view of another lockable articulation joint of another embodiment of the present invention.

FIGS. 62-64 illustrate another lockable articulation joint 3000 of various embodiments of the present invention. As can be seen in those Figures, various embodiments may include a proximal spine segment 3010 that extends from the handle assembly (not shown) and may be supported thereby in any one of a number of known arrangements without departing from the spirit and scope of the present invention. The proximal spine segment 3010 has a distal end 3012 that has a neck portion 3014 protruding therefrom that has a substantially ball-shaped member 3016 formed thereon. As can be seen in FIGS. 63 and 64, the ball-shaped member 3016 has a series of slots 3018 therein that serve to define a series of ball segments 3020. As shown in FIG. 62, the ball-shaped member 3016 may be sized to be received in a socket 3034 formed in a proximal end 3032 of a distal spine segment 3030. The ball-shaped member 3016 and socket 3034 collectively form a ball joint, generally designated as 3040 that affords the distal spine segment 3030 with the ability to articulate in multiple directions relative to the proximal spine segment 3010. A sufficient amount of clearance 3042 may be provided between the proximal end 3032 of the distal spine segment 3030 and the distal end 3012 of the proximal spine segment 3010 to enable the distal spine segment 3030 to articulate in a desired range of motion relative to the proximal spine segment 3010. In various embodiments, the distal spine segment 3030 may be attached to the channel assembly (not shown) to which the anvil (not shown) is pivotally attached.

As can be seen in FIG. 62, an actuation member 3050 may be used to selectively radially extend the ball segments 3020 to expand and lock the ball-shaped member 3016 in the socket 3034. In one embodiment (FIGS. 62-64), the actuation member has a hollow shaft portion 3052 that extends through a passage 3015 in the neck portion 3014 of the proximal spine segment 3010 and also through a passage 3017 in the ball-shaped member 3016. The distal end 3054 of the actuation member 3050 has a substantially cone-shaped portion 3056 that is received in a cone-shaped actuation pocket 3018 in the ball-shaped member 3016 as shown. As the actuation member 3050 is drawn in the proximal direction PD, the cone-shaped portion 3056 causes the ball segments 3020 to extend radially outward and lock the ball-shaped member 3016 within the socket 3034. Various trigger and locking arrangements (not shown) in the handle may be employed to selectively axially move the actuation member in the proximal PD and distal DD directions and lock the actuation member 3050 in position to retain the ball-shaped member 3016 in an expanded/locked condition.

To use this embodiment, the clinician positions the tool assembly 100 in the patient and then applies an articulation force to the tool assembly with another surgical instrument or by bringing the tool assembly 100 into contact with a portion of the patient to articulate the tool assembly to a desired position before drawing the actuation member 3050 in the proximal direction PD. After the tool assembly 100 has been articulated to the desired position, the clinician draws the actuation member 3050 in the proximal direction to cause the ball segments 3020 to expand radially outwardly and lock the ball-shaped member 3016 in that orientation within the socket 3034 to thereby retain the distal spine segment 3030 (and the tool assembly 100 attached thereto) in that articulated position. Such system employs a "passive" articulation technique.

FIGS. 65-67 depict another lockable articulation joint 3100 of various embodiments of the present invention that is substantially identical in operation as articulation joint 3000 described above, except for the actuation member 3150 and the ball-shaped member 3116. As can be seen in those Figures, the ball-shaped member 3116 has at least one and preferably three radially extendable portions 3120 formed therein. The actuation member 3150 has a hollow shaft portion 3152 that extends through a passage 3015 in the neck portion 3014 of the proximal spine segment 3010 and also through a passage 3017 in the ball-shaped member 3116. The distal end 3154 of the actuation member 3150 has a cone-shaped wedge portion 3156 that corresponds to each of the radially extendable portions 3120 in the ball-shaped member 3116 that extends into a cone-shaped actuation pocket 3118 in the ball-shaped member 3116 as shown. As the actuation member 3150 is drawn in the proximal direction PD, the cone-shaped wedge portions 3156 causes the corresponding radially extendable portions 3120 to expand radially outward and lock the ball-shaped member 3116 within the socket 3034. Various trigger and locking arrangements (not shown) in the handle may be employed to selectively move the actuation member in the proximal PD and distal DD directions and lock the member in position to retain the ball-shaped member 3116 in a expanded/locked condition.

To use this embodiment, the clinician positions the tool assembly 100 in the patient and then applies an articulation force to the tool assembly with another surgical instrument or by bringing the tool assembly 100 into contact with a portion of the patient to articulate the tool assembly to a desired position before drawing the actuation member 3150 in the proximal direction PD. After the tool assembly 100 has been articulated to the desired position, the clinician draws the actuation member 3150 in the proximal direction to cause the radially extendable portions 3120 to extend radially outwardly and lock the ball-shaped member 3116 in that orientation within the socket 3034 to thereby retain the distal spine segment 3030 (and the tool assembly 100 attached thereto) in that articulated position. Such system employs a "passive" articulation technique.

Figure 68:
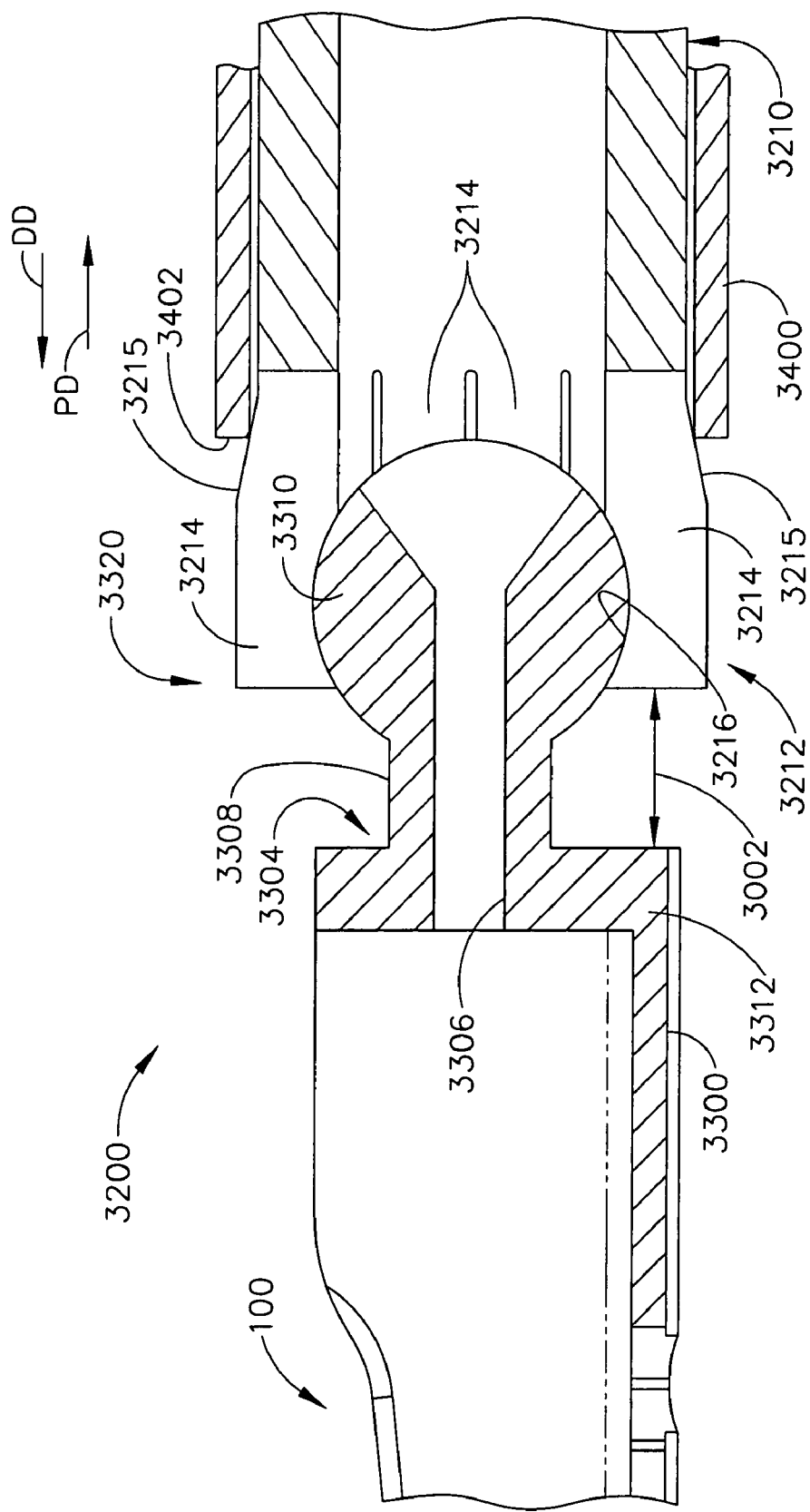
FIG. 68 a cross-sectional view of another lockable articulation joint of another embodiment of the present invention.

FIGS. 68-70 illustrate another lockable articulation joint 3200 of various embodiments of the present invention. As can be seen in those Figures, various embodiments may include a proximal spine segment 3210 that extends from the handle assembly (not shown) and may be supported thereby in any one of a number of known arrangements without departing from the spirit and scope of the present invention. The proximal spine segment 3210 may have a distal end 3212 that has a plurality of radially contractable portions in the form of, for example, flexible socket fingers 3214 that define a socket 3216 therein. As can also be seen in these FIG. 68, a ball-shaped member 3310 may be formed on a proximal end 3312 of a distal spine segment 3300. The ball-shaped member 3310 may be formed on the end of a neck portion 3308 sized to be received in a socket 3216 formed by the socket fingers 3214. The ball-shaped member 3310 and socket 3216 collectively form a ball joint, generally designated as 3320, that affords the distal spine segment 3300 with the ability to articulate in multiple directions relative to the proximal spine segment 3210. A sufficient amount of clearance 3002 may be provided between the proximal end 3304 of the distal spine segment 3300 and the distal end 3212 of the proximal spine segment 3210 to enable the distal spine segment 3300 to articulate in a desired range of motion relative to the proximal spine segment 3210. In various embodiments, the distal spine segment 3300 may be attached to the channel assembly (not shown) to which the anvil (not shown) is pivotally attached. In addition, a hollow passage 3306 may be provided through the ball-shaped member 3310 and a neck portion 3308 to facilitate passage of cables or other actuation instruments/components therethrough.

As can also be seen in FIGS. 68-70, this embodiment may also include a closure ring 3400 that is selectively slidably and axially movable on the proximal spine segment 3210 in the proximal and distal directions. The various systems and components described above may be employed to selectively move the closure ring 3400 in the distal and proximal directions. As can be most particularly seen in FIG. 68, the socket fingers 3214 have a sloped or tapered end surface 3215 to enable the distal end portion 3402 of the closure ring 3400 to slide thereupon and cause the closure fingers to 3214 to close upon the ball-shaped member 3310 and lock it in position.

To use this embodiment, the clinician positions the tool assembly 100 in the patient and then applies an articulation force to the tool assembly with another surgical instrument or by bringing the tool assembly 100 into contact with a portion of the patient to articulate the tool assembly to a desired position before advancing the closure ring 3400 distally. After the tool assembly 100 has been articulated to the desired position, the clinician advances the closure ring 3400 distally to cause the closure fingers 3214 to closure upon the ball-shaped member 3310 and lock the ball-shaped member 3310 in that orientation within the socket 3216 to thereby retain the distal spine segment 3300 (and the tool assembly 100 attached thereto) in that articulated position. Such system employs a "passive" articulation technique.

Figure 71:
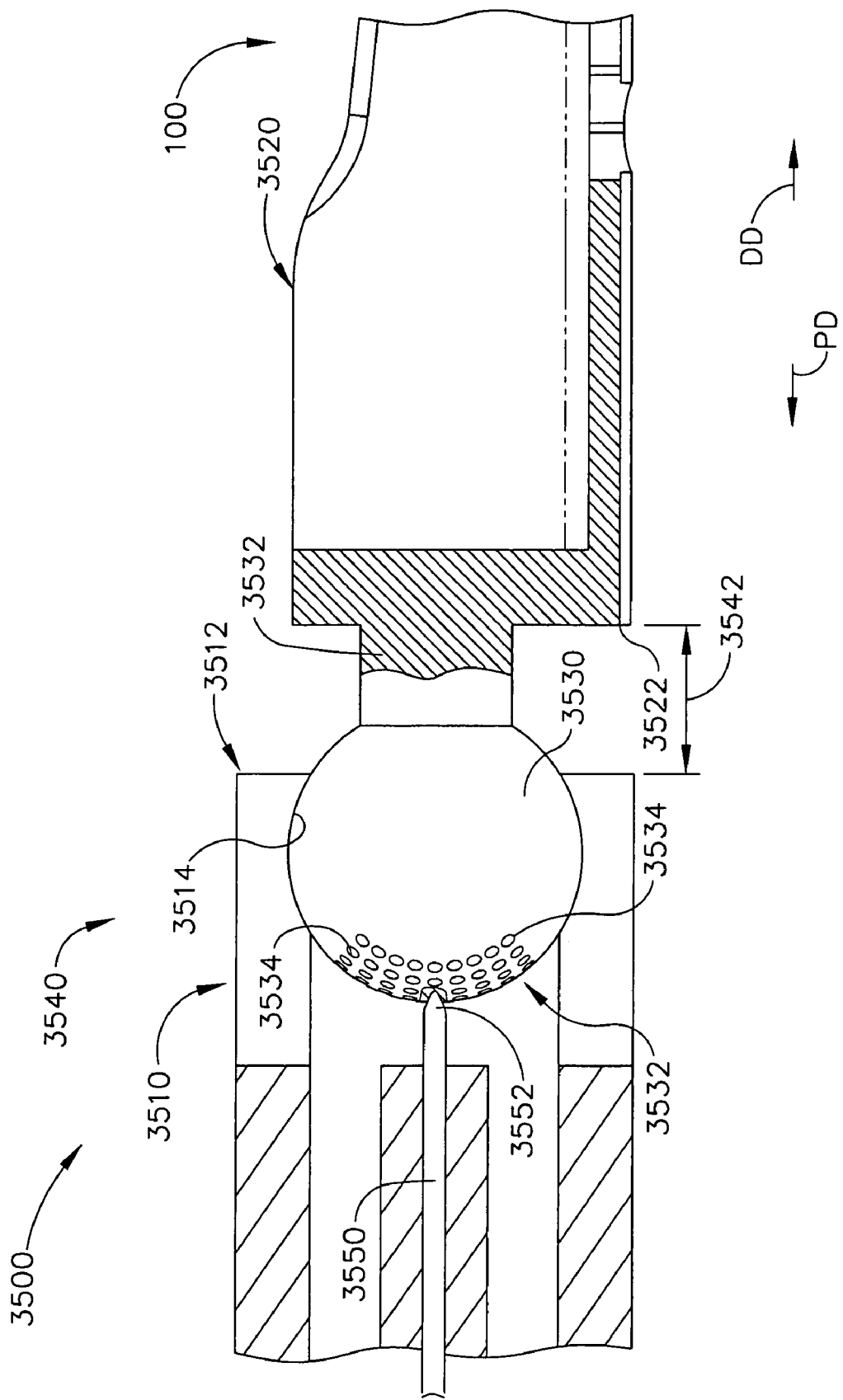
FIG. 71 a cross-sectional view of another lockable articulation joint of another embodiment of the present invention.

FIG. 71 illustrates another passive articulation joint 3500 of various embodiments of the present invention. As can be seen in those Figures, various embodiments may include a proximal spine segment 3510 that extends from the handle assembly (not shown) and may be supported thereby in any one of a number of known arrangements without departing from the spirit and scope of the present invention. The proximal spine segment 3510 may have a distal end 3512 that has a socket 3514 therein. As can also be seen in FIG. 71, a ball-shaped member 3530 is formed on a neck portion 3532 formed on the proximal end 3522 of a distal spine segment 3520. The ball-shaped member 3530 and socket 3514 collectively form a ball joint, generally designated as 3540, that affords the distal spine segment 3520 with the ability to articulate in multiple directions relative to the proximal spine segment 3510. In alternative embodiments, the socket may be formed in the distal spine segment and the ball-shaped member may be formed in the proximal spine segment. A sufficient amount of clearance 3542 may be provided between the proximal end 3522 of the distal spine segment 3520 and the distal end 3512 of the proximal spine segment 3510 to enable the distal spine segment 3520 to articulate in a desired range of motion relative to the proximal spine segment 3510. In various embodiments, the distal spine segment 3520 is attached to the channel assembly (not shown) to which the anvil (not shown) is pivotally attached.

As can be further seen in FIG. 71, the proximal facing face 3532 of the ball-shaped member 3530 has a plurality of detents 3534 formed therein. A locking pin 3550 is operably supported within the proximal spine segment 3510 and is oriented for engagement with the detents 3534. The locking pin 3550 may be spring biased toward the proximal facing face 3532 of the ball-shaped member 3530 such that as the distal spine segment 3520 is articulated relative to the proximal spine segment 3510, the locking pin snaps into a corresponding one of the detents 3534 to retain the distal spine segment 3520 in that position.

To use this embodiment, the clinician positions the tool assembly 100 in the patient and then applies an articulation force to the tool assembly with another surgical instrument or by bringing the tool assembly 100 into contact with a portion of the patient to articulate the tool assembly to a desired position or another surgical tool may be used to apply an articulation force to the tool assembly to cause the tool assembly 100 to move to a desired direction. As the tool assembly is articulated, the distal end 3552 of the locking pin will snap into and out of detents 3534 until the desired articulation position is achieved. Such system employs a "passive" articulation technique.

Figure 72:
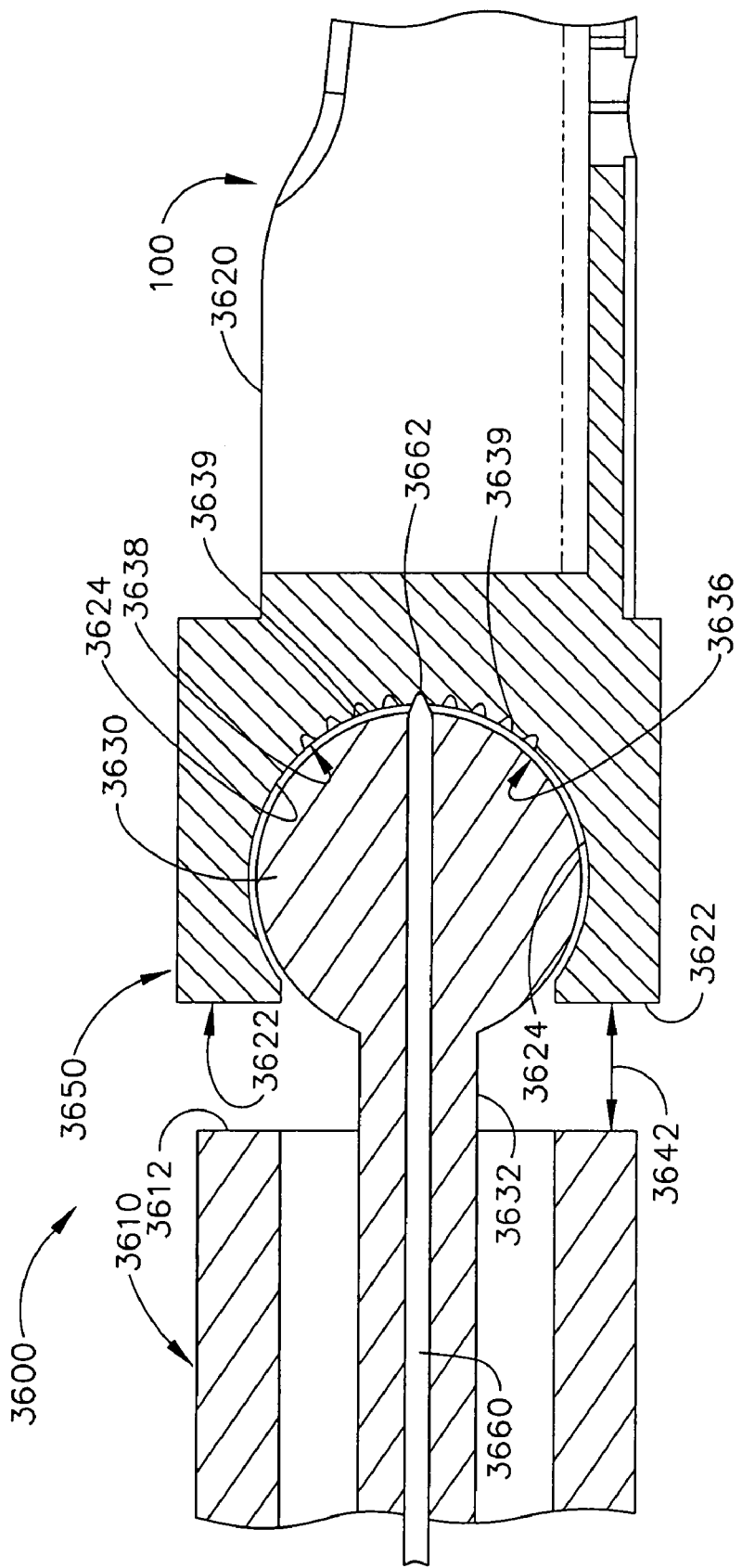
FIG. 72 a cross-sectional view of another lockable articulation joint of another embodiment of the present invention.

FIG. 72 illustrates another passive articulation joint 3600 of various embodiments of the present invention that is somewhat similar to the articulation joint 3500 described above except for the differences discussed below. In this embodiment for example, the ball-shaped member 3630 may be formed on a neck portion 3632 that protrudes distally from the proximal spine segment 3610. The proximal spine segment 3610 may extend from the handle assembly (not shown) and may be supported thereby in any one of a number of known arrangements without departing from the spirit and scope of the present invention. The distal spine segment 3620 has a socket 3624 therein. The ball-shaped member 3630 and socket 3622 collectively form a ball joint, generally designated as 3650 that affords the distal spine segment 3620 the ability to articulate in multiple directions relative to the proximal spine segment 3610. A sufficient amount of clearance 3642 is provided between the proximal end 3622 of the distal spine segment 3620 and the distal end 3612 of the proximal spine segment 3610 to enable the distal spine segment 3620 to articulate in a desired range of motion relative to the proximal spine segment 3610. In various embodiments, the distal spine segment 3620 is attached to the channel assembly (not shown) to which the anvil (not shown) is pivotally attached.

As can be further seen in FIG. 72, a portion 3638 of the socket face 3636 may have a plurality of detents 3639 formed therein. A locking pin 3660 is operably supported within the proximal spine segment 3610 and is oriented for engagement with the detents 3639. The locking pin 3660 may be spring biased toward the face 3636 such that as the distal spine segment 3620 is articulated relative to the proximal spine segment 3610, the locking pin 3660 snaps into a corresponding one of the detents 3639 to retain the distal spine segment 3620 in that position.

To use this embodiment, the clinician positions the tool assembly 100 in the patient and then applies an articulation force to the tool assembly with another surgical instrument or by bringing the tool assembly 100 into contact with a portion of the patient to articulate the tool assembly to a desired position or another surgical tool may be used to apply an articulation force to the tool assembly to cause the tool assembly 100 to move to a desired direction. As the tool assembly is articulated, the distal end 3662 of the locking pin 3660 will snap into and out of detents 3639 until the desired articulation position is achieved. Such system employs a "passive" articulation technique.

Various surgical stapling instrument embodiments of the present invention may be designed to accommodate tool assemblies that are designed to be discarded after a single use. After the stapling operation is completed, the tool assembly is discarded and the instrument may be re-sterilized in preparation for another operation. In such applications, it is often desirable, therefore, to employ a joint arrangement that facilitates quick attachment and detachment of the tool assembly to the instrument. FIGS. 73-83 illustrate a surgical instrument 4000 that is constructed for use in connection a surgical tool assembly 100" that can perform a surgical action. In various embodiments, the tool assembly 100" is constructed to cut and staple tissue my means of the cable-powered dynamic clamping member/knife arrangement described above. In other embodiments, different drive arrangements may be employed to drive the dynamic clamping member/knife through the elongate channel portion of the tool assembly 100".

In some embodiments, the tool assembly 100" comprises a portion of a disposable reload unit 4002. In other embodiments, the tool assembly 100" may be permanently attached to the other portions of the instrument 4000 and capable of reuse in connection with staple cartridge assemblies. The disposable reload unit 4002 may further include a connector segment 4004 for coupling the disposable reload unit 4002 to the instrument 4000. In various embodiments, the tool assembly 100" may be articulatable relative to the connector portion 4004 by means of an articulation joint 4006.

Figure 73A:
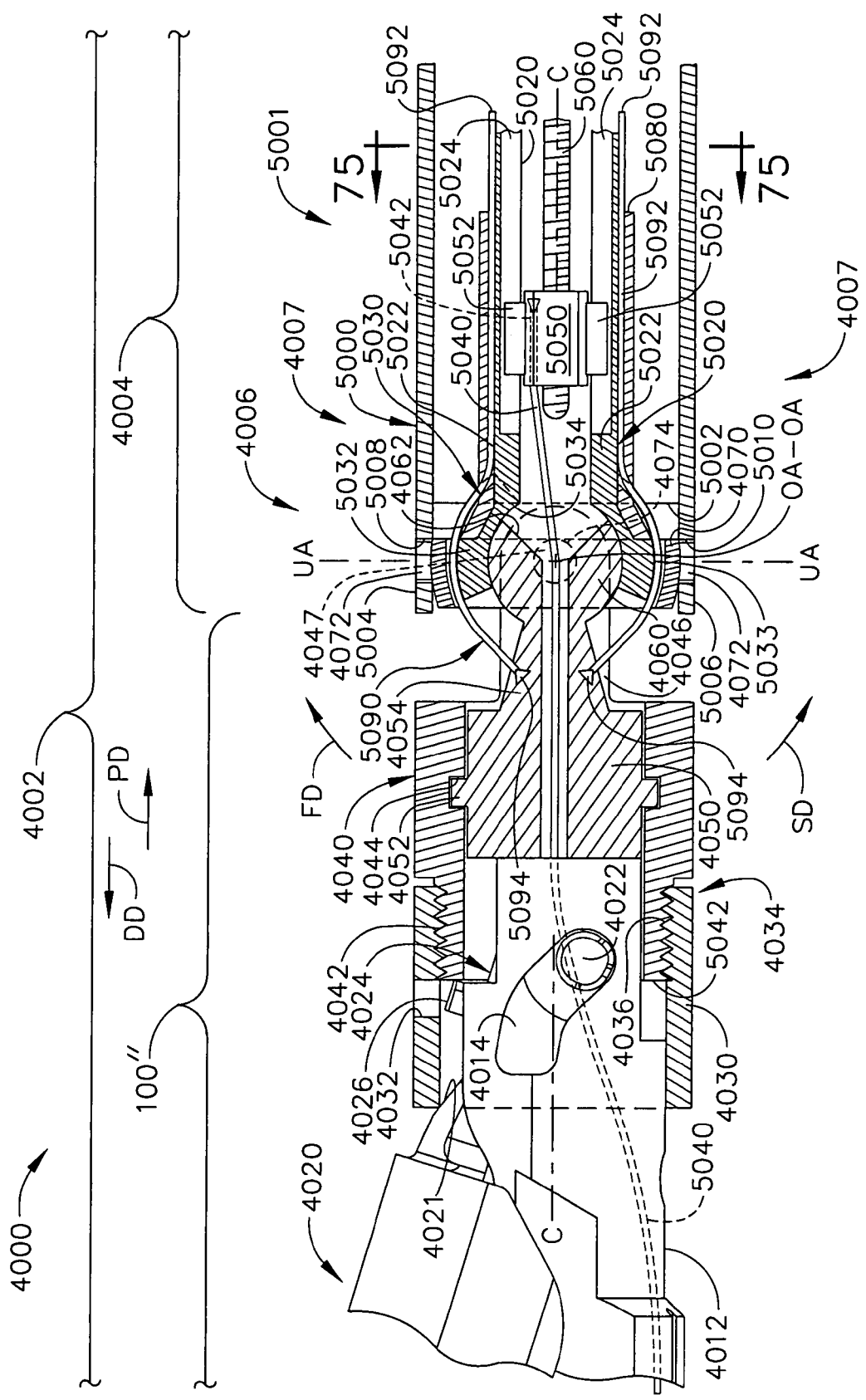
FIG. 73A is a partial cross-sectional view of a tool assembly and articulation joint of another surgical instrument embodiment of the present invention.

As can be most particularly see in FIG. 73A, one tool assembly 100" embodiment may include an elongate channel assembly 4012 that has an anvil assembly 4020 pivotally coupled thereto. For example, in one embodiment, the anvil assembly 4020 may have a pair of trunnions 4022 that are adapted to be received in corresponding slots 4014 in the walls of the elongate channel assembly 4012 as shown. The anvil assembly 4020 may be formed with an anvil closure tab 4026 on a proximal end 4024 thereof for selective contact by a closure ring 4030. The non-rotating closure ring 4030 is keyed to the elongate channel assembly 4012 and/or anvil assembly 4020 such that the closure ring 4030 cannot rotate relative to the elongate channel 4012. A tab clearance opening 4032 may be provided through the closure ring 4030 to receive the anvil closure tab 4026 when the anvil assembly 4020 is in the closed (clamped) position. A series of internal threads 4036 may be provided in the proximal end 4034 of the non-rotating closure ring 4030 for threadably receiving a threaded distal end 4042 of a distal closure tube segment 4040. As will be discussed in further detail below, as the distal closure tube segment 4040 is rotated, the closure ring 4030 is driven axially in the distal direction DD. As the closure ring 4030 moves in the distal direction DD, it rides up a ramp 4021 on the proximal end of anvil assembly 4020 to cause the anvil assembly 4020 to pivot to a closed position. Such arrangement represents a vast improvement over prior arrangements wherein the closure ring is pulled by a cable in the distal direction.

The surgical instrument 4000 may further include an elongate closure tube assembly 5000 that houses a variety of components and which is operably attached to a handle assembly as will be discussed in further detail below. In various embodiments of the present invention, the closure tube assembly 5000 may comprise an intermediate closure tube segment 5001 and a proximal closure tube segment 5020. In some embodiments, the tool assembly 100" may be coupled to the intermediate closure tube segment 5001 of closure tube assembly 5000 by an articulation joint 4006 that facilitates travel of the tool assembly 100" relative to the closure tube assembly 5000 about two axes UA-UA and OA-OA that are substantially orthogonal to each other as will be discussed in further detail below. Also, various embodiments may include a means for actively controlling the pivotal travel of the tool assembly 100" as well as having the capability of passive articulation while also having the ability to lock the tool assembly in the desired articulated position. These unique and novel features and advantages will become further apparent as the present Detailed Description proceeds.

In various embodiments, for example, the distal closure tube segment 4040 may be formed with a pair of opposed universal pivot arms 4046 that protrude in the proximal direction therefrom. The distal end 5002 of the intermediate closure tube segment 5001 may be formed with two opposing fastener arms 5004, 5006 that protrude distally therefrom. See FIGS. 73A and 74B. Fastener arm 5004 has a pivot hole 5008 therethrough and fastener arm 5006 has a pivot hole 5010 that is substantially coaxially aligned with the pivot hole 5008 to define the universal pivot axis UA-UA. Positioned between the fastener arms 5004 and 5006 is a universal ring 4070 that has two pairs of pins 4072, 4074 protruding therefrom wherein each pin may be spaced ninety degrees from each other about the circumference of the universal ring 4070 (one pin 4074 is shown in dashed lines in FIGS. 73A and 74A). As shown in FIG. 73A, one pin 4072 is pivotally received in upper pivot hole 5008 in the fastener arm 5004 and the other pin 4072 is pivotally received in the lower pivot hole 5010 in the fastener arm 5006. Such arrangement enables the universal ring 4070 to pivot about the universal axis UA-UA relative to the closure tube assembly 5000. Each of the opposed universal pivot arms 4046 protruding from the distal closure tube 4040 has a hole 4047 therein to pivotally receive a corresponding one of the pins 4074 therein to enable the distal closure tube 4040 to pivot relative to the universal ring 4070 and closure tube assembly 5000 about an orthogonal axis OA-OA (shown in FIG. 75) in a first pivotal direction represented by arrow FD in FIG. 73A and second pivotal direction represented by arrow SD in FIG. 73A. Axis UA-UA and OA-OA may be substantially orthogonal to each other.

Thus, the person of ordinary skill in the art will appreciate that the above-described universal ring 4070 arrangement facilitates the articulation of the distal closure tube 4040 and ultimately tool assembly 100" which is attached thereto about multiple axes UA-UA and OA-OA relative to the closure tube assembly 5000. In addition, as will be further described below, in various embodiments, the closure tube assembly 5000 may be rotatably supported by the handle assembly such that it may be rotated around the shaft axis C-C. Because the tool assembly 100" is affixed to the closure tube assembly 5000 (through the articulation joint 4006), the tool assembly 100" is also rotated therewith. Such arrangement, therefore, provides a tool assembly 100" that may have a cable driven knife assembly therein and a non-cable driven anvil closure arrangement with the ability to be articulated about several axes.

Figure 74A:
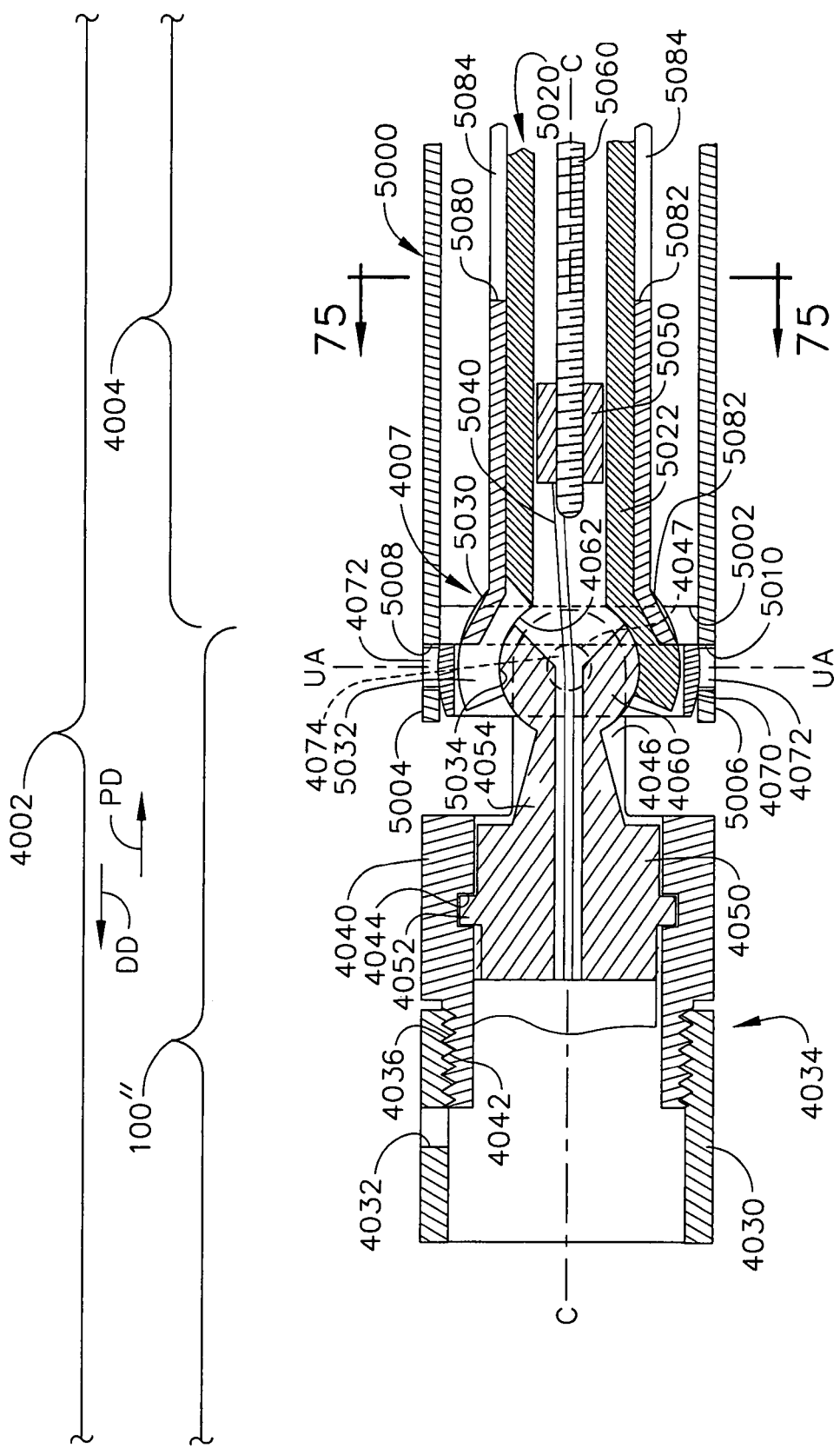
FIG. 74A is another partial cross-sectional view of a tool assembly and articulation joint of the surgical instrument of FIGS. 73A and 73B.

As can also be seen in FIGS. 73A and 74A, this embodiment may further include a distal spine segment 4050 that may have an annular retaining flange 4052 formed thereon that is received in a locating groove 4044 in the distal closure tube 4040. In various embodiments, the articulation joint 4006 may also include an articulation joint locking assembly, generally designated as 4007, which facilitates the locking of the articulation joint 4006 after the tool assembly 100" has been articulated to a desired orientation. Such locking assembly 4007 may include a ball-shaped member 4060 that is formed on a neck portion 4054 of the distal spine segment 4050. The locking assembly 4007 may further include a serrated socket member 5030 that is formed on the distal end 5022 of an intermediate spine segment 5020 located in a connector segment 4004. Serrated socket member 5030 may comprise a plurality of radially contractable fingers 5032 that define a socket 5034 therebetween in which the ball-shaped member 4060 may articulate in multiple directions. The serrated socket member 5030 is mounted within the universal ring 4070.

In various embodiments, a socket locking tube 5080 may be coaxially received on the disposable spine segment 5020 such that it is axially movable relative thereto as will be discussed in further detail below. The distal end 5082 of the locking tube 5080 may be tapered for selective axial contact with the serrated socket member 5030 as the locking tube 5080 is axially advanced in the distal direction DD to cause the serrated fingers 5032 to radially contract and close around the ball-shaped member 4060 to lock the distal spine segment 4050 (and tool assembly 100") in position relative to the elongate closure tube assembly 5000.

Figure 73B:
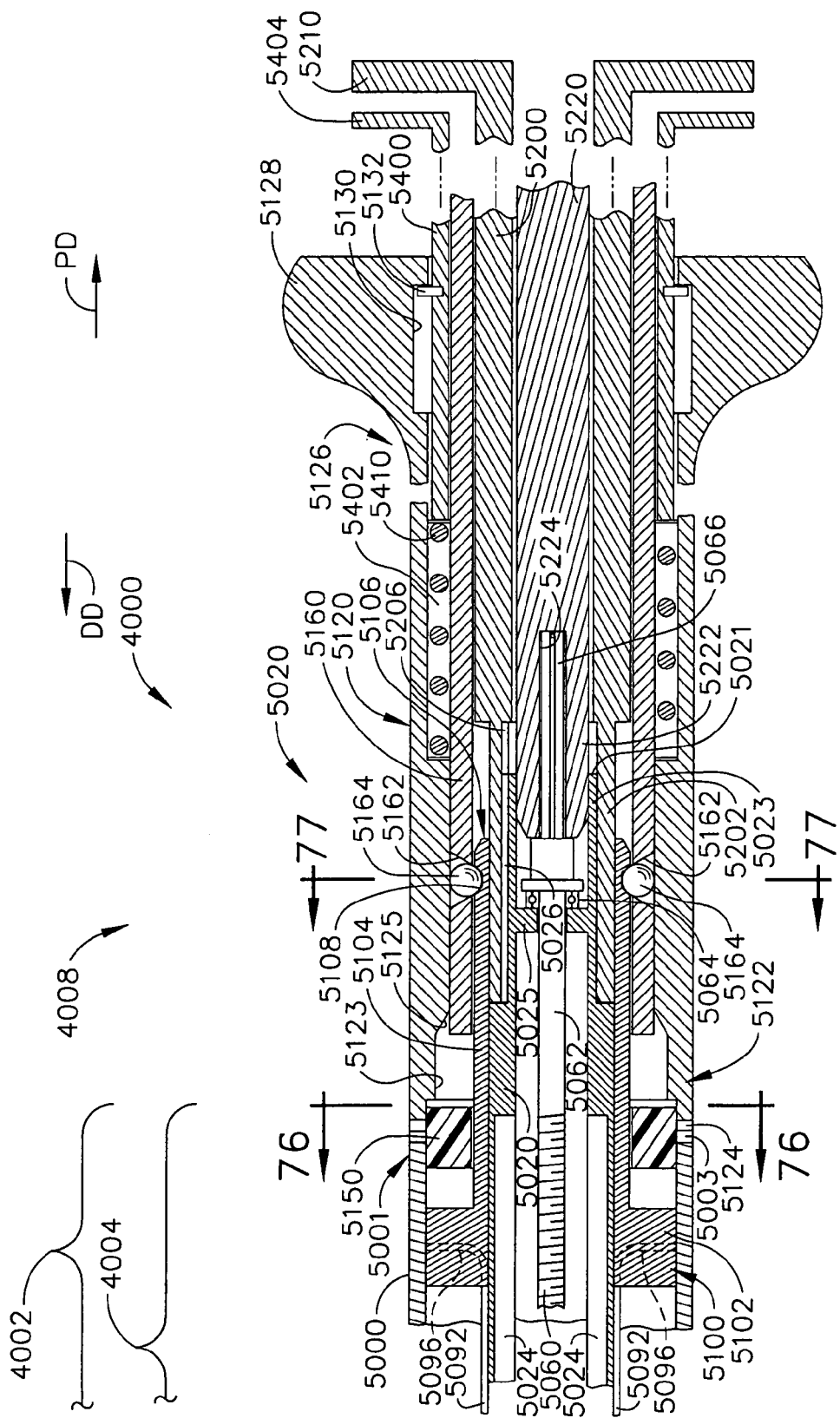
FIG. 73B is a partial cross-sectional view of the closure tube assembly of the surgical instrument of FIG. 73A.

The surgical instrument 4000 of various embodiments of the present invention may further include an active articulation system generally designated as 5090 for actively applying articulation motions to the distal spine segment 4050. In various embodiments, for example, the active articulation system 5090 may include four articulating wires 5092 that may be fabricated from spring steel or the like and be sufficiently stiff to transfer a compression force applied to a proximal end portion thereof without collapsing. The wires 5092 may be spaced around the serrated socket 5030 at ninety degree intervals from each other and be received within corresponding grooves 5033 in the outer surface of the corresponding radially contractable fingers 5032. The distal end 5094 of each wire 5092 may be attached to the neck portion 4054 of the distal spine segment 4050 and the proximal ends 5096 of each wire 5092 may be attached to a hub portion 5102 of a distal wire mount 5100 received within the closure tube 5000 as shown in FIG. 73B. As will be discussed in further detail below, the distal spine segment 4050 (and tool assembly 100" attached thereto) may be actively articulated by pulling and pushing the wires 5092.

Figure 75:
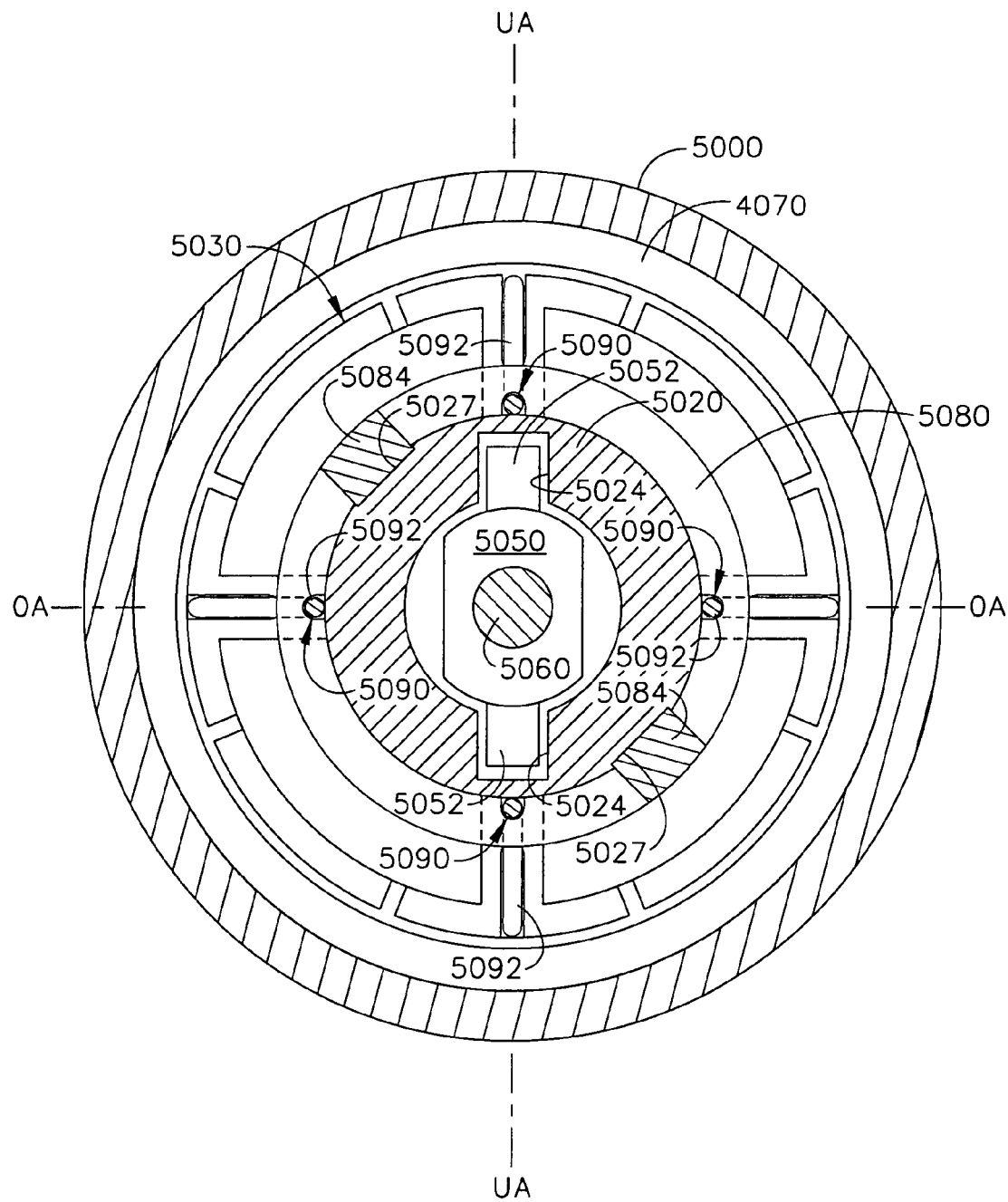
FIG. 75 is a cross-sectional view through the closure tube assembly depicted in FIG. 74A taken along line 75-75 in FIG. 74A.

Also in various embodiments, the proximal facing portion of ball-shaped member 4060 may have a substantially conical shaped cavity 4062 therein to accommodate one or more knife actuation cables 5040 that are attached to a dynamic clamping member (not shown) and/or knife (not shown) mounted within the disposable tool assembly 100". The proximal end 5042 (FIG. 73A) of the cable 5040 may be attached to a knife nut 5050 that is threadably journaled on a knife screw 5060. As can be seen in FIGS. 73A and 75, the knife nut 5050 has a pair of laterally protruding tabs 5052 that are axially received in corresponding axially extending slots 5024 in the disposable spine segment 5020. The person of ordinary skill in the art will appreciate that such arrangement permits the knife nut 5050 to move axially in the proximal direction PD or distal direction DD as the knife screw 5060 is rotated.

Figure 74B:
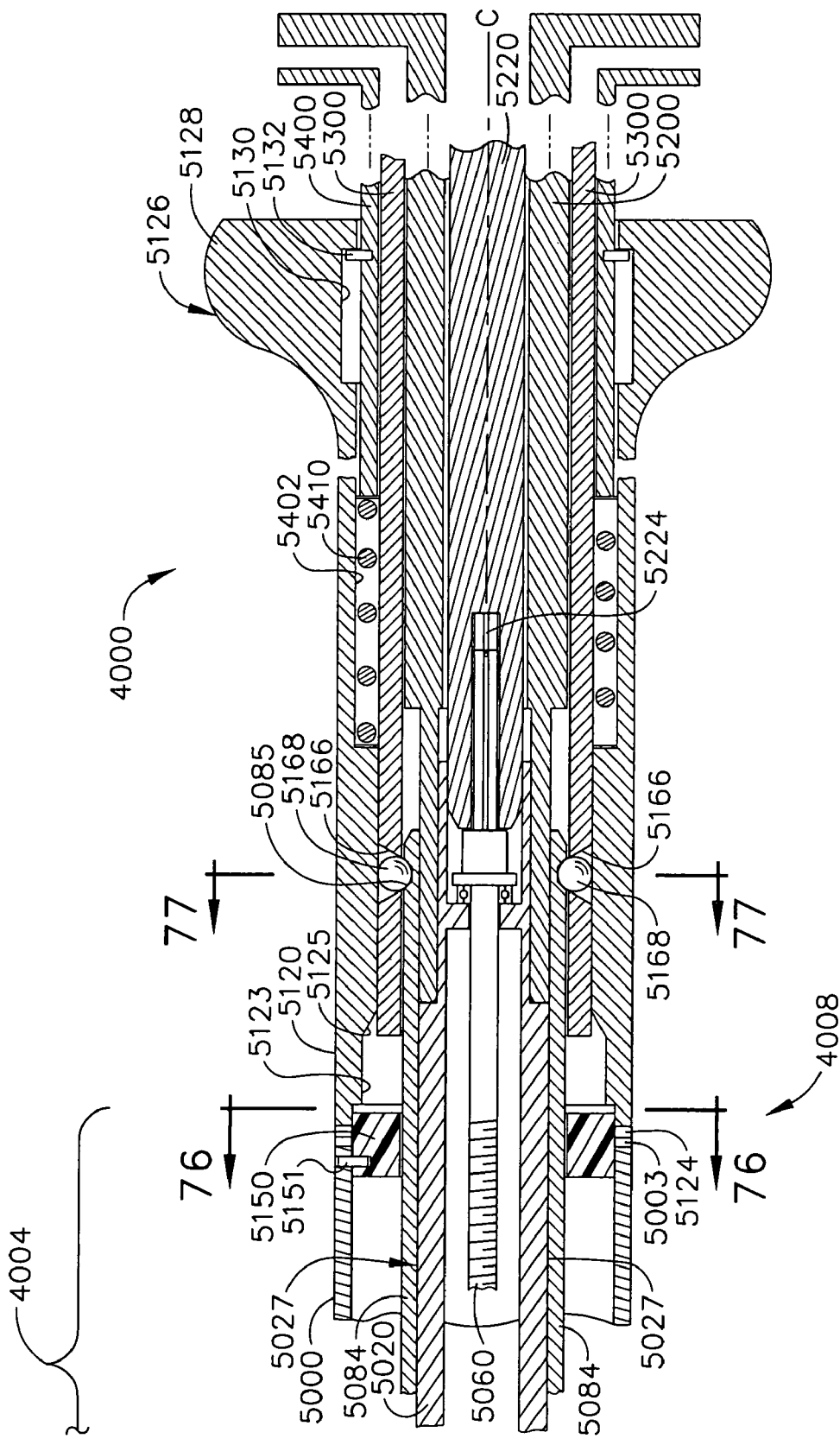
FIG. 74B is another partial cross-sectional view of the closure tube assembly of the surgical instrument of FIGS. 73A and 73B.
Figure 76:
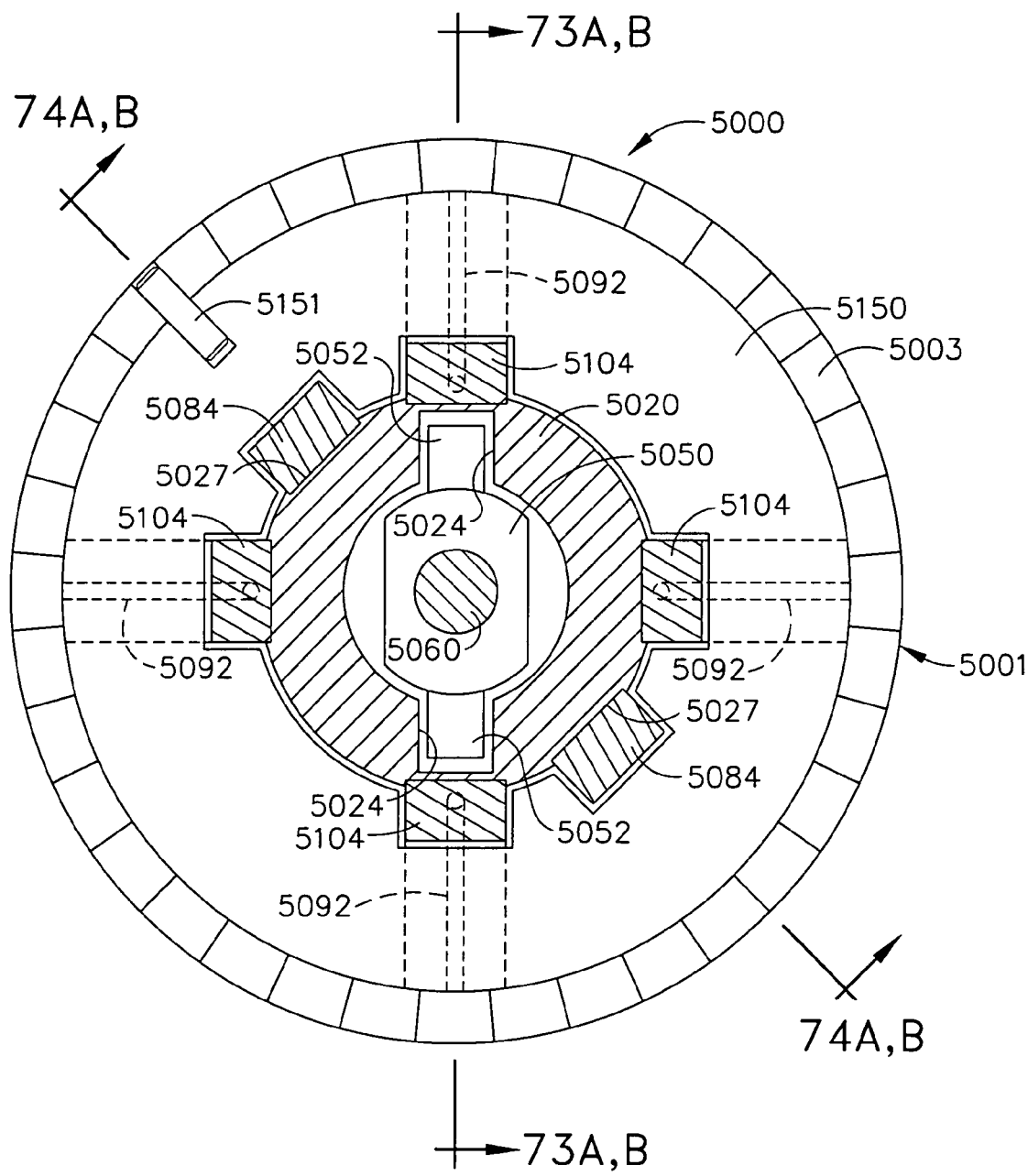
FIG. 76 is another cross-sectional view of the closure tube assembly depicted in FIG. 74B taken along line 76-76 in FIG. 74B.
Figure 77:
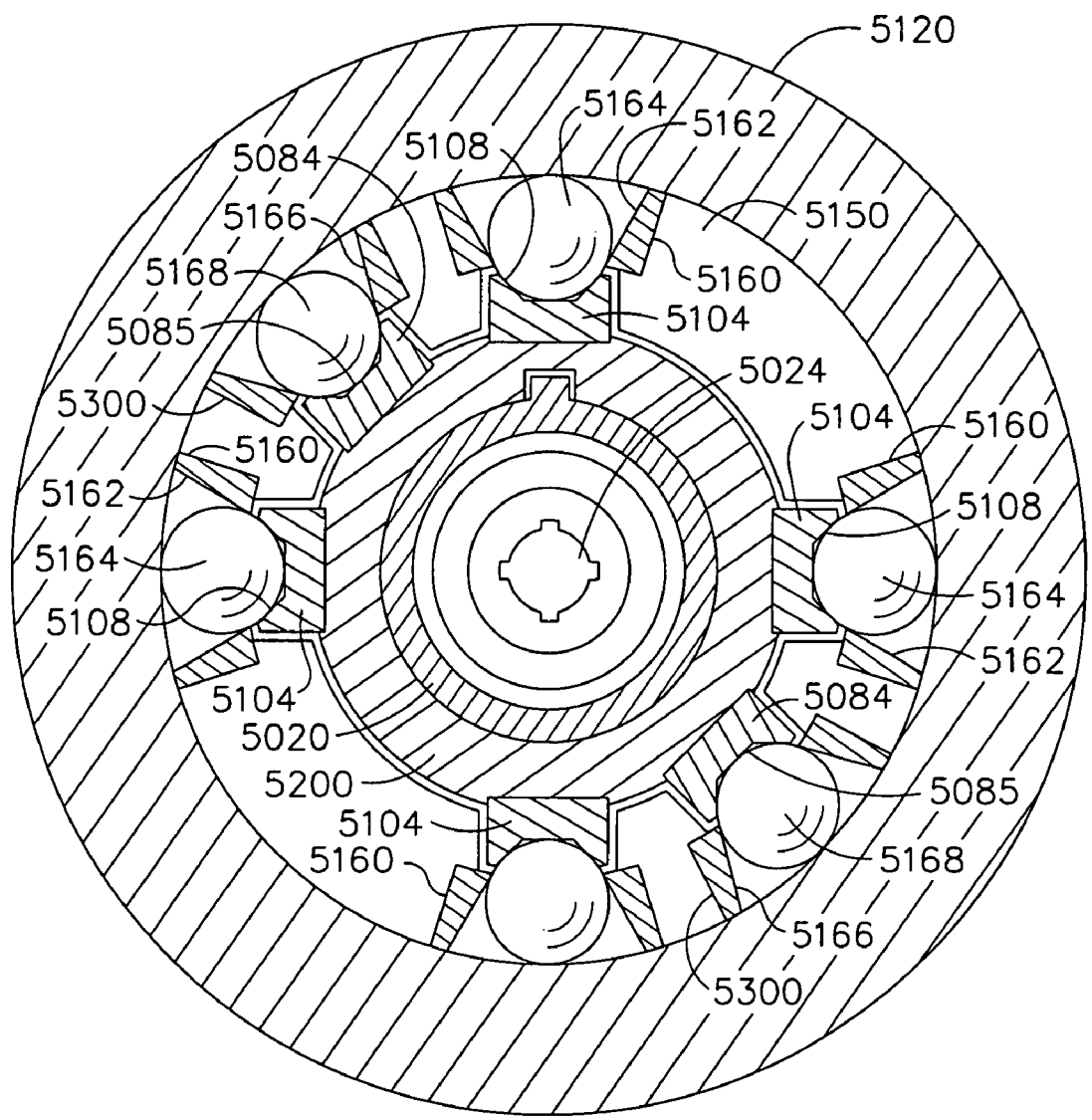
FIG. 77 is another cross-sectional view of the closure tube assembly depicted in FIG. 74B taken along line 77-77 in FIG. 74B.

As indicated above, the disposable reload unit 4002 in various embodiments may be constructed to be disposable after one use. To facilitate quick detachment of a reload unit 4002 and reattachment of a new reload unit 4002 without the use of tools, a quick disconnect joint 4008 may be employed. As used herein, the term "quick disconnect" refers to the ability to detach one component from another component without the use of tools. The operation and construction of various embodiments of the quick disconnect joint 4008 may be understood from reference to FIGS. 73B, 74B, and 76. As can be seen in FIGS. 73B and 74B, the closure tube assembly 5000 comprises an intermediate closure tube segment 5001 and a proximal closure tube segment 5020. As can be seen in FIGS. 73B and 76, the proximal end of the intermediate closure tube segment 5001 has a series of radial gear teeth 5003 formed thereon for meshing engagement with gear teeth 5124 (not shown in FIG. 76) on a distal end 5122 of a proximal closure tube segment 5120 (not shown in FIG. 76) when the disposable reload unit 4002 is attached the proximal closure tube segment 5120.

To support the removable interconnection between the disposable reload unit 4002 and the proximal closure tube segment 5120, a connection spider 5150 may be employed. The connection spider 5150 may be partially received within the proximal end of the intermediate closure tube segment 5001 and protrude therefrom such that when the intermediate closure tube segment 5001 is coupled to the proximal closure tube segment 5120, a portion of the connection spider 5150 protrudes into the distal end 5122 of the proximal closure tube segment 5120. In various embodiments, the connection spider may be pinned within the proximal end of the intermediate closure tube segment 5001 by a pin 5151, adhesive or other suitable fastener arrangements. See FIG. 76.

In various embodiments, the connection spider 5150 may also be journaled on a disposable spine segment 5020 and configured to receive corresponding actuator bars 5104 that protrude from a distal wire mount 5100. The proximal end 5106 of each actuator bar 5104 may contain a tapered detent to facilitate interconnection with a plurality of proximal wire connector members 5160. In one embodiment for example, four proximal wire connector members are employed. The plurality of actuator bars 5104 may be provided with a detent 5108 for receiving a corresponding connector ball 5164 mounted within tapered bore detent 5162 in each of the proximal wire connectors 5160. See FIGS. 73B and 77. Thus, four connector balls 5164 are employed—one for each proximal wire connector 5160. As can also be seen in FIG. 73B, 78, and 79, the proximal end 5021 of the disposable spine segment 5020 has a proximally extending connection portion 5023 that may have an internal collar portion 5025 formed therein to support a proximal end portion 5062 of the knife screw 5060. In addition, the proximally extending connection portion 5023 may have an external spine key 5026 formed thereon for receipt in a key slot 5206 formed in a distal end 5202 of the proximal spine segment 5200. The proximal end 5062 of the knife screw 5060 may be supported in a bearing 5064 and have a splined drive portion 5066 for non-rotatable receipt in a spline drive cavity 5224 in the distal end 5222 of a knife drive shaft 5220. See FIG. 78

Turning next to FIGS. 74A and 74B, the attachment of the locking tube 5080 may be understood. As can be seen in FIG. 74A, the locking tube 5080 a pair of brake actuator arms 5084 protrude proximally therefrom. FIG. 74B is a cross-section that is rotated approximately 45 degrees from the cross-section shown in FIG. 73B. As can be seen in FIG. 74B, each brake actuator arm 5084 has a detent 5085 formed therein for receiving connector balls 5168 mounted within tapered bore detents 5166 in a corresponding proximal brake actuator arm 5300. See FIGS. 74B and 77. To provide the brake actuator arm 5084 with sliding lateral support, each brake actuator arm 5084 may be slidably received in a corresponding groove 5027 in the disposable spine segment 5020. See FIGS. 75 and 76.

Figure 78:
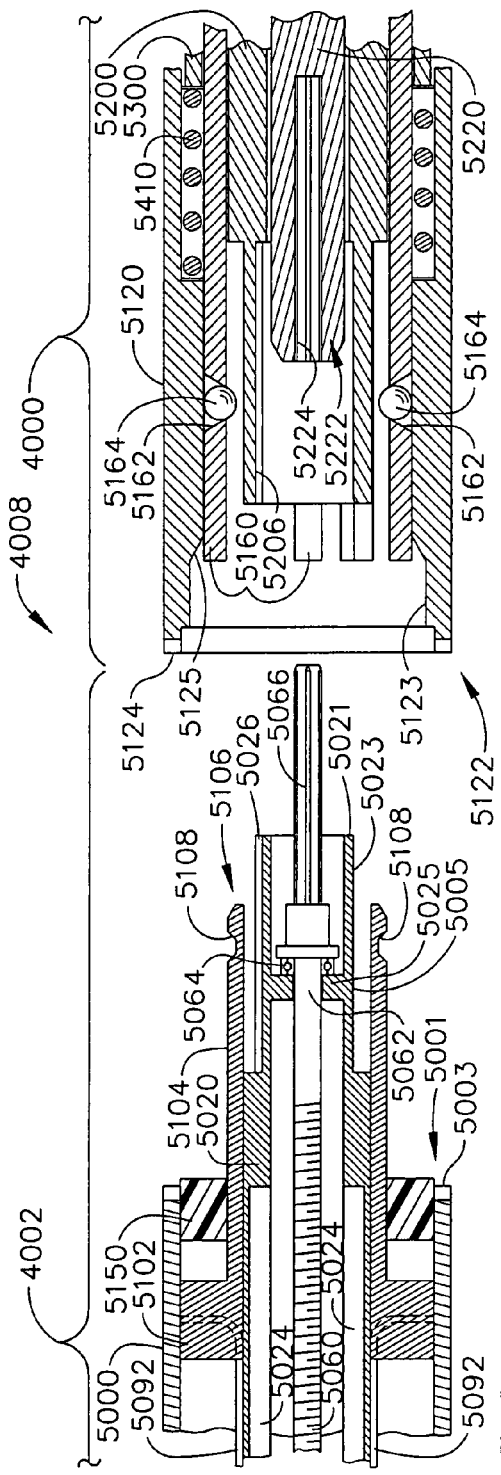
FIG. 78 is a partial exploded assembly view of a quick disconnect joint of an embodiment of the present invention with the components thereof shown in cross-section.
Figure 79:
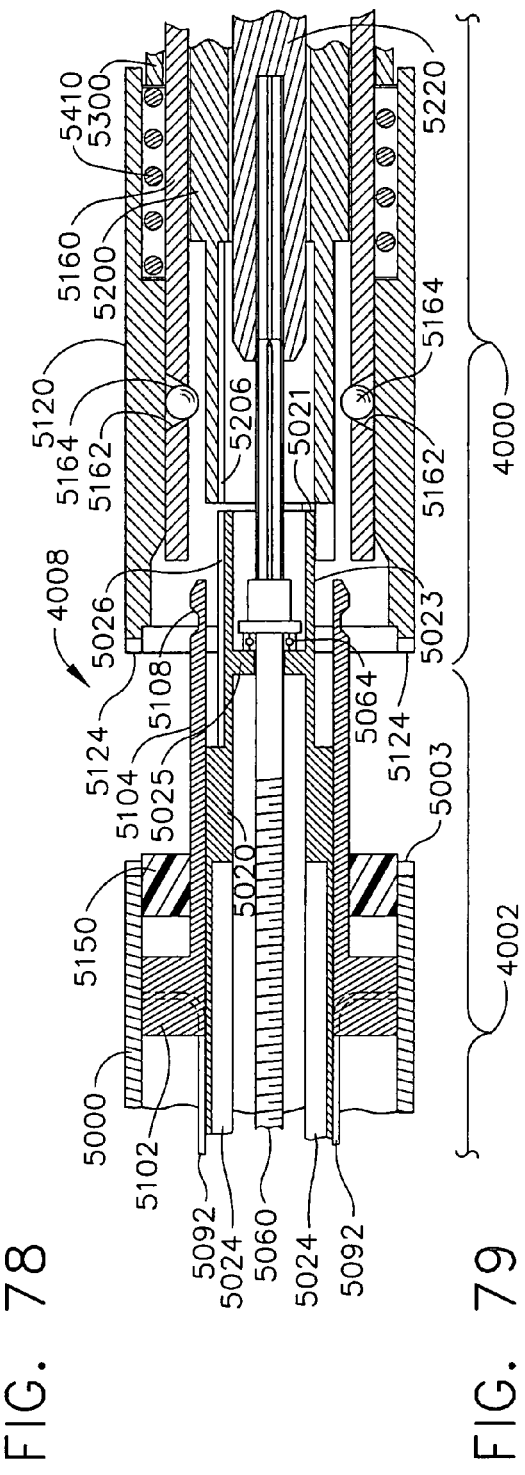
FIG. 79 is another partial exploded assembly view of the quick disconnect joint of FIG. 78.
Figure 80:
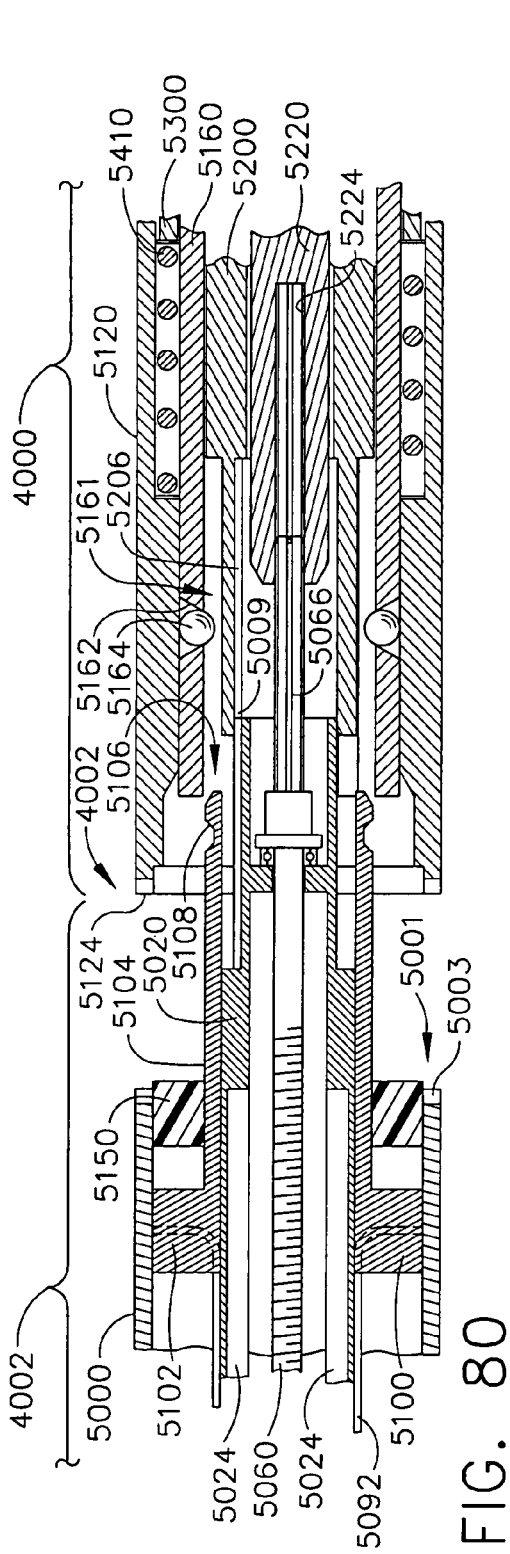
FIG. 80 is another partial exploded assembly view of the quick disconnect joint of FIGS. 78 and 79.
Figure 81:
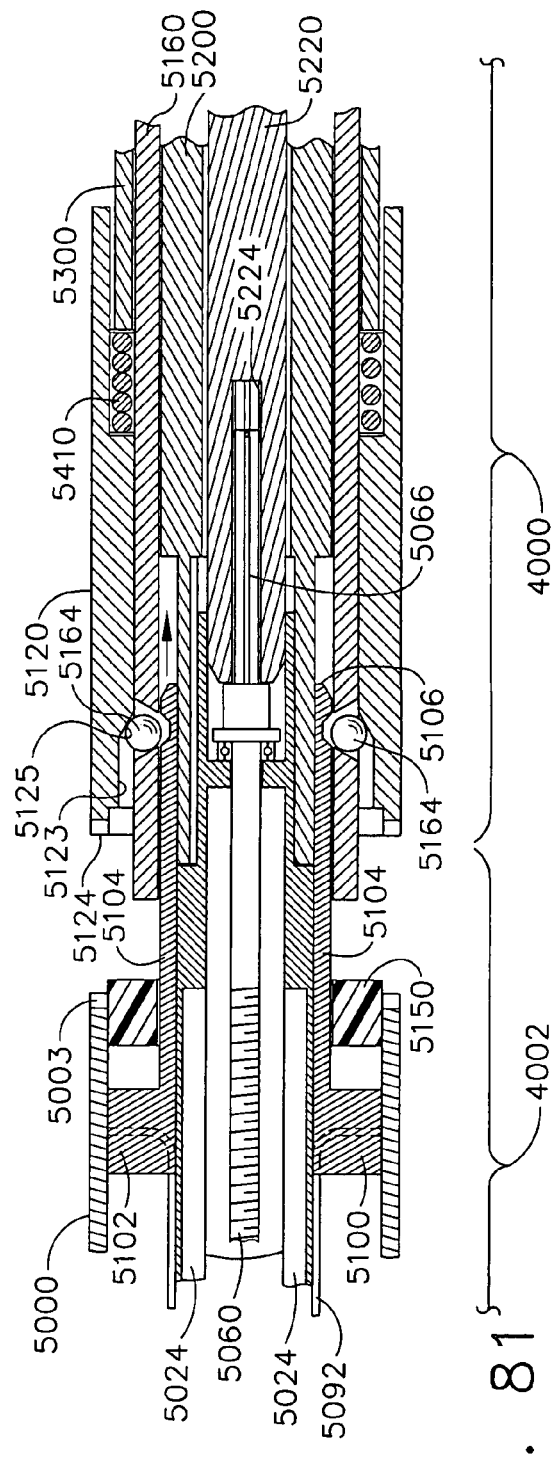
FIG. 81 is another partial exploded assembly view of the quick disconnect joint of FIGS. 78-80.

As can also be seen in FIG. 73B, an outer proximal spine segment 5400 may be received within the proximal closure tube 5120 and cooperates therewith to define a spring cavity 5402 for receiving a closure tube spring 5410 therein. The proximal end 5126 of the proximal closure tube segment 5120 may have an enlarged knob portion 5128 thereon to facilitate the application of control motions thereto by the clinician. A pocket 5130 may be formed in the knob portion 5128 for receiving a clip ring 5132 therein that is affixed to the outer proximal spine segment 5400. Thus, the closure tube spring 5410 serves to bias the proximal closure tube segment 5120 into meshing engagement with the disposable closure tube segment 5000. As can be seen in FIGS. 73B and 78, the distal end 5122 of the proximal closure tube segment 5120 has a larger internal diameter 5123 that has a tapered surface 5125 To disengage the tool assembly 100" from the instrument 4000, the clinician draws the knob 5128 in the proximal direction PD against the force of the spring 5410 until the larger internal diameter portion 5123 is oriented in registration with the connector balls 5164 to enable the connector balls 5164 to move out of engagement with the detents 5108 in the proximal ends 5106 of the actuator bars 5104 of the distal wire mount 5100 when the user applies a removal force to the tool assembly 100" pulling it in the distal direction DD.

FIGS. 78-81 illustrate the attachment of a disposable reload unit 4002 to the instrument portion 4000. With particular reference to FIG. 78, the clinician orients the unit 4002 such that the spline portion 5066 of the knife screw 5060 is aligned with the internal spline cavity 5224 in the knife drive shaft 5220 and inserts the proximal end of the spline drive portion 5066 therein. See FIG. 79. Thereafter, the clinician aligns the spine key 5026 on the proximal end 5021 of the disposable spine segment with the key slot 5206 in the proximal spine segment 5200. See FIGS. 79 and 80. The clinician then continues to insert the proximal end 5106 into the area 5161 between the four proximal wire connectors 5160 and the proximal spine segment 5200. See FIG. 80. The clinician may then move the closure knob 5128 in the proximal direction to enable the connector balls 5164 to move radially outward as the proximal ends 5106 of the actuator bars 5104 are pushed proximally into position. The clinician then releases the knob 5128 to permit the proximal closure tube 5120 to move distally locking the connector balls 5164 in the detents 5108 in the actuator bars 5104 of the distal wire mount 5100 to affix the four proximal wire connectors 5160 to the distal wire mount 5100 and also lock the connector balls 5168 in the detents 5085 in the brake actuator arms 5084. In addition, the radial gears 5003, 5124 are retained in meshing engagement with each other.

Figure 82:
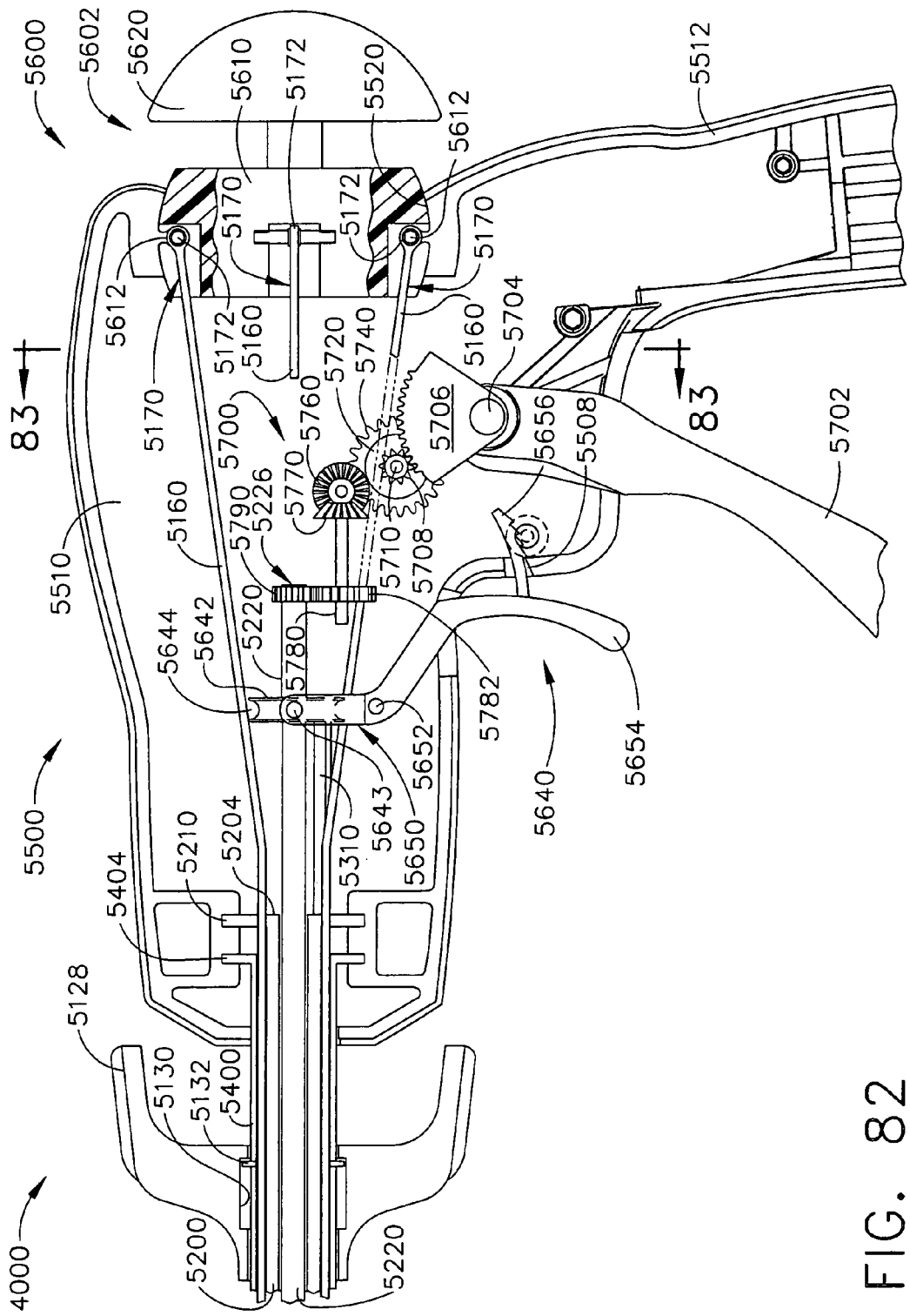
FIG. 82 is a cross-sectional view of another handle assembly embodiment of the present invention.
Figure 83:
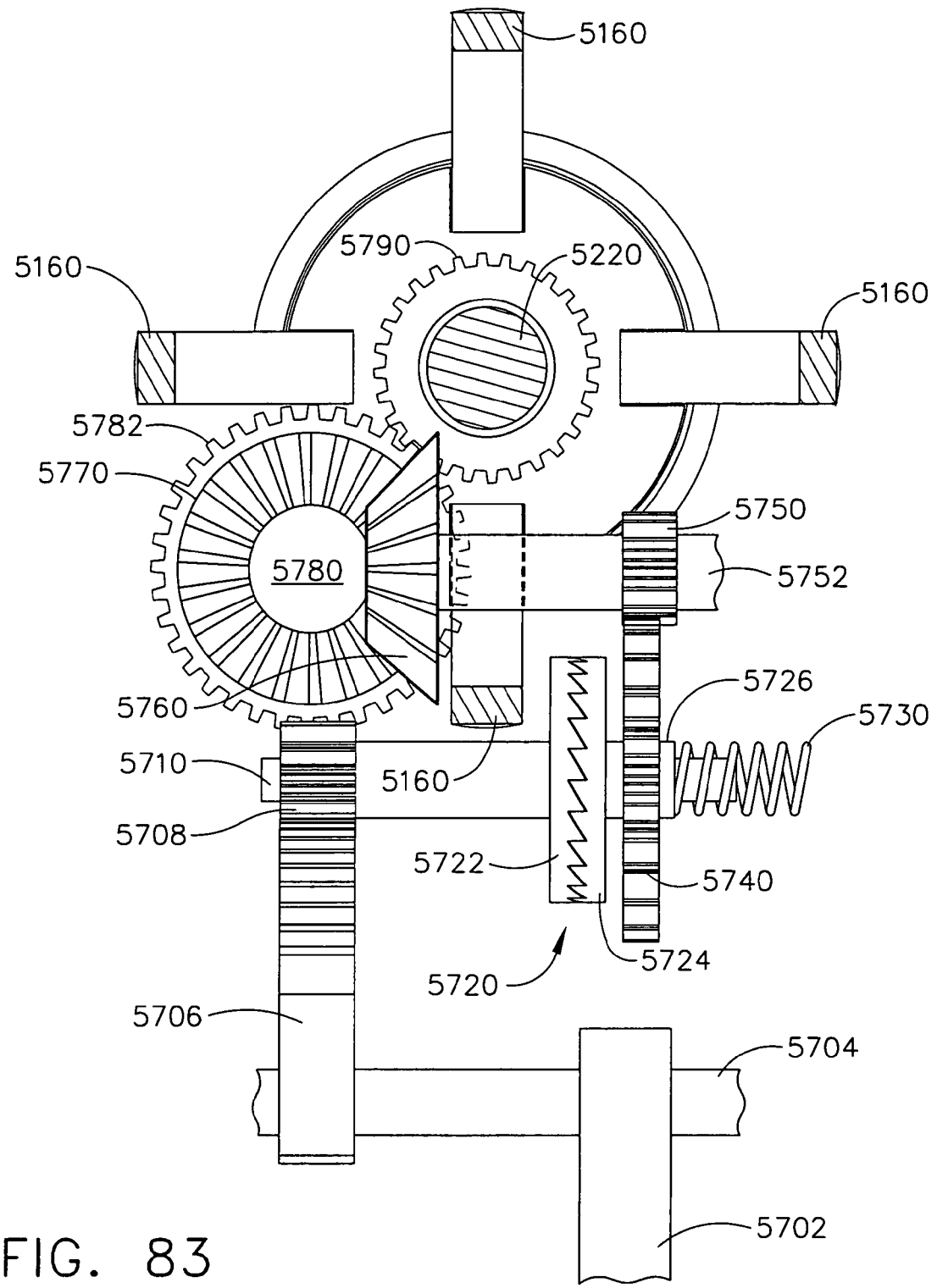
FIG. 83 is a diagrammatic end view of a drive system of various embodiments of the present invention.
Figure 84:
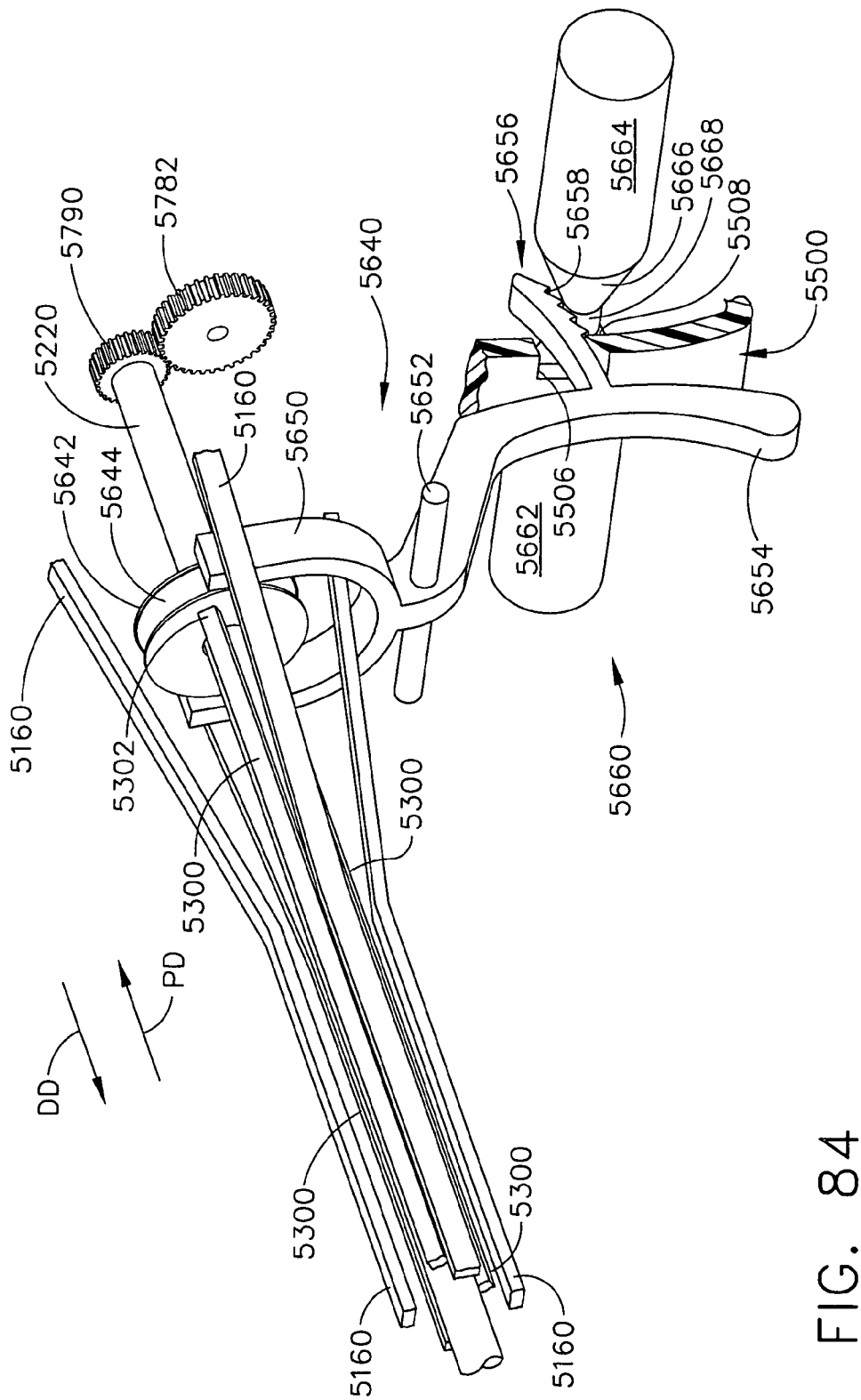
FIG. 84 is a partial perspective view of a brake release mechanism of various embodiments of the present invention.

FIGS. 82-84 depict one embodiment that may be used to articulate the tool assembly 100" relative to the connector segment 4004 and provide actuation thereto. As can be seen in FIG. 82, the instrument 4000 may further include a handle assembly 5500 that may be formed from two housing sections 5510 (only one housing section 5510 is shown in FIG. 82) that may be connected together by screws, snaps, adhesive, etc. In various embodiments, the handle assembly 5500 may take the form of a "pistol-grip" type housing with a hand grip portion 5512. As can be seen in FIG. 82, an attachment flange 5404 may be formed on the proximal end of the outer proximal spine segment 5400 for affixing the outer proximal spine segment 5400 to the handle assembly 5500. The flange 5404 may be attached to the handle housing 5500 by adhesive or other mechanical fastener arrangements, screws, snaps, slots, etc. Likewise, the proximal end 5204 of the proximal spine segment 5200 may have a flange 5210 for affixing the proximal spine segment 5200 to the handle assembly 5500. The flange 5210 may be attached to the handle housing 5500 by adhesive or other mechanical fastener arrangements, screws, snaps, slots, etc.

In various embodiments, the active articulation system 5090 may further comprise an articulation control system, generally designated as 5600, that is operably supported by the handle assembly 5500 and interfaces with the articulation wires 5092. As can be seen in FIG. 82, articulation control system 5600 may comprise a joy stick assembly 5602 to which the proximal ends 5170 of each of the proximal wire connectors 5160 are pivotally connected. In one embodiment, for example, a joy stick assembly 5602 may include an articulation ball 5610 that is rotatably supported in a socket 5520 in the handle assembly 5500. In various embodiments, each proximal end 5170 of the proximal wire connectors 5160 may have a spherical ball bearing 5172 supported thereon to receiving a bearing mount pin 5612 to attach the proximal wire connectors 5160 to the articulation ball 5610. Other fastener arrangements could also be employed however. In addition, an articulation knob 5620 may be attached to the articulation ball 5610.

Thus, to articulate the tool assembly 100" relative to the connector segment 4004, the clinician can grasp the hand grip portion 5512 in one hand and the articulation knob 5620 in the other hand. By manipulating the articulation knob 5620, the clinician can apply articulation motions to the distal wire mount 5100 and ultimately to the four articulation wires 5092 attached thereto which, in turn, impart the articulation motion to the distal spine segment 4050 which will cause the tool assembly 100" to articulate relative to the connector segment 4004 of the disposable reload unit 4002. Thus, the clinician can effectively steer the tool assembly 100" through use of the joy stick assembly 5602.

The position of the tool assembly 100" may be locked in position by a brake control system generally designated as 5640. As can be seen in FIGS. 82 and 84, a brake control system 5640 may include a driver disc 5642 that is movably journaled on the knife drive shaft 5220 for selective axial movement there along without impeding the rotation of the knife drive shaft 5220. As can be seen in FIG. 84, each proximal brake actuator arm 5300 has a proximal end 5302 that is affixed to the drive disc 5642. A brake yoke 5650 may be coupled to the driver disc 5642 by a pair of pins 5643 that protrude into circumferentially extending groove 5644 formed in the driver disc 5642. The brake yoke 5650 may be pivotally supported by the housing assembly 5500 on a brake yoke pivot pin 5652. As can be seen in FIG. 84, in various embodiments, a brake trigger 5654 is formed on the lower portion of the brake yoke 5650. The brake trigger 5654 may have a lock arm 5656 protruding therefrom into an opening 5506 in the housing assembly 5500. A lower portion of the lock arm 5656 may have lock teeth 5658 formed thereon to engage a locking wall portion 5508 of the housing assembly 5500.

Various embodiments of the present invention may also employ a brake release mechanism 5660 for locking and unlocking the brake trigger 5654. As can be seen in FIG. 84, one form of a release mechanism 5660 may include a locking button 5662 that has a release button portion 5664 and is movably supported by the handle assembly 5500 in the position illustrated in FIG. 84. As can be seen in that Figure, the locking button 5664 may have a conical shaped end portion 5666 that has a neck that extends to a conical portion (not shown) of the release button portion 5664. When the clinician pushes the release button portion 5664 in a first direction, the conical portion 5666 contacts the lock arm 5656 and lifts it out of engagement with the locking wall portion 5508 to thereby enable the trigger 5654 to pivot. A spring (not shown) could be used to retain the locking button 5662 in the locked position. Once the trigger 5654 is pivoted to the desired position, the user simply pushes the release portion 5664 in an opposite direction to move the conical portion 5666 out of engagement with the lock arm 5656 to permit it to engage the locking wall portion 5508 once again. Thus, once the clinician has articulated the tool assembly 100" to the desired position, the clinician squeezes the brake trigger 5654 toward the handle assembly 5500. Such action causes the brake yoke 5650 and the driver disc 5642 to move the brake arms 5300 in the distal direction DD which drives the locking tube 5080 in the distal direction DD to lock the fingers 5032 around the ball-shaped member 4060. Once the fingers 5032 have been locked around the ball-shaped member 4060, the clinician can push the locking button in a direction which permits one of the teeth 5658 on the locking arm 5656 to engage the locking wall portion 5508 and retain the brake release mechanism in the locked position. When the clinician desires to unlock the tool assembly 100" and perhaps rearticulate it, the clinician simply pushes the locking trigger release button portion to permit the trigger 5654 to be pivoted away from the handle assembly 5500 and thereby move the brake arms 5300 proximally.

In various embodiments of the present invention, rotational motion may be applied to the knife drive shaft 5220 by means of a drive system generally designated as 5700. As can be seen in FIGS. 82 and 83, in one embodiment, the drive system 5700 may include a firing handle 5702 that is pivotally or otherwise actuatably coupled to the handle assembly 5500. In one embodiment for example, the firing handle 5702 may be pivotably attached to the handle assembly 5500 by a pivot pin 5704. Attached to the firing handle is a firing gear 5706 that is oriented to pivot with the firing handle 5702. The firing gear 5706 may be in meshing engagement with a ratchet drive gear 5708 that is mounted to a ratchet drive shaft 5710. Ratchet drive shaft 5710 may be attached to a ratchet clutch assembly 5720.

In various embodiments, a ratchet clutch assembly 5720 may include a first clutch plate 5722 that is attached to the ratchet shaft 5710 and which is in meshing engagement with a second ratchet clutch plate 5724 that is mounted to an output shaft 5726. The second clutch plate 5724 may be biased into meshing engagement with the first clutch plate 5722, by ratchet spring 5730. A ratchet output gear 5740 may be attached to the ratchet output shaft 5726 which is arranged for meshing engagement with a drive gear 5750 mounted to a bevel drive shaft 5752. An input bevel gear 5760 may be mounted on the bevel drive shaft 5752 and be in meshing engagement with an output bevel gear 5770 that is mounted to an output shaft 5780. An output gear 5782 is mounted to the output shaft 5780 and is in meshing engagement with a knife drive gear 5790 attached to the proximal end 5226 of the knife drive shaft 5220.

Thus, to rotate the knife drive shaft 5220 and drive the knife nut 5050 in the proximal direction PD and actuate the dynamic clamping assembly (not shown) and knife arrangement (not shown) by means of the knife actuation cables 5040, the clinician grasps the handle assembly and ratchets the firing handle 5702 back and forth toward the grip portion 5512. Movement of the firing handle 5512 in that manner will cause the drive system 5700 to impart a rotary motion to the knife drive shaft 5220 and ultimately to the knife screw 5060 to cause the knife nut 5050 to move in the proximal direction. After the firing sequence has been completed, the clinician can detach the reload unit 4002 and reattach another reload unit and repeat the process. In alternative embodiments, the knife drive shaft may be rotated by means of a motor and planetary gear drive. The motors may be battery powered or powered with alternating current. Other drive arrangements could also be employed.

Figure 85:
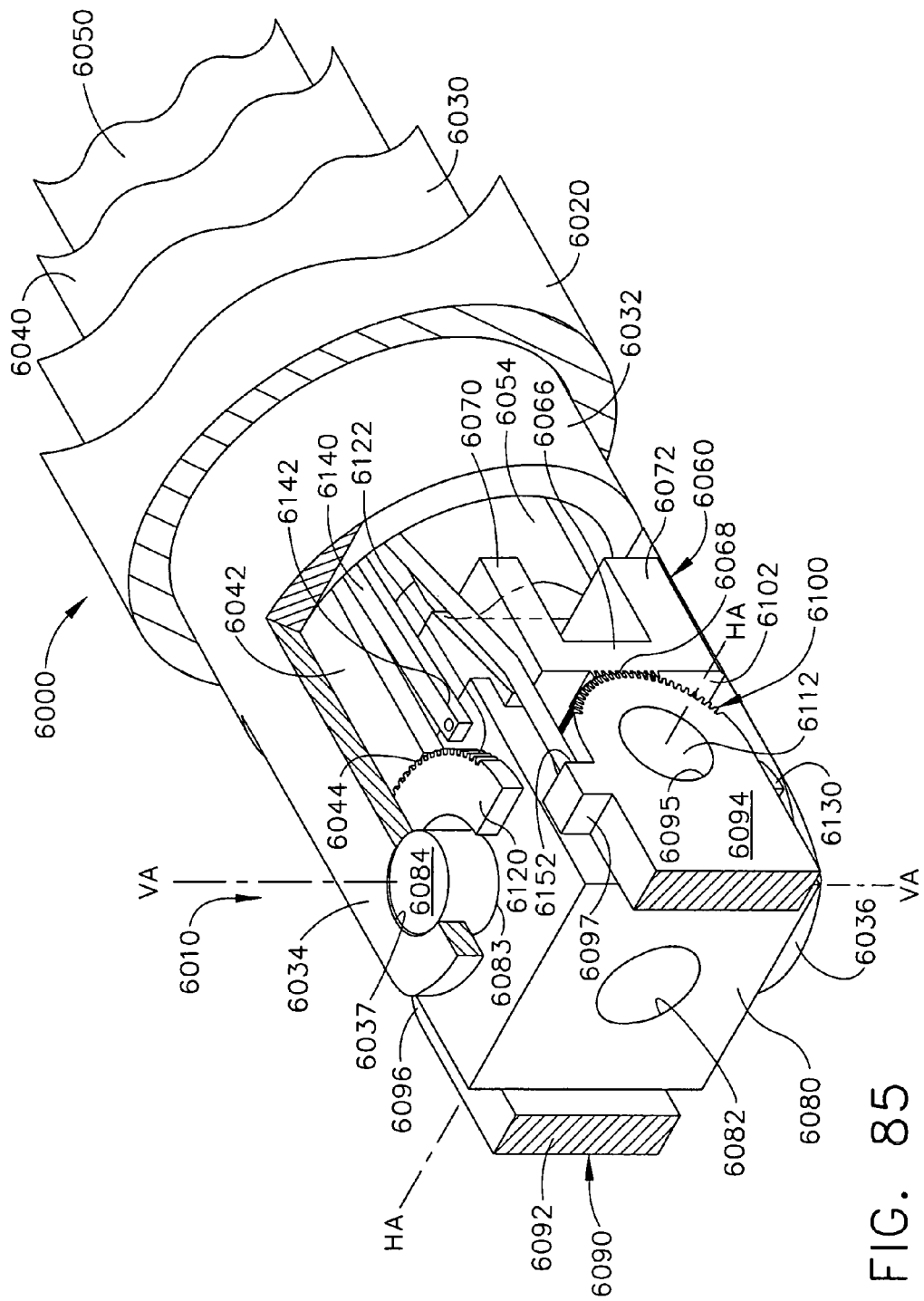
FIG. 85 is a partial perspective view of another articulation joint embodiment of various embodiments of the present invention.
Figure 86:
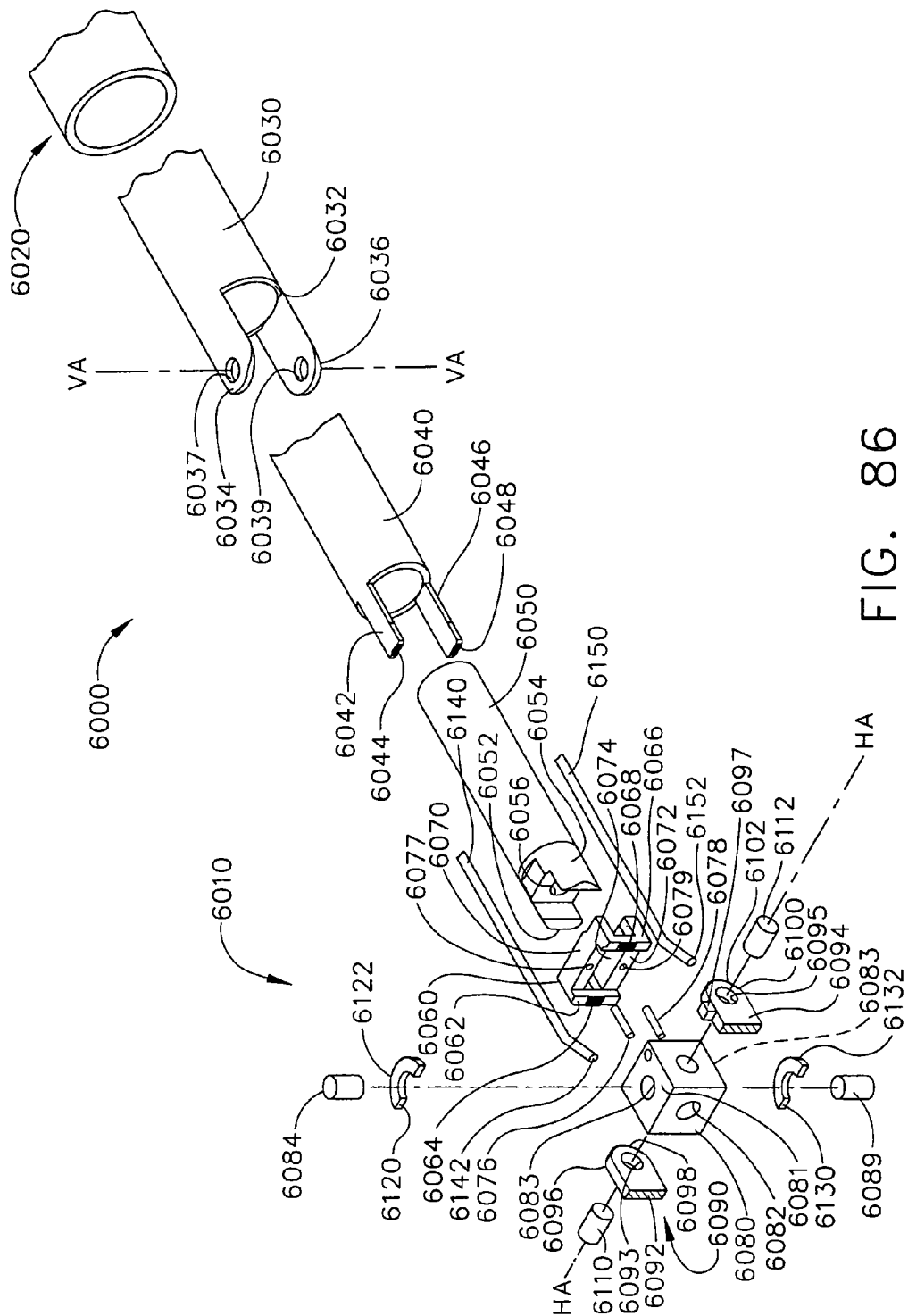
FIG. 86 is an exploded assembly view of the articulation joint of FIG. 85.
Figure 87:
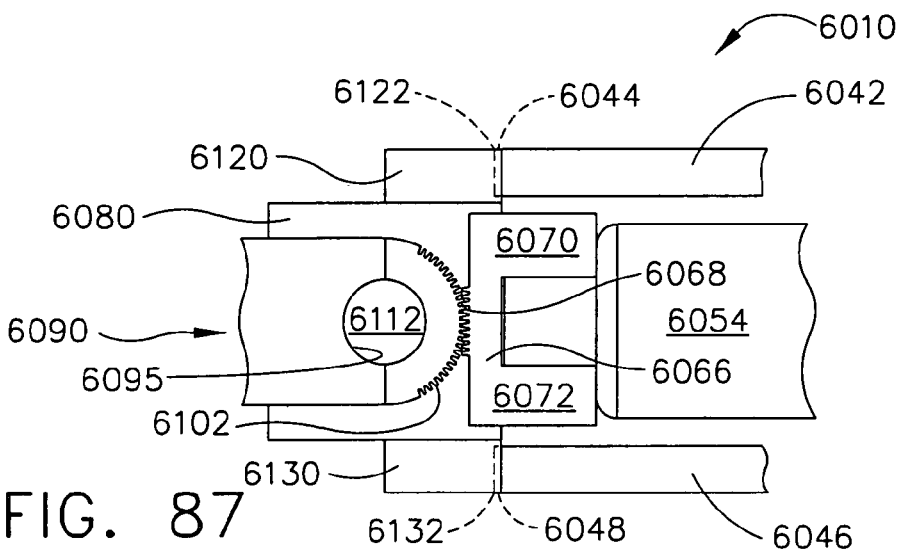
FIG. 87 is a partial side elevational view of the articulation joint of FIGS. 85 and 86.
Figure 88:
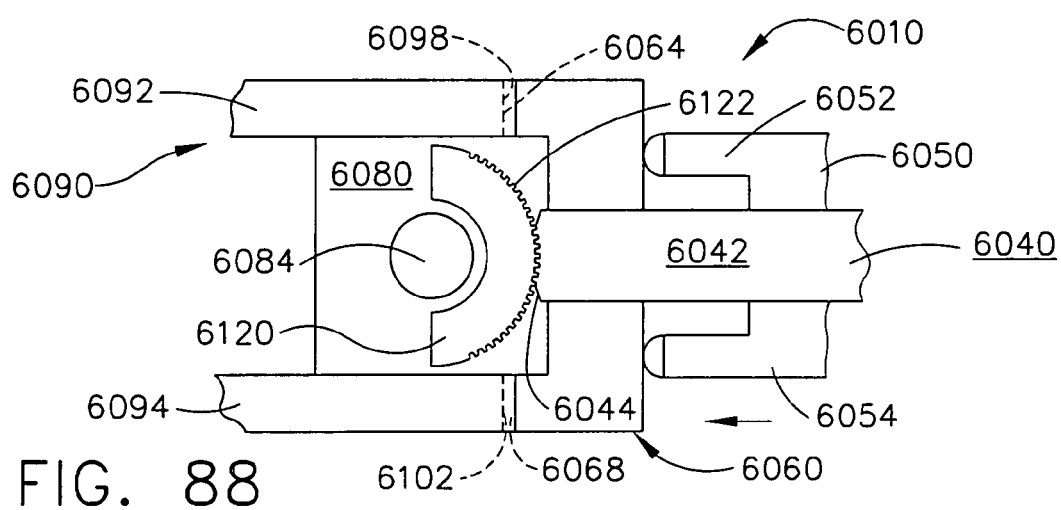
FIG. 88 is a top view of the articulation joint of FIG. 87.
Figure 89:
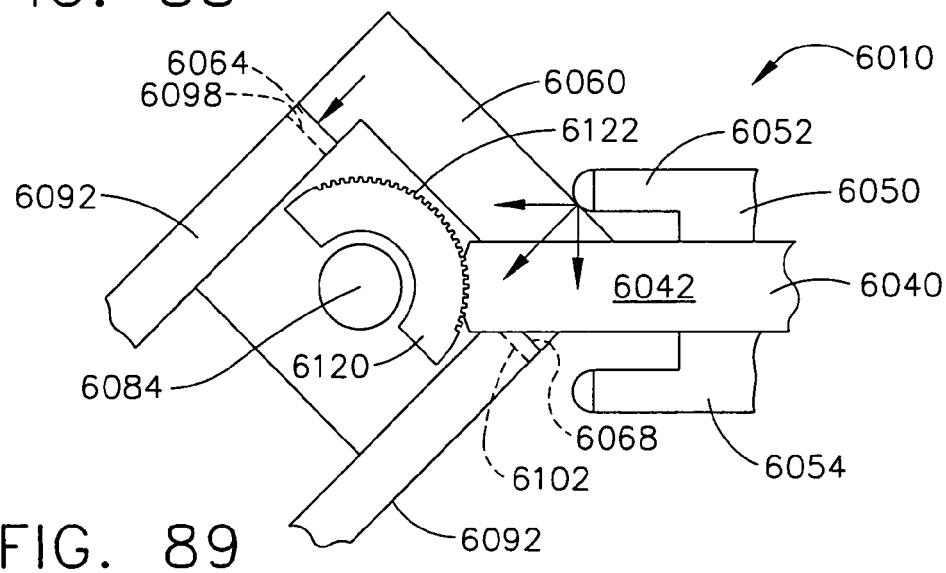
FIG. 89 is another top view of the articulation joint of FIGS. 87 and 88 in an articulated position.

FIGS. 85-89 illustrate another surgical instrument embodiment 6000 that employs an active or controllable articulation joint arrangement 6010. As can be seen in FIGS. 85 and 86, one embodiment may employ a closure tube 6020 of the type and construction described above. The closure tube 6020 has a proximal end (not shown) that may interface with various closure tube control mechanisms supported by the handle assembly for providing actuation forces thereto. The closure tube 6020 may also interface with one of the various tool assemblies described above to apply opening or opening and closing forces to the anvil assembly thereof. Also in this embodiment, a spine member 6030 may extend from the handle assembly (not shown) through the closure tube 6020. Again, the proximal end (not shown) of the spine member 6030 may be operably supported by the handle assembly (not shown) in the various manners described above or in other known manners. In various embodiments, the distal end 6032 of the spine member 6030 may be formed with a top spine arm 6034 and a bottom spine arm 6036 that protrude in the distal direction DD from the distal end 6032 of the spine member 6030. The top spine arm 6034 has a pivot hole 6037 therethrough and the bottom spine arm 6036 has a pivot hole 6039 that is substantially coaxially aligned with the pivot hole 6037 along a vertical axis VA-VA.

The various embodiments may also include a horizontal locking tube 6040 that extends through the spine member 6030. The horizontal locking tube 6040 has a proximal end (not shown) that is supported by the handle assembly (not shown) and which may interface with an actuation arrangement (not shown) for axially advancing the horizontal locking tube 6040 axially in the proximal direction PD and distal direction DD within the spine member 6030 and for selectively retaining or locking the horizontal locking tube 6040 in a desired axial position. In addition, the actuation arrangement for the horizontal locking tube 6040 may also employ a spring or other arrangement for biasing the horizontal locking tube 6040 in the proximal direction PD after the horizontal locking tube 6040 has been unlocked. As can be seen in FIG. 86, the horizontal locking tube 6040 has a top or first locking bar 6042 that has a series of top or first teeth 6044 formed therein. The horizontal locking bar 6040 further has a bottom or second locking bar 6046 that has a series of bottom or second teeth 6048 formed in the distal end thereof.

Also in these embodiments, a vertical locking tube 6050 may extend through the horizontal locking tube 6040. The vertical locking tube 6050 has a proximal end (not shown) that is supported by the handle assembly (not shown) and which may interface with an actuation arrangement (not shown) for axially advancing the vertical locking tube 6050 axially in the proximal direction PD and distal direction DD within the horizontal locking tube 6040 and for selectively retaining or locking the vertical locking tube 6050 in a desired axial position. In addition, the actuation arrangement for the vertical locking tube 6050 may also employ a spring or other arrangement for biasing the vertical locking tube 6050 in the proximal direction PD after the vertical locking tube 6050 has been unlocked. In various embodiments, for example, the actuation arrangement employed may be configured to actuate, lock and release the horizontal locking tube 6040 and the vertical locking tube 6050 in simultaneous motions.

As can be seen in FIG. 86, in various embodiments, for example, the vertical locking tube 6050 has a first vertical lock tine 6052 and a second vertical lock tine 6054. Various embodiments may employ a tool assembly of the types described above that use a cable driven dynamic clamping member and/or knife arrangement. The vertical locking tube may have a cable passage 6056 therethrough to accommodate the drive cables (not shown) that pass from the tool assembly to the handle assembly.

In various embodiments, the first and second vertical locking tines 6052, 6054 are oriented for engagement with a vertical locking block 6060. In one embodiment, for example, the vertical locking block 6060 may have a first lateral locking column 6062 that has a series of first lateral teeth 6064 thereon and a second lateral column 6066 that has a series of second lateral teeth 6068 thereon. The first lateral locking column 6062 and the second lateral locking column 6066 are arranged in a spaced apart relation to each other by an upper or first lateral cross bar 6070 and a bottom or second lateral cross bar 6072 that are arranged in a spaced apart relationship to each other to define an actuator-receiving passage 6074 therebetween. In various embodiments, the vertical locking block 6060 may be configured for axial travel in the proximal direction PD and distal direction DD relative to an articulation member or block 6080 in response to an actuation motion from the vertical locking tube 6050. The vertical locking block 6060 may be supported for axial travel toward and away from the articulation block 6080 by a pair of pins 6076 and 6078 that extend into holes 6077, 6079 in the vertical lock block 6060 and holes (not shown) in articulation block 6080.

As can be seen in FIGS. 85 and 86, the articulation block 6080 may have a longitudinal passage 6082 therethrough for accommodating the drive cables (not shown). In addition, a first vertical pin 6084 is received in a hole 6083 in the articulation block and protrudes therefrom to be received in the first pivot hole 6037 in the top or first upper arm 6037 of the spine member 6030. Likewise, a lower pin 6089 protrudes from the bottom surface of the articulation block 6080 to be pivotally received in the bottom or second pivot hole in the bottom or second arm 6036 of the spine member 6030 such that the articulation block 6080 may selectively pivot about the vertical axis VA-VA. Also in various embodiments, a proximal end of an elongate channel assembly 6090 that may comprise a portion of the tool assembly may have a first clevis portion or arm 6092 and a second clevis portion or arm 6094 extending in the proximal direction therefrom. The proximal facing face 6096 of the first clevis arm 6092 has a first set of horizontal locking teeth 6068 formed thereon for selective engagement with a corresponding set of second horizontal locking teeth 6064 on the first lateral locking column 6062. Likewise, the proximal facing face 6100 of the second clevis arm 6094 has another set of first horizontal locking teeth 6102 formed thereon for selective meshing engagement with another corresponding set of second horizontal locking teeth 6068 on the second lateral locking column 6062 on the vertical lock block 6060. The first clevis arm 6092 may have a first pivot hole 6093 therethrough that is adapted to pivotally receive a pivot pin 6110 protruding from the articulation block 6080 and the second clevis arm 6094 may have a second pivot hole 6095 therethrough for pivotally receiving a second pivot pin 6112 protruding from the articulation block 6080 such that the channel assembly 6090 may selectively pivot relative to the articulation block 6080 about horizontal axis HA-HA.

As can also be seen in FIG. 86, a first horizontal lock segment 6120 may be attached or integrally formed on an upper surface 6081 of the articulation block 6080 and have a series of first vertical locking teeth 6122 formed therein for engagement with a corresponding set of second vertical locking teeth 6044 formed in the top or first horizontal locking bar 6042. Likewise, a second horizontal lock segment 6130 may be attached to or integrally formed with a bottom surface 6083 of the articulation block 6080 and have another series of first vertical locking teeth 6132 formed therein for engagement with a corresponding set of second vertical locking teeth 6048 on the second or bottom locking bar 6046.

To enable the user to actively articulate the tool assembly (channel assembly 6090) the articulation joint 6010 may be provided with a horizontal actuator bar 6140 and a vertical actuator bar 6150. The horizontal actuator bar 6140 may be fabricated from plastic material, spring steel, etc., for example. The distal end 6142 of the horizontal actuator bar 6140 may be formed with a spherical ball bearing arrangement of the type described above and be pinned to or otherwise attached to the articulation block 6080. The proximal end (not shown) of the horizontal actuator bar 6140 may be operably attached to a joy stick assembly of the type described above operably supported in the handle assembly or other actuation arrangement for applying pushing and pulling motions to the horizontal actuator bar 6140. As can be seen in FIGS. 85 and 86, the distal end 6152 of the vertical actuator bar 6150 may be coupled to an extension block 6097 formed on the second clevis arm 6094. The distal end 6152 may be fixedly attached to the extension block 6097 or have a spherical ball bearing formed thereon to be pivotally attached thereto. The proximal end (not shown) of the vertical actuator bar 6150 may be operably attached to a joy stick assembly of the type described above operably supported in the handle assembly or other actuation arrangement for applying pushing and pulling motions to the vertical actuator bar 6150. In alternative embodiments, either the vertical actuator bar 6150 or the horizontal actuator bar 6140 may be omitted. In those embodiments, for example, if the horizontal actuator bar 6140 is omitted, the vertical actuator bar 6150 can be employed to articulate the channel assembly 6090 (and tool assembly) about the horizontal axis HA-HA and the clinician can articulate the channel assembly 6090 (and tool assembly) about the vertical axis by releasing (unlocking) the horizontal locking tube 6040 and bringing the tool assembly into contact with a portion of the patient's body or another surgical instrument to apply a pivoting force to the channel assembly (and tool assembly) to cause them to pivot about vertical axis VA-VA until they are positioned in the desired position at which time the horizontal locking tube 6040 may be advanced into locking engagement with the horizontal lock members 6120, 6130. Similarly, if the vertical actuator bar is omitted, the horizontal actuator bar can be employed to articulate the channel assembly 6090 (and tool assembly) about the vertical axis VA-VA and the clinician can articulate the channel assembly 6090 (and tool assembly) about the horizontal axis HA-HA by releasing (unlocking) the vertical locking tube 6050 and bringing the tool assembly into contact with a portion of the patient's body or another surgical instrument to apply a pivoting force to the channel assembly 6090 (and tool assembly) to cause them to pivot about horizontal axis HA-HA until they are positioned in the desired position at which time the vertical locking tube 6050 may be advanced into locking engagement with the horizontal locking teeth 6068, 6102 on the channel devises 6092, 6094, respectively.

Figure 90:
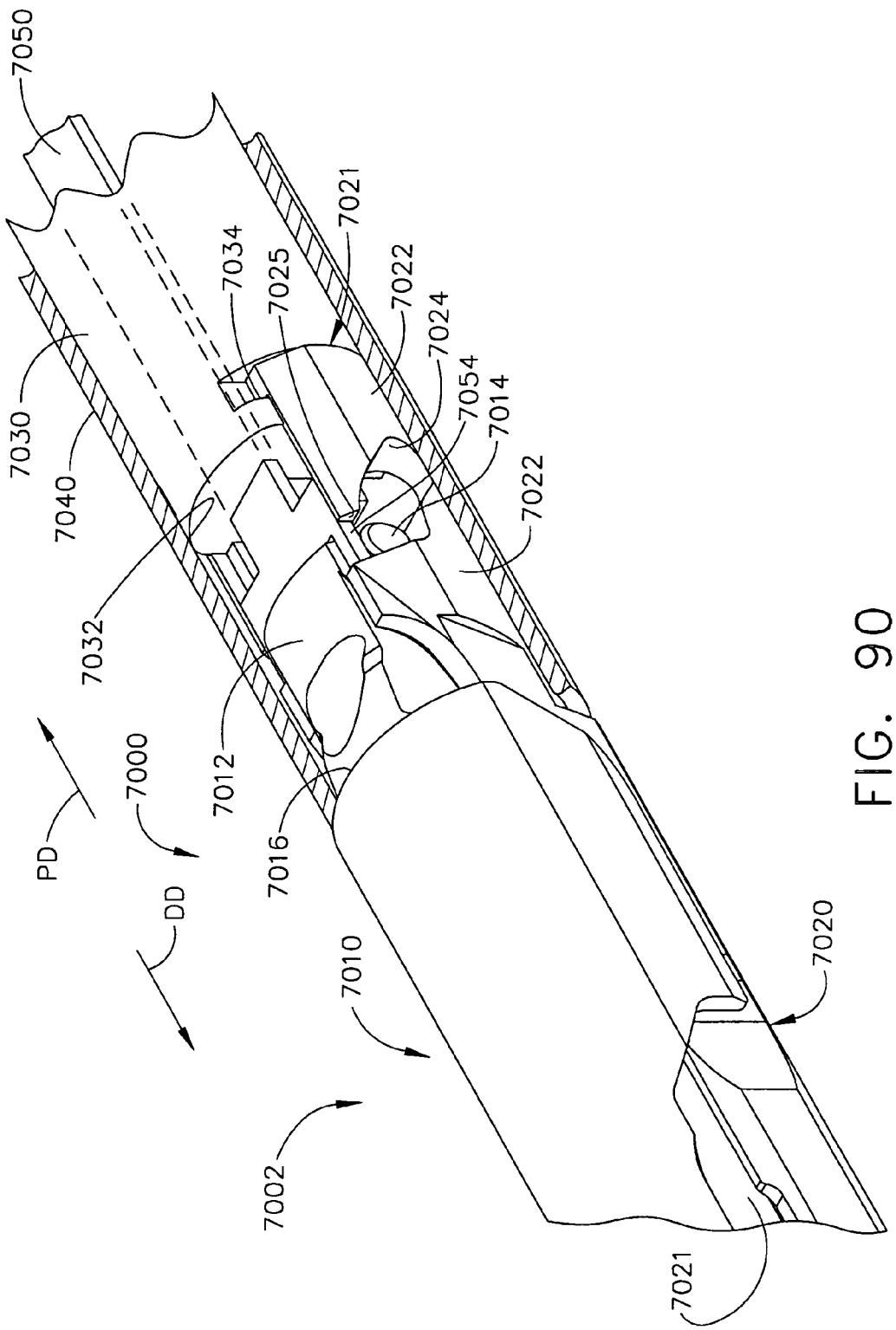
FIG. 90 is a partial perspective view of another tool assembly and closure tube arrangement of various embodiments of the present invention with a portion of the closure tube shown in cross-section.

FIGS. 90-105 illustrate another surgical instrument embodiment 7000 of the present invention, that may be disposed of after use. However, the unique and novel features of these embodiments may be employed in connection with several of the embodiments discussed above without departing from the spirit and scope of the present invention. As can be seen in FIG. 90, the tool assembly 7002 includes an anvil assembly 7010 that is pivotally coupled to a channel assembly 7020 of the type and construction described above for operably receiving a staple cartridge 7021 therein. The anvil assembly 7020 has a proximal end 7012 that has two anvil trunnions 7014 protruding therefrom that are adapted to be received within corresponding open ended slots 7024 in the walls 7022 of the proximal end 7021 of the channel assembly 7020. As can also be seen in FIGS. 90-95, the instrument 7000 may further include a spine member 7030 that has a distal end 7032 that may be attached to the proximal end 7021 of the channel assembly 7020.

These embodiments may also employ a closure tube 7040 that may be constructed and operated in any one of the above-described manners. For example, the distal end 7042 may be constructed for selective axial contact with a proximal facing ledge 7016 formed in the anvil assembly 7010 such that as the closure tube 7040 is moved in the distal direction DD, the distal end 7042 contacts the ledge 7016 and causes the anvil assembly 7010 to pivot to the closed position (FIGS. 90-92) while the trunnions 7014 are constrained to pivot in their respective slots 7024 by a trunnion lock bar 7050 as will be discussed in further detail below. The proximal end (not shown) of the closure tube 7040 may be supported by actuation components of the type and construction described above in the handle assembly (not shown) to selectively control the axial movement of the closure 7040 in the distal direction DD and proximal direction PD.

As can be seen in FIG. 90, the trunnion lock bar 7050 may be slidably supported in an axial slot 7034 provided in the spine 7030. The proximal end (not shown) of the trunnion lock bar 7050 may interact with actuation members in the handle assembly to move the trunnion lock bar 7050 in the distal direction DD and the proximal direction PD and selectively retain the bar 7050 in those positions. As can be further seen in FIGS. 92 and 94, the distal end 7052 of the trunnion lock bar 7050 may have two trunnion retention arms 7054 protruding therefrom.

Figure 95:
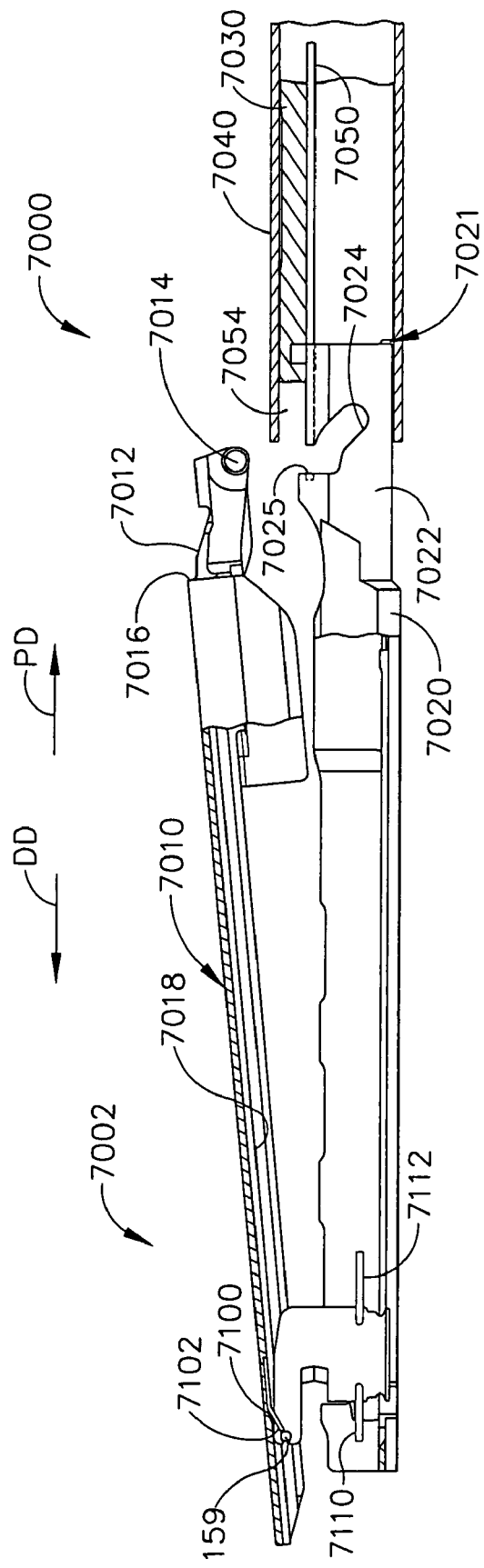
FIG. 95 is a cross-sectional elevational view of the tool assembly and closure tube arrangement of FIGS. 90-92 with the trunnion lock bar in an unlocked position and the trunnions moved out of the trunnion slots in the elongate channel assembly.

FIGS. 90-92 illustrate the trunnion lock bar 7050 in the locked position wherein the trunnion retention arms 7054 retain the trunnions in their respective open ended slots 7024 in the channel assembly 7020. As can be seen in those Figures, when in that position, the anvil assembly 7010 may be in the closed (clamped) position. After the stapling procedure has been completed (e.g., after the dynamic clamping member/knife assembly has been driven from the proximal end 7004 of the tool assembly 7002 to the distal end 7006 of the tool assembly 7002), the clinician can retract the closure tube and the trunnion lock bar 7050 in the proximal direction to permit the trunnions 7014 to popup through the open end 7025 of each slot 7024 as shown in FIG. 95. When the proximal end 7012 of the anvil assembly 7010 is in the position illustrated in FIG. 95, the person of ordinary skill in the art will understand that the tissue that was once clamped between the anvil assembly 7010 and the staple cartridge 7021 can now be released therefrom.

FIGS. 104 and 105 illustrate an alternative surgical instrument 4000' embodiment that may have portions that are substantially identical in construction and operation as the surgical instrument 4000 described above. In the embodiment depicted in FIGS. 104 and 105, however, the slots 4014' are opened ended to permit the trunnions 4022' to become disengaged therefrom. As can be seen in FIG. 104, when the closure ring 4030 has been advanced to its distal-most position to close the anvil assembly 4020, the closure ring 4030 also serves to retain the anvil assembly 4020' in the clamped position by virtue of its bearing on the proximal end portion 4024' of the anvil assembly 4020'. When the closure ring 4030 is advanced to its proximal-most position as shown in FIG. 105, the trunnions 4022' are free to move out of the open ended slots 4014' in the elongate channel assembly 4012'. Surgical instrument 4000' may otherwise operate in an identical manner as surgical instrument 4000 which was described in detail above.

Also in various embodiments, to completely release the anvil assembly 7010, the anvil assembly 7010 may be provided with a spring member 7100 that is attached to the underside 7011 of the anvil assembly 7010 as shown in FIG. 95. As can be seen in that Figure, the dynamic clamping member 150 which is configured to be driven by one or more drive cables 7110, 7112 within the elongate channel assembly 7020 by drive cables may be provided with a pin 159 that is oriented to be slidably received in a slot 7018 in the anvil assembly 7010. The pin 159 serves to draw the anvil assembly 7010 toward to the elongate channel assembly 7020 as the dynamic clamping assembly 150 is driven in the distal direction DD through the elongate channel assembly 7010. As can be seen in FIG. 95, the distal end 7102 of the spring member 7120 extends downwardly to engage the pin 159 when the dynamic clamping assembly 150 has reached its distal-most position as illustrated in FIG. 95. Thereafter, pulling or otherwise moving the dynamic clamping assembly 150 in the proximal direction will result in the spring 7102 dislodging the pin 159 from the slot 7018.

Various embodiments of a dynamic clamping assembly 150 are illustrated in FIGS. 96-103. As can be seen in those Figures, a dynamic clamping member 150 may include an upper portion 157, a central support or upward extension 151, and a bottom portion 152 which cooperates to slidingly retain dynamic clamping member 150 along an ideal cutting path during longitudinal, distal movement thereof within the elongate channel assembly 7020. The leading cutting edge 155, here, knife blade 155a, is dimensioned to ride within a slot formed in the staple cartridge 7021 and separate tissue once stapled. It is envisioned that leading edge 155 of the dynamic clamping member 150 may be serrated, beveled or notched to facilitate tissue cutting. The dynamic clamping member 150 may be driven by one or more drive cables 7100, 7112. To facilitate attachment of said drive cables 7110, 7112, the dynamic clamping assembly 150 may be provided with attachment apertures 7130 and ledges 7132. However, other attachment arrangements and drive configurations could be employed.

Figure 96:
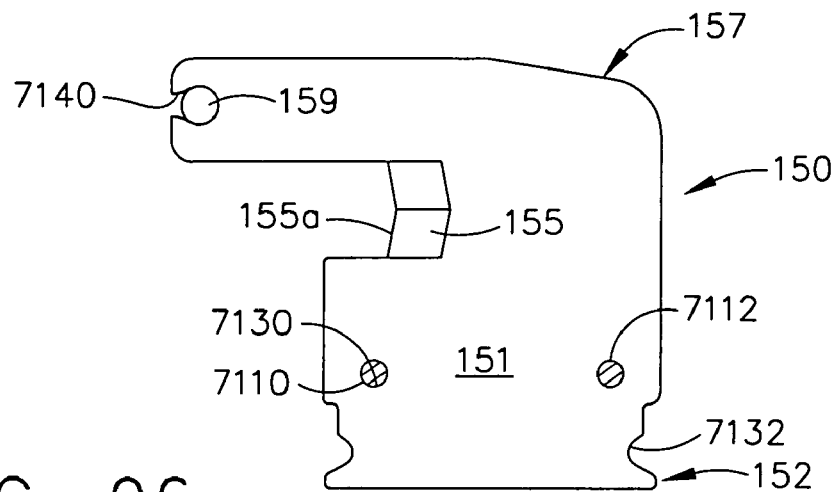
FIG. 96 is a side elevational view of a dynamic clamping assembly of various embodiments of the present invention.
Figure 97:
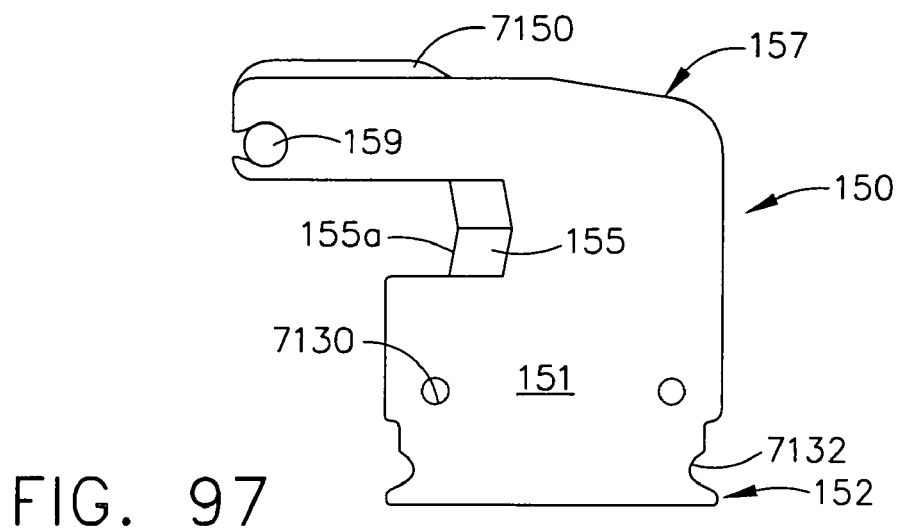
FIG. 97 is a side elevational view of another dynamic clamping assembly of various embodiments of the present invention.
Figure 98:
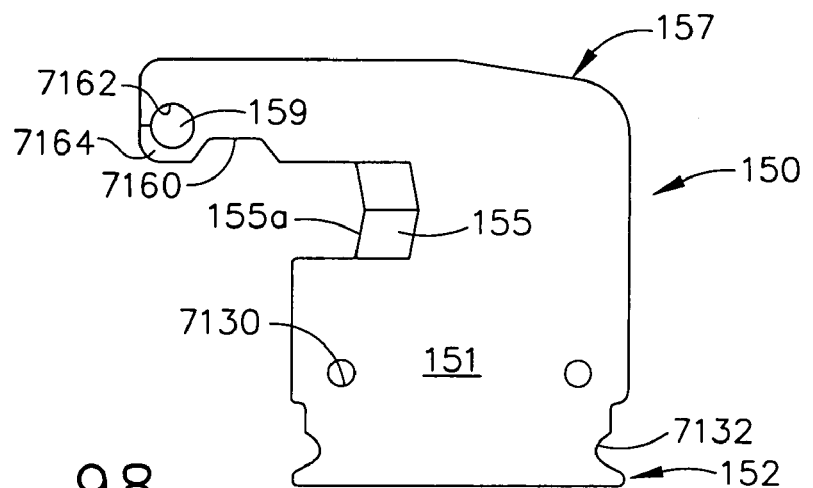
FIG. 98 is a side elevational view of another dynamic clamping assembly of various embodiments of the present invention.
Figure 99:
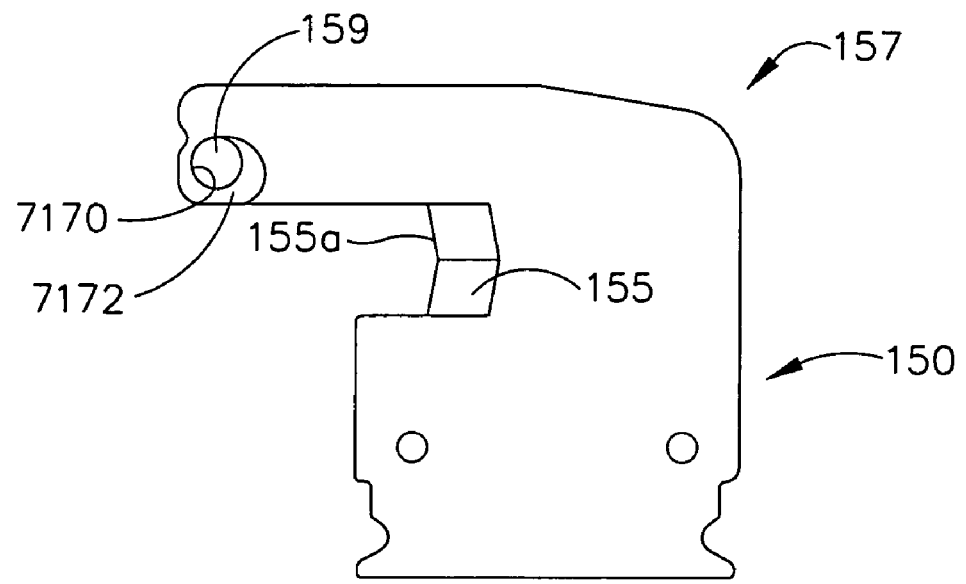
FIG. 99 is a side elevational view of another dynamic clamping assembly of various embodiments of the present invention.
Figure 100:
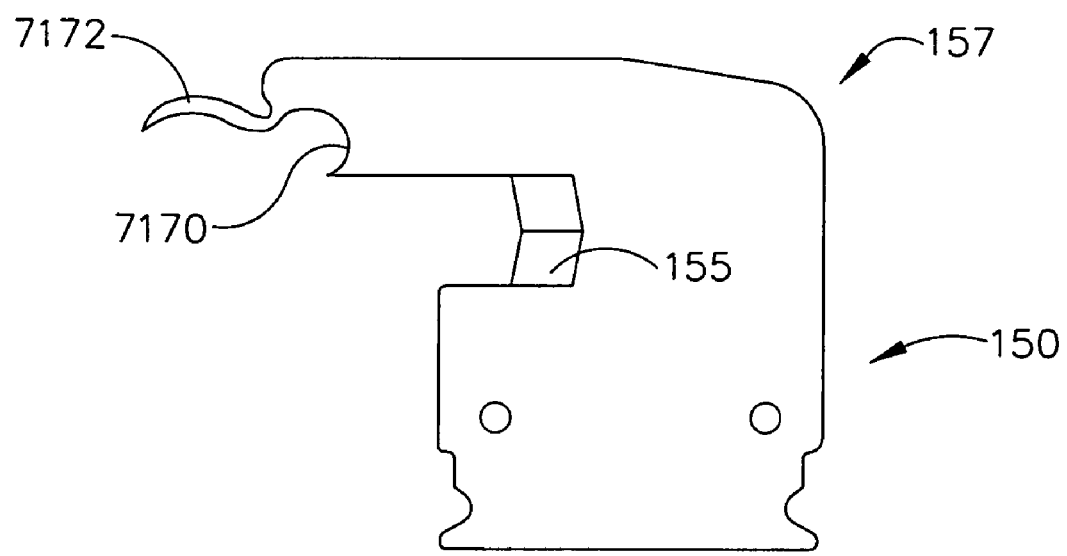
FIG. 100 is another side elevational view of the dynamic clamping assembly of FIG. 99 after the slot has been opened and the pin removed.
Figure 101:
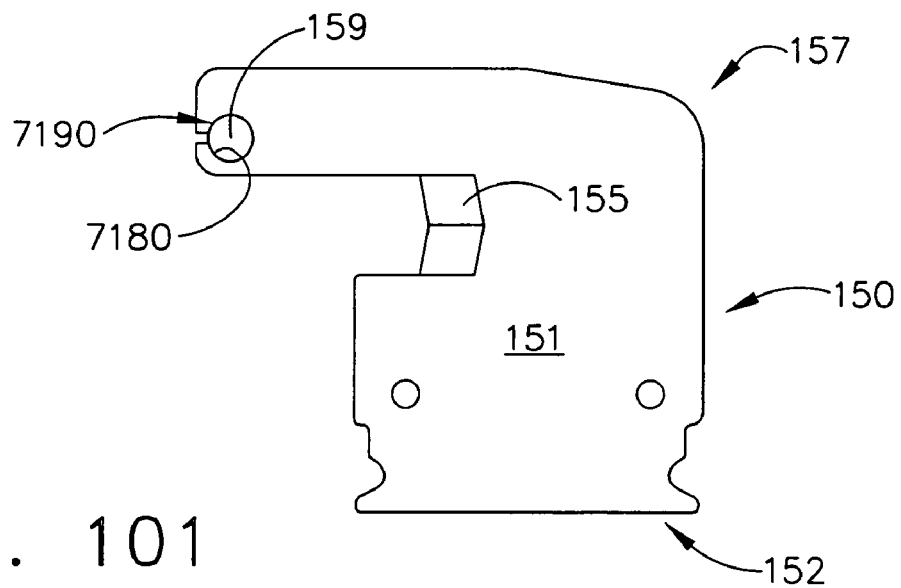
FIG. 101 is a side elevational view of another dynamic clamping assembly of various embodiments of the present invention.
Figure 102:
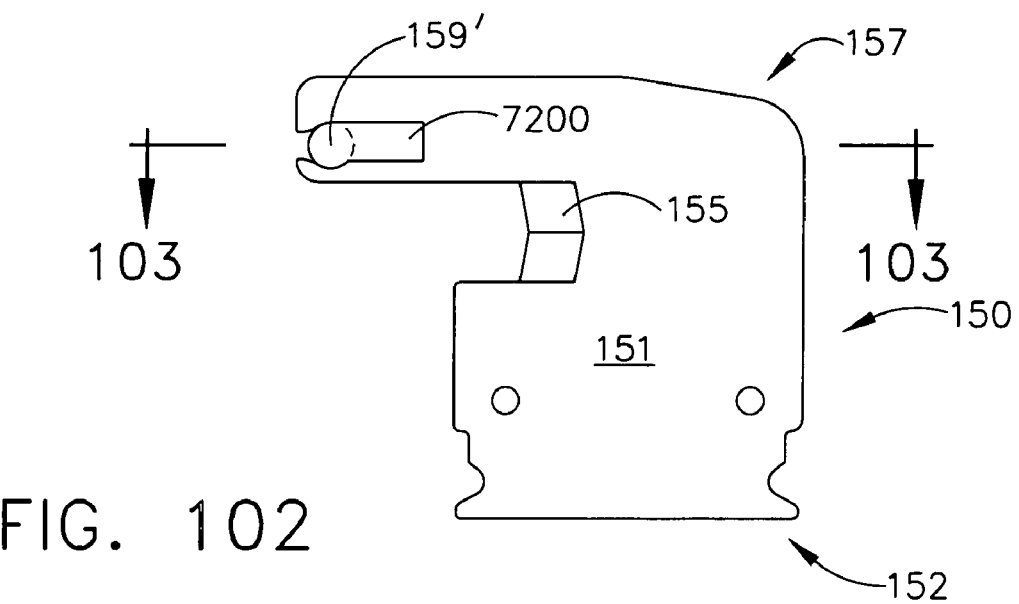
FIG. 102 is a side elevational view of another dynamic clamping assembly of various embodiments of the present invention.
Figure 103:
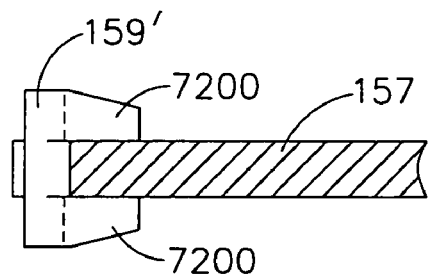
FIG. 103 is a partial cross-sectional view of the dynamic clamping assembly of FIG. 102 taken along line 103-103 in FIG. 102.

Turning to FIG. 96, the upper portion 157 of the dynamic clamping member is provided with an open ended slot 7140 for receiving the pin 159 therein. Once the pin 159 contacts the spring 7100, the pin 159 may be forced out of the open ended slot 7140. The dynamic clamping member embodiment of FIG. 97 is substantially identical to the embodiment of FIG. 96, except that the upper portion 157 has a reinforcement member 7150 formed thereon. In the embodiment of FIG. 98, an undercut portion 7160 is provided in the upper portion and the slot 7162 is initially crimped closed. When the pin 159 contacts the spring 7100, the bottom portion 7164 forming the slot is permitted to bend downward to release the pin 159. In the embodiment depicted in FIG. 99, the slot 7170 supporting the pin 159 is defined by a bendable flap 7172 that can be bent or deformed to open the slot 7170 to permit the pin to be removed therefrom as illustrated in FIG. 100. The embodiment depicted in FIG. 101 has a second slot 7190 that communicates with the first pin slot 7180 that enables the first pin slot to be opened to a point wherein the pin can be released therefrom. In the embodiments depicted in FIGS. 96-101, the pin 159 has a substantially circular cross-sectional shape. In the embodiment depicted in FIGS. 102 and 103, the pin 159' is provided with lateral wings or gussets 7200 to provide additional support to the pin 159' and minimize any likelihood of the pin bending as the dynamic clamping member 150 is driven through the elongate channel assembly 7020.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device may be reconditioned for reuse after at least one use. Reconditioning may include any combination of the steps of disassembly of the device, followed by cleaning or replacement of particular pieces, and subsequent reassembly. In particular, the device may be disassembled, and any number of particular pieces or parts of the device can be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical instrument comprising:
   an elongate channel assembly having a distal end and a proximal end, said elongate channel assembly constructed to operably support a staple cartridge assembly therein;
   a knife assembly oriented for travel within said elongate channel assembly;
   a first distal cable transition support operably mounted to said distal end of said elongate channel assembly;
   at least one second cable transition support operably attached to said knife assembly; and
   a first cable having a distal end affixed to said distal end of said elongate channel assembly, said first cable extending around said second cable transition support on said knife assembly and said first distal cable transition support and having a proximal end interfacing with a winch assembly;
   a second distal cable transition support operably mounted to said distal end of said elongate channel assembly; and
   a second cable having a distal end affixed to said distal end of said elongate channel assembly, said second cable extending around said second cable transition support on said knife assembly and said second distal cable transition support and having a proximal end interfacing with said winch assembly.

2. The surgical instrument of claim 1 wherein said first and second distal cable transition supports are selected from the group of cable transition supports consisting of pulleys, rods, and capstans.

3. The surgical instrument of claim 2 wherein said second cable transition support comprises a double pulley.

4. The surgical instrument of claim 1 wherein said winch assembly comprises:
   a first rotatable spool to which said first cable is attached; and
   a second rotatable spool to which said second cable is attached.

5. The surgical instrument of claim 4 wherein said first rotatable spool has a decreasing diameter along its axial direction and wherein said second rotatable spool has a decreasing diameter along its axial direction.

6. The surgical instrument of claim 4 wherein said first rotatable spool has a diameter in a central portion that is larger than diameters of the end portions thereof and wherein said second rotatable spool has a diameter in a central portion that is larger than the diameters on the end portions thereof.

7. The surgical instrument of claim 4 wherein said first and second spools are driven by an actuation system selected from the group of actuation systems consisting of manually driven actuators, electrical powered motors, alternating current powered motors, and air powered motors.

8. The surgical instrument of claim 4 wherein said first rotatable spool is rotatable in directions that are opposite from other directions in which said rotatable second spool rotates.

9. The surgical instrument of claim 8 further comprising a transmission assembly communicating with said winch assembly for selectively changing between directions in which the first and second rotatable spools rotate.

10. A method for processing an instrument for surgery, the method comprising:
    obtaining the surgical instrument comprising an elongate channel assembly having a distal end and a proximal end, said elongate channel assembly constructed to operably support a staple cartridge assembly therein; a knife assembly oriented for travel within said elongate channel assembly; a first distal cable transition support operably mounted to said distal end of said elongate channel assembly; at least one second cable transition support operably attached to said knife assembly; and a first cable having a distal end affixed to said distal end of said elongate channel assembly, said first cable extending around said second cable transition support on said knife assembly and said first distal cable transition support and having a proximal end interfacing with a winch assembly;
    a second distal cable transition support operably mounted to said distal end of said elongate channel assembly; and a second cable having a distal end affixed to said distal end of said elongate channel assembly, said second cable extending around said second cable transition support on said knife assembly and said second distal cable transition support and having a proximal end interfacing with said winch assembly;
    sterilizing the surgical instrument; and
    storing the instrument in a sterile container.

11. A surgical instrument, comprising:
    an elongate channel assembly having a distal end and a proximal end and constructed to operably support a staple cartridge therein;
    a knife assembly oriented for travel within said elongate channel assembly;
    first and second distal cable transition supports on said distal end of said elongate channel assembly;
    first and second proximal cable transition supports operably attached to said proximal end of said elongate channel assembly;
    a reciprocatable drive member;
    a first cable attached to said knife assembly and said reciprocatable drive member, said first cable operably supported on said first distal cable transition support and said first proximal cable transition support;
    a second cable having one end attached to said knife assembly and another end attached to said reciprocatable drive member, said second cable operably supported on said second distal transition support and said second proximal transition support; and
    at least one retract cable attached to said knife assembly and said reciprocatable drive member and extending therebetween.

12. The surgical instrument of claim 11 wherein said first and second distal cable transition members and said first and second proximal cable transition members are selected from the group of cable transition members consisting of pulleys, rods, and capstans.

13. The surgical instrument of claim 11 wherein said reciprocatable drive member is selectively driven by a drive system selected from the group of drive systems consisting of manually driven actuator, electrical powered motors, alternating current powered motors, and air powered motors.

14. The surgical instrument of claim 13 wherein said drive system comprises:

a rack coupled said drive member; and a driven pinion gear for selectively driving said rack in axial directions.

15. The surgical instrument of claim 14 further comprising a transmission assembly operably communicating with said driven pinion gear for selectively controlling a direction of rotation thereof.

16. A method for processing an instrument for surgery, the method comprising:

obtaining the surgical instrument comprising an elongate channel assembly having a distal end and a proximal end and constructed to operably support a staple cartridge therein; a knife assembly oriented for travel within said elongate channel assembly; first and second distal cable transition supports on said distal end of said elongate channel assembly; first and second proximal cable transition supports operably attached to said proximal end of said elongate channel assembly; a reciprocatable drive member; a first cable attached to said knife assembly and said reciprocatable drive member, said first cable operably supported on said first distal cable transition support and said first proximal cable transition support; a second cable having one end attached to said knife assembly and another end attached to said reciprocatable drive member, said second cable operably supported on said second distal transition support and said second proximal transition support; and at least one retract cable attached to said knife assembly and said reciprocatable drive member and extending therebetween;

sterilizing the surgical instrument; and storing the instrument in a sterile container.

17. A surgical instrument, comprising:

a handle assembly;

an elongate closure tube assembly operably coupled to said handle assembly;

an elongate channel assembly having a proximal end operably interfacing with said elongate closure tube assembly, said elongate channel assembly constructed to operably support a staple cartridge therein;

a knife assembly oriented for travel within said elongate channel assembly;

two first distal cable transition supports operably attached to a distal end of said elongate channel assembly;

at least one second cable transition support operably attached to said knife assembly;

a first cable having a first anchor segment affixed to a first point of attachment on said distal end of said elongate channel assembly, said first cable extending from said first point of attachment around one of said first cable transition supports and said second cable transition support to interface with a winch assembly operably supported by said handle assembly; and a second cable having a second anchor segment affixed to a second point of attachment on said distal end of said elongate channel assembly, said second cable extending from said second point of attachment around the other one of said first cable transition supports and said second cable transition support to interface with said winch assembly.

18. The surgical instrument of claim 17 further comprising an articulation joint in said elongate closure tube assembly.

* * * * *